(12) United States Patent
Ozawa et al.

(10) Patent No.: US 12,303,505 B2
(45) Date of Patent: May 20, 2025

(54) TUMOR-TREATING PHARMACEUTICAL COMPOSITION

(71) Applicant: Eisai R&D Management Co., Ltd., Tokyo (JP)

(72) Inventors: Yoichi Ozawa, Tsukuba (JP); Yusaku Hori, Tokyo (JP); Kazuhiko Yamada, Tsukuba (JP); Hiroshi Kamiyama, Tsukuba (JP); Masahiro Matsuki, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/465,277

(22) PCT Filed: Feb. 6, 2018

(86) PCT No.: PCT/JP2018/004007
§ 371 (c)(1),
(2) Date: May 30, 2019

(87) PCT Pub. No.: WO2018/147275
PCT Pub. Date: Aug. 16, 2018

(65) Prior Publication Data
US 2019/0388420 A1 Dec. 26, 2019

(30) Foreign Application Priority Data
Feb. 8, 2017 (JP) .................. 2017-021542

(51) Int. Cl.
| A61K 31/4985 | (2006.01) |
| A61K 31/53 | (2006.01) |
| A61P 35/00 | (2006.01) |

(52) U.S. Cl.
CPC .......... *A61K 31/4985* (2013.01); *A61K 31/53* (2013.01); *A61P 35/00* (2018.01)

(58) Field of Classification Search
CPC ...... A61K 31/4985; A61K 31/53; A61P 35/00
USPC .......... 512/312; 514/312; 514/243; 546/153; 544/184
See application file for complete search history.

(56) References Cited

U.S. PATENT DOCUMENTS

| | | |
|---|---|---|
| 4,000,278 A | 12/1976 | Curran |
| 4,526,988 A | 7/1985 | Hertel |
| 4,563,417 A | 1/1986 | Albarella et al. |
| 4,582,789 A | 4/1986 | Sheldon, III et al. |
| 4,656,027 A | 4/1987 | Sjoovist |
| 4,742,003 A | 5/1988 | Derynck et al. |
| 4,743,450 A | 5/1988 | Harris et al. |
| 4,764,454 A | 8/1988 | Ichijima et al. |
| 5,009,894 A | 4/1991 | Hsiao |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,633,006 A | 5/1997 | Catania et al. |
| 5,650,376 A | 7/1997 | Badaye et al. |
| 5,656,454 A | 8/1997 | Lee et al. |
| 5,658,374 A | 8/1997 | Glover |
| 5,686,104 A | 11/1997 | Mills et al. |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,262,046 B1 | 7/2001 | Alker et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |

(Continued)

FOREIGN PATENT DOCUMENTS

| AU | 2012246490 | 8/2016 |
| CA | 2 361 057 | 7/2000 |

(Continued)

OTHER PUBLICATIONS

Cecil Textbook of Medicine, edited by Bennet, J.C., and Plum F., 20th edition,vol. 1, 1004-1010, 1996.*

(Continued)

*Primary Examiner* — Erich A Leeser
(74) *Attorney, Agent, or Firm* — Fish & Richardson P.C.

(57) ABSTRACT

Provided is a pharmaceutical composition for treating a tumor, which is used in combination therapy of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

21 Claims, 22 Drawing Sheets

(56) References Cited

U.S. PATENT DOCUMENTS

| | | |
|---|---|---|
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 6,984,403 B2 | 1/2006 | Hagen et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,175,856 B2 | 2/2007 | Ullah et al. |
| 7,211,587 B2 | 5/2007 | Kubo et al. |
| 7,253,286 B2 | 8/2007 | Funahashi et al. |
| 7,312,243 B1 | 12/2007 | Pravda |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,683,172 B2 | 3/2010 | Naito et al. |
| 7,725,303 B2 | 5/2010 | Tramontana |
| 7,759,518 B2 | 7/2010 | Maderna et al. |
| 7,790,885 B2 | 9/2010 | Nagai et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,994,159 B2 | 8/2011 | Yamamoto et al. |
| 7,998,948 B2 | 8/2011 | Obaishi et al. |
| 8,044,240 B2 | 10/2011 | Dimock |
| 8,063,049 B2 | 11/2011 | Koh et al. |
| 8,080,657 B2 | 12/2011 | Chung et al. |
| 8,101,799 B2 | 1/2012 | Madema et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,293,743 B2 | 10/2012 | Kahn |
| 8,309,126 B2 | 11/2012 | Holman et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,492,560 B2 | 7/2013 | Stokes et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 8,871,450 B2 | 10/2014 | Hacker |
| 8,962,650 B2 | 2/2015 | Narita et al. |
| 8,969,379 B2 | 3/2015 | Furitsu et al. |
| 8,992,915 B2 | 3/2015 | Heider et al. |
| 9,174,988 B2 | 11/2015 | Snyder et al. |
| 9,174,998 B2 | 11/2015 | Inoue et al. |
| 9,945,862 B2 | 4/2018 | Funahashi et al. |
| 10,259,791 B2 | 4/2019 | Nakamura et al. |
| 10,259,817 B2 | 4/2019 | Kushida et al. |
| 10,407,393 B2 | 9/2019 | Nakamura et al. |
| 10,583,133 B2 | 3/2020 | Math et al. |
| 10,822,307 B2 | 11/2020 | Nakamura et al. |
| 2002/0010203 A1 | 1/2002 | Lipson et al. |
| 2002/0032217 A1 | 3/2002 | Fanara et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0124129 A1 | 7/2003 | Oliner |
| 2003/0187019 A1 | 10/2003 | Ullah et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0198806 A1 | 10/2004 | Littlefield et al. |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0243205 A1 | 12/2004 | Keravel et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0261337 A1 | 11/2005 | Wang et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0018909 A1 | 1/2006 | Oliner et al. |
| 2006/0057159 A1 | 3/2006 | Huang et al. |
| 2006/0057195 A1 | 3/2006 | Nonomura et al. |
| 2006/0079494 A1 | 4/2006 | Santi et al. |
| 2006/0104984 A1 | 5/2006 | Littlefield et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0198885 A1 | 9/2006 | Dharmadhikari et al. |
| 2006/0246071 A1 | 11/2006 | Green et al. |
| 2006/0247259 A1 | 11/2006 | Funahashi et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0043052 A1 | 2/2007 | Moon et al. |
| 2007/0078159 A1 | 4/2007 | Matsushima |
| 2007/0117842 A1 | 5/2007 | Arimoto et al. |
| 2007/0129353 A1 | 6/2007 | Kahn |
| 2007/0214604 A1 | 9/2007 | Yi |
| 2007/0254930 A1 | 11/2007 | Ryu et al. |
| 2007/0292515 A1 | 12/2007 | Schobel et al. |
| 2007/0298111 A1 | 12/2007 | Ueki |
| 2008/0114039 A1 | 5/2008 | Hirawat et al. |
| 2008/0207617 A1 | 8/2008 | Miwa et al. |
| 2008/0214557 A1 | 9/2008 | Ueki et al. |
| 2008/0214604 A1 | 9/2008 | Furitsu et al. |
| 2008/0214606 A1 | 9/2008 | Szakacs et al. |
| 2008/0241835 A1 | 10/2008 | Mehraban et al. |
| 2008/0246404 A1 | 10/2008 | Shelton et al. |
| 2008/0267971 A1 | 10/2008 | Green et al. |
| 2008/0286282 A1 | 11/2008 | Semba et al. |
| 2009/0028858 A1 | 1/2009 | Wang et al. |
| 2009/0042213 A1 | 2/2009 | Hoofnagle et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0069421 A1 | 3/2009 | Kasai et al. |
| 2009/0104285 A1 | 4/2009 | Littlefield et al. |
| 2009/0171112 A1 | 7/2009 | Naito et al. |
| 2009/0191212 A1 | 7/2009 | Oliner et al. |
| 2009/0202541 A1 | 8/2009 | Bruns et al. |
| 2009/0209580 A1 | 8/2009 | Matsui |

(56) References Cited

U.S. PATENT DOCUMENTS

| | | |
|---|---|---|
| 2009/0217401 A1 | 8/2009 | Korman et al. |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2009/0311175 A1 | 12/2009 | Brose |
| 2010/0048503 A1 | 2/2010 | Yamamoto |
| 2010/0048620 A1 | 2/2010 | Yamamoto |
| 2010/0069333 A1 | 3/2010 | Kahn |
| 2010/0092490 A1 | 4/2010 | Uenaka et al. |
| 2010/0105031 A1 | 4/2010 | Matsui et al. |
| 2010/0197911 A1 | 8/2010 | Funahashi et al. |
| 2010/0239688 A1 | 9/2010 | Yamamoto |
| 2010/0286094 A1 | 11/2010 | Chung et al. |
| 2010/0324087 A1 | 12/2010 | Yamamoto |
| 2011/0020410 A1 | 1/2011 | Nonomura et al. |
| 2011/0060049 A1 | 1/2011 | Vernier et al. |
| 2011/0028498 A1 | 2/2011 | Ryan et al. |
| 2011/0092459 A1 | 4/2011 | Odagami et al. |
| 2011/0104161 A1 | 5/2011 | Burgess et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0172446 A1 | 7/2011 | Littlefield et al. |
| 2011/0207756 A1 | 8/2011 | Matsui |
| 2011/0288115 A1 | 11/2011 | Kelbe |
| 2011/0293615 A1 | 12/2011 | Yamamoto |
| 2011/0311546 A1 | 12/2011 | Oliner et al. |
| 2012/0022076 A1 | 1/2012 | Maderna et al. |
| 2012/0052073 A1 | 3/2012 | Green et al. |
| 2012/0053177 A1 | 3/2012 | Ibrahim et al. |
| 2012/0077837 A1 | 3/2012 | Okamoto et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0071403 A1 | 3/2013 | Rolland et al. |
| 2013/0085152 A1 | 4/2013 | Matsui et al. |
| 2013/0108626 A1 | 5/2013 | Delmar et al. |
| 2013/0121999 A1 | 5/2013 | De Haas et al. |
| 2013/0123274 A1 | 5/2013 | Nakagawa et al. |
| 2013/0133091 A1 | 5/2013 | Korman et al. |
| 2013/0142799 A1 | 6/2013 | Oliner et al. |
| 2013/0171135 A1 | 7/2013 | Andres et al. |
| 2013/0171160 A1 | 7/2013 | Green et al. |
| 2013/0183300 A1 | 7/2013 | Andres et al. |
| 2013/0183301 A1 | 7/2013 | Delmar et al. |
| 2013/0183302 A1 | 7/2013 | De Haas et al. |
| 2013/0183303 A1 | 7/2013 | De Haas et al. |
| 2013/0195857 A1 | 8/2013 | Delmar et al. |
| 2013/0196972 A1 | 8/2013 | Chung et al. |
| 2013/0225581 A1 | 8/2013 | Furuta et al. |
| 2013/0237565 A1 | 9/2013 | Furitsu et al. |
| 2013/0243758 A1 | 9/2013 | Andres et al. |
| 2013/0267482 A1 | 10/2013 | Odagami et al. |
| 2013/0296365 A1 | 11/2013 | Bando |
| 2013/0309250 A1 | 11/2013 | Cogswell et al. |
| 2013/0336959 A1 | 12/2013 | Andres et al. |
| 2013/0336960 A1 | 12/2013 | Andres et al. |
| 2013/0344059 A1 | 12/2013 | Andres et al. |
| 2013/0344060 A1 | 12/2013 | Andres et al. |
| 2014/0017231 A1 | 1/2014 | Andres et al. |
| 2014/0017232 A1 | 1/2014 | Andres et al. |
| 2014/0023639 A1 | 1/2014 | Andres et al. |
| 2014/0023640 A1 | 1/2014 | Andres et al. |
| 2014/0031384 A1 | 1/2014 | Narita et al. |
| 2014/0051706 A1 | 2/2014 | Kouji et al. |
| 2014/0056874 A1 | 2/2014 | Andres et al. |
| 2014/0056875 A1 | 2/2014 | Andres et al. |
| 2014/0056876 A1 | 2/2014 | Andres et al. |
| 2014/0148483 A1 | 5/2014 | Semba et al. |
| 2014/0193397 A1 | 7/2014 | Andres et al. |
| 2014/0212422 A1 | 7/2014 | Korman et al. |
| 2014/0234296 A1 | 8/2014 | Sharma et al. |
| 2014/0243316 A1 | 8/2014 | Takaishi et al. |
| 2014/0294852 A1 | 10/2014 | Korman et al. |
| 2014/0302019 A1 | 10/2014 | Delmar et al. |
| 2014/0328833 A1 | 11/2014 | Korman et al. |
| 2014/0348743 A1 | 11/2014 | Korman et al. |
| 2015/0005343 A1 | 1/2015 | Nomoto et al. |
| 2015/0125455 A1 | 5/2015 | Green et al. |
| 2015/0165025 A1 | 6/2015 | Korman et al. |
| 2015/0175615 A1 | 6/2015 | Inoue et al. |
| 2015/0210769 A1 | 7/2015 | Freeman et al. |
| 2015/0283145 A1 | 10/2015 | Kouji et al. |
| 2015/0366866 A1 | 12/2015 | Ali et al. |
| 2015/0374731 A1 | 12/2015 | Maio et al. |
| 2016/0222118 A1 | 8/2016 | Chen et al. |
| 2017/0088615 A1 | 3/2017 | Korman et al. |
| 2017/0191137 A1 | 7/2017 | Semba et al. |
| 2017/0233344 A1 | 8/2017 | Nakamura et al. |
| 2018/0038868 A1 | 2/2018 | Gajewski et al. |
| 2018/0092901 A1 | 4/2018 | Denker et al. |
| 2018/0141950 A1 | 5/2018 | Kushida et al. |
| 2019/0388420 A1 | 12/2019 | Ozawa et al. |
| 2020/0375975 A1 | 12/2020 | Kremer et al. |
| 2022/0023285 A1 | 1/2022 | Denker et al. |

FOREIGN PATENT DOCUMENTS

| | | |
|---|---|---|
| CA | 2606719 | 12/2006 |
| CA | 3044658 | 8/2018 |
| CH | 656535 | 7/1986 |
| CL | 201102116 | 3/2009 |
| CL | 200003576 | 10/2009 |
| CL | 201402511 | 4/2012 |
| CL | 201502363 | 2/2013 |
| CL | 201601367 | 2/2013 |
| CN | 1083728 | 3/1994 |
| CN | 1293041 | 5/2001 |
| CN | 1473041 | 2/2004 |
| CN | 1478078 | 2/2004 |
| CN | 1585770 | 2/2005 |
| CN | 1634043 | 7/2005 |
| CN | 1642415 | 7/2005 |
| CN | 1744881 | 3/2006 |
| CN | 1772052 | 5/2006 |
| CN | 1878751 | 12/2006 |
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101337931 | 1/2009 |
| CN | 101443009 | 5/2009 |
| CN | 101454286 | 6/2009 |
| CN | 101454311 | 6/2009 |
| CN | 101616671 | 12/2009 |
| CN | 101827849 | 9/2010 |
| CN | 101848895 | 9/2010 |
| CN | 101896485 | 11/2010 |
| CN | 102036962 | 4/2011 |
| CN | 102046628 | 5/2011 |
| CN | 102470133 | 5/2012 |
| CN | 102958523 | 3/2013 |
| CN | 103003262 | 3/2013 |
| CN | 103209982 | 7/2013 |
| CN | 103402519 | 11/2013 |
| CN | 105338977 | 2/2016 |
| CN | 107305202 | 10/2017 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |
| EP | 0 870 842 | 10/1998 |

(56) References Cited

FOREIGN PATENT DOCUMENTS

| | | |
|---|---|---|
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 473 043 | 11/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 719 763 | 11/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 058 302 | 5/2009 |
| EP | 2 062 886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2206517 | 7/2010 |
| EP | 2 218 712 | 8/2010 |
| EP | 2 293 071 | 3/2011 |
| EP | 2628741 | 8/2013 |
| EP | 2 711 433 | 3/2014 |
| EP | 2821066 | 1/2015 |
| EP | 2 700 403 | 11/2015 |
| EP | 3 088 401 | 11/2016 |
| EP | 3384901 | 10/2018 |
| EP | 3 524 595 A1 | 8/2019 |
| EP | 3 524 595 B1 | 8/2022 |
| EP | 4147689 | 3/2023 |
| ES | 2282299 | 10/2007 |
| GB | 2253848 | 9/1992 |
| GB | 2456907 | 8/2009 |
| IL | 148756 | 10/2007 |
| IN | 236500 | 11/2009 |
| IN | 201747040368 | 11/2017 |
| JP | 61-148115 | 7/1986 |
| JP | 63-028427 | 6/1988 |
| JP | 1-022874 | 1/1989 |
| JP | 2-291295 | 12/1990 |
| JP | 4-341454 | 11/1992 |
| JP | H05194259 | 8/1993 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-518384 | 6/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-033472 | 2/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-514968 | 5/2006 |
| JP | 2006-515884 | 6/2006 |
| JP | 2006-230816 | 9/2006 |
| JP | 2006-340714 | 12/2006 |
| JP | 2007-153894 | 6/2007 |
| JP | 2008-546797 | 12/2008 |
| JP | 2009-515890 | 4/2009 |
| JP | 2009-132660 | 6/2009 |
| JP | 2009-263298 | 11/2009 |
| JP | 2010-502209 | 1/2010 |
| JP | 2010-535233 | 11/2010 |
| JP | 2011-500666 | 1/2011 |
| JP | 2011-522037 | 7/2011 |
| JP | 2013-540774 | 11/2013 |
| JP | 2014-509298 | 4/2014 |
| JP | 2014-521308 | 8/2014 |
| JP | 2016-528162 | 9/2016 |
| JP | 2018-512391 A | 5/2018 |
| JP | 6788600 B2 | 11/2020 |
| KR | 10-2003-0040552 | 5/2003 |
| KR | 2003-40552 | 5/2003 |
| KR | 10-0589032 | 11/2005 |
| KR | 10-2006-0113759 | 11/2006 |
| KR | 10-2007-0053205 | 5/2007 |
| KR | 20070116217 | 12/2007 |
| KR | 10-2008-0008374 | 1/2008 |
| RU | 2192863 | 11/2002 |
| RU | 2264389 | 11/2005 |
| RU | 2328489 | 7/2008 |
| RU | 2404992 | 10/2008 |
| RU | 2362771 | 7/2009 |
| RU | 2385867 | 4/2010 |
| RU | 2448708 | 6/2010 |
| RU | 2457210 | 7/2012 |
| RU | 2470024 | 12/2012 |
| RU | 2512538 | 4/2014 |
| RU | 2582964 | 4/2016 |
| RU | 2669805 | 10/2018 |
| TW | I304061 | 12/2008 |
| WO | WO 1986/003222 | 6/1986 |
| WO | WO 1992/020642 | 11/1992 |
| WO | WO 1993/011748 | 6/1993 |
| WO | WO 1994/009010 | 4/1994 |
| WO | WO 1995/015758 | 6/1995 |
| WO | WO 1995/017181 | 6/1995 |
| WO | WO 1995/019774 | 7/1995 |
| WO | WO 1996/009294 | 3/1996 |

(56) References Cited

FOREIGN PATENT DOCUMENTS

| | | |
|---|---|---|
| WO | WO 1996/026997 | 9/1996 |
| WO | WO 1996/030347 | 10/1996 |
| WO | WO 1996/033980 | 10/1996 |
| WO | WO 1996/039145 | 12/1996 |
| WO | WO 1996/040080 | 12/1996 |
| WO | WO 1996/040142 | 12/1996 |
| WO | WO 1997/003069 | 1/1997 |
| WO | WO 1997/013760 | 4/1997 |
| WO | WO 1997/013771 | 4/1997 |
| WO | WO 1997/017329 | 5/1997 |
| WO | WO 1997/021437 | 6/1997 |
| WO | WO 1997/038984 | 10/1997 |
| WO | WO 1997/048693 | 12/1997 |
| WO | WO 1998/000134 | 1/1998 |
| WO | WO 1998/002434 | 1/1998 |
| WO | WO 1998/002437 | 1/1998 |
| WO | WO 1998/002438 | 1/1998 |
| WO | WO 1998/013350 | 4/1998 |
| WO | WO 1998/014437 | 4/1998 |
| WO | WO 1998/023613 | 6/1998 |
| WO | WO 1998/029137 | 7/1998 |
| WO | WO 1998/032436 | 7/1998 |
| WO | WO 1998/035958 | 8/1998 |
| WO | WO 1998/037079 | 8/1998 |
| WO | WO 1998/050346 | 11/1998 |
| WO | WO 1998/052558 | 11/1998 |
| WO | WO 1998/056787 | 12/1998 |
| WO | WO 1999/000357 | 1/1999 |
| WO | WO 1999/003854 | 1/1999 |
| WO | WO 1999/032106 | 7/1999 |
| WO | WO 1999/032110 | 7/1999 |
| WO | WO 1999/032111 | 7/1999 |
| WO | WO 1999/032436 | 7/1999 |
| WO | WO 1999/035132 | 7/1999 |
| WO | WO 1999/035146 | 7/1999 |
| WO | WO 1999/043654 | 9/1999 |
| WO | WO 1999/062890 | 12/1999 |
| WO | WO 2000/019985 | 4/2000 |
| WO | WO 2000/031048 | 6/2000 |
| WO | WO 2000/042012 | 7/2000 |
| WO | WO 2000/043366 | 7/2000 |
| WO | WO 2000/043384 | 7/2000 |
| WO | WO 2000/044728 | 8/2000 |
| WO | WO 2000/047212 | 8/2000 |
| WO | WO 2000/050405 | 8/2000 |
| WO | WO 2000/071097 | 11/2000 |
| WO | WO 2001/002369 | 1/2001 |
| WO | WO 2001/023375 | 4/2001 |
| WO | WO 2001/027081 | 4/2001 |
| WO | WO 2001/032926 | 5/2001 |
| WO | WO 2001/036403 | 5/2001 |
| WO | WO 2001/040217 | 6/2001 |
| WO | WO 2001/045689 | 6/2001 |
| WO | WO 2001/046196 | 6/2001 |
| WO | WO 2001/047890 | 7/2001 |
| WO | WO 2001/047931 | 7/2001 |
| WO | WO 2001/060814 | 8/2001 |
| WO | WO 2002/016348 | 2/2002 |
| WO | WO 2002/032872 | 4/2002 |
| WO | WO 2002/036117 | 5/2002 |
| WO | WO 2002/041882 | 5/2002 |
| WO | WO 2002/044156 | 6/2002 |
| WO | WO 2002/072578 | 9/2002 |
| WO | WO 2002/080975 | 10/2002 |
| WO | WO 2002/088110 | 11/2002 |
| WO | WO 2002/092091 | 11/2002 |
| WO | WO 2002/096361 | 12/2002 |
| WO | WO 2003/000660 | 1/2003 |
| WO | WO 2003/006462 | 1/2003 |
| WO | WO 2003/013529 | 2/2003 |
| WO | WO 2003/024386 | 3/2003 |
| WO | WO 2003/027102 | 3/2003 |
| WO | WO 2003/028711 | 4/2003 |
| WO | WO 2003/031448 | 4/2003 |
| WO | WO 2003/033472 | 4/2003 |
| WO | WO 2003/050090 | 6/2003 |
| WO | WO 2003/074045 | 9/2003 |
| WO | WO 2003/075840 | 9/2003 |
| WO | WO 2003/079020 | 9/2003 |
| WO | WO 2003/087026 | 10/2003 |
| WO | WO 2003/099771 | 12/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | WO 2004/076412 | 9/2004 |
| WO | WO 2004/078144 | 9/2004 |
| WO | WO 2004/080462 | 9/2004 |
| WO | WO 2004/080966 | 9/2004 |
| WO | WO 2004/087096 | 10/2004 |
| WO | WO 2004/089286 | 10/2004 |
| WO | WO 2004/093828 | 11/2004 |
| WO | WO 2004/096214 | 11/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/070891 | 8/2005 |
| WO | WO 2005/082854 | 9/2005 |
| WO | WO 2005/082855 | 9/2005 |
| WO | WO 2005/092896 | 10/2005 |
| WO | WO 2005/116032 | 12/2005 |
| WO | WO 2005/117867 | 12/2005 |
| WO | WO 2005/117887 | 12/2005 |
| WO | WO 2006/004636 | 1/2006 |
| WO | WO 2006/014325 | 2/2006 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/038552 | 4/2006 |
| WO | WO 2006/062984 | 6/2006 |
| WO | WO 2006/090930 | 8/2006 |
| WO | WO 2006/090931 | 8/2006 |
| WO | WO 2006/105798 | 10/2006 |
| WO | WO 2006/123517 | 11/2006 |
| WO | WO 2006/137474 | 12/2006 |
| WO | WO 2007/000347 | 1/2007 |
| WO | WO 2007/002325 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/061874 | 5/2007 |
| WO | WO 2007/136103 | 11/2007 |
| WO | WO 2008/023698 | 2/2008 |
| WO | WO 2008/026577 | 3/2008 |
| WO | WO 2008/026748 | 3/2008 |
| WO | WO 2008/053602 | 5/2008 |
| WO | WO 2008/088088 | 7/2008 |
| WO | WO 2008/093855 | 8/2008 |
| WO | WO 2008/102870 | 8/2008 |
| WO | WO 2008/155387 | 12/2008 |
| WO | WO 2009/018238 | 2/2009 |
| WO | WO 2009/051397 | 4/2009 |
| WO | WO 2009/060945 | 5/2009 |
| WO | WO 2009/077874 | 6/2009 |
| WO | WO 2009/096377 | 8/2009 |

(56) References Cited

FOREIGN PATENT DOCUMENTS

| | | |
|---|---|---|
| WO | WO 2009/114335 | 9/2009 |
| WO | WO 2009/140549 | 11/2009 |
| WO | WO 2009/148192 | 12/2009 |
| WO | WO 2009/150256 | 12/2009 |
| WO | WO 2010/006225 | 1/2010 |
| WO | WO 2010/044485 | 4/2010 |
| WO | WO 2010/048304 | 4/2010 |
| WO | WO 2010/086964 | 8/2010 |
| WO | WO 2010/101849 | 9/2010 |
| WO | WO 2010/120112 | 10/2010 |
| WO | WO 2010/128685 | 11/2010 |
| WO | WO 2011/017583 | 2/2011 |
| WO | WO 2011/021597 | 2/2011 |
| WO | WO 2011/022335 | 2/2011 |
| WO | WO 2011/162343 | 12/2011 |
| WO | WO 2012/019300 | 2/2012 |
| WO | WO 2012/029913 | 3/2012 |
| WO | WO 2012/115286 | 8/2012 |
| WO | WO 2012/144463 | 10/2012 |
| WO | WO 2012/154935 | 11/2012 |
| WO | WO 2012/157672 | 11/2012 |
| WO | WO 2012/166899 | 12/2012 |
| WO | WO 2013/019906 | 2/2013 |
| WO | WO 2013/132044 | 9/2013 |
| WO | WO 2013/151708 | 10/2013 |
| WO | WO 2014/055648 | 4/2014 |
| WO | WO 2014/061826 | 4/2014 |
| WO | WO 2014/087230 | 6/2014 |
| WO | WO 2014/113729 | 7/2014 |
| WO | WO 2014/128245 | 8/2014 |
| WO | WO 2014/130869 | 8/2014 |
| WO | WO 2014/133022 | 9/2014 |
| WO | WO 2014/151006 | 9/2014 |
| WO | WO 2014/185540 | 11/2014 |
| WO | WO 2014/208774 | 12/2014 |
| WO | WO 2015/098853 | 7/2015 |
| WO | WO 2015/098855 | 7/2015 |
| WO | WO 2015/119944 | 8/2015 |
| WO | WO 2015/144934 | 10/2015 |
| WO | WO 2016/141218 | 9/2016 |
| WO | WO 2016/180781 | 11/2016 |
| WO | WO 2016/196389 | 12/2016 |
| WO | WO 2016/204193 | 12/2016 |
| WO | WO 2016/208576 | 12/2016 |
| WO | WO 2018/147275 | 8/2018 |
| WO | WO 2021/086909 | 5/2021 |
| WO | WO 2022/031952 | 2/2022 |

OTHER PUBLICATIONS

Freshney et al.,Culture of Animal Cells, A Manual of Basic Technique, Alan R. Liss, Inc., 1983, New York, p. 4.*
Dermeret al., Bio/Technology, 1994, 12:320.*
"Carboxymethyl Cellulose Sodium." Chemical Land 21. Retrieved Apr. 24, 2012. <http://www.chemicalland21.comlindustrialchem/perfonnancepolymer/CARBOXYMETHYL%20CELLULOSE%20S0DIUM%20SAL T.htm>.
"Carboxymethylcellulose Sodium." Merck Index: An Encyclopedia of Chemicals, Drugs, & Biologicals: 13th Ed. New Jersey: Merck & Co (2001), p. 308.
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter. com, 4 pages (2005).
"Current Protocols in Molecular Biology", John Wiley & Sons Section 11.4-11.13 (1987), 62, pages.
"FDA-AACR Oncology Dose Finding Workshop—Session 3 Transcript [URL:https://www.aacr.org/AdvocacyPolicy/GovernmentAffairs/Documents/6.13.16%20FDA-AACR%20Oncology%20Dose%20Finding%20Workshop%20Session%203%20Transcript.pdf]", Jun. 13, 2016, 27 pages.
"FMC BioPolymer; http://www.fmcbiopolymer.com/portals/pharm/content/docs/fmc_alubra_brochurefinal.podf," Mar. 16, 2015, 6 pages.
"Impurities in New Drug Substances Q3A (R2)", ICH Harmonized—Tripartite Guideline, Oct. 25, 2006.
"IN 1571/CHENP/2007", Aug. 31, 2007, 50 pages (English Translation).
"IN 2045/CHENP/2006", Jun. 1, 2007, 13 pages (English Translation).
"IN 2572/CHENP/2006", Jun. 8, 2007, 74 pages (English Translation).
"IN 383/CHENP/2008", Sep. 19, 2008, 26 pages (English Translation).
"Mix: Merriam-Webster Dictionary (Year: 2018)," 2018.
"Molecular Targets and Cancer Therapeutics," Poster Session A, A92, Nov. 6, 2015, p. 64.
"Patent Term Extension document filed before the USPTO in respect of the U.S. Pat. No. 7,253,286," Apr. 8, 2015, 89 pages.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
"Prescribing Information of AFINITOR (everolimus) tables for oral administration, AFINITOR DISPERZ (everolimus tables for oral suspension) [Retrieved on Jun. 12, 2017 URL:https://www.accessdata. fda.gov/drugsatfda_docs/label/2016/022334s036lbl.pdf,2.2,]", Novartis Pharmaceuticals Corporation, Feb. 2016, 42 pages.
"Prescribing Information of LENVIMA (lenvatinib) capsules, for oral use, Eisai Inc. [URL:https://www.accessdata.fda.gov/drugsatfda_docs/label/2015/206947s000lbl.pdf,2.1,2.2,8.6,8.7,Tables1-3]", Feb. 2015, 25 pages.
"Recent Results and Ongoing Trials with Panitumumab (ABX-EGF), a Fully Human Anti-Epidermal Growth Factor Receptor Antibody, in Metastatic Colorectal Cancer," Clinical Colorectal Cancer. 2005; 5(1):21-3.
"Specification: Test Procedures and Acceptance Criteria for New Drug Substances and New Drug Products: Chemical Substances," Q6A, ICH Harmonized—Tripartite Guideline, Oct. 6, 1999, 35 pages.
[No Author], "Crossover Study to Evaluate the Relative Bioavailability and Palatability of a Lenvatinib Suspension Compared to the Capsule Formulation in Adult Healthy Volunteers," ClinicalTrials. gov, Jun. 8, 2016, 11 pages, retrieved from: URL<https://clinicaltrials.gov/ct2/show/NCT02792829?term=NCT02792829&rank=1>.
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium und Beruf, DT. Apotheker-Verl, Stuttgart; DE, Jan. 1, 2000, p. 40-p. 52, XP008143620 (English translation).
AACR American Association Cancer Research, 92nd Annual Meeting, 42:583, Mar. 24-28, 2001, New Orleans, LA, USA, 3126.
Abrams et al., SU11248 Inhibits KIT and Platelet-derived Growth Factor Receptor Beta in Preclinical Models of Human Small Cell Lung Cancer*Molecular Cancer Therapeutics*., 2: 471-478, 2003.
Abuzar et al., "Synthesis of some new 7-chloro-4-substituted quinolines as potential antiparasitic agents," Eur. J. Med. Chem., 21(1):5-8 (1986).
Additional Response in IL Application No. 188670, dated Oct. 25, 2011, 4 pages (with English translation).
Advisory Action for U.S. Appl. No. 12/092,539 dated Jun. 28, 2011.
Advisory Action in U.S. Appl. No. 12/315,291, dated Mar. 24, 2011, 10 pages.
Agarwal et al., "Binding of discoidin domain receptor 2 to collagen I: an atomic force microscopy investigation," Biochemistry, 41(37):11091-11098 (2002).
Agnieszka et al., "Emergence of potential biomarkers of response to anti-angiogenic anti-tumor agents," Int J Cancer, Sep. 2010, 127(6):1251-1258.
Almarsson et al., "High-Throughput Surveys of Crystal Form Diversity of Highly Polymorphic Pharmaceutical Compounds," Crystal Growth & Design, Sep. 10, 2003, 3(6):927-933.

(56) References Cited

OTHER PUBLICATIONS

Altschul et al., "Basic Local Alignment Search Tool", J. Mol. Biol. 215:403-410 (1990).
Amended Claims filed in European Application No. 11798224.9, filed Aug. 2, 2013, 35 pages.
Amended Claims filed in Korean Application No. 10-2010-7011023, filed Jul. 17, 2013, 15 pages, with English translation.
Amended Claims filed in Russian Application No. 2013140169, dated Aug. 29, 2013, 17 pages, with English translation.
Amended Claims in Brazilian Application No. BR112012003592-4, dated Oct. 23, 2014, 12 pages, with English translation.
Amended claims in European Application No. 04807580.8, dated Jun. 16, 2014, 7 pages.
Amended Claims in Malaysian Application No. PI2011700172, dated in Jul. 3, 2014, 15 pages.
Amended description filed after receipt of search report in European Patent App. No. 10809938.3, filed Dec. 8, 2011.
Amended description filed after receipt of search report in European Patent App. No. 10809938.3, filed Sep. 14, 2010.
Amended Drawing in Filipino Application No. 1-2011-502441, dated Oct. 17, 2014, 2 pages.
Amended Drawing in Israeli Application No. 217197, dated Oct. 22, 2014, 4 pages, with English translation.
Amended Drawings in European Application No. 10809938.3, dated Nov. 11, 2014, 14 pages.
Amended set of Claims in European Application No. 11798224.9, dated Sep. 19, 2014, 53 pages.
Amended Specification filed in Australian Application No. 2012246490, filed Aug. 2, 2013, 15 pages.
Amendment after Allowance dated Jan. 4, 2011 in CA Application No. 2426461.
Amendment and Argument dated Apr. 27, 2012 in response to the Japanese Office Action in JP2007-542863, 13 pages and English translation.
Amendment and RCE submission documents filed in U.S. Appl. No. 12/039,381, dated Oct. 23, 2013, 13 pages.
Amendment and Request in Continued Examiner in U.S. Appl. No. 13/083,338, dated Oct. 10, 2014, 5 pages.
Amendment and Response filed in U.S. Appl. No. 11/997,543, dated Dec. 19, 2013, 38 pages.
Amendment and Response to Final Office Action in U.S. Appl. No. 12/092,539, dated Jun. 15, 2011.
Amendment and Response to Final Office Action in U.S. Appl. No. 12/864,817, dated Dec. 5, 2011.
Amendment and Response to Non-Final Office Action in U.S. Appl. No. 11/997,543, dated Aug. 19, 2011.
Amendment and Response to Office Action dated Apr. 2, 2013 in U.S. Appl. No. 13/083,338, 9 pages.
Amendment and Response to Office Action in U.S. Appl. No. 11/997,543, dated Jan. 9, 2012.
Amendment and Response to Office Action in U.S. Appl. No. 11/997,719, dated Dec. 23, 2010.
Amendment and Response to Office Action in U.S. Appl. No. 12/092,539, dated Mar. 11, 2011.
Amendment and Response to Office Action in U.S. Appl. No. 12/439,339, dated Aug. 22, 2013, 14 pages.
Amendment and Response to Office Action in U.S. Appl. No. 12/439,339, dated Feb. 7, 2012.
Amendment and Response to Office Action in U.S. Appl. No. 12/439,339, dated Jul. 30, 2012.
Amendment and Response to Office Action in U.S. Appl. No. 12/524,754, dated Feb. 17, 2012.
Amendment and Response to Office Action in U.S. Appl. No. 12/741,682, dated Jul. 30, 2012.
Amendment and Response to Office Action in U.S. Appl. No. 12/864,817, dated Aug. 9, 2011.
Amendment and Response to Office Action in U.S. Appl. No. 13/205,328, dated Apr. 11, 2012.
Amendment dated Apr. 11, 2006 in Chinese Application No. 01819710.8, with English translation.
Amendment dated Apr. 17, 2002 in Taiwanese Application No. 90125928, with English translation.
Amendment dated Apr. 19, 2005 in Japanese Application No. 2002-536056, with English translation.
Amendment dated Aug. 13, 2013 in Japanese Application No. P2009-540099, 8 pages, with English translation.
Amendment dated Aug. 17, 2004 in South African Application No. 2003/3567.
Amendment dated Aug. 29, 2013 in Chinese Application No. 201280010898.X, 24 pages, with English translation.
Amendment dated Aug. 4, 2004 in South African Application No. 2003/3567.
Amendment dated Aug. 6 2013, in Japanese Application No. 2009-551518, 6 pages, with English translation.
Amendment dated Dec. 12, 2011 in JO Patent App. No. 55/2011, with English translation.
Amendment dated Dec. 15, 2011 in VN Application No. 1-2011-03484, with English translation.
Amendment dated Dec. 22, 2011 in South African Application No. 2011/08697.
Amendment dated Feb. 9, 2011 in Taiwanese Application No. 100104281.
Amendment dated Jan. 11, 2010 in Chinese Application No. 200580026468.7, with English translation.
Amendment dated Jan. 26, 2010 in Chinese Application No. 200710007097.9, with English translation.
Amendment dated Jul. 2, 2009 in Chinese Application No. 200710007097.9, with English translation.
Amendment dated Jun. 22, 2010 in Chinese Application No. 200710007097.9, with English translation.
Amendment dated Mar. 20, 2012 in Korean Patent App. No. 10-2012-7003846.
Amendment dated Mar. 23, 2009 in Japanese Application No. 2005-124034, with English translation.
Amendment dated Mar. 6, 2006 in Korean Application No. 10-2003-7005506, with English translation.
Amendment dated Mar. 7, 2005 in Japanese Application No. 2002-536056, with English translation.
Amendment dated Mar. 8, 2006 in Korean Application No. 10-2005-7020292, with English translation.
Amendment dated May 10, 2012 in Japanese Patent Application No. 2011-527665.
Amendment dated May 21, 2009 in Japanese Application No. 2005-124034, with English translation.
Amendment dated May 28, 2003 in Chinese Application No. 01819710.8, with English translation.
Amendment dated Nov. 19, 2009 in Chinese Application No. 200710007097.9, with English translation.
Amendment dated Nov. 24, 2011 in Korean Application No. 10-2007-7001347, with English translation.
Amendment dated Oct. 1, 2013 in Indian Application No. 10502/CHENP/2012, 10 pages.
Amendment dated Oct. 25, 2005 in Korean Application No. 10-2003-7005506, with English translation.
Amendment dated Oct. 28, 2011 in LB Patent App. No. 9292.
Amendment dated Oct. 9, 2006 in Chinese Application No. 01819710.8, with English translation.
Amendment dated Sep. 13, 2005 in Chinese Application No. 01819710.8, with English translation.
Amendment dated Sep. 23, 2009 in Chinese Application No. 200580026468.7, with English translation.
Amendment dated Sep. 23, 2013 in Australian Application No. 2011270165, 35 pages.
Amendment filed in Brazilian Application No. BR112012032462-4, dated Nov. 4, 2013, 21 pages, with English translation.
Amendment filed in European Application No. 12774278.1, filed Aug. 13, 2013, 12 pages.
Amendment filed in European Application No. 12793322.4, dated Nov. 28, 2013, 6 pages.
Amendment filed in Japanese Application No. 2008-532141, filed Jul. 5, 2013, 2 pages, with English translation.
Amendment filed in Korean Application No. 10-2008-7027527, dated Jan. 27, 2014, 12 pages, with English translation.

(56) References Cited

OTHER PUBLICATIONS

Amendment filed in Korean Application No. 10-2008-7029472, dated May 1, 2014, 14 pages, with English translation.
Amendment filed in Korean Application No. 10-2008-7029472, dated Nov. 20, 2013, 81 pages, with English translation.
Amendment filed in Korean Application No. 10-2009-7005657, dated May 7, 2014, 15 pages, with English translation.
Amendment filed in Korean Application No. 10-2009-7017694, dated Feb. 28, 2014, 7 pages.
Amendment filed in Korean Application No. 10-2013-7020616, dated Nov. 22, 2013, 22 pages, with English translation.
Amendment filed in U.S. Appl. No. 13/805,826, dated Sep. 9, 2013, 14 pages.
Amendment in Australian Application No. 2005217325, dated Aug. 9, 2006, 11 pages.
Amendment in Australian Application No. 2005217328, dated Aug. 9, 2006, 10 pages.
Amendment in Australian Application No. 2006282456, dated Apr. 26, 2012, 6 pages.
Amendment in Australian Application No. 2006282456, dated Jan. 25, 2008, 26 pages.
Amendment in Australian Application No. 2007289787, dated Apr. 7, 2009, 16 pages.
Amendment in Bangladesh Application No. 184/2006, dated May 6, 2008, 3 pages.
Amendment in Bangladesh Application No. 184/2006, dated Sep. 26, 2007, 4 pages.
Amendment in Brazilian Application No. PI0616799/3, dated May 29, 2012, 6 pages.
Amendment in Canadian Application No. 2828946, dated Aug. 30, 2013, 14 pages.
Amendment in Chinese Application No. 200580001760.3, dated May 15, 2007, 31 pages, with English translation.
Amendment in Chinese Application No. 200680021939.X, dated Dec. 18, 2007, 23 pages, with English translation.
Amendment in Chinese Application No. 200780019520.5, dated Nov. 27, 2008, 10 pages, with English translation.
Amendment in Chinese Application No. 2008800045113, dated Aug. 7, 2009, 36 pages, with English translation.
Amendment in Chinese Patent Application No. 201080030508.6 dated Feb. 7, 2013, 17 pages, with English translation.
Amendment in European Application No. 05719973.9, dated Oct. 30, 2006, 2 pages.
Amendment in European Application No. 06796594.7, dated Apr. 19, 2012, 3 pages.
Amendment in European Application No. 06796594.7, dated Jan. 11, 2008, 3 pages.
Amendment in European Application No. 06796594.7, dated Nov. 16, 2007, 3 pages.
Amendment in European Application No. 07793075.8, dated Jan. 26, 2011, 12 pages.
Amendment in European Application No. 07793075.8, dated Mar. 3, 2009, 5 pages.
Amendment in European Application No. 08711837.8, dated Sep. 8, 2009, 23 pages.
Amendment in European Application No. 09713617.0, dated Sep. 1, 2010, 3 pages.
Amendment in European Patent Application No. 12793322.4, dated Sep. 15, 2017, 20 pages.
Amendment in Filipino Application No. 1-2007-502319, dated May 14, 2012, 3 pages.
Amendment in Indian Application No. 1424/CHENP/2008, dated Apr. 27, 2012, 4 pages.
Amendment in Indian Application No. 2371/CHENP/2012, dated Oct. 30, 2014, 2 pages.
Amendment in Indian Application No. 7026/CHENP/2013, dated Sep. 5, 2013, 8 pages.
Amendment in Israeli Application No. 188670, dated May 2, 2012, 7 pages, with English translation.
Amendment in Israeli Application No. 197002, dated Feb. 11, 2009, 4 pages.
Amendment in Israeli Application No. 200090, dated Oct. 2, 2013, 10 pages, with English translation.
Amendment in Israeli Application No. 200466, dated Aug. 18, 2009, 28 pages.
Amendment in Israeli Application No. 217197, dated Dec. 24, 2015, 5 pages, with English translation.
Amendment in Japanese Application No. 2007-532099, dated Dec. 25, 2007, 6 pages, with English translation.
Amendment in Japanese Application No. 2007-532099, dated Sep. 25, 2007, 28 pages, with English translation.
Amendment in Japanese Application No. 2008-530917, dated Dec. 13, 2012, 6 pages, with English translation.
Amendment in Japanese Application No. 2009-554285, dated Aug. 19, 2010, 7 pages, with English translation.
Amendment in Japanese Application No. P2009-510543, dated Nov. 9, 2009, 25 pages, with English translation.
Amendment in JO Application No. 280/2006, dated Oct. 19, 2007, 3 pages, with English translation.
Amendment in Korean Application No. 10-2006-7013907, dated Sep. 28, 2007, 10 pages, with English translation.
Amendment in Korean Application No. 10-2006-7013940, dated Oct. 1, 2007, 43 pages, with English translation.
Amendment in Korean Application No. 10-2007-7026886, dated Dec. 27, 2007, 4 pages, with English translation.
Amendment in Korean Application No. 10-2007-7026886, dated Nov. 21, 2007, 9 pages, with English translation.
Amendment in Korean Application No. 10-2007-7026886, dated Oct. 27, 2009, 4 pages, with English translation.
Amendment in Korean Application No. 10-2008-7029577, dated Apr. 1, 2009, 6 pages, with English translation.
Amendment in Korean Application No. 10-2009-7013723, dated Aug. 10, 2009, 17 pages, with English translation.
Amendment in Korean Application No. 10-2010-7011023, dated Oct. 21, 2014, 31 pages.
Amendment in Korean Application No. 10-2010-7018835, dated Dec. 1, 2014, 18 pages, with English translation.
Amendment in Korean Application No. 10-2012-7003846, dated Nov. 26, 2014, 20 pages, with English translation.
Amendment in Korean Application No. 10-2012-7033886, dated Sep. 27, 2013, 34 pages, with English translation.
Amendment in Malaysian Application No. PI20071922, dated Jul. 17, 2008, 243 pages.
Amendment in Mexican Application No. MX/a/2012/014776, dated Oct. 21, 2013, 5 pages.
Amendment in Norwegian Application No. 20080460, dated May 14, 2012, 4 pages, with English translation.
Amendment in Russian Application No. 2012158142, dated Oct. 17, 2013, 48 pages, with English translation.
Amendment in Saudi Arabian Application No. 06270287, dated Oct. 22, 2007, 12 pages.
Amendment in Singapore Application No. 200718614/1, dated Aug. 24, 2010, 13 pages.
Amendment in Taiwanese Application No. 100104281, dated Oct. 22, 2014, 8 pages.
Amendment in TH Application No. 0601004017, dated Sep. 25, 2007, 6 pages, with English translation.
Amendment in U.S. Appl. No. 11/065,631, dated May 28, 2008, 16 pages.
Amendment in U.S. Appl. No. 11/662,425, dated Sep. 2, 2014, 6 pages.
Amendment in U.S. Appl. No. 11/892,785, dated Dec. 17, 2008, 17 pages.
Amendment, Response to Office Action under 37 C.F.R. § 1.111 and Information Disclosure Statement for U.S. Appl. No. 13/624,278, filed Jun. 28, 2013, 23 pages.
Amendments received before examination for EP Application No. 01976786.2, dated Sep. 10, 2004.
Amendments to the specification filed on Mar. 26, 2012 for AU Patent Appl. No. 2010285740.

(56) References Cited

OTHER PUBLICATIONS

American Association for Cancer Research, "Redefining the Frontiers of Science," 94th Annual Meeting, vol. 44, 2nd Edition, Washington Convention Center, Washington, DC (Jul. 11-14, 2003).
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 200.
Anderson and Flora, "Preparation of Water-Soluble Compounds Through Salt Formation," Practice of Medicinal Chem., 1996, pp. 739-754.
Anderson et al, "Clinical, Safety, and Economic Evidence in Radioactive Iodine-Refractory Differentiated Thyroid Cancer: A Systematic Literature Review", Thyroid, 23(4):392-407, 2013.
Anderson et al., "Preparation of Water-soluble Compounds through Salt Formation. The Practice of Medicinal Chemistry," Technomics, 347-349 and 355-356 (Sep. 25, 1999).
Ang , "Role of the fibroblast growth factor receptor axis in cholangiocarcinoma", Journal of Gastroenterology and Hepatology, 2015 vol. 30, p. 1116-p. 1122.
Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143).
Antibodies: A Laboratory Manual, E. Harlow and D. Lane, ed. Cold Spring Harbor Laboratory (Cold Spring Harbour, NY, 1988), 190 pages.
Appeal for Reversal in CO Application No. 12-022608, dated Jan. 28, 2014, 17 pages (with English translation).
Appeal in SA Application No. 06270287, dated Jun. 23, 2010, 4 pages (with English translation).
Applicant Interview Summary Under 37 C.F.R. § 1.133(b) for U.S. Appl. No. 12/439,339, dated May 31, 2013, 7 pages.
Applicant Observation for CN Application No. 200780017371.9, filed May 29, 2013, 6 pages (with English translation).
Application for Patent Term Adjustment in U.S. Appl. No. 12/439,339, dated Dec. 18, 2014, 8 pages.
Approval of request for amendments for EP Application No. 04025700.8, dated Mar. 13, 2008.
Argument and Amendment for JP Application No. 2008-556208, filed Mar. 21, 2013, 15 pages (with English translation).
Argument and Amendment for CN 200880002425.9 filed on Jul. 18, 2011, 8 pages with English translation.
Argument and Amendment for JP Application No. 2008-532141, filed Nov. 29, 2012, 12 pages (with English translation).
Argument and Amendment for JP. Application No. 2008-516724, filed Nov. 28, 2012, 22 pages (with English translation).
Argument and Amendment for JP. Application No. 2009-123432, dated Jun. 12, 2012, 12 pages (with English translation).
Argument and Amendment for JP. Application No. 2009-529019, dated Jul. 3, 2012, 14 pages (with English translation).
Argument Brief filed in KR Application No. 10-2008-7029577, dated Feb. 27, 2014, 30 pages (with English translation).
Argument Brief filed on Mar. 6, 2006 for KR Application No. 10-2003-7005506 (with English translation).
Argument Brief filed on Mar. 8, 2006 for KR Application No. 10-2005-7020292 (with English translation).
Argument Brief filed on Nov. 24, 2011 for KR Application No. 10-2007-7001347 (with English translation).
Argument Brief filed on Oct. 25, 2005 for KR Application No. 10-2003-7005506 (with English translation).
Argument Brief in KR Application No. 10-2007-7026886, dated Oct. 27, 2009, 7 pages (with English translation).
Argument filed in KR Application No. 10-2009-7017694, dated Feb. 28, 2014, 48 pages.
Argument filed on Apr. 19, 2005 for JP Application No. 2002-536056 (with English translation).
Argument filed on Aug. 13, 2013 in JP Application No. 2009-540099, 10 pages (with English translation).
Argument filed on Aug. 6, 2013 for JP Patent Application No. 2009-551518, 18 pages (with English translation).
Argument filed on Mar. 23, 2009 for JP Application No. 2005-124034 (with English translation).
Argument filed on May 21, 2009 for JP Application No. 2005-124034 (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Asano et al., "Broad-spectrum preclinical combination activity of eribulin combined with various anticancer agents in human breast cancer, lung cancer, ovarian cancer, and melanoma xenograft models," European J Cancer, 50(Suppl 6):20, Nov. 19, 2014.
Asu no Shinyaku ("The New Drugs of Tomorrow"), editing/printing by Technomics, Inc., 81-83 (Dec. 2006) (English translation), 14 pages.
Auburn University, "Thyroid Cancer," (as of Feb. 25, 2006, using Wayback machine), Feb. 25, 2006, 8 pages.
Australian ("AU") Notice of Allowance dated Nov. 22, 2010 for corresponding AU Application No. 2006285673.
Australian ("AU") Office Action dated May 19, 2010 for corresponding AU Application No. 2006285673.
Australian ("AU") Office Action dated May 7, 2009 for corresponding AU Application No. 2006285673.
Australian ("AU") Office Action dated Oct. 29, 2009 for corresponding AU Application No. 2006285673.
Australian Notice of Allowance in Application No. 2011270165, dated Dec. 14, 2015, 3 pages.
Australian Office Action directed at Appl. No. 2007252506 dated Jan. 13, 2012, 2 pages.
Australian Office Action directed at Appl. No. 2007252506 dated Nov. 7, 2011, 5 pages.
Australian Office Action for Application No. 2008205847, dated Apr. 11, 2012.
Australian Office Action for Application No. 2008211952, dated Apr. 3, 2012.
Australian Office Action for Application No. AU2006309551 dated Apr. 28, 2011.
Australian Office Action in Application No. 2011271065, dated Nov. 6, 2015, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012.
Australian Second Statement of Proposed Amendments in Application No. 2011270165, dated Dec. 4, 2015, 5 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Bajwa et al., "Antimalarials 1 Heterocyclic Analogs of N-Substituted Naphthalenebisoxazines," J Med Chem., 16(2):134-138, Aug. 9, 1972.
Baker et al., "Blockade of vascular endothelial growth factor receptor and epidermal growth factor receptor signaling for therapy of metastatic human pancreatic cancer," Cancer Res., 62:1996-2003 (2002).
Banker et al., "Modern Pharmaceutics," 4th Edition, Marcel Dekker Inc., 2002, p. 172-174.
Barker and Clevers, "Mining the Wnt pathway for cancer therapeutics," Reviews Drug Discovery, Dec. 2006, 5:997-1014.
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).

(56) References Cited

OTHER PUBLICATIONS

Bavin, "Polymorphism in process development," Chemistry & Industry, 1989, 21:527-529.
Beebe et al., "Pharmacological Characterization of CP-547,632, a Novel Vascular Endothelial Growth Factor Receptor-2 Tyrosine Kinase Inhibitor for Cancer Therapy 1", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Besson et al., "PTEN/MMAC1/TEP1 in signal transduction and tumorigenesis," EP J Biochem., 1999, 263:605-611.
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Board of Appeal of the European Patent Office, "Decision—T1212/01 3.3.2," dated Feb. 3, 2015, 55 pages.
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Boss et al., "A Phase I study of E7080, a multitargeted tyrosine kinase inhibitor, in patients with advanced solid tumours," British Journal of Cancer, 106:1598-1604 (2012).
Bramhall, S., "The Matrix Metalloproteinases and Their Inhibitors in Pancreatic Cancer", International J. Pancreatol., 21, 1-12, 1997.
Brazilian Office Action in Application No. PI0418200-6, dated Jun. 16, 2015, 1 page.
Brief communication to applicant for EP Application No. 01976786.2, dated Sep. 9, 2005.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.

Bruheim et al., "Antitumour activity of oral E7080, a novel inhibitor of multiple tyrosine kinases, in human sarcoma xenografts," XP002789540, International Journal of Cancer, 2011, 129(3):742-750.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Burwell, Jr, "The Cleavage of Ethers," Chem Rev., 54(4):615-685, Feb. 26, 1954.
Bussolino et al., "Role of Soluble Mediators in Angiogenesis," Eur. J. Cancer, 32A(14):2401-2412 (1996).
Byrn et al., "Pharmaceutical Solids: A Strategic Approach to Regulatory Considerations," Pharmaceutical Research, 1995, 12(7):945-954.
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action dated Jan. 14, 2010 for corresponding CA Application No. 2,620,594.
Canadian ("CA") Office Action dated Jan. 6, 2011 for corresponding CA Application No. 2,620,594.
Canadian Notice of Allowance in Application No. 2676796, dated Oct. 8, 2015, 1 page.
Canadian Office Action for Application No. 2426461, dated Dec. 6, 2007.
Canadian Office Action for Application No. 2426461, dated Feb. 10, 2010.
Canadian Office Action for Application No. 2426461, dated May 8, 2009.
Canadian Office Action for Application No. 2426461, dated Nov. 20, 2008.
Canadian Office Action in Application No. 2828946, dated Nov. 30, 2015, 4 pages.
Canadian Office Action in Application No. 2704000, dated Jan. 14, 2016, 3 pages.
Canadian Office Action in Application No. 2704000, dated Jul. 14, 2015, 3 pages.
Canadian Response to Office Action in Application No. 2802644, dated Apr. 18, 2016, 9 pages.
Canadian Submission Documents in Application No. 2713930, dated Jun. 22, 2015, 8 pages.
CancerCare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999)
Carey, "Organic Chemistry 4e: Chapter 24: Phenols," McGraw Hill, http://www.mhhe.com/physsci/chemistry/carey/student/olc/ch24reactionsarylethers.html Oct. 3, 2014, 2000, 4 pages.
Carlomagno et al., "Point Mutation of the RET Proto-Oncogene in the TT Human Medullary Thyroid Carcinoma cell Line", Biochemical and Biophysical Research Communications, 207,1022-1028 (1995).
Carlomagno et al., "BAY 43-9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carr et al., "Phase II Study of Daily Sunitinib in FDG-PET-Positive, Iodine-Refractory Differentiated Thyroid Cancer and Metastatic Medullary Carcinoma of the Thyroid with Functional Imaging Correlation," XP055539627, Clinical Cancer Research, 2010, 16(21):5260-5268.
Carter et al., "Inhibition of drug-resistant mutants of ABL, KIT and EGF receptor kinases", Proceedings of the National Academy of Sciences of the United States of America., 102, 11011-11016, 2005.

(56) References Cited

OTHER PUBLICATIONS

Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Chaki et al., "mGlu2/3 and mGlu5 receptors: Potential targets for novel antidepressants," Neuropharmacology, 2013, 66:40-52.
Chemical & Engineering News, "The Top Pharmaceuticals That Changed the World," 83, [cited: Mar. 29, 2016], Jun. 20, 2005, 3 pages.
Chen et al., "Solid-state nuclear magnetic resonance and its application in research of drug polymorphs," Chinese Journal of New Drugs, 2013, 22(16):1921-1924, 1955 (with English Translation).
Chen et al., "FGFR3 as a therapeutic target of the small molecule inhibitor PKC412 in hematopoietic malignancies," Oncogene, 24:8259-8267 (2005).
Chen et al., "Small molecule-mediated disruption of Wnt-dependent signaling in tissue regeneration and cancer," Nat Chem Biol., Feb. 2009, 5(2):100-107.
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chilean Response to Examiner's Report in Application No. 2012-00412, dated Mar. 30, 2015, 16 pages, with English translation.
Chinese ("CN") Office Action dated Dec. 4, 2009 for corresponding CN Application No. 200680036592.6, with English translation.
Chinese Notice of Allowance in Application No. 201280010898.X, dated Sep. 2, 2015, 4 pages.
Chinese Office Action directed at Appl. No. 200780017371.9 dated Oct. 20, 2010, 13 pages with English translation.
Chinese Office Action for Application No. 200580026468.7, dated Jun. 26, 2009.
Chinese Office Action for Application No. 200710007097.9, dated Mar. 6, 2009.
Chinese Office Action for Application No. 200780017371.9, dated Mar. 7, 2012, with English translation.
Chinese Office Action for Application No. 200880002425.9, dated Mar. 7, 2012, with English translation.
Chinese Office Action for Application No. 200880003336.6, dated May 24, 2011, with English translation.
Chinese Office Action for Application No. 200880115011.7, dated Feb. 20, 2012, with English translation.
Chinese Office Action for Application No. 201080030508.6, dated Nov. 30, 2012.
Chinese Office Action for Application No. 200680041355.9 dated Aug. 24, 2010 with English translation.
Chinese Office Action for Application No. 200680041355.9 dated Mar. 5, 2010 with English translation.
Chinese Office Action in Application No. 201280010898.X, dated Mar. 30, 2015, 13 pages, with English translation.
Chinese Office Action with the English translation dated Feb. 29, 2012, for Application No. 200680036592.6.
Chinese Response in Reexamination and Invalidation Procedure in Application No. 200780017371.9, dated Jan. 19, 2015, 8 pages, with English translation.
Chinese Response to Office Action directed at Appl. No. j200780017371.9 filed on Feb. 24, 2011, 10 pages with English translation.
Chinese Response to Office Action for Application No. 200680041355.9 filed on Jul. 19, 2010 with English translation.
Chinese Response to Office Action for Application No. 200680041355.9 filed on Nov. 8, 2010 with English translation.
Chinese Response to the Chinese Decision of Rejection, filed on Feb. 7, 2013, for corresponding Chinese Application No. 200680036592.6.
Chinese Submission Documents in Application No. 201280010898.X, dated Jun. 15, 2015, 12 pages.
Chinese Voluntary Amendment in Application No. 201510031628.2, dated Oct. 10, 2015, 5 pages, with English translation.
Ciardiello et al., "ZD1839 (IRESSA), an EGFR-selective tyrosine kinase inhibitor, enhances taxane activity in bcl-2 overexpressing, multidrug-resistant MCF-7 ADS human breast cancer cells," Int. J. Cancer, 98:463-469 (2002).
CIPO Notice of Allowance for Appl. No. 2,620,594 dated May 3, 2012.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors ," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action dated Oct. 13, 2010 with English translation.
CN200780032071.8 Response to Office Action filed on Feb. 16, 2011 with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for Application No. 12-022608, dated Oct. 7, 2013, 10 pages (with English translation).
Colombian Official Notification in Application No. 12-022608, dated Jan. 6, 2015, 8 pages, with English translation.
Comments re Board of Appeal in EP Application No. 04807580.8, dated Jul. 7, 2014, 3 pages.
Communication about intention to grant a European patent for EP Application No. 01976786.2, dated Sep. 4, 2006.
Communication about intention to grant a European patent for EP Application No. 04025700.8, dated Oct. 15, 2007.
Communication about intention to grant a European patent for EP Application No. 05783232.1, dated Nov. 20, 2008.
Communication about intention to grant a European patent for EP Application No. 06023078.6, dated Jul. 18, 2008.
Communication from the Examining Division for EP Application No. 01976786.2, dated Aug. 17, 2005.
Communication from the Examining Division for EP Application No. 01976786.2, dated Mar. 21, 2006.
Communication from the Examining Division for EP Application No. 01976786.2, dated Sep. 19, 2005.
Communication from the Examining Division for EP Application No. 04025700.8, dated Apr. 10, 2006.
Communication from the Examining Division for EP Application No. 04025700.8, dated Oct. 23, 2006.
Communication from the Examining Division for EP Application No. 05783232.1, dated Feb. 7, 2008.
Communication from the Examining Division for EP Application No. 06023078.6, dated Aug. 2, 2007.
Communication from the Examining Division for EP Application No. 06023078.6, dated Sep. 26, 2007.
Communication re Intention to Grant Patent in EP Application No. 07793075.8, dated Nov. 9, 2012, 97 pages.
Communication re Intention to Grant Patent in EP Application No. 07805959.9, dated Jun. 21, 2011, 70 pages.
Communication regarding the expiry of opposition period for EP Application No. 01976786.2, dated Jan. 4, 2008.

(56) References Cited

OTHER PUBLICATIONS

Communication regarding the expiry of opposition period for EP Application No. 04025700.8, dated May 7, 2009.
Communication regarding the expiry of opposition period for EP Application No. 05783232.1, dated Feb. 19, 2010.
Communication regarding the expiry of opposition period for EP Application No. 06023078.6, dated Nov. 4, 2009.
Complete Specification in Indian Patent Application No. 2371/CHENP/2012, dated May 17, 2013, 15 pages.
Continuation Patent Application, Preliminary Amendment and Information Disclosure Statement for U.S. Appl. No. 13/923,858, filed Jun. 21, 2013, 97 pages.
Cooper et al., "Revised American Thyroid Association Management Guidelines for Patients with Thyroid Nodules and Differentiated Thyroid Cancer the American Thyroid Association (ATA) Guidelines Taskforce on Thyroid Nodules and Differentiated Thyroid Cancer Background," XP055539610, Thyroid, 2009, 19(11):1167-1214.
Corbin et al., "Sensitivity of oncogenic KIT mutants to the kinase inhibitors MLN518 and PD180970", Blood., 104, 3754-3757, 2004.
Correction Request in CO Application No. 12-022608, dated Dec. 24, 2014, 3 pages (with English translation).
Corvi et al., "RET IPCM-1: a novel fusion gene in papillary thyroid carcinoma", Oncogene, 19:4236-4242 (2000).
Coupling Reagents, "Advanced Automated Peptide Protein Technologies," Published Aug. 3, 2007, 4 pages.
Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," J. Clin. Endocrinol. Metab., 88:5438-5443 (2003).
Dankort et al., "Braf V660E cooperates with Pten loss to induce metastic melanoma," Nature Genetics, 2009, 41(5):544-552.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
Davies et al., "Mutations of the BRAF gene in human cancer," Nature, Jun. 27, 2002, 417:949-954.
De Lange et al., "Phase II trial of cisplatin and gemcitabine in patients with advanced gastric cancer," Annals of Oncology, 15:484-488 (2004).
De Robertis et al., "Identification and characterization of a small-molecule inhibitor of Wnt signaling in gliobastoma cells," Mol Cancer Ther, 2013, 12:1180-1189.
Decision of Final Rejection issued in CN Application No. 200780017371.9, dated Jul. 3, 2013, 16 pages (with English translation).
Decision of Grant in RU Application No. 2008110932, dated Feb. 6, 2009, 29 pages (with English translation).
Decision of Rejection dated Oct. 30, 2012 issued for corresponding Chinese Application No. 200680036592.6 with full English language translation.
Decision to grant a European patent for EP Application No. 01976786.2, dated Feb. 1, 2007.
Decision to grant a European patent for EP Application No. 04025700.8, dated Jun. 5, 2008.
Decision to grant a European patent for EP Application No. 05783232.1, dated Mar. 19, 2009.
Decision to grant a European patent for EP Application No. 06023078.6, dated Dec. 4, 2008.
Decision to Grant Patent in EP Application No. 05719973.9, dated Jun. 1, 2012, 1 page.
Decision to Grant Patent in EP Application No. 07805959.9, dated Nov. 4, 2011, 2 pages.
Decision to Grant Patent in JP Application No. 2007-532099, dated Jan. 8, 2008, 5 pages (with English translation).
Decision to Grant Patent in JP Application No. 2008-530917, dated Jan. 15, 2013, 6 pages (with English translation).
Decision to Grant Patent in JP Application No. 2008-532065, dated Nov. 13, 2012, 6 pages (with English translation).
Decision to Grant Patent in JP Application No. P2009-510543, dated Feb. 2, 2010, 6 pages (with English translation).
Deficiencies in sequence listing for EP Application No. 06023078.6, dated Dec. 5, 2006.
Demand for Appeal Trial filed in JP Application No. 2008-532141, filed Jul. 5, 2013, 10 pages (with English translation).
Deplanque et al., "Anti-Angiogenic Agents: Clinical Trial Design and Therapies in Development," European Journal of Cancer, 36:1713-1724 (2000).
Dermer, "Another Anniversary for the War on Cancer," Bio/Technology, 12:320 (1994).
Dezso et al., Systems biology analysis to identify biomarkers for lenvatinib in the preclinical cancer cell line panels. Abstract of the presentation #6 (abstract 1371), AACR Annual Meeting, 2015, 2 pages.
Di Raimondo et al., "Antiogenic Factors in multiple myeloma: higher levels in bone than in peripheral blood," Haematologica, 85:800-805 (2000).
Dias et al., "IL-12 Regulates VEGF and MMPs in a Murine Breast Cancer Model", International J. Cancer., 78, 361-5, 1998.
Dietrich, "BRAF Inhibition in Refractory Hairy-Cell Leukemia," N Eng J Med, 366(21):2038-2040, May 24, 2012.
DiLorenzo et al., "Targeted Therapy in the Treatment of Metastatic Renal Cell Cancer," Oncology, 77(suppl 1):122-131 (2009).
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005
Egyptian Submission Documents in Application No. PCT 283/2012, dated Jan. 18, 2015, 26 pages, with English translation.
Eisai Co., Ltd., "Phase II Study Results Showed Eisai's Lenvatinib (E7080) Demonstrated an Objective Response Rate of 59% in Advance Radioiodine-Refractory Differentiated Thyroid Cancer", News Release: 2011 PR Department, Eisai Coi., Ltd.,No. 11-44, https://www.eisai.co.jp/news/news201144.html, Jun. 2, 2011, p. 11-p. 44.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Emami et al., "A small molecule inhibitor of β-catenin /CREB-binding protein transcription," PNAS, Aug. 24, 2004, 101(34):12682-12687.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Emoto et al., "Localization of the VEGF and angiopoietin genes in uterine carcinosarcoma," Gynecologic Oncology, 95:474-482 (2004).
EP Communication under Rule 71(3) EPC for Application No. 06832529.9 dated Nov. 25, 2011.
EP07806561.2 Office Action dated Dec. 9, 2011.
EP07806561.2 Office Action dated Feb. 7, 2011, 1 page.
EP07806561.2 Office Actions dated Jan. 19.
EP07806561.2 Response to Office Action filed on Aug. 9, 2011.
Erber et al., "Combined inhibition of VEGF and PDGF signaling enforces tumor vessel regression by interfering with pericyte-mediated endothelial cell survival mechanisms," FASEB J., 18(2):338-340 (2004).

(56) References Cited

OTHER PUBLICATIONS

Erdem et al, "Correlation of E-cadherin, VEGF, COX-2 expression to prognostic parameters in papillary thyroid carcinoma", Experimental Mole Pathol., 90:312-317, Feb. 16, 2011.
European Notice of Allowance in Application No. 07743994.1, dated May 8, 2015, 51 pages.
European Notice of Allowance in Application No. 10809938.3, dated Jan. 8, 2016, 2 pages.
European Notice of Allowance in Application No. 10809938.3, dated Sep. 3, 2015, 30 pages.
European Notice of Allowance in Application No. 11798224.9, dated Sep. 29, 2015, 37 pages.
European Notice of Allowance in Application No. 12774278.1, dated Jun. 29, 2015, 34 pages.
European Office Action in Application No. 04719054.1, dated Oct. 30, 2009.
European Office Action in Application No. 04807580.8, dated Apr. 18, 2011.
European Office Action in Application No. 04807580.8, dated Dec. 3, 2010.
European Office Action in Application No. 04807580.8, dated Oct. 25, 2011.
European Office Action in Application No. 04818213.3, dated Feb. 2, 2012.
European Office Action in Application No. 06832529.9, dated Oct. 15, 2009.
European Office Action in Application No. 06832529.9, dated Sep. 12, 2011.
European Office Action in Application No. 07743994.1, dated Oct. 10, 2012.
European Office Action in Application No. 12786619.2, dated Dec. 8, 2015, 4 pages.
European Response to Communication Pursuant to Article 94(3) EPC in Application No. 10809938.3, dated Apr. 13, 2015, 12 pages.
European Response to EESR in Application No. 07743994.1-2123, dated Nov. 23, 2010, 22 pages.
European Response to Office Action in Application No. 06832529.9, dated Apr. 22, 2010.
European Response to Office Action in Application No. 06832529.9, dated Oct. 4, 2011.
European Response to Office Action in Application No. 12786619.2, dated May 12, 2015, 99 pages.
European Search Report in Application No. 03791389.4, dated Jul. 7, 2011.
European Search Report in Application No. 04025700.8, dated Jan. 13, 2005.
European Search Report in Application No. 04719054.1, dated Apr. 17, 2009.
European Search Report in Application No. 04818213.3, dated Jul. 30, 2007.
European Search Report in Application No. 05783232.1, dated Sep. 7, 2007.
European Search Report in Application No. 06023078.6, dated Mar. 16, 2007.
European Search Report in Application No. 06767145.3, dated May 23, 2011.
European Search Report in Application No. 06768437.3, dated Oct. 11, 2010.
European Search Report in Application No. 06782407.8, dated Jul. 23, 2010.
European Search Report in Application No. 06832529.9, dated Jul. 29, 2009.
European Search Report in Application No. 06833681.7, dated Nov. 24, 2010.
European Search Report in Application No. 07743994.1, dated May 4, 2010.
European Search Report in Application No. 07806561.2, dated Jan. 19, 2011.
European Search Report in Application No. 10015141.4, dated Sep. 9, 2011.
European Search Report in Application No. 10809938.3, dated Jan. 2, 2013.
European Search Report in Application No. 12793322.4, dated May 26, 2015, 9 pages.
European Search Report in Application No. 12793322.4, dated Sep. 10, 2015, 13 pages.
European Search Report in Application No. 13865671.5, dated May 23, 2016, 7 pages.
European Search Report in EP 08704376.6 dated Jun. 14, 2012, 12 pages.
European Submission Document in Application No. 09705712.9, dated Feb. 24, 2015, 196 pages.
Examination Report in Australian Application No. 2001295986, dated May 4, 2006.
Examination Report in Australian Application No. 2001295986, dated Sep. 20, 2005.
Examination Report in Australian Application No. 2005217325, dated Aug. 1, 2007, 2 pages.
Examination Report in Australian Application No. 2005217328, dated Aug. 1, 2007, 2 pages.
Examination Report in Australian Application No. 2006203099, dated Feb. 21, 2008.
Examination Report in Australian Application No. 2006236039, dated Mar. 26, 2008.
Examination Report in Australian Application No. 2007288793, dated Dec. 22, 2011, 2 pages.
Examination Report in Australian Application No. 2007289787, dated Nov. 25, 2011, 2 pages.
Examination Report in Australian Application No. 2008217931, dated Jun. 28, 2012, 3 pages.
Examination Report in Australian Application No. 2008325608, dated Nov. 24, 2012.
Examination Report in Australian Application No. 2009210098, dated Jan. 30, 2013 10 pages.
Examination Report in New Zealand Application No. 525324, dated Feb. 18, 2005.
Examination Report in New Zealand Application No. 525324, dated Oct. 13, 2003.
Examination Report in New Zealand Application No. 525324, dated Sep. 2, 2004.
Examination Report in Pakistan Application No. 155/2005, dated Mar. 11, 2009, 2 pages.
Experimental Medicine, Supplementary Volume, "A New Handbook of Genetic Engineering", Section 4, Yodosha, 2003(Japanese).
Explanation of Circumstances Concerning Accelerated Examination filed May 10, 2012 for JP Patent Application No. 2011-527665, 21 pages (with English Translation).
Extended European Search Report in Application No. 06796594.7, dated Sep. 7, 2011, 5 pages.
Extended European Search Report in Application No. 06797249.7, dated Dec. 7, 2012.
Extended European Search Report in Application No. 07793075.8, dated Sep. 8, 2010, 6 pages.
Extended European Search Report in Application No. 07805959.9, dated Nov. 16, 2010, 6 pages.
Extended European Search Report in Application No. 08711837.8, dated Mar. 28, 2011, 5 pages.
Extended European Search Report in Application No. 09713617.0, dated Apr. 28, 2011, 5 pages.
Extended European Search Report in Application No. 12195436.6, dated Feb. 21, 2013 8 pages.
Extended European Search Report in Application No. 12786619.2, dated Nov. 25, 2014, 6 pages.
Extended European Search Report in Application No. 16755489.8, dated Jul. 30, 2018, 8 pages.
Ezzat et al., "Dual Inhibition of RET and FGFR4 Retains Medullary Thyroid Cancer Cell Growth," Clinical Cancer Research, Feb. 2005, 11:1336-1341.
Fala et al., "Lenvima (Lenvatinib), a Multireceptor Tyrosine Kinase Inhibitor, Approved by the FDA for the Treatment of Patients with Differentiated Thyroid Cancer," XP002789351, American Health & Drug Benefits, 2015, 8(Special Feature):176-179.

(56) References Cited

OTHER PUBLICATIONS

Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
Ferrara, "Vascular Endothelial Growth Factor: Basic Science and Clinical Progress," Endocrine Reviews, 25(4):581-611, Aug. 2004.
FGBU [online], "Research Institute of Influenza of the Ministry of Health of the Russian Federation, Federal Center for Influenza and ARD, National Center for Influenza, WHO Guidelines for the Treatment and Prevention of Influenza in Adults," St. Petersburg, 2014, 42 pages, retrieved from: URL<http://gkb12.mznso.ru/media/cms_page_media/2149/rekomendaciipo-diagnostike-i-iecheniyu-grippa-u-vzroslyh_2.dpf,> (with English Translation).
Filipino Office Action in Application No. 1-2011-502441, dated May 8, 2015, 2 pages.
Filipino Submission Documents in Application No. 1-2011-502441, dated May 22, 2015, 25 pages.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
First Office Action dated Mar. 6, 2012 for the corresponding JP application, JP2007-542863, 17 pages and English translation.
Folkman et al., "Angiogenesis," The Journal of Biological Chemistry, 267(16):10931-10934 (1992).
Folkman et al., "Seminars in Medicine of the Beth Israel Hospital, Boston: Clinical Applications of Research on Angiogenesis," The England Journal of Medicine, 333(26):1757-1763 (1995).
Folkman et al., "What is the Evidence That Tumors are Angiogenesis Dependent?," Journal of the National Cancer Institute, 82(1):4-6 (1990).
Folkman, "What is the evidence that tumors are angiogenesis dependent," J Nat Can Inst 82(1), 1990.
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of ρ-aminosalicylic acid and its salts," International Journal of Pharmaceutics, 126:199-208 (1995).
Formality Requirement dated Jun. 18, 2003 for PH Application No. 1-2003-500266.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Angiogenesis Inhibitor/Keldcan 19:220-227 Shinsei Sogaiyaku," Clin Gastroenterol., May 25, 2004, 19:220-227.
Fujii et al., "MP-412, a dual EGFR/HER2 tyrosine kinase inhibitor: 2. In vivo antitumor effects," Am. Assoc. Cancer Research, A3394, 2005, 2 pages.
Funahashi et al., "ASCO Annual Meeting Abstracts," Jounral of Clinical Oncology, 1(29):8566, 2011.
Funahashi et al., "P-2123, Lenvatinib treatment of differentiated thyroid cancer (DTC): Analysis to identify biomarkers associated with response," The 71st Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," J. Clin. Invest., 92:1736-1744 (1993).
Furitsu et al., "Stable medicinal compositions of quinolinecarboxamide derivative," Database Caplus Chemical Abstracts Service, Columbus, OH, US (2006) (XP002520305).
Furuta et al., "Synthesis and Biological Evaluation of Selective Inhibitors of PDGF Receptor Auto Phosphorylation," #64, American Chemical Society, 226th ACS National Meeting, New York, NY (Sep. 7-11, 2003).
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," Acta Chimica Hungarica, 112(2):241-247 (1983).
Gardner et al., "In Vitro Activity Sorghum-Selective Fluorophenyl Urea Herbicides," Pesticide Biochemistry and Physiology, 24(3):285-297 (1985).
Gaspar et al., "Single-agent Dose-finding Cohort of a Phase 1/2 Study of Lenvatinib in Children and Adolescents With Refractory or Relapsed Solid Tumors", ASCO 2017 Poater 301, ITCC-50 Study, Jun. 2-6, 2017.
Gaspar et al., "Single-agent expansion cohort of lenvatinib (LEN) and combination dose-finding cohort of LEN + etoposide (ETP) + ifosfamide (IFM) in patients (pts) aged 2 to ≤25 years with relapsed/refractory osteosarcoma (OS)," Journal of Clinical Oncology, 2018, 36(15):11527.
Gaspar et al., "Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS)," Presentation at American Society of Clinical Oncology Annual Meeting, 2018, 1 page.
Gaspar et al., Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS), International Society for Paediatric Oncology, 2018, 1 page.
Gatzemeier et al., "Phase III comparative study of high-dose cisplatin versus a combination of paclitaxel and cisplatin in patients with advanced non-small-cell lung cancer," J. Clin. Oncol., 18(19):3390-3399 (2000).
Gayed et al., "Prospective evaluation of plasma levels of ANGPT2, TuM2PK, and VEGF in patients with renal cell carcinoma", BMC Urology, Biomed Central, London, GB, vol. 15, No. 1, Apr. 3, 2015, p. 24, XP021217372.
Genitourinary Cancers, Prostate Cancer Genitourinary, http://www.merkmanuals.com/professional/print/sec17/ch241/ch241e.html Mar. 16, 2011.
Gentet et al., "Ifosfamide and etoposide in childhood osteosarcoma. A phase II study of the French Society of Paediatric Oncology", European Journal of Cancer, vol. 33, 1997, p. 232-p. 237.
Gild et al, "Multikinase inhibitors: a new option for the treatment of thyroid cancer", Nature Reviews Endocrinol., 7:617-624, Oct. 2011.
Giles, "The vascular endothelial growth factor (VEGF) signaling pathway: a therapeutic target in patients with hematologic malignancies," Oncologist, 6(suppl 5):32-39 (2001).
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Glen et al., "432 Correlative analyses of serum biomarkers and clinical outcomes in the phase 2 study of lenvatinib, everolimus, and the combination, in patients with metastatic renal cell carcinoma following 1 VEGF-targeted therapy", European Journal of Cancer, vol. 51, Sep. 1, 2015, p. S89, XP055510094.
Glen et al., "Correlative Analyses of Serum Biomarkers and Clinical Outcomes in the Phase 2 Study of Lenvatinib, Everolimus, and the Combination, in Patients With a Metastatic Renal Cell Carcinoma Following 1 VEGF-Targeted Therapy", Poster presentation at 18th ECCO—40th ESMO European Cancer Congress, Vienna, Sep. 25-29, 2015.
Glen, "Pre-clinical investigation and clinical development of E7080, a multi-targeted tyrosine kinase inhibitor: implications for melanoma," Ph.D. thesis submitted to the Faculty of Medicine, Division of Cancer Sciences and Molecular Pathology, University of Glasgow, Aug. 11, 2010, 2 pages.

(56) References Cited

OTHER PUBLICATIONS

Goede, "Identification of serum angiopoietin-2 as a biomarker—for clinical outcome of colorectal cancer patients treated with bevacizumab-containing therapy," Br J Cancer, 103(9):1407-1414, Oct. 2010.
Golkar et al., "Mastocytosis," Lancet, 349:1379-1385 (1997).
Gong et al., "Expression of CC Chemokine Receptor 4 in Human Follicular Thyroid Carcinoma," Academic Journal of Military Medical University, 28:701-703, 2007 English Translation.
Goorin et al., "Phase II/III trial of etoposide and high-dose ifosfamide in newly diagnosed metastatic osteosarcoma: a pediatric oncology group trial," XP009511743, Journal of Clinical Oncology: Official Journal of the American Society of Clinical Oncology, 2002, 20(2):426-433.
Gould, "Salt Selection for Basic Drugs," International Journal of Pharmaceutics, 33:201-217, (1986) (XP025813036).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Grier et al., "Addition of Ifosfamide and Etoposide to Standard Chemotherapy for Ewing's Sarcoma and Primitive Neuroectodermal Tumor of Bone", The New England Journal of Medicine, vol. 348, 2003, p. 694-p. 701.
Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Guo, "Dose Optimization Study: E7080-G000-218 [URL:https://www.aacr.org/AdvocacyPolicy/GovernmentAffairs/Documents/6.13.16%20FDA-AACR%20Dose%20Finding%20for%20Online.pdf]", Presentation slides at FDA-AACR: Oncology Dose-finding Workshop, Jun. 13, 2016, 25 pages.
Gura, "Cancer Models Systems for Identifying new drugs are often faulty," Science, 278:1041-1042 (1997).
Gurney et al., "Wnt pathway inhibition via the targeting of Frizzled receptors results in decreased growth and tumorigenicity of human tumors," PNAS, Jul. 17, 2012, 109(29):11717-11722.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Haleblian,"Characterization of habits and crystalline modification of solids and their pharmaceutical applications," J. Pharm. Sci., 64(8):1269-1288 (1975).
Haller, "Chemotherapy for advanced pancreatic cancer," Int. J. Radiation Oncol. Biol. Phys., 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).
Hancock et al., "Molecular Mobility of Amorphous Pharmaceutical Solids Below Their Glass Transition Temperatures," Pharmaceutical Research, 1995, 12(6):799-806.
Hao et al., "Targeted Inhibition of β-Catenin/CBP Signaling Ameliorates Renal Interstitial Fibrosis," J Am Soc Nephrol., 2011, 22:1642-1653.
Hara et al., "Amplification of c-myc, K-sam, and c-met in Gastric Cancers: Detection by Fluorescence In Situ Hybridization", Laboratory Investigation, 78, 1143-1153, 1998.
Hattori et al., "Immunohistochemical detection of K-sam protein in stomach cancer," Clin. Cancer Res., 2(8):1373-1381 (1996).
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Hayamo et al., "Pericytes in experimental MDA-MB231 tumor angiogenesis," Histochemistry and Cell Biology, 117(6):527-534, Abstract (Jun. 2002).

Hayato, "In-silico trial to evaluate the utility of a postmarketing trial for dose optimization-Lenvatinib in Renal Cell Carcinoma—[URL:https://insp.memberclicks.net/mcdatafiles/receiptattach/insp/11395454/7966299/ACOP7_Session4a_SeiichiHayato_19Oct2016.pptx]", Presentation slides at the Seventh American Conference on Pharmacometrics, Oct. 25, 2016, 17 pages.
Hayek et al., "An In Vivo Model for Study of the Angiogenic Effects of Basic Fibroblast Growth Factor," Biochemical and Biophysical Research Communications, 147(2):876-880 (1987).
Hearing Notice issued May 4, 2012, in India Patent Application No. 383/CHENP/2008.
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Heinrich et al., "Inhibition of c-kit receptor tyrosine kinase activity by STI 571, a selective tyrosine kinase inhibitor," Blood, 96(3):925-932 (2000) (XP001097629).
Heinrich et al., "Inhibition of KIT tyrosine kinase activity: a novel molecular approach to the treatment of KIT-positive malignancies," J. Clin. Oncol., 20(6):1692-1703 (2002).
Helfrich et al., "Angiopoietin-2 Levels Are Associated with Disease Progression in Metastatic Malignant Melanoma," Clin Cancer Res 15(4):1384-1392, Feb. 15, 2009.
Henderson, Jr. et al., "Inhibition of Wnt/β-catenin/CREB binding protein(CBP) signaling reverses pulmonary fibrosis," PNAS, Aug. 10, 2010, 107(32):14309-14314.
Hennequin et al., "Design and Structure-Activity Relationship of a New Class of Potent VEGF Receptor Tyrosine Kinase Inhibitors", Journal of Medicinal Chemistry., 42: 5369-5389, 1999Wedge.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst and Khuri et al., "Mode of action of docetaxel—a basis for combination with novel anticancer agents," Cancer Treat Rev, 29:407-415, 2003.
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.
Hertel LW., et al., "Evaluation of the Antitumor Activity of Gemcitabine (2',2'-Difluoro-2'-deoxycytidine)", Cancer Research, 50, 4417-4422, 1990.
Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012).
Hines et al., "Coexpression of the c-kit and Stem Cell Factor Genes in Breast Carcinomas," Cell Growth & Differentiation, 6:769-779 (1995).
Hogaboam et al., "Novel Role of Transmembrane SCF for Mast Cell Activation and Eotaxin Production in Mast Cell-Fibroblast Interactions," J. Immunol., 160:6166-6171 (1998).
Hori et al., "Suppression of Solid Tumor Growth by Immunoneutralizing Monoclonal Antibody against Human Basic Fibroblast Growth Factor", Cancer Research., 51, 6180-4, 1991.
Huang et al., "Tankyrase inhibition stabilizes axin and antagonizes Wnt signaling," Nature, 2009, 461:614-620.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hungarian Amendment to the Specification in Application No. P0302603, dated Jul. 7, 2015, 45 pages, with English translation.
Hungarian Notice of Allowance in Application No. P0302603, dated Aug. 19, 2015, 4 pages, with English translation.
Hungarian Office Action in Application No. P0302603, dated Apr. 7, 2015, 5 pages, with English translation.

(56) References Cited

OTHER PUBLICATIONS

Hungarian Office Action in Application No. P0302603, dated Nov. 26, 2015, 4 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al, "A Phase 2 Study of Lenvatinib Monotherapy as Second-line Treatment in Unresectable Biliary Tract Cancer: Primary Analysis Results", ESMO 2017 Congress, Sep. 8-12, 2017.
Ikeda et al., "Changes in Phenotype and Proliferative Potential of Human Acute Myeloblastic Leukemia Cells in Culture with Stem Cell Factor," Experimental Hematology, 21:1686-1694 (1993).
Ikeda et al., "Expression and Functional Role of the Proto-Oncogene c-kit in Acute Myeloblastic Leukemia Cells," Blood, 78(11):2962-2968 (1991).
Ikuta et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
Inai et al., "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
Indian Office Action for Application No. 1571/CHENP/2007, dated Oct. 30, 2012.
Indian Office Action in Application No. 2365/CHENP/2015, dated Sep. 6, 2018, 6 pages (with English Translation).
Indian Office Action in Application No. 6415/CHENP/2008, dated Oct. 3, 2013, 2 pages.
Indian Patent Application No. 2572/CHENP/2006 filed Jul. 13, 2006.
Information about decision on request for EP Application No. 06023078.6, dated Mar. 21, 2007.
Inoue et al., "Molecular Target Therapy Targeting Angiogenesis Pathways," The Nishinihon Journal of Urology, 66:425-432 (2004).
International Adjuvant Lung Cancer Trial Collaborative Group, "Cisplatin-Based Adjuvant Chemotherapy in Patients with Completely Resec," The New England Journal of Medicine, 350(4):351-360, Jan. 22, 2004.
International Preliminary Report in International Application No. PCT/IB2008/003880, dated Aug. 11, 2009, 4 pages.
International Preliminary Report in International Application No. PCT/JP2007/066185, dated Mar. 5, 2009, 6 pages.
International Preliminary Report in International Application No. PCT/JP2007/066635, dated Mar. 12, 2009, 9 page.
International Preliminary Report in International Application No. PCT/JP2008/053066, dated Sep. 11, 2009, 12 pages.
International Preliminary Report in International Application No. PCT/JP2008/071881, dated Jul. 14, 2011, 7 pages pages.
International Preliminary Report in International Application No. PCT/JP2009/0524001, dated Oct. 14, 2010, 5 pages.
International Preliminary Report in Patentability in International Application No. PCT/JP2006/316331, dated Feb. 26, 2008, 5 pages.
International Preliminary Report on Patentability and Written Opition of the International Searching Authroity for Application No. PCT/JP2006/312487, dated Dec. 24, 2007.
International Preliminary Report on Patentability for Application No. PCT/JP01/09221, dated Jan. 8, 2003.
International Preliminary Report on Patentability for Application No. PCT/JP2004/003087, dated Feb. 13, 2006.
International Preliminary Report on Patentability for Application No. PCT/JP2005/016941, dated Mar. 20, 2007.
International Preliminary Report on Patentability for Application No. PCT/JP2010/063804, dated Mar. 13, 2012.
International Preliminary Report on Patentability for Application No. PCT/JP2011/064430, dated Jan. 24, 2013, 6 pages.
International Preliminary Report on Patentability for Application No. PCT/JP2018/018810, dated Aug. 7, 2018, 10 pages.
International Preliminary Report on Patentability for International Application No. PCT/JP2003/010964 dated Aug. 10, 2004, 7 pages.
International Preliminary Report on Patentability for International Application No. PCT/JP2007/060560 dated Nov. 18, 2008, 6 pages with English translation.
International Preliminary Report on Patentability for International Application No. PCT/JP2007/060560, dated Dec. 10, 2008, 7 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability for International Application No. PCT/JP2008/051697, dated Aug. 4, 2009, 18 pages.
International Preliminary Report on Patentability for International Application No. PCT/JP2008/070321, dated May 11, 2010, 15 pages with English translation.
International Preliminary Report on Patentability for International Application No. PCT/JP2009/051244 dated Aug. 31, 2010, 12 pages (with English translation).
International Preliminary Report on Patentability in Application No. PCT/JP2013/084052, dated Jul. 2, 2015, 7 pages.
International Preliminary Report on Patentability in International Application No. PCT/JP2005/003701, dated Sep. 16, 2006, 7 pages.
International Preliminary Report on Patentability in International Application No. PCT/JP2005/003704, dated Sep. 19, 2006, 7 pages.
International Preliminary Report on Patentability in International Application No. PCT/JP2006/315563 dated Feb. 5, 2008, 10 pages with English translation.
International Preliminary Report on Patentability in International Application No. PCT/JP2006/315698 dated Feb. 5, 2008, 17 pages English translation.
International Preliminary Report on Patentability in International Application No. PCT/JP2006/322514 dated May 7, 2008, 8 pages.
International Preliminary Report on Patentability in International Application No. PCT/JP2006/322516 dated May 7, 2008,8 pages.
International Preliminary Report on Patentability in International Application No. PCT/JP2012/060279, dated Oct. 23, 2013, 11 pages.
International Preliminary Report on Patentability in International Application No. PCT/JP2012/062509, dated Nov. 28, 2013, 11 pages.
International Preliminary Report on Patentability in International Patent Application No. PCT/JP2014/083932, dated Jul. 7, 2016, 5 pages.
International Preliminary Report on Patentability in International Patent Application No. PCT/JP2016/068381, dated Jan. 4, 2018, 9 pages (English Translation).
International Preliminary Report on Patentability in International Patent Application No. PCT/JP2016/002562, dated Aug. 9, 2016, 4 pages (English Translation).
International Preliminary Report on Patentability in International Application No. PCT/JP2016/055268, dated Sep. 8, 2017, 9 pages [English Translation].
International Preliminary Report on Patentability in International Patent Application No. PCT/JP2015/073946, dated Mar. 9, 2017, 8 pages (English Translation).
International Preliminary Report on Patentability in International Patent Application No. PCT/JP2016/074090, dated Mar. 1, 2018, 6 pages (English Translation).
International Preliminary Report on Patentability in PCT Application No. PCT/US2012/040183, dated Apr. 3, 2014, 9 pages.
International Search Report and International Preliminary Report on Patentability for PCT Application No. PCT/JP2011/064430, dated Sep. 13, 2011, 8 pages.
International Search Report and Written Opinion in Application No. PCT/JP2014/063134, dated Sep. 9, 2014, 8 pages.
International Search Report and Written Opinion in International Application No. PCT/JP2008/071881, dated Jan. 27, 2009, 12 pages.

(56) References Cited

OTHER PUBLICATIONS

International Search Report and Written Opinion in International Application No. PCT/JP2009/0524001, dated Mar. 10, 2009, 9 pages.
International Search Report and Written Opinion in International Application No. PCT/JP2014/083932, dated Mar. 17, 2015, 9 pages.
International Search Report and Written Opinion in International Application No. PCT/JP2017/015461, dated Jun. 27, 2017, 8 pages.
International Search Report for Application No. PCT/JP01/09221, dated Jan. 15, 2002.
International Search Report for Application No. PCT/JP2004/003087, dated Jul. 13, 2004.
International Search Report for Application No. PCT/JP2005/016941, dated Nov. 15, 2005.
International Search Report for Application No. PCT/JP2006/315563, dated Sep. 5, 2006.
International Search Report for Application No. PCT/JP2006/315698, dated Oct. 17, 2006.
International Search Report for Application No. PCT/JP2006/322514, dated Jan. 23, 2007.
International Search Report for Application No. PCT/JP2006/323881, dated Jan. 23, 2007.
International Search Report for Application No. PCT/JP2007/060560, dated Sep. 11, 2007.
International Search Report for Application No. PCT/JP2007/063525, dated Sep. 4, 2007.
International Search Report for Application No. PCT/JP2007/067088, dated Nov. 20, 2007.
International Search Report for Application No. PCT/JP2008/051024, dated Apr. 1, 2008.
International Search Report for Application No. PCT/JP2008/051697, dated Mar. 4, 2008.
International Search Report for Application No. PCT/JP2008/070321, dated Jun. 20, 2009.
International Search Report for Application No. PCT/JP2009/051244, dated Mar. 24, 2009.
International Search Report for Application No. PCT/JP2010/063804, dated Sep. 14, 2010.
International Search Report for International Application No. PCT/JP2006/317307, dated Dec. 12, 2006, 3 pages.
International Search Report for PCT/JP2012/060279, dated May 29, 2012.
International Search Report in International Application No. PCT/IB2008/003880, dated Aug. 11, 2009, 7 pages.
International Search Report in International Application No. PCT/JP2005/003701, dated May 31, 2005, 6 pages (with English translation).
International Search Report in International Application No. PCT/JP2005/003704, dated May 31, 2005, 6 pages (with English translation).
International Search Report in International Application No. PCT/JP2006/316331, dated Oct. 17, 2006, 5 pages (with English translation).
International Search Report in International Application No. PCT/JP2006/322516 dated Jan. 23, 2007, 5 pages.
International Search Report in International Application No. PCT/JP2007/066185, dated Sep. 25, 2007, 4 pages.
International Search Report in International Application No. PCT/JP2007/066635, dated Oct. 16, 2007, 5 pages.
International Search Report in International Application No. PCT/JP2008/053066, dated May 20, 2008, 8 pages.
International Search Report in International Application No. PCT/JP2013/084052, dated Mar. 4, 2014, 2 pages.
International Search Report in International Patent Application No. PCT/JP2016/068381, dated Sep. 6, 2016, 2 pages (English Translation).
International Search Report in International Patent Application No. PCT/JP2015/073946, dated Dec. 1, 2015, 3 pages.
International Search Report in International Patent Application No. PCT/JP2016/055268, dated May 17, 2016, 2 pages (English Translation).
International Search Report in International Patent Application No. PCT/JP2016/002562, dated Aug. 9, 2016, 2 pages (English Translation).
International Search Report in International Patent Application No. PCT/JP2018/004007, dated Apr. 3, 2018, 4 pages (English Translation).
Interview Summary in U.S. Appl. No. 12/558,982, dated Oct. 20, 2011, 3 pages.
Invitation to declare maintenance of the application for EP Application No. 01976786.2, dated Jul. 12, 2004.
Invitation to declare maintenance of the application for EP Application No. 05783232.1, dated Sep. 25, 2007.
Invitation to declare maintenance of the application for EP Application No. 06023078.6, dated May 2, 2007.
Israel 200090 Office Actions dated Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 dated Jan. 26, 2010, 4 pages with English translation.
Israel Office Action directed at Appl. No. 205512 dated Nov. 13, 2011, 4 pages with English translation.
Israel Response (IDS List) to Office Action directed at Appl. No. 195282 filed on May 3, 2010, 6 pages with English translation.
Israeli Notice of Allowance in Application No. 205512, dated Feb. 15, 2015, 5 pages, with English translation.
Israeli Office Action dated Mar. 27, 2012 for Israeli Application No. 189589 with English translation.
Israeli Office Action for Application No. 155447, dated Oct. 16, 2007 (with English translation).
Israeli Office Action for Application No. 189677, dated Feb. 18, 2009 (with English translation).
Israeli Office Action for Application No. 195282, dated Feb. 5, 2012 (with English translation).
Israeli Office Action for Application No. 199907, dated Apr. 22, 2012 (with English translation).
Israeli Office Action in Application No. 217197, dated Oct. 25, 2015, 4 pages.
Israeli Office Action in Application No. 223695, dated Aug. 25, 2015, 6 pages, with English translation.
Israeli Office Action in Application No. 223695, dated Feb. 16, 2015, 5 pages, with English translation.
Israeli Office Action in Application No. 227558, dated Aug. 2, 2015, 5 pages, with English translation.
Israeli Office Action in Application No. 238463, dated Oct. 28, 2015, 5 pages, with English translation.
Israeli Office Action dated May 16, 2010 for corresponding Israeli Application No. 189589, with English translation.
Israeli Response to Office Action in Application No. 217197, dated Dec. 24, 2015, 6 pages.
Israeli Submission Documents in Application No. 223695, dated May 4, 2015, 4 pages, with English translation.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 5 pages.
Issue Notification in U.S. Appl. No. 12/558,982, dated Sep. 26, 2012, 1 page.
Issued Notification in U.S. Appl. No. 11/892,785, dated Aug. 18, 2010, 1 page.
Itoh et al., "Preferential alternative splicing in cancer generates a K-sam messenger RNA with higher transforming activity," Cancer Res., 54:3237-3241 (1994).
Jain, "Normalizing tumor vasculature with anti-angiogenic therapy: A new paradigm for combination therapy," Nature Medicine 7(9):987-989, Sep. 2001.

(56) References Cited

OTHER PUBLICATIONS

Jakeman et al., "Developmental Expression of Binding Sites and Messenger Ribonucleic Acid for Vascular Endothelial Growth Factor Suggests a Role for This Protein in Vasculogenesis and Angiogenesis," Endocrinology, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Allowance for Application No. P2005-515330, dated Apr. 21, 2009.
Japanese Allowance for Application No. P2005-516605, dated Dec. 7, 2010.
Japanese Classification of Gastric Carcinoma "Igan-Toriatsukai Kiyaku" (Jun. 1999, 13th ed.) and an English translation, 10 pages.
Japanese Decision to Grant a Patent dated Jan. 30, 2013 for Japanese Application No. 2007-533350, with English translation.
Japanese Notice of Allowance in Application No. P2011-206481, dated Aug. 4, 2015, 7 pages, with English translation.
Japanese Notice of Reasons for Rejection dated May 15, 2012 for Japanese Application No. 2007-533350 with English translation.
Japanese Office Action dated Apr. 11, 2005 for Application No. 2002-536056 (with English translation).
Japanese Office Action dated Jun. 19, 2018 for Application No. P2016-214593, 7 pages (with English translation).
Japanese Office Action for Application No. 2007-522356, dated Feb. 8, 2011.
Japanese Office Action for Application No. P2005-516605, dated Nov. 4, 2009.
Japanese Office Action for Application No. P2008-516724, dated Oct. 9, 2012 (with English translation).
Japanese Office Action in Application No. P2011-206481, dated Jun. 2, 2015, 7 pages, with English translation.
Japanese Office Action in Application No. P2012-521531, dated Mar. 3, 2015, 6 pages, with English translation.
Japanese Office Action in Application No. P2012-521531, dated Sep. 29, 2015, 4 pages, with English translation.
Japanese Office Action in Application No. P2013-510994, dated Jul. 28, 2015, 5 pages, with English translation.
Japanese Office Action in Application No. P2013-510994, dated Jun. 9, 2015, 6 pages, with English translation.
Jhiang, "The RET proto-oncogene inn human cancers," Oncogene, 19:5590-5597 (2000).
Jiang et al., "Inactivating mutations of RNF43 confer Wnt dependency in pancreatic ductal adenocarcinoma," PNAS, Jul. 30, 2013, 110(31):12649-12654.
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," J. Clin. Endocrinol. Metab., 89:4142-4145 (2004).
Joao et al., "Somatic trinucleotide change encompassing codons 882 and 883 of the RET proto-oncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Randomized phase II trial comparing bevacizumab plus carboplatin and paclitaxel with carboplatin and paclitaxel alone in previously untreated locally advanced or metastatic non-small-cell lung cancer," J Clin Oncol 22(11):2184-2191, Jun. 1, 2004.
Johnson et al., "Paclitaxel plus carboplatin in advanced non-small-cell lung cancer: a phase II trial," J. Clin. Oncol., 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," Eur. J. Cancer, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," Ann Rheum. Dis., 64:1126-1131 (2005).
Kanai et al., "Development Status and Future Prospects of Novel Molecular Target Drugs for Hepatocellular Carcinoma", Journal of the Japanese Society of Gastroenterology, 106:1727-1735 (2009).
Kanai et al., "Current status and future perspective of molecular targeted therapy for hepatocellular carcinoma," Journal of the Japanese Society of Gastroenterology, 106:1727-1735 (2009) (English translation).
Kanakura et al., "Expression, Function and Activation of the Proto-Oncogene c-kit Product in Human Leukemia Cells," Leukemia and Lymphorma, 10:35-41 (1993).
Kashuk et al., "Phenotype-genotype correlation in Hirschsprung disease is illuminated by comparative analysis of the RET protein sequence," PNAS, 102(25):8949-8954 (2005).
Kato et al., "Effects of lenvatinib on tumor-associated macrophages enhance antitumor activity of PD-1 signal Inhibitors," Molecular Targets and Cancer Therapeutics, Abstract A92, Nov. 6, 2015, 1 page.
Kawano et al., "Presentation Abstract, Abstract No. 1619, Combination of VEGFR inhibitor lenvatinib (E7080) and Met/EphB4inhibitor golvatinib (E7050) overcomes VEGFR inhibitor-resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," Int. Arch. Allergy Immunol., 113:196-199 (1997).
Kelly et al., "Randomized phase III trial of paclitaxel plus carboplatin versus vinorelbine plus cisplatin in the treatment of patients with advanced non-small-cell lung cancer: a Southwest Oncology Group trial," J. Clin. Oncol., 19(13):3210-3218 (2001).
Kharkyevitch, "Farmakologiya," Third addition, and revised supplemented, Moscow, "Meditsina," 1987, partial translation, 5 pages.
Kibbe, Handbook of Pharmaceutical Excipients. Third Edition, 2000, pp. 6-1 through 6-6.
Kim et al., "RET Oligonucleotide Microarray for the Detection of RET Mutations in Multiple Endocrine Neoplasia Type 2 Syndromes", Clinical Cancer Research, 8,457-463, (2002).
Kim et al., "A phase II study of irinotecan plus cisplatin for patients with advanced stage IIIB or IV NSCLC previously treated with nonplatinum-based chemotherapy," Cancer, 107(4):799-805 (2006).
Kim et al., "An orally administered multitarget tyrosine kinase inhibitor, SU11248, is a novel potent inhibitor of thyroid oncogenic RET/papillary thyroid cancer kinases," J. Clin. Endocrinol. Metlab., 91(10):4070-4076 (2006).
Kim, "Technology evaluation: Matuzumab, Merck KGaA", Curr Opin Mol Ther. 2004; 6(1 ):96-103.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Kitamura et al., "Regulation of Development, Survival and Neoplastic Growth of Mast Cells through the c-kit Receptor," Int. Arch Allergy Immunol., 107:54-56 (1995).
Kitteringham et al., "A Simple Method for the Synthesis of Unsymmetrical Ureas," Synthetic Communications, 30(11):1937-1943 (2000).
Kleespies et al., "Tyrosine kinase inhibitors and gemcitabine: New treatment options in pancreatic cancer,?" Drug Resistance Updates, 9:1-18 (2006).
Klein et al, "Vascnlar endothelial growth factor gene and protein: strong expression in thyroiditis and thyroid carcinoma", Journal of endocrinology, Nov. 30, 1999, 41-49.

(56) References Cited

OTHER PUBLICATIONS

Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Klugbauer et al., "Detection of a Novel Type of RET Rearrangement (PTC5) in Thyroid Carcinomas after Chernobyl and Analysis of the Involved RET-fused Gene RFG5", Cancer Research, 58:198-203 (1998).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," Biochimica et Biophysica Acta, 1333:F217-F248 (1997).
Konno, "Physical and Chemical Changes of Medicinals in Mixtures with Adsorbents in the Solid State IV," Study on Reduced-Pressure Mixing for Practical Use of Amorphous Mixtures of Flufenamic Acid, Chem. Pharm Bull, 1990, p. 2003.
Korean ("KR") Notice of Allowance dated Aug. 25, 2010 corresponding KR Application No. 10-2008-7005195, with English translation.
Korean ("KR") Office Action dated Dec. 24, 2009 for corresponding KR Application No. 10-2008-7005195, with English translation.
Korean ("KR") Office Action dated May 29, 2010 for corresponding KR Application No. 10-2008-7005195, with English translation.
Korean Notice of Allowance in Application No. 10-2010-7011023, dated Mar. 24, 2015, 3 pages, with English translation.
Korean Office Action for Application No. 10-2003-7005506, dated Jan. 5, 2006 (with English translation).
Korean Office Action for Application No. 10-2005-7020292, dated Dec. 8, 2005 (with English translation).
Korean Office Action for Application No. 10-2006-7013993, dated Jul. 31, 2007 (with English translation).
Korean Office Action for Application No. 10-2007-7001347, dated Apr. 27, 2012 (with English translation).
Korean Office Action for Application No. 10-2007-7001347, dated Sep. 28, 2011 (with English translation).
Korean Office Action for Application No. 10-2009-7005657, dated Sep. 30, 2013, 27 pages (with English translation).
Korean Office Action in KR Application No. 10-2008-7029472, dated Sep. 30, 2013, 27 pages (with English translation).
Korean Request for Examination in Application No. 10-2012-7033886, dated Aug. 26, 2015, 12 pages, with English translation.
Kotva et al., "Substances with Antineoplastic Activity, LIII. N-(δ-(4-Pyrrolo[2,3-d]Pyrimidinylthio) Valeryl]} Amino Acids and Analogous Derivatives of Di- and Triglycine," Collection Czechoslov. Chem. Commun., 38:1438-1444 (1973).
Koyama et al, "Anti-tumor effect of E7080, a novel angiogenesis inhibitor," Folia Pharmacol. Japan., 2008, 132: 100-104 (with English translation).
Kremer, "Lenvatinib Advisory Board", The presentation document, American Society of Clinical Oncology, Annual meeting 2014, May 31, 2014, 138 pages.
Kruckeberg et al., "Pyrosequencing Technology as a Method for the Diagnosis of Multiple Endocrine Neoplasia Type 2", Clinical Chemistry, 50, 522-529, 2004.
Krystal et al., "Indolinone Tyrosine Kinase Inhibitors Block Kit Activation and Growth of Small Cell Lung Cancer Cells", Cancer Research., 61, 3660-3668, 2001.
Kubo et al., "a novel series of 4-phenoxyquinolines: potent and highly selective inhibitors of pdgf receptor autophosphorylation", Bioorganic and Medicinal Chemistry Letters., 7, 2935-2940, 1997.
Kubo et al., "Novel Potent Orally Active Selective VEGFR-2 Tyrosine Kinase Inhibitors: . . . ureas", Journal of Medicinal Chemistry., 48, 1359-1366, 2005.

Kumar et al., "Survival and failure outcomes in primary thyroid lymphomas: A single centre experience of combined modality approach," Journal of Thyroid Research, vol. 2013, Jun. 18, 2013, 6 pages.
Kumar et al., "Discovery and biological evaluation of GW654652: A pan inhibitor of VEGF receptors," Proceedings of the American Association for Cancer Research, 44, 9, (Abstract 39), 2003, 2 pages.
Laird et al., "SU6668 Is a Potent Antiangiogenic and Antitumor Agent That Induces Regression of Established Tumorsl", Cancer Research., 60, 4152-4160, 2000.
Lam et al., "Extemporaneous Compounding of Oral Liquid Dosage Formulations and Alternative Drug Delivery Methods for Anticancer Drugs," Reviews of Therapeutics, Pharmacotherapy, 2011, 31(2):164-192.
Lam et al., "High prevalence of RET proto-oncogene activation (RET/PTe) in papillary thyroid carcinomas", Eur J Endocrinology, 147: 741-745 (2002).
Lam et al., "β-catenin signaling: a novel mediator of fibrosis and potential therapeutic target," Curr Opin Rheumatol., 2011, 23(6):562-567 (Author Manuscript).
Lasota et al., "Mutations in Exons 9 and 13 of KIT Gene Are Rare Events in Gastrointestinal Stromal Tumors," American Journal of Pathology, 157(4):1091-1095 (2000).
LeDoussal et al. "bispecific-antibody-mediated targeting of radiolabeled bivalent haptens: theoretical, experimental and clinical results", Int. J. Cancer Suppl. 7: 58-62, 1992.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Lehtio et al., "Tankyrases as drug targets," FEBS J., 2013, 280:3576-3593.
Lennartsson et al., The Stem Cell Factor Receptor/c-Kit as a Drug Target in Cancer, Current Cancer Drug Targets, 6:p. 65-75 (2006).
Lenvatinib in Wikipedia: The Free Encyclopedia, http://en/wikipeida/org/wiki/Lenvatinib (accessed Dec. 18, 2013), 2 pages.
Leow et al. "MEDI3617, a human anti-angiopoietin 2 monoclonal antibody, inhibits angiogenesis and tumor growth in human tumor xenograft models", International Journal of Oncology, Demetrios A. Spandidos Ed. & Pub, GR, vol. 40, No. 5, May 1, 2012, p. 1321-1330, XP002721374.
Lesueur et al., "Polymorphisms in RET and its coreceptors and ligands as genetic modifiers of multiple endocrine neoplasia type 2A," Cancer Res., 66:1177-1180 (2006).
Leukemias, Hematology, and Oncology, http://www.merkmanuals.com/professional/print/sec11/ch142a.html Mar. 16, 2011, 5 pages.
Lev et al., "A Specific Combination of Substrates is Involved in Signal Transduction by the Kit-Encoded Receptor," The EMBO Journal, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).
Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026.
Liu et al., "Dose Adjustment Integrated Exposure Response Analysis (DAIER) for Dose Optimization Lenvatinib Renal Call Carcinoma [URL:https://www.aacr.org/AdvocacyPolicy/GovernmentAffairs/Documents/6.13.I6%20FDA-AACR%20Dose%20Finding%20for%Online.pdf]", Presentation slides at FDA-AACR: Oncology Dose-finding Workshop, Jun. 13, 2016, 19 pages.
Liu et al., "Structure of Human Methionine Aminopeptidase-2 Complexed with Fumagillin", Science., 282, 1324-1327, 1998.
Liu, "Water-Insoluble Drug Formation," Interpharm Press, 2000, p. 525, 557-561.

(56) References Cited

OTHER PUBLICATIONS

Llovet et al., "Plasma biomarkers as predictors of outcome in patients with advanced hepatocellular carcinoma," Clinical Cancer Res, 2012, 18(8):2290-2300.

Logie et al., "Activating mutations of the tyrosine kinase receptor FGFR3 are associated with benign skin tumors in mice and humans," Mol. Genet., 14:1153-1160 (2005).

Longley et al., "Altered Metabolism of Mast-Cell Growth Factor (c-kit Ligand) in Cutaneous Mastocytosis," The New England Journal of Medicine, 328(18):1302-1307 (1993).

Longley et al., "Classes of c-KIT activating mutations: proposed mechanisms of action and implications for disease classification and therapy," Leuk. Res., 25:571-576 (2001).

Longley et al., "Somatic c-KIT Activating Mutation in Urticaria Pigmentosa and Aggressive Mastocytosis: Establishment of Clonality in a Human Mast Cell Neoplasm," Nature Genetics, 12:312-314 (1996).

Lu et al., "Tailoring in Vitro Selection for a Picomolar Affinity Human Antibody Directed Against Vascular Endothelial Growth Factor Receptor 2 for Enhanced Neutralizing Activity," J Biol Chem., 2003, 278(44):43496-43507.

Lukacs et al., "Stem Cell Factor (c-kit Ligand) Influences Eosinophil Recruitment and Histamine Levels in Allergic Airway Inflammation," J. Immunol., 156:3945-3951 (1996).

Macedonian Notice of Allowance in Application No. P/2015/231, dated Oct. 13, 2015, 2 pages, with English translation.

Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).

Maintenance and Response to EP Search Report in EP Application No. 06796594.7, dated Dec. 21, 2011, 43 pages.

Maintenance of the application for EP Application No. 01976786.2, dated Sep. 6, 2004.

Maintenance of the application for EP Application No. 05783232.1, dated Nov. 9, 2007.

Maintenance of the application for EP Application No. 06023078.6, dated Jun. 19, 2007.

Marchetti et al., "Clinical Features and Outcome of Patients with Non-Small-Cell Lung Cancer Harboring BRAF Mutations," J Clin Oncol, 29(26):3574-3579, Aug. 8, 2011.

Marzioni et al., "Clinical Implications of novel aspects of biliary pathophysiology," XP026942498, 20th National Congress of Digestive Diseases/Digestive and Liver Disease, 2010, 42(4):238-244.

Masferrer et al., "COX-2 Inhibitors a New Class of Antiangiogenic Agents", Annals of N.Y. Acad. Science., 889:84-6, 1999.

Matsui et al, "a novel multi-targeted tyrosine kinase inhibitor, exhibits anti-angiogenic activity via inhibition of KIT signaling in a small cell lung cancer xenograft model", European Journal of Cancer, Sep. 29, 2004, p. 47.

Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.

Matsui et al., "E7080 (ER-203492-00), a Novel VEGF Receptor )Tyrosine Kinase Inhibitor-I. Characterization as an Angiogenesis Inhibitor," Abstract # 51, AACR, Washington, USA (Jul. 11-14, 2003).

Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003).

Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).

Matsui et al., "E7080, a novel multi-receptor Tyrosine Kinase Inhibitor, inhibited in vitro / in vivo VEGF- and SCF-driven angiogenesis SCLC cell line," Abstract #146, EORTC-NCI-AACR, Geneva, Switzerland (Sep. 28-Oct. 1, 2004).

Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.

Matsui et al., "Quantitative analysis of the profile of tumor vessels may be useful as predictive biomarkers for E7080," Abstract #4631, 98th AACR annual meeting, Los Angeles, CA, (Apr. 14-18, 2007).

Matsui et al., "VEGFRs inhibitor E7080 inhibits lymph node metastasis of human breast carcinoma, by preventing murine lymphatic endothelial cells from lymphangiogenesis," Abstract #PD12-8, 18$^{th}$ EORTC-NCI-AACR Symposium on "Molecular Targets and Cancer Therapeutics," Prague, Czech Republic (Nov. 7-10, 2006).

Matsui, "Extracellular matrix of linitis plastica as a possible new therapeutic target," Surgical Treatment, Sep. 2003, 89(3):301-306 (with English translation).

Matsuki et al., "Antitumor activity of a combination of lenvatinib mesilate, ifosfamide, and etoposide against human pediatric osteosarcoma cell lines," XP009511737, Cancer Research; 107th Annual Meeting of the American-Association-of-CancerResearch (AACR), American Association for Cancer Research, 2016, 76(Suppl. 14):3266.

Matsushima et al., "Preparation of pyridine and pyrimidine derivatives as inhibitors of hepatocyte growth factor receptor (HGFR)," Hcaplus, 2005, 977021.

McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).

McCulloch et al., "Astragalus-based Chinese herbs and platinum-based chemotherapy for advanced non-small-cell lung cancer: meta-analysis of randomized trials," J. Clin. Oncol., 24(3):419-430 (2006).

Medicines.org.uk [online], "Lenvima 4 mg hard capsules," XP002789352, Electronic Medicines Compendium, Jun. 2015, [Retrieved on Jan. 3, 2019], retrieved from: URL<https://www.medicines.org.uk/emc/product/6840/smpc/print>, 23 pages.

Meltzer, "The Pharmacological Basis for the Treatment of Perennial Allergic Rhinitis and Non-Allergic Rhinitis with Topical Corticosteroids," Allergy, 52:33-40 (1997).

Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Clin. Cancer Res., 9:327-337 (2003).

Metcalfe et al., "Lineage Commitment in the Progeny of Murine Hematopoietic Prepogenitor Cells: Influence of Thrombopoietin and Interleukin 5," Proc. Nat'l Acad. Sci. USA, 95:6408-6412 (1998).

Metcalfe et al., "Mast cells," Physiol. Rev., 77(4):1033-1079 (1997).

Metcalfe, "Classification and Diagnosis of Mastocytosis: Current Status," J. Invest. Dermatol., 96:2S-4S (1991).

Mexican Notice of Allowance in Application No. MX/a/2012/014776, dated Mar. 18, 2015, 3 pages, with English translation.

Mexican Notice of Allowance in Application No. MX/a/2013/009931, dated Jun. 29, 2015, 3 pages, with English translation.

Mexican Office Action in Application No. MX/a/2010/008187, dated Aug. 21, 2013, 6 pages (with English translation).

Mexican Office Action in Application No. MX/a/2013/009931, dated Apr. 9, 2015, 3 pages, with English translation.

Mexican Office Action in Application No. MX/a/2014/010594, dated Oct. 13, 2015, 8 pages, with English translation.

Mexican Submission Documents in Application No. MX/a/2014/010594, dated Oct. 8, 2015, 10 pages, with English translation.

Mexican Submission Documents in Application No. MX/a/2014/010594, dated Sep. 24, 2015, 2 pages, with English translation.

Micke et al., "Characterization of c-kit expression in small cell lung cancer: prognostic and therapeutic implications," Clin. Cancer Res., 9:188-194 (2003).

Mikms et al., "AARY-334543, a potent, orally active small molecule inhibitor of EGFR and ErbB-2," Am. Assoc. Cancer Res. Abstract 3399, 2005, 2 pages.

(56) References Cited

OTHER PUBLICATIONS

Miller et al., "Genomic amplification of MET with boundaries within fragile site FRA7G and upregulation of MET pathways in esophageal adenocarcinoma," Oncogene, 2005, 25(3):409-418.
Miller et al., "Paclitaxel plus bevacizumab versus paclitaxel alone for metastatic breast cancer," N. Engl. J. Med., 357(26):2666-2676 (2007).
Millstein and Cuello, "Hybrid hybridomas and their use in immunohistochemistry", Nature 305: 537-9, 1983.
Mitchell et al, "The influence of additives on the cloud point, disintegration and dissolution of hydroxypropylmethylcellulose gels and matrix tablets," International iournal of pharmaceutics, 1990, vol. 66, No. 1/3, pp. 233-242.
Miyauchi et al., "Two Germline Missense Mutations of Co dons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003).
Mohammadi et al., "Crystal structure of an angiogenesis inhibitor bound to the FGF receptor tyrosine kinase domain", EMBO J., 17, 5896-5904, 1998.
Molina et al., "A phase 1b clinical trial of the multitargeted tyrosine kinase inhibitor lenvatinib (E7080) in combination with everolimus for treatment of metastatic renal cell carcinoma (RCC)", Cancer Chemotherapy and Pharmacology, Jan. 2014, vol. 73, No. 1, p. 181-p. 189.
Mologni et al., "Inhibition of RET tyrosine kinase by SU5416," J. Mol. Endocrinol., 37(2):199-212.
Montalbetti and Falque, "Tetrahedron report No. 740: Amide bond formation and peptide coupling," Tetrahedron, 2005, 61:10827-10852.
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 21(21):3955-3964 (2003).
Morikawa et al., "Angiogenesis and Pericytes," The Cell, 37(4):164-168 (2005) (English translation).
Morris et al., "An Integrated Approach to the Selection of optimal Salt Form for a New Drug Candidate," International Journal of Pharmaceutics, 105:209-217 (1994) (XP023724810).
Mototsugu, "mTOR inhibitors," Nippohn Rinsho, Jun. 2010, 68(6):1067-1072 (with English abstract).
Motzer et al., "Investigation of novel circulating proteins, germ line single nucleotide polymorphisms, and molecular tumor markers as potential efficacy biomarkers of first-line sunitinib therapy for advanceed renal cell carcinoma," Cancer Chemotherapy and Pharmacology, Aug. 7, 2014, vol. 74 No. 4, p. 739-p. 750.
Motzer et al., "Lenvatinib, everolimus, and the combination in patients with metastatic renal cell carcinoma: a randomised, phase 2, open-label, multicentre trial," Lancet Oncol, (2015), 11(16):1473-1482.
Motzer et al., "Randomized phase 2 three-arm trial of lenvatinib (LEN), everolimus (EVE), and LEN+EVE in patients (pts) with metastatic renal cell carcinoma (mRCC)," Oral presentation at ASCO Annual Meetingm, Chicago, May 29-Jun. 2, 2015.
Motzer et al., "Randomized phase II, three-arm trial of lenvatinib (LEN), everolimus (EVE), and LEN+EVE in patients pts) with metastatic renal cell carcinoma (mRCC)," Journal of Clinical Oncology, May 20, 2015, vol. 33, Issue 15S, p. 248.
Myers et al., "The Preparation and SAR of 4-(Anilino), 4-(Phenoxy), and 4-(Thiophenoxy)-Quinazolines: Inhibitors of p56 1ck and EGF-R Tyrosine Kinase Activity," Bioorgan. & Med. Chem. Letters, 7:417-420 (1997).

Naclerio et al., "Rhinitis and Inhalant Allergens," JAMA, 278(22):1842-1848 (1997).
Nagata et al., "Elevated Expression of the Proto-Oncogene c-kit in Patients with Mastocytosis," Leukemia, 12:175-181 (1998).
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.
Nakagawa, Takayuki et al., "Lenvatinib in combination with golvatinib overcomes hepatocyte growth factor pathway-induced resistance to vascular endothelial growth factor receptor inhibitor", Cancer Science, Jun. 2014, vol. 105, No. 6, p. 723-p. 730.
Nakamura et al., "In Vitro selectivity and potency of KRN951, a novel inhibitor of VEGF receptor tyrosine kinases", Cancer Research, cited Jul. 13, 2016, 2 pages.
Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor—II. Effects on Growth of Human Tumor Xenografts and Life Span of Mice in Colon 38 Orthotopic Transplantation Model," Abstract #52, AACR, Toronto, Canada (Apr. 5-9, 2003).
Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.
Nakanishi, "Molecular diversity of glutamate receptors and implications for brain function," Science, 1992, pp. 597-603.
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Nakazawa et al., "Multitargeting strategy using lenvatinib and golvatinib: Maximizing anti-angiogenesis activity in a preclinical cancer model", Cancer Science, Feb. 2015, vol. 106, No. 2, p. 201-p. 207.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Naran eta l., "Inhibition of HGF/MET as therapy for malignancy," Expert Opin. Ther. Targets, 2009, p. 569-581.
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).
Naski et al., "Graded activation of fibroblast growth factor receptor 3 by mutations causing achondroplasia and thanatophoric dysplasia," Nat. Genet., 13:233-237 (1996).
Natali et al., "Breast Cancer is Associated with Loss of the c-kit Oncogene Product," Int. J. Cancer, 52:713-717 (1992).
NCBI GenBank Accession No. NM_000222, Coffey et al. (Feb. 11, 2008).
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Nishikawa et al., "Cys611Ser mutation in RET proto-oncogene in a kindred with medullary thryroid carcinoma and Hirschsprung's disease", European Journal of Human Genetics, 11,364-368 (2003).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," Cold Spring Harbor Laboratory Press, 3:816-826 (1989) (XP002522472).
Noriyuki et al., "Anti-tumor effect of E7080, a novel angiogenesis inhibitor," Database BIOSIS [Online] Biosciences Information Ser-

(56) References Cited

OTHER PUBLICATIONS vice, Philadelphia, PA, US: Database accession No. PREV200800475929, Aug. 2008, XP002677323.
Norwegian Office Action in Application No. 20063383, dated Apr. 15, 2015, 2 pages, with English translation.
Notice of Acceptance dated Aug. 10, 2004 for ZA Patent App. No. 2003/3567.
Notice of Acceptance dated Aug. 3, 2006 for AU Application No. 2001295986.
Notice of Acceptance dated May 13, 2008 for AU Application No. 2006236039.
Notice of Acceptance for AU Application No. 2009210098, dated Jun. 4, 2013, 3 pages.
Notice of Acceptance in AU Application No. 2005217325, dated Nov. 20, 2007, 3 pages.
Notice of Acceptance in AU Application No. 2005217328, dated Sep. 24, 2007, 3 pages.
Notice of Acceptance in AU Application No. 2006282456, dated Aug. 17, 2009, 1 page.
Notice of Acceptance in AU Application No. 2007288793, dated Apr. 10, 2012, 3 pages.
Notice of Acceptance in AU Application No. 2007289787, dated Mar. 16, 2012, 3 pages.
Notice of Acceptance in DB Application No. 60/2005, dated Nov. 16, 2006, 1 page.
Notice of Acceptance in NZ Application No. 547517, dated Mar. 6, 2009, 1 page.
Notice of Acceptance in NZ Application No. 566793, dated Feb. 12, 2010, 2 pages.
Notice of Acceptance of Complete Specification dated Mar. 4, 2005 for NZ Application No. 525324.
Notice of Allowability dated Nov. 28, 2007 for PH Application No. 1-2003-500266.
Notice of Allowability in PH Application No. 1-2007-502319, dated Feb. 29, 2012, 1 page.
Notice of Allowance dated Apr. 19, 2005 for RU Application No. 2003114740 (with English translation).
Notice of Allowance dated Apr. 19, 2011 for JP Application No. 2007-522356.
Notice of Allowance dated Apr. 24, 2012 for U.S. Appl. No. 12/524,754.
Notice of Allowance dated Apr. 29, 2010 for AU Application No. 2005283422.
Notice of Allowance dated Aug. 2, 2005 for JP Application No. 2002-536056 (with English translation).
Notice of Allowance dated Aug. 7, 2012 for Japanese Application No. P2007-529565 (with English translation).
Notice of Allowance dated Dec. 15, 2006 for CN Application No. 01819710.8.
Notice of Allowance dated Dec. 26, 2007 for IL Application No. 155447 (with English translation).
Notice of Allowance dated Feb. 15, 2013 for NZ Application No. 598291, 1 page.
Notice of Allowance dated Feb. 27, 2009 for U.S. Appl. No. 11/293,785.
Notice of Allowance dated Feb. 5, 2010 for CN Application No. 200580026468.7 (with English translation).
Notice of Allowance dated Jul. 17, 2012 for JP Application No. P2011-527665 (with English translation).
Notice of Allowance dated Jul. 21, 2009 for JP Application No. 2005-124034 (with English translation).
Notice of Allowance dated Jun. 13, 2006 for U.S. Appl. No. 10/420,466.
Notice of Allowance dated Jun. 20, 2012 for EP Application No. 06782407.8.
Notice of Allowance dated Jun. 25, 2012 for EP Application No. 07806561.2.
Notice of Allowance dated Jun. 3, 2008 for U.S. Appl. No. 11/293,785.
Notice of Allowance dated Mar. 14, 2010 for IL Application No. 189677 (with English translation).
Notice of Allowance dated Mar. 16, 2007 for U.S. Appl. No. 10/420,466.
Notice of Allowance dated Mar. 21, 2013 for EP Application No. 07793075.8, 2 pages.
Notice of Allowance dated Mar. 22, 2012 for U.S. Appl. No. 12/986,638.
Notice of Allowance dated Mar. 8, 2013 for CA Application No. 2627598, 1 page.
Notice of Allowance dated May 16, 2013 for EP Application No. 06796594.7, 2 pages.
Notice of Allowance dated May 18, 2009 for U.S. Appl. No. 11/293,785.
Notice of Allowance dated May 6, 2013 for EP Application No. 04818213.3, 22 pages.
Notice of Allowance dated Nov. 14, 2011 for IL Application No. 181697 (with English translation).
Notice of Allowance dated Nov. 19, 2008 for U.S. Appl. No. 11/293,785.
Notice of Allowance dated Nov. 2, 2012 for EP Application No. 06782407.8.
Notice of Allowance dated Nov. 2, 2012 for EP Application No. 07806561.2.
Notice of Allowance dated Oct. 14, 2010 for CA Application No. 2426461.
Notice of Allowance dated Oct. 17, 2011 for CA Application No. 2579810.
Notice of Allowance dated Oct. 18, 2006 for MX Application No. PA/a/2003/003362 (with English translation).
Notice of Allowance dated Oct. 20, 2008 for TW Application No. 90125928 (with English translation).
Notice of Allowance dated Oct. 31, 2008 for NO Application No. 20031731 (with English translation).
Notice of Allowance dated Oct. 9, 2010 for CN Application No. 200710007097.9 (with English translation).
Notice of Allowance dated Sep. 12, 2005 for U.S. Appl. No. 10/420,466.
Notice of Allowance dated Sep. 20, 2011 for JP Application No. 2006-535174.
Notice of Allowance dated Sep. 25, 2012 for U.S. Appl. No. 12/986,638.
Notice of Allowance dated Sep. 4, 2012 in JP Application No. P2009-123432 (with English translation).
Notice of Allowance for CN Application No. 200980103218.7, dated May 27, 2013, 4 pages (with English translation).
Notice of Allowance for JP Application No. 2008-516724, dated Jan. 22, 2013, 4 pages, with English translation.
Notice of Allowance for JP Application No. P2008-532141, dated Sep. 10, 2013, 5 pages (with English translation).
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in AU Application No. 2010285740, dated Nov. 19, 2014, 1 page.
Notice of Allowance in Australian Patent Application No. 2012246490, dated Jul. 25, 2016, 4 pages.
Notice of Allowance in Australian Patent Application No. 2014371148, dated Jul. 26, 2018, 4 pages (English Translation).

(56) References Cited

OTHER PUBLICATIONS

Notice of Allowance in CA Application No. 2605854, dated Apr. 7, 2010, 1 page.
Notice of Allowance in CA Application No. 2652442, dated Apr. 16, 2014, 1 page.
Notice of Allowance in CA Application No. 2661333, dated Dec. 19, 2013, 1 page.
Notice of Allowance in CA Application No. 2661702, dated Sep. 26, 2013, 1 page.
Notice of Allowance in CA Application No. 2771403, dated Oct. 22, 2014, 1 page.
Notice of Allowance in Canadian Patent Application No. 2704000, dated Jul. 7, 2016, 1 page.
Notice of Allowance in Canadian Patent Application No. 2802644, dated Aug. 5, 2016, 1 page.
Notice of Allowance in Canadian Patent Application No. 2828946, dated Feb. 22, 2016, 1 page.
Notice of Allowance in Chilean Patent Application No. 2012-00412, dated Jan. 29, 2019, 21 pages (with English Translation).
Notice of Allowance in Chinese Patent Application No. 201480026871.9, dated Jun. 28, 2017, 8 pages (English Translation).
Notice of Allowance in Chinese Patent Application No. 201480067017.7, dated Sep. 13, 2018, 4 pages (English Translation).
Notice of Allowance in CN Application No. 200680021939.X, dated Jan. 11, 2012, 4 pages (with English translation).
Notice of Allowance in CN Application No. 200780019200.X, dated Jan. 15, 2013, 4 pages (with English translation).
Notice of Allowance in CN Application No. 200780019520.5, dated Apr. 27, 2011, 4 pages (with English translation).
Notice of Allowance in CN Application No. 201180030568.2, dated Sep. 9, 2014, 4 pages (with English translation).
Notice of Allowance in EP Application No. 04807580.8, dated Dec. 15, 2014, 103 pages.
Notice of Allowance in EP Application No. 04818213.3, dated Sep. 19, 2013, 2 pages.
Notice of Allowance in EP Application No. 07743994.1, dated May 8, 2015, 51 pages.
Notice of Allowance in EP Application No. 08704376.6, dated Aug. 19, 2014, 62 pages.
Notice of Allowance in EP Application No. 08846814.5, dated Jan. 8, 2015, 36 pages.
Notice of Allowance in European Patent Application No. 12786619.2, dated Sep. 30, 2016, 155 pages.
Notice of Allowance in European Patent Application No. 12793322.4, dated Feb. 14, 2018, 82 pages.
Notice of Allowance in European Patent Application No. 12793322.4, dated Jun. 4, 2018, 7 pages.
Notice of Allowance in European Patent Application No. 14727633.1, dated Feb. 9, 2018, 72 pages.
Notice of Allowance in European Patent Application No. 14873998.0, dated Oct. 17, 2018, 141 pages.
Notice of Allowance in Gulf Cooperation Council Patent Application No. GC2014-28624, dated May 9, 2018, 2 pages (English Translation).
Notice of Allowance in ID App. Ser No. W-00 2008 00601, dated Oct. 17, 2012, 12 pages (with English translation).
Notice of Allowance in IL Application No. 195282, dated Aug. 11, 2014, 5 pages (with English translation).
Notice of Allowance in IL Application No. 197141, dated Oct. 27, 2013, 2 pages (with English translation).
Notice of Allowance in IL Application No. 200090, dated Nov. 18, 2013, 5 pages (with English translation).
Notice of Allowance in IL Application No. 207089, dated Nov. 10, 2014, 5 pages (with English translation).
Notice of Allowance in Indonesian Patent Application No. W-00201201031, dated Dec. 28, 2016, 5 pages (English Translation).
Notice of Allowance in Israeli Patent Application No. 217197, dated Jun. 26, 2016, 3 pages, (English translation).

Notice of Allowance in Israeli Patent Application No. 223695, dated Apr. 4, 2017, 3 pages (English Translation).
Notice of Allowance in Israeli Patent Application No. 227558, dated May 8, 2017, 6 pages (English Translation).
Notice of Allowance in Israeli Patent Application No. 242519, dated Dec. 13, 2017, 6 pages (English Translation).
Notice of Allowance in Israeli Patent Application No. 245961, dated Jul. 26, 2018, 15 pages (English Translation).
Notice of Allowance in Japanese Patent Application No. P2012-521531, dated Mar. 1, 2016, 6 pages (English Translation).
Notice of Allowance in Japanese Patent Application No. P2013-515178, dated May 17, 2016, 6 pages (English Translation).
Notice of Allowance in Japanese Patent Application No. P2014-513691, dated Oct. 4, 2016, 6 pages (English Translation).
Notice of Allowance in Japanese Patent Application No. P2015-554886, dated Jan. 24, 2017, 6 pages, (English Translation).
Notice of Allowance in Japanese Patent Application No. P2015-555882, dated Sep. 4, 2018, 6 pages (English Translation).
Notice of Allowance in Japanese Patent Application No. P2016-214593, dated Sep. 4, 2018, 6 pages (English Translation).
Notice of Allowance in Japanese Patent Application No. P2016-572771, dated Apr. 4, 2017, 6 pages (English Translation).
Notice of Allowance in Jordan Patent Application No. 55/2011, dated Apr. 16, 2017, 2 pages (English Translation).
Notice of Allowance in JP Application No. P2009-540099, dated Oct. 21, 2014, 6 pages (with English translation).
Notice of Allowance in JP Application No. P2009-551518, dated Oct. 22, 2013, 5 pages (with English translation).
Notice of Allowance in Korean Patent Application No. 10-2012-7033886, dated Oct. 18, 2016, 3 pages (English Translation).
Notice of Allowance in Korean Patent Application No. 10-2013-7020616, dated Jun. 29, 2017, 3 pages (English Translation).
Notice of Allowance in KR Application No. 10-2006-7013907, dated Jan. 14, 2008, 3 pages (with English translation).
Notice of Allowance in KR Application No. 10-2006-7013940, dated Jan. 14, 2008, 3 pages (with English translation).
Notice of Allowance in KR Application No. 10-2008-7013685, dated Nov. 29, 2013, 3 pages (with English translation).
Notice of Allowance in KR Application No. 10-2008-7027527, dated Mar. 3, 2014, 4 pages (with English translation).
Notice of Allowance in KR Application No. 10-2008-7029472, dated Sep. 16, 2014, 3 pages (with English translation).
Notice of Allowance in KR Application No. 10-2009-7005657, dated Sep. 19, 2014, 3 pages (with English translation).
Notice of Allowance in KR Application No. 10-2009-7017694, dated Jul. 28, 2014, 3 pages (with English translation).
Notice of Allowance in KR Application No. 10-2010-7018835, dated Jan. 20, 2015, 3 pages (with English translation).
Notice of Allowance in KR Application No. 10-2012-7003846, dated Feb. 3, 2015, 3 pages.
Notice of Allowance in Mexican Patent Application No. MX/a/2014/010594, dated Nov. 17, 2016, 3 pages (English Translation).
Notice of Allowance in MX Application No. MX/a/2008/002156, dated Oct. 15, 2010, 3 pages (with English translation).
Notice of Allowance in MX Application No. MX/a/2010/008187, dated Jul. 17, 2014, 3 pages (with English translation).
Notice of Allowance in MY Application No. PI20071922, dated Jan. 15, 2010, 3 pages.
Notice of Allowance in Pakistani Patent Application No. 907/2014, dated May 2, 2018, 1 page (English Translation).
Notice of Allowance in PK Application No. 1024/2006, dated Nov. 2, 2010, 1 page.
Notice of Allowance in PK Application No. 375/2008, dated Nov. 2, 2010, 1 page.
Notice of Allowance in RU Application No. 2006134254, dated Jan. 14, 2008, 30 pages (with English translation).
Notice of Allowance in RU Application No. 2012103471, dated Dec. 19, 2014, 12 pages (with English translation).
Notice of Allowance in RU Application No. 2012158142, dated May 5, 2015, 15 pages (with English translation).
Notice of Allowance in Russian Patent Application No. 2015148193, dated Apr. 23, 2018, 15 pages (English Translation).

(56) References Cited

OTHER PUBLICATIONS

Notice of Allowance in Russian Patent Application No. 2016122867, dated Aug. 31, 2018, 30 pages (English Translation).
Notice of Allowance in Singapore Patent Application No. 11201509278X, dated Nov. 22, 2017, 5 pages (English Translation).
Notice of Allowance in Singaporean Patent Application No. 11201604496Y, dated Nov. 23, 2016, 5 pages.
Notice of Allowance in South African Patent Application No. 2016/03956, dated Nov. 2, 2017, 2 pages.
Notice of Allowance in TW Application No. 095130665, dated Sep. 7, 2012, 4 pages (with English translation).
Notice of Allowance in U.S. Appl. No. 10/797,903, dated Mar. 10, 2011, 22 pages.
Notice of Allowance in U.S. Appl. No. 13/870,507, dated Jul. 26, 2016, 13 pages.
Notice of Allowance in U.S. Appl. No. 14/577,660, dated Jul. 9, 2015, 10 pages.
Notice of Allowance in U.S. Appl. No. 15/750,712, dated Apr. 1, 2019, 125 pages.
Notice of Allowance in UA Application No. a201203132, dated Mar. 21, 2014, 6 pages.
Notice of Allowance in Ukraine Patent Application No. a201606261, dated Feb. 22, 2018, 18 pages (English Translation).
Notice of Allowance in U.S. Appl. No. 11/892,785, dated Apr. 5, 2010, 23 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in U.S. Appl. No. 11/508,322, dated Sep. 15, 2009, 6 pages.
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 11/997,719, dated Jun. 5, 2014, 14 pages.
Notice of Allowance in U.S. Appl. No. 12/031,568, dated Jun. 1, 2012, 23 pages.
Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/439,339, dated Apr. 1, 2014, 17 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/524,754, dated Sep. 18, 2014, 35 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 12/741,682, dated Feb. 7, 2014, 11 pages.
Notice of Allowance in U.S. Appl. No. 12/741,682, dated May 15, 2014, 13 pages.
Notice of Allowance in U.S. Appl. No. 12/741,682, dated Oct. 21, 2013, 12 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/083,338, dated Feb. 6, 2014, 15 pages.
Notice of Allowance in U.S. Appl. No. 13/083,338, dated Jul. 10, 2014, 22 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in U.S. Appl. No. 13/624,278, dated Oct. 31, 2014, 14 pages.
Notice of Allowance in U.S. Appl. No. 13/624,278, dated Sep. 16, 2013, 20 pages.
Notice of Allowance in U.S. Appl. No. 13/805,826, dated Dec. 17, 2014, 15 pages.
Notice of Allowance in U.S. Appl. No. 13/983,891, dated Mar. 20, 2014, 9 pages.
Notice of Allowance in U.S. Appl. No. 14/002,018, dated Oct. 24, 2014, 70 pages.
Notice of Allowance in U.S. Appl. No. 14/122,339, dated Dec. 21, 2017, 8 pages.
Notice of Allowance in U.S. Appl. No. 14/890,207, dated Nov. 21, 2018, 12 pages.
Notice of Allowance in U.S. Appl. No. 15/503,108, dated Apr. 11, 2018, 7 pages.
Notice of Allowance in U.S. Appl. No. 15/503,108, dated Dec. 12, 2018, 8 pages.
Notice of Allowance in U.S. Appl. No. 15/503,108, dated Feb. 7, 2019, 4 pages.
Notice of Allowance in U.S. Appl. No. 15/503,108, dated Jan. 4, 2019, 6 pages.
Notice of Allowance in Vietnamese Patent Application No. 1-2016-02104, dated Aug. 27, 2018, 2 pages (English Translation).
Notice of Allowance in VN Application No. 1-2008-00723, dated Aug. 19, 2010, 2 pages (with English translation).
Notice of Allowance in VN Application No. 1-2011-03484, dated Apr. 28, 2014, 2 pages.
Notice of Allowance in ZA Application No. 2007/09572, dated Mar. 12, 2009, 1 pages.
Notice of Allowance issued in CN Application No. 200880115011.7, dated Aug. 5, 2013, 4 pages (with English translation).
Notice of Allowance issued in CN Application No. 201080030508.6, dated Jul. 4, 2013, 4 pages (with English translation).
Notice of Allowance issued in EP Application No. 10015141.4, dated Jul. 1, 2013, 41 pages.
Notice of Allowance issued in IL Application No. 175363, dated Aug. 13, 2013, 2 pages (with English translation).
Notice of Allowance issued in JP Application No. P2008-556208, dated Jul. 9, 2013, 4 pages (with English translation).
Notice of Allowance issued in U.S. Appl. No. 12/524,754, dated Jul. 19, 2013, 11 pages.
Notice of Appeal in European Patent Application No. 08846814.5, dated Jul. 5, 2017, 3 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Notice of decision for patent dated Apr. 17, 2006 for KR Application No. 10-2005-7020292, (with English translation).
Notice of decision for patent dated Jun. 12, 2006 for KR Application No. 10-2003-7005506 (with English translation).
Notice of Final Rejection in KR Application No. 10-2009-7013723, dated Jul. 29, 2011, 4 pages (with English translation).
Notice of Grant in KR Application No. 10-2007-7026886, dated Dec. 31, 2009, 5 pages (with English translation).
Notice of Non-Substantive Deficiencies Prior to Allowance in IL Application No. 197141, dated Feb. 3, 2013, 16 pages (with English translation).
Notice of Reasons for Rejection issued in JP Application No. P2009-540099, dated Jul. 2, 2013, 7 pages (with English translation).

(56) References Cited

OTHER PUBLICATIONS

Notice of Reasons for Rejection dated Nov. 13, 2012 issued for corresponding Japanese Application No. 2007-533350 with full English language translation.
Notice Prior to Allowance in IL Application No. 188670, dated Sep. 12, 2011, 2 pages (with English translation).
Notice Prior to Allowance in IL Application No. 197002, dated Oct. 28, 2012, 2 pages (with English translation).
Notice Prior to Examination dated Jun. 29, 2008 for IL Application No. 189677 (with English translation).
Notice Prior to Examination dated Mar. 9, 2009 for IL Application No. 181697 (with English translation).
Notice Prior to Examination in IL Application No. 188670, dated Aug. 13, 2009, 3 pages (with English translation).
Notice Prior to Examination in IL Application No. 197002, dated Mar. 23, 2010, 3 pages (with English translation).
Notice Prior to Examination in IL Application No. 197141, dated Mar. 23, 2010, 3 pages (with English translation).
Notice Prior to Examination in IL Application No. 200466, dated Jun. 22, 2010, 3 pages (with English translation).
Notification dated Apr. 25, 2008 for PH Application No. 1-2003-500266.
Notification of Defects for IL Application No. 195282, dated Apr. 10, 2013, 4 pages (with English Translation).
Notification of Non-Compliant Amendment filed on Jan. 13, 2005 for U.S. Appl. No. 10/420,466.
Noy et al., "Tumor-Associated Macrophages: From Mechanisms to Therapy," Immunity 41:49-61, Jul. 17, 2014.
Nugiel et al., "Synthesis and evaluation of indenopyrazoles as cyclin-dependent kinase inhibitors. 2. Probing the indeno ring substituent pattern," J. Med. Chem., 45(24):5224-5232 (2002).
Nyati et al., "Radiosensitization by Pan ErbB Inhibitor CI-1033 in Vitro and in Vivo", Clinical Cancer Research., 10:691-700, 2004.
Observation for CN Application No. 200880115011.7, dated Apr. 11, 2013, 10 pages (with English translation).
Observations for CN Application No. 201080030508.6, dated May 27, 2013, 7 pages (with English translation).
Ocqueteau et al., Expression of the CD117 antigen (C-Kit) on normal and myelomatous plasma cells, Br. J. Haematol., 95:489-493 (1996).
Office Action dated May 13, 2005 for Chinese Application No. 01819710.8 (with English translation).
Office Action dated May 16, 2008 for Norwegian Application No. 20031731 (with English translation).
Office Action dated May 3, 2013 for Canadian Application No. 2661702, 2 pages.
Office Action dated Nov. 13, 2012 for Japanese Application No. P2008-532141 (with English translation).
Office Action dated Nov. 20, 2009 for Chinese Application No. 200580026468.7 (with English translation).
Office Action dated Nov. 26, 2007 for Mexican Application No. PA/a/2005/013764 (with English translation).
Office Action dated Oct. 11, 2007 for Taiwanese Application No. 90125928 (with English translation).
Office Action dated Oct. 15, 2012 for Israeli Application No. 200090 (with English translation).
Office Action dated Oct. 15, 2012 for New Zealand Application No. 598291.
Office Action dated Oct. 4, 2005 for Mexican Application No. PA/a/2003/003362 (with English translation).
Office Action dated Oct. 4, 2007 for Norwegian Application No. 20031731 (with English translation).
Office Action dated Sep. 11, 2009 for Chinese Application No. 200710007097.9 (with English translation).
Office Action dated Sep. 19, 2012 for Canadian Application No. 2627598.
Office Action dated Sep. 28, 2011 for Korean Application No. 10-2007-7001347 (with English translation).
Office Action dated Sep. 28, 2012 for Chinese Application No. 200780017371.9 (with English translation).
Office Action dated Sep. 29, 2012 for Chinese Application No. 200980103218.7 (with English translation).
Office Action dated Sep. 5, 2008 for Norwegian Application No. 20031731 (with English translation).
Office Action dated Sep. 5, 2012 for Chinese Application No. 200880003336.6 (with English translation).
Office Action dated Sep. 5, 2012 for Chinese Application No. 200880115011.7 (with English translation).
Office Action dated Sep. 7, 2007 for Filipino Application No. 1-2003-500266.
Office Action for Canadian Application No. 2,620,594, dated Aug. 15, 2011.
Office Action for Canadian Application No. 2579810 dated Jul. 15, 2011.
Office Action for Canadian Application No. 2652442, dated Apr. 16, 2013 2 pages.
Office Action for Chinese Application No. 01819710.8 dated Feb. 10, 2006 (with English translation).
Office Action for Chinese Application No. 01819710.8, dated Aug. 11, 2006 (with English translation).
Office Action for Chinese Application No. 200580026468.7 dated Jun. 26, 2009 (with English translation).
Office Action for Chinese Application No. 200680020317.5, dated Aug. 3, 2012 (with English translation).
Office Action for Chinese Application No. 200710007096.4 dated Jul. 24, 2009 (with English translation).
Office Action for Chinese Application No. 200710007097.9 dated Apr. 27, 2010 (with English translation).
Office Action for Chinese Application No. 200710007097.9 dated Dec. 25, 2009 (with English translation).
Office Action for Chinese Application No. 200710007097.9 dated Mar. 6, 2009 (with English translation).
Office Action for Chinese Application No. 200780017371.9, dated Mar. 14, 2013 9 pages (with English translation).
Office Action for Chinese Application No. 201080030508.6, dated Apr. 9, 2013, 6 pages (with English translation).
Office Action for EP Application No. 08846814.5, dated Apr. 16, 2013, 5 pages.
Office Action for Filipino Application No. 1-2003-500266 dated Aug. 8, 2003.
Office Action for Filipino Application No. 1-2003-500266 dated Jul. 21, 2006.
Office Action for Filipino Application No. 1-2003-500266 dated Jun. 27, 2007.
Office Action for Filipino Application No. 1-2003-500266 dated Mar. 21, 2007.
Office Action for IL 199907 dated Jun. 17, 2010, 3 pages with English translation.
Office Action for Israeli Application No. 181697 dated Dec. 20, 2010 (with English translation).
Office Action for Israeli Application No. 217197, dated Apr. 11, 2013 4 pages (with English translation).
Office Action for Japanese Application No. 2005-124034 dated Apr. 28, 2009 (with English translation).
Office Action for Japanese Application No. 2005-124034 dated Jan. 27, 2009 (with English translation).
Office Action for Japanese Application No. 2009-123432 dated Jun. 5, 2012 (with English translation).
Office Action for Korean Application No. 10-2003-7005506 dated Jul. 27, 2005 (with English translation).
Office Action for Mexican Application No. PA/a/2003/003362 dated Jun. 7, 2006 (with English translation).
Office Action for Norwegian Application No. 20031731 dated Mar. 7, 2007 (with English translation).
Office Action for U.S. Appl. No. 11/997,719, dated Apr. 8, 2013 55 pages.
Office Action for U.S. Appl. No. 13/624,278, dated Mar. 29, 2013 73 pages.
Office Action in Algerian Patent Application No. 120036, dated Dec. 31, 2017, 2 pages (English Translation).
Office Action in Argentine Patent Application No. P110100513, dated Mar. 11, 2019, 10 pages (with English Translation).

(56) References Cited

OTHER PUBLICATIONS

Office Action in AU Application No. 2006282456, dated Jun. 12, 2009, 1 pages.
Office Action in AU Application No. 2010285740, dated Aug. 22, 2014, 3 pages.
Office Action in Australian Patent Application No. 2012246490, dated Apr. 20, 2016, 3 pages.
Office Action in Australian Patent Application No. 2012246490, dated Feb. 5, 2016, 3 pages.
Office Action in Australian Patent Application No. 2013364953, dated Apr. 19, 2017, 3 pages.
Office Action in Australian Patent Application No. 2013364953, dated Feb. 16, 2017, 3 pages.
Office Action in Australian Patent Application No. 2014371148, dated Mar. 28, 2018, 2 pages.
Office Action in Australian Patent Application No. 2015309862, dated Apr. 2, 2019, 3 pages.
Office Action in BD Application No. 184/2006, dated May 11, 2007, 2 pages.
Office Action in Brazilian Patent Application No. PI0418200-6, dated Apr. 24, 2019, 27 pages (with English Translation.
Office Action in Canadian Application No. 2543859, dated Aug. 19, 2008, 5 pages.
Office Action in Canadian Application No. 2543861, dated Aug. 19, 2008, 4 pages.
Office Action in Canadian Application No. 2605854, dated Jul. 29, 2009, 2 pages.
Office Action in Canadian Application No. 2652442, dated Oct. 4, 2013, 2 pages.
Office Action in Canadian Application No. 2676796, dated Dec. 30, 2013, 5 pages.
Office Action in Canadian Application No. 2676796, dated Jan. 29, 2015, 5 pages.
Office Action in Canadian Application No. 2704000, dated Nov. 4, 2014, 3 pages.
Office Action in Canadian Application No. 2713930, dated Jan. 30, 2015, 5 pages.
Office Action in Canadian Application No. 2771403, dated Jul. 16, 2014, 3 pages.
Office Action in Canadian Patent Application No. 2704000, dated Mar. 27, 2015, 3 pages.
Office Action in Canadian Patent Application No. 2713930, dated Mar. 7, 2016, 5 pages.
Office Action in Chilean Patent Applciation No. 2012-00412, dated Jan. 23, 2017, 4 pages (English Translation).
Office Action in Chilean Patent Application No. 2012-00412, dated Jan. 28, 2015, 17 pages, with English translation.
Office Action in Chilean Patent Application No. 201601419, dated Feb. 13, 2018, 18 pages (English Translation).
Office Action in Chinese Application No. 200680020317.5, dated Mar. 4, 2014, 13 pages.
Office Action in Chinese Application No. 200680020317.5, dated Nov. 28, 2013, 8 pages (with English translation).
Office Action in Chinese Application No. 200680021939.X, dated Mar. 30, 2011, 7 pages (with English translation).
Office Action in Chinese Application No. 200680021939.X, dated May 27, 2010, 9 pages (with English translation).
Office Action in Chinese Application No. 200680021939.X, dated Sep. 2, 2010, 10 pages (with English translation).
Office Action in Chinese Application No. 200780017371.9, dated Dec. 11, 2014, 9 pages (with English translation).
Office Action in Chinese Application No. 200780017371.9, dated May 15, 2015, 17 pages (with English translation).
Office Action in Chinese Application No. 200780019200.X, dated Apr. 6, 2012, 9 pages (with English translation).
Office Action in Chinese Application No. 200780019520.5, dated Dec. 21, 2010, 7 pages (with English translation).
Office Action in Chinese Application No. 200780019520.5, dated Sep. 27, 2010, 8 pages (with English translation).
Office Action in Chinese Application No. 2008800045113, dated Jul. 5, 2011, 10 pages (with English translation).
Office Action in Chinese Application No. 201180030568.2, dated Mar. 24, 2014, 8 pages (with English translation).
Office Action in Chinese Application No. 201180030568.2, dated Oct. 12, 2013, 11 pages (with English translation.
Office Action in Chinese Application No. 201280010898.X, dated Aug. 11, 2014, 14 pages (with English translation).
Office Action in Chinese Patent Application No. 201380054667.3 dated Aug. 9, 2017, 11 pages (English Translation).
Office Action in Chinese Patent Application No. 201380054667.3, dated Feb. 14, 2017, 9 pages (English Translation.
Office Action in Chinese Patent Application No. 201380054667.3, dated Jul. 18, 2016, 18 pages (English Translation).
Office Action in Chinese Patent Application No. 201480026871.9, dated Feb. 21, 2017, 10 pages (English Translation).
Office Action in Chinese Patent Application No. 201480067017.7, dated Mar. 1, 2017, 11 pages (English Translation).
Office Action in Chinese Patent Application No. 201510031628.2, dated Apr. 5, 2017, 8 pages (English Translation).
Office Action in Chinese Patent Application No. 201510031628.2, dated Dec. 12, 2017, 11 pages (English Translation).
Office Action in Chinese Patent Application No. 201510031628.2, dated Jul. 19, 2018, 11 pages (English Translation).
Office Action in Chinese Patent Application No. 201510031628.2, dated Jun. 2, 2016, 11 pages (English Translation).
Office Action in Chinese Patent Application No. 201580042365.3, dated Mar. 5, 2019, 21 pages (with English Translation).
Office Action in Chinese Patent Application No. 201680022734.2, dated Oct. 22, 2018, 12 pages (English Translation).
Office Action in Chinese Patent Application No. 201680030060.5, dated Jan. 30, 2019, 15 pages (with English Translation).
Office Action in CL Application No. 2012-00412, dated Sep. 3, 2014, 22 pages (with English translation).
Office Action in CO Application No. 12-022608, dated Dec. 17, 2013, 12 pages (with English translation).
Office Action in Colombian Patent Application No. 16147681, dated Jun. 27, 2018, 16 pages (English Translation).
Office Action in DB Application No. 60/2005, dated Jul. 25, 2006, 2 pages.
Office Action in Egyptian Patent Application No. PCT 283/2012, dated Feb. 19, 2018, 10 pages (English Translation).
Office Action in Egyptian Patent Application No. PCT 283/2012, dated Apr. 28, 2019, 9 pages (with English Translation).
Office Action in European Application No. 03791389.4, dated Dec. 2, 2014, 5 pages.
Office Action in European Application No. 03791389.4, dated Jun. 10, 2014, 4 pages.
Office Action in European Application No. 04807580.8, dated Mar. 18, 2014, 12 pages.
Office Action in European Application No. 05719973.9, dated Feb. 11, 2011, 7 pages.
Office Action in European Application No. 05719973.9, dated Nov. 2, 2011, 4 pages.
Office Action in European Application No. 07743994.1, dated Sep. 9, 2014, 8 pages.
Office Action in European Application No. 07793075.8, dated Mar. 1, 2011, 3 pages.
Office Action in European Application No. 08704376.6, dated Feb. 24, 2014, 4 pages.
Office Action in European Application No. 08846814.5, dated Jun. 4, 2014, 4 pages.
Office Action in European Application No. 10809938.3, dated Feb. 10, 2015, 4 pages.
Office Action in European Application No. 10809938.3, dated Oct. 16, 2014, 5 pages.
Office Action in European Patent Application No. 07743994.1, dated Apr. 18, 2017, 5 pages.
Office Action in European Patent Application No. 07743994.1, dated Mar. 8, 2017, 5 pages.
Office Action in European Patent Application No. 08846814.5, dated Apr. 29, 2016, 28 pages.

(56) References Cited

OTHER PUBLICATIONS

Office Action in European Patent Application No. 08846814.5, dated Sep. 13, 2017, 19 pages.
Office Action in European Patent Application No. 08846814.5, dated Sep. 28, 2016, 14 pages.
Office Action in European Patent Application No. 09705712.9, dated Apr. 11, 2018, 5 pages.
Office Action in European Patent Application No. 12774278.1, dated Mar. 9, 2015, 6 pages.
Office Action in European Patent Application No. 12793322.4, dated May 19, 2017, 4 pages.
Office Action in European Patent Application No. 13865671.5, dated Mar. 7, 2017, 4 pages.
Office Action in European Patent Application No. 14727633.1, dated Oct. 13, 2016, 4 pages.
Office Action in European Patent Application No. 15836577.5, dated Mar. 23, 2018, 9 pages.
Office Action in Gulf Cooperation Council Patent Application No. GC2011-17812, dated Aug. 2, 2018, 8 pages (English Translation).
Office Action in Gulf Cooperation Council Patent Application No. GC2015-29939, dated Feb. 22, 2018, 16 pages (English Translation).
Office Action in Gulf Cooperation Council Patent Application No. GC2014-28624, dated Jan. 7, 2018, 7 pages (English Translation).
Office Action in ID App. Ser No. W-00 2008 00601, dated Jan. 13, 2012, 4 pages (with English translation).
Office Action in Indian Application No. 1424/CHENP/2008, dated Sep. 19, 2011, 18 pages.
Office Action in Indian Application No. 1571/CHENP/2007, dated Oct. 23, 2013, 2 pages.
Office Action in Indian Application No. 1571/CHENP/2007, dated Dec. 9, 2013, 2 pages.
Office Action in Indian Application No. 1908/DELNP/2008, dated Feb. 2, 2012.
Office Action in Indian Patent Application No. 10502/CHENP/2012, dated Dec. 29, 2017, 5 pages (English Translation).
Office Action in Indian Patent Application No. 10502/CHENP/2012, dated Apr. 16, 2019, 2 pages (with English Translation).
Office Action in Indian Patent Application No. 1511/CHENP/2009, dated Feb. 27, 2017, 7 pages (English Translation).
Office Action in Indian Patent Application No. 2371/CHENP/2012, dated Jul. 27, 2017, 5 pages (English Translation).
Office Action in Indian Patent Application No. 2371/CHENP/2012, dated Jun. 18, 2018, 3 pages (English Translation).
Office Action in Indian Patent Application No. 2371/CHENP/2012, dated Oct. 29, 2018, 1 page (English Translation).
Office Action in Indian Patent Application No. 2371/CHENP/2012, dated Sep. 17, 2018, 3 pages (English Translation).
Office Action in Indian Patent Application No. 2793/CHENP/2013, dated Feb. 28, 2018, 2 pages (English Translation).
Office Action in Indian Patent Application No. 2793/CHENP/2013, dated Sep. 13, 2017, 12 pages (English Translation).
Office Action in Indian Patent Application No. 3334/CHENP/2010, dated Feb. 6, 2017, 13 pages (English Translation).
Office Action in Indian Patent Application No. 5022/CHENP/2009, dated Jun. 28, 2016, 7 pages.
Office Action in Indian Patent Application No. 5022/CHENP/2009, dated Jun. 29, 2017, 3 pages (English Translation).
Office Action in Indian Patent Application No. 5287/CHENP/2010, dated Mar. 15, 2017, 8 pages (English Translation).
Office Action in Indian Patent Application No. 5287/CHENP/2010, dated Mar. 22, 2018, 2 pages (English Translation).
Office Action in Indian Patent Application No. 6415/CHENP/2008, dated Jan. 19, 2017, 5 pages (English Translation).
Office Action in Indian Patent Application No. 7026/CHENP/2013, dated Mar. 8, 2018, 7 pages (English Translation).
Office Action in Indian Patent Application No. 7026/CHENP/2013, dated Feb. 5, 2019, 4 pages (English Translation).
Office Action in Indonesian Patent Application No. W-00201201031, dated Mar. 14, 2016, 4 pages (English translation).
Office Action in Israeli Application No. 175363, dated Jan. 2, 2013, 2 pages, with English translation.
Office Action in Israeli Application No. 188670, dated Jul. 3, 2011, 2 pages (with English translation).
Office Action in Israeli Application No. 197002, dated Feb. 8, 2012, 2 pages (with English translation).
Office Action in Israeli Application No. 197141, dated Feb. 22, 2012, 18 pages (with English translation).
Office Action in Israeli Application No. 200090, dated Jul. 24, 2013, 5 pages (with English translation).
Office Action in Israeli Application No. 205512, dated Dec. 20, 2012, 8 pages, with English translation.
Office Action in Israeli Application No. 205512, dated Oct. 28, 2013, 5 pages (with English translation).
Office Action in Israeli Application No. 205512, dated Sep. 22, 2014, 5 pages (with English translation).
Office Action in Israeli Application No. 207089, dated Jan. 6, 2013, 5 pages (with English translation).
Office Action in Israeli Application No. 207089, dated Nov. 25, 2013, 6 pages (with English translation).
Office Action in Israeli Application No. 217197, dated Oct. 22, 2014, 4 pages (with English translation).
Office Action in Israeli Application No. 255564, dated Aug. 15, 2018, 5 pages (English Translation).
Office Action in Israeli Patent Application No. 227558, dated Mar. 13, 2016, 5 pages (English Translation).
Office Action in Israeli Patent Application No. 238463, dated Feb. 1, 2018, 6 pages (English Translation).
Office Action in Israeli Patent Application No. 242519, dated Aug. 9, 2017, 7 pages (English Translation).
Office Action in Israeli Patent Application No. 245961, dated Jul. 20, 2016, 5 pages (English Translation).
Office Action in Israeli Patent Application No. 250454, dated Feb. 11, 2018, 4 pages (English Translation).
Office Action in Israeli Patent Application No. 253946, dated Oct. 17, 2018, 5 pages (with English Translation).
Office Action in Israeli Patent Application No. 255564, dated Apr. 11, 2019, 7 pages (with English Translation).
Office Action in Israeli Patent Application No. 257292, dated Jan. 8, 2019, 5 pages (with English Translation).
Office Action in Israeli Patent Application No. 257433, dated Jan. 8, 2019, 5 pages (with English Translation).
Office Action in Japanese Application No. 2008-530917, dated Oct. 23, 2012, 4 pages (with English translation).
Office Action in Japanese Application No. 2008-556208, dated Jan. 22, 2013, 8 pages, with English translation.
Office Action in Japanese Application No. P2005-516605 dated Jun. 1, 2010, 3 pages.
Office Action in Japanese Application No. P2008-532141, dated May 21, 2013, 4 pages (with English translation).
Office Action in Japanese Application No. P2009-510543, dated Sep. 29, 2009, 7 pages (with English translation).
Office Action in Japanese Application No. P2009-540099, dated Mar. 25, 2014, 6 pages (with English translation).
Office Action in Japanese Application No. P2009-551518, dated Jun. 18, 2013, 5 pages (with English translation).
Office Action in Japanese Application No. P2014-553200, dated Jun. 6, 2017, 6 pages (with English tranlsation).
Office Action in Japanese Patent Application No. P2014-513691, dated Jun. 21, 2016, 4 pages, (English Translation).
Office Action in Japanese Patent Application No. P2014-513691, dated Mar. 8, 2016, 6 pages (English Translation).
Office Action in Japanese Patent Application No. P2015-555882, dated Mar. 27, 2018, 4 pages (English Translation).
Office Action in Japanese Patent Application No. P2016-214593, dated Oct. 17, 2017, 9 pages (English Translation).
Office Action in Japanese Patent Application No. P2016-572771, dated Feb. 7, 2017, 6 pages (English Translation).
Office Action in Jordan Patent Application No. 55/2011, dated Feb. 16, 2017, 2 pages (English Translation).
Office Action in JP2007-542863 dated May 29, 2012, 8 pages with English translation.

(56) References Cited

OTHER PUBLICATIONS

Office Action in Korean Application No. 10-2006-7013907, dated Jul. 28, 2007, 7 pages (with English translation).
Office Action in Korean Application No. 10-2006-7013940, dated Jul. 31, 2007, 19 pages (with English translation).
Office Action in Korean Application No. 10-2007-7026886, dated Aug. 27, 2009, 5 pages (with English translation).
Office Action in Korean Application No. 10-2008-7013685, dated May 20, 2013, 10 pages (with English translation).
Office Action in Korean Application No. 10-2008-7027527, dated Dec. 9, 2013, 6 pages (with English translation).
Office Action in Korean Application No. 10-2008-7029472, dated Mar. 28, 2014, 6 pages (with English translation).
Office Action in Korean Application No. 10-2008-7029577, dated Dec. 30, 2013, 7 pages (with English translation).
Office Action in Korean Application No. 10-2009-7005657, dated Mar. 28, 2014, 6 pages (with English translation).
Office Action in Korean Application No. 10-2009-7013723, dated May 19, 2011, 10 pages (with English translation).
Office Action in Korean Application No. 10-2009-7017694, dated Jan. 29, 2014, 26 pages (with English translation).
Office Action in Korean Application No. 10-2010-7011023, dated Sep. 3, 2014, 14 pages (with English translation).
Office Action in Korean Application No. 10-2010-7018835, dated Sep. 30, 2014, 6 pages (with English translation).
Office Action in Korean Application No. 10-2012-7003846, dated Oct. 7, 2014, 7 pages.
Office Action in Korean Patent Application No. 10-2013-7020616, dated Dec. 19, 2016, 12 pages (English Translation).
Office Action in Mexican Application No. MX/a/2010/008187, dated Apr. 28, 2014, 4 pages (with English translation).
Office Action in Mexican Application No. MX/a/2010/008187, dated Dec. 5, 2013, 8 pages (with English translation).
Office Action in Mexican Application No. MX/a/2012/002011, dated Apr. 28, 2014, 10 pages (with English translation).
Office Action in Mexican Application No. MX/a/2012/002011, dated Nov. 21, 2013, 8 pages (with English translation).
Office Action in Mexican Application No. MX/a/2012/014776, dated Apr. 4, 2014, 22 pages (with English Translation).
Office Action in Mexican Application No. MX/a/2012/014776, dated Oct. 15, 2014, 15 pages (with English translation).
Office Action in Mexican Application No. MX/a/2013/009931, dated Sep. 5, 2014, 15 pages (with English translation).
Office Action in Mexican Patent Application No. MX/a/2014/010594, dated Aug. 17, 2016, 10 pages (English Translation).
Office Action in Mexican Patent Application No. MX/a/2015/015605, dated Apr. 15, 2019, 8 pages (with English Translation).
Office Action in New Zealand Patent Application No. 714049, dated May 21, 2019, 3 pages.
Office Action in Norwegian Patent Office Application No. 20063383, dated Mar. 15, 2016, 6 pages (English Translation) [citation change Dec. 1, 2017].
Office Action in NZ Application No. 566793, dated Dec. 4, 2009, 1 page.
Office Action in Pakistan Patent Application No. 548/2015, dated Oct. 18, 2017, 2 pages (English Abstract).
Office Action in Pakistani Patent Application No. 907/2014, dated Aug. 11, 2016, 2 pages.
Office Action in Peruvian Patent Application No. 2081-2011, dated Jul. 15, 2016, 12 pages (English Translation).
Office Action in PH Application No. 1-2007-502319, dated Dec. 16, 2011, 1 page.
Office Action in PH Application No. 1-2011-502441 dated Oct. 1, 2013, 1 page.
Office Action in PH Application No. 1-2011-502441, dated Feb. 19, 2014, 2 pages.
Office Action in PK Application No. 1024/2006, dated Dec. 12, 2007, 3 pages.
Office Action in PK Application No. 1024/2006, dated Feb. 24, 2009, 2 pages.
Office Action in PK Application No. 1024/2006, dated Oct. 21, 2008, 2 pages.
Office Action in PK Application No. 155/2005, dated Nov. 17, 2007, 2 pages.
Office Action in PK Application No. 375/2008, dated Feb. 24, 2009, 1 page.
Office Action in PK Application No. 375/2008, dated Jul. 20, 2009, 2 pages.
Office Action in PK Application No. 375/2008, dated Oct. 21, 2008, 3 pages.
Office Action in Russian Application No. 2006134254, dated Oct. 13, 2006, 4 pages (with English translation).
Office Action in Russian Application No. 2006134254, dated Sep. 18, 2007, 9 pages (with English translation).
Office Action in Russian Application No. 2008110932, dated Dec. 3, 2008, 6 pages (with English translation).
Office Action in Russian Application No. 2012103471, dated May 20, 2014, 5 pages (with English translation).
Office Action in Russian Application No. 2012103471, dated Sep. 16, 2014, 5 pages (with English translation).
Office Action in Russian Application No. 2013139556, dated Dec. 2, 2013, 6 pages (with English translation).
Office Action in Russian Patent Application No. 2015115397, dated Oct. 26, 2017, 16 pages (English Translation).
Office Action in Russian Patent Application No. 2015148193, dated Dec. 25, 2017, 13 pages (English Translation).
Office Action in Russian Patent Application No. 2015148193, dated Jan. 27, 2016, 4 pages, (English Translation).
Office Action in Russian Patent Application No. 2015148193, dated May 10, 2016, 3 pages (English Translation).
Office Action in Russian Patent Application No. 2016122867, dated Jun. 18, 2018, 13 pages (English Translation).
Office Action in Russian Patent Application No. 2017104496, dated Mar. 26, 2019, 15 pages (with English Translation).
Office Action in Russian Patent Application No. 2017128583, dated Feb. 28, 2019, 30 pages (with English Translation).
Office Action in Singaporean Patent Application No. 11201706630U, dated Apr. 30, 2018, 8 pages (English Translation).
Office Action in Taiwanese Application No. 095130665, dated Mar. 2, 2012, 8 pages (with English translation).
Office Action in Taiwanese Application No. 100104281, dated Dec. 9, 2014, 13 pages (with English translation).
Office Action in Taiwanese Patent Application No. 103144928, dated Jun. 7, 2018, 7 pages (English Translation).
Office Action in Taiwanese Patent Application No. 103144928, dated Nov. 13, 2018, 6 pages (English Translation).
Office Action in Taiwanese Patent Application No. 104127982, dated Apr. 30, 2019, 12 pages (with English Translation).
Office Action in U.S. Appl. No. 11/065,631, dated Feb. 28, 2008, 12 pages.
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 11/662,425, dated Feb. 27, 2014, 152 pages.
Office Action in U.S. Appl. No. 11/662,425, dated Jun. 5, 2014, 30 pages.
Office Action in U.S. Appl. No. 11/662,425, dated Sep. 17, 2014, 3 pages.
Office Action in U.S. Appl. No. 11/997,543, dated Mar. 11, 2014, 20 pages.
Office Action in U.S. Appl. No. 12/031,568, dated Aug. 13, 2010, 15 pages.
Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/039,381, dated Jan. 9, 2014, 16 pages.
Office Action in U.S. Appl. No. 12/039,381, dated May 29, 2014, 78 pages.

(56) References Cited

OTHER PUBLICATIONS

Office Action in U.S. Appl. No. 12/039,381, dated Sep. 12, 2013, 15 pages.
Office Action in U.S. Appl. No. 12/315,291, dated Jan. 12, 2011, 9 pages.
Office Action in U.S. Appl. No. 12/315,291, dated Jun. 7, 2010, 20 pages.
Office Action in U.S. Appl. No. 12/439,339, dated May 23, 2013, 15 pages.
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/864,817, dated Aug. 15, 2014, 79 pages.
Office Action in U.S. Appl. No. 12/867,646, dated Oct. 26, 2011, 37 pages.
Office Action in U.S. Appl. No. 13/083,338, dated Jan. 3, 2013, 9 pages.
Office Action in U.S. Appl. No. 13/238,085, dated Nov. 12, 2013, 74 pages.
Office Action in U.S. Appl. No. 13/238,085, dated Sep. 6, 2013, 10 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/805,826, dated Sep. 23, 2014, 25 pages.
Office Action in U.S. Appl. No. 13/870,507, dated Dec. 12, 2014, 10 pages.
Office Action in U.S. Appl. No. 13/923,858, dated Apr. 18, 2014, 64 pages.
Office Action in U.S. Appl. No. 13/923,858, dated Dec. 5, 2014, 67 pages.
Office Action in U.S. Appl. No. 13/983,891, dated Jan. 22, 2014, 11 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Office Action in U.S. Appl. No. 14/862,349, dated Mar. 10, 2016, 11 pages.
Office Action in U.S. Appl. No. 13/870,507, dated Feb. 17, 2016, 28 pages.
Office Action in U.S. Appl. No. 13/923,858, dated Feb. 22, 2018, 16 pages.
Office Action in U.S. Appl. No. 13/923,858, dated May 4, 2017, 31 pages.
Office Action in U.S. Appl. No. 13/923,858, dated May 16, 2019, 13 pages.
Office Action in U.S. Appl. No. 13/923,858, dated Oct. 4, 2018, 16 pages.
Office Action in U.S. Appl. No. 14/117,276, dated May 20, 2016, 11 pages.
Office Action in U.S. Appl. No. 14/122,339, dated Aug. 10, 2017, 10 pages.
Office Action in U.S. Appl. No. 14/122,339, dated Jan. 2, 2018, 3 pages.
Office Action in U.S. Appl. No. 14/122,339, dated Jul. 8, 2016, 12 pages.
Office Action in U.S. Appl. No. 15/460,629, dated Feb. 6, 2019, 27 pages.
Office Action in U.S. Appl. No. 15/460,629, dated Sep. 28, 2018, 10 pages.
Office Action in U.S. Appl. No. 15/503,108, dated Nov. 14, 2017, 12 pages.
Office Action in U.S. Appl. No. 15/550,124, dated May 3, 2018, 124 pages.
Office Action in U.S. Appl. No. 15/554,577, dated Jan. 3, 2019, 26 pages.
Office Action in U.S. Appl. No. 15/573,197, dated Apr. 8, 2019, 133 pages.
Office Action in U.S. Appl. No. 15/748,980, dated Jan. 2, 2019, 9 pages.
Office Action in U.S. Appl. No. 15/750,712, dated Jan. 11, 2019, 7 pages.
Office Action in U.S. Appl. No. 16/038,710, dated May 2, 2019, 21 pages.
Office Action in U.S. Appl. No. 16/038,710, dated Nov. 20, 2018, 124 pages.
Office Action in U.S. Appl. No. 16/229,805, dated Mar. 29, 2019, 120 pages.
Office Action in Vietnamese Patent Application No. 1-2016-02104, dated Apr. 26, 2018, 4 pages (English Translation).
Office Action in VN Application No. 1-2011-03484, dated Dec. 31, 2013, 2 pages (with English translation).
Office Action in Yemen Patent Application No. 592/2011, dated Jan. 16, 2017, 2 pages (English Translation).
Office Action Israel Application No. 207089 dated Nov. 13, 2011, 4 pages (with English translation).
Office Action issued for CN 200880002425.9 dated Mar. 2, 2011, 10 pages with English translation.
Office Action issued for EP 06768437.3 (EPO Form1224) dated Oct. 28, 2010, 47 pages.
Office Action issued for European Search Report for European Application No. 06782407 dated Sep. 29, 2011, 6 pages.
Office Action issued for Japanese Application No. 2007-529565 dated Dec. 13, 2011, 7 pages with English full translation.
Office Action issued for JP Appl. No. 2007-529565 dated May 8, 2012, 6 pages with English translation.
Office Action issued in MX Application No. MX/a/2012/002011, dated Jul. 17, 2013, 6 pages (with English translation).
Office Action dated Jan. 7, 2011, in U.S. Appl. No. 12/092,539.
Office Communication dated Sep. 13, 2004 for U.S. Appl. No. 10/420,466.
Office Letter Confirmation of Amendment After Allowance dated Jan. 11, 2011 for CA Application No. 2426461.
Office Letter re Notice of Allowance dated May 25, 2012 for ZA Application No. 201108697.
Official Letter and Notice of Allowance for AU Application No. 2008211952, dated Jul. 10, 2012.
Official Letter and Notice of Allowance for AU Application No. 2008325608, dated Feb. 27, 2013, 7 pages.
Official Letter in AU Application No. 2006282456, dated May 15, 2012, 1 page.
Official Letter in AU Application No. 2006282456, dated Sep. 24, 2012, 259 pages.
Official Letter in BD Application No. 184/2006, dated Feb. 2, 2012, 1 page.
Official Letter re Deficiencies in sequence listing in EP Application No. 06796594.7, dated Mar. 10, 2008, 3 pages.
Official Letter re Grant of Request for Correction of Specification for SG Application No. 201108602-2, dated Aug. 8, 2012.
Official Letter re Granting Patent in EP Application No. 06796594.7, dated Sep. 25, 2012, 270 pages.
Official Letter re Intention to Grant Patent in EP Application No. 05719973.9, dated Feb. 6, 2012, 553 pages.
Official Letter re invitation to declare maintenance in EP Application No. 06796594.7, dated Sep. 26, 2011, 1 page.
Official Letter re invitation to declare maintenance in EP Application No. 07793075.8, dated Sep. 27, 2010, 1 page.
Official Letter re invitation to declare maintenance in EP Application No. 07805959.9, dated Dec. 3, 2010, 1 page.
Official Notification in Australian Patent Application No. 2005283422, dated Jul. 14, 2016, 8 pages.
Official Notification in Australian Patent Application No. 2005283422, dated Oct. 20, 2016, 1 page.

(56) References Cited

OTHER PUBLICATIONS

Official Notification in Brazilian Patent Application No. BR112012003592-4, dated Apr. 15, 2019, 6 pages (with English Translation).
Official Notification in CA Application No. 2771403, dated Dec. 16, 2014, 1 page.
Official Notification in Chilean Patent Application No. 201601419, dated Sep. 21, 2018, 17 pages (English Translation).
Official Notification in EP Application No. 04807580.8, dated Jun. 16, 2014, 1 pages.
Official Notification in EP Application No. 04807580.8, dated Jun. 27, 2014, 17 pages.
Official Notification in European Patent Application No. 07743994.1, dated Jul. 22, 2016, 18 pages.
Official Notification in European Patent Application No. 14727633.1, dated Jun. 21, 2018, 2 pages.
Official Notification in Gulf Cooperation Council Patent Application No. GC2014-28624, dated Apr. 5, 2018, 298 pages (English Translation).
Official Notification in Indian Patent Application No. 10502/CHENP/2012, dated Apr. 26, 2019, 2 pages (with English Translation).
Official Notification in Indian Patent Application No. 1511/CHENP/2009, dated Nov. 26, 2018, 173 pages.
Official Notification in Indian Patent Application No. 1511/CHENP/2009, dated Oct. 13, 2017, 105 pages.
Official Notification in Indian Patent Application No. 201747004829, dated Mar. 20, 2018, 87 pages (English Translation).
Official Notification in Indian Patent Application No. 201747028834, dated Jan. 9, 2018, 63 pages.
Official Notification in Indian Patent Application No. 2371/CHENP/2012, dated Jan. 25, 2018, 3 pages (English Translation).
Official Notification in Indian Patent Application No. 5287/CHENP/2010, dated Apr. 6, 2018, 2 pages (English Translation).
Official Notification in Indian Patent Application No. 6415/CHENP/2008, dated Apr. 28, 2017, 5 pages (English Translation).
Official Notification in Israeli Patent Application No. 223695, dated May 29, 2017, 1 page (English Translation).
Official Notification in Israeli Patent Application No. 253946, dated Feb. 10, 2019, 3 pages (with English Translation).
Official Notification in Jordan Patent Application No. 55/2011, dated Feb. 12, 2018, 2 pages (English Translation).
Official Notification in U.S. Appl. No. 13/923,858, dated Jul. 23, 2018, 15 pages.
Official Notification re Decision on Petition in U.S. Appl. No. 11/997,719, dated Sep. 23, 2014, 1 page.
Official Notification re Interview Summary in U.S. Appl. No. 14/002,018, dated Oct. 6, 2014, 2 pages.
Ohe et al, "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," Annals of Oncology 18(2):317-323, Nov. 1, 2006.
Okayama et al., "Activation of Eosinophils with Cytokines Produced by Lung Mast Cells," Int Arch Allergy Immunol., 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," Eur. J. Immunol., 28:708-715 (1998).
Okura et al., "Effects of monoclonal anti-c-kit antibody (ACK2) on melanocytes in newborn mice," J. Invest. Dermatol., 105(3):322-328 (1995).
Okusaka et al., "Chemotherapy for biliary tract cancer", biliary tract, 2013 vol. 27 No. 1, p. 124-p. 134 (Machine Translation).
Olaso et al., "DDR2 receptor promotes MMP-2-mediated proliferation and invasion by hepatic stellate cells," J. Clin. Invest., 108(9):1369-1378 (2001).
O'Reilly et al., "Hydrolysis of tert-Butyl Methyl Ether (MTBE) in Dilute Aqueous Acid," Environ. Sci. Technol., 2001, 35:3954-3961.

Ozawa et al., "E7386, an orally active CBP/beta-catenin modulator, effects tumor microenvironment, resulting to the enhancement of antitumor activity of lenvatinib," Eisai, 2017, 1 page.
Ozols et al., "Phase III trial of carboplatin and paclitaxel compared with cisplatin and paclitaxel in patients with optimally resected stage III ovarian cancer: a Gynecologic Oncology Group study," J. Clin. Oncol., 21(17):3194-3200 (2003).
Pacini, "38th Annual Meeting of the European Thyroid Association", European Thyroid Association, Santiago de Compostela, Spain, Aug. 15, 2014, p. 73-p. 226.
Pakistani Office Action for Application No. 94/2011, dated May 9, 2012.
Pal et al., "A Phase 2 Trial of Lenvatinib 18 mg vs 14 mg Once Daily (QD) in Combination With Everolimus (5 mg QD) in Renal Cell Carcinoma", A poster presentation at 16th International Kidney Cancer Symposium, Miami, FL, USA, Nov. 3-4, 2017, 1 page.
Pandey et al., "Identification of Orally Active, Potent, and Selective 4-Piperazinylquinazolines as Antagonists of the Platelet-Derived Growth Factor Receptor Tyrosine Kinase Family", *Journal of Medicinal Chemistry.*, 45, 3772-3793, 2002.
Papai et al., "The efficacy of a combination of etoposide, ifosfamide, and cisplatin in the treatment of patients with soft tissue sarcoma", Cancer, Jul. 2000, vol. 89, No. 1, p. 177-p. 180.
Park et al., "Serum Angiopoietin-2 as a Clinical Marker for Lung Cancer," Chest 132(1):200-206, Jul. 2007.
Partial European Search Report for Application No. 01976786.2, dated Apr. 6, 2004.
Patel et al., "The effect of excipients on the stability of levothyroxine sodium pentahydrate tablets," Int'l J Pharm., 2003, 264:35-43.
Paterson et al., "Preclinical studies of fibroblast growth factor receptor 3 as a therapeutic target in multiple myeloma," British Journal of Haematology, 124:595-603 (2004).
Paulus, "Preparation and Biomedical Applications of Bispecific Antibodies", Behring Inst. Mitt. 78: 118-132 (1985).
Payment of Final Fee and Amendment after Allowance in CA Application No. 2771403, dated Nov. 24, 2014, 3 pages.
Paz et al., "Development of angiogenesis inhibitors to vascular endothelial growth factor receptor 2. Current status and future perspective," Frontiers in Bioscience, 10:1415-1439 (May 1, 2005).
Pearson, "Rapid and Sensitive Sequence Comparison with FASTP and FASTA", Methods in Enzymology 183 :63-98 (1990).
Peruvian Office Action in Application No. 2081-2011, dated Mar. 23, 2016, 12 pages, with English translation.
Petition in JP Application No. 2007-532099, dated Dec. 25, 2007, 3 pages (with English translation).
Petition in JP Application No. 2007-532099, dated Sep. 25, 2007, 3 pages (with English translation).
Petition in JP Application No. 2009-554285, dated Aug. 19, 2010, 3 pages (with English translation).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Pilaniya et al., "Recent trends in the impurity profile of pharmaceuticals", J Adv Pharm Technol Res.; 1(3): 302-310, Jul.-Sep. 2010.
Pisters et al, "Induction chemotherapy before surgery for early-stage lung cancer: A novel approach," J Thoracic Cardiovasc Surg 119(3):429-439, Mar. 2000.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood.,103, 3474-3479, 2004.
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011.
Preliminary Amendment and Response to Restriction Requirement in U.S. Appl. No. 13/083,338, filed Apr. 30, 2012.

(56) References Cited

OTHER PUBLICATIONS

Preliminary Amendment dated Apr. 26, 2013 for U.S. Appl. No. 13/870,507, 10 pages.
Preliminary Amendment filed in EP Application No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Preliminary Amendment filed on Apr. 18, 2003 for U.S. Appl. No. 10/420,466.
Preliminary Amendment filed on Dec. 2, 2005 for U.S. Appl. No. 10/420,466.
Preliminary Amendment filed on Feb. 3, 2006 for U.S. Appl. No. 11/293,785.
Preliminary Amendment filed on May 23, 2003 for KR Application No. 10-2003-7005506 (with English translation).
Preliminary Amendment filed on Oct. 27, 2003 for U.S. Appl. No. 10/420,517.
Preliminary Amendment for U.S. Appl. No. 13/624,278, filed Sep. 21, 2012, 7 pages.
Preliminary Amendment in U.S. Appl. No. 10/577,043, dated Apr. 24, 2006, 12 pages.
Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.
Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.
Pritzker, "Cancer Biomarkers: Easier Said Than Done," Clinical Chemistry, 48(8):1147-1150 (2002).
Ramsden, "Angiogenesis in the thyroid gland," Journal of endocrinology, Apr. 11, 2000, 475-480.
Reasons for Reexamination dated Sep. 11, 2012 for CN Application No. 200680020317.5 (with English translation).
Reexamination filed on May 25, 2004 for TW Application No. 90125928 (with English translation).
Reexamination filed on Nov. 25, 2004 for TW Application No. 90125928 (with English translation).
Registered dated Feb. 24, 2009 for PH Application No. 1-2003-500266.
Registry's Letter in MT Application No. 3723, dated Sep. 29, 2007, 1 page.
Rejection dated Apr. 26, 2004 for TW Application No. 90125928 (with English translation).
Remington, "The Science and Practice of Pharmacy," Remington, 20th Edition, 2000, pp. 1123-1124.
Ren "Advances in Medical Therapy of Melanoma," J of Practical Oncology, 25(2):137-140, Dec. 31, 2010.
Reply to communication from the Examining Division for EP App. Ser. 06023078.6, dated Feb. 4, 2008.
Reply to communication from the Examining Division for EP App. Ser. 06023078.6, dated Sep. 11, 2007.
Reply to communication from the Examining Division for EP Application No. 01976786.2, dated Jan. 25, 2006.
Reply to communication from the Examining Division for EP Application No. 01976786.2, dated Jul. 19, 2006.
Reply to communication from the Examining Division for EP Application No. 04025700.8, dated Feb. 15, 2007.
Reply to communication from the Examining Division for EP Application No. 04025700.8, dated Jan. 26, 2007.
Reply to communication from the Examining Division for EP Application No. 04025700.8, dated Sep. 12, 2006.
Reply to Examination Report dated Feb. 8, 2013 for EP Application No. 07743994.1, 4 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Notice of Allowance in U.S. Appl. No. 11/662,425, dated Jan. 20, 2015, 5 pages.
Reply to Notice of Non-Compliant Amendment in U.S. App. No. 12/315,291, dated Nov. 12, 2010, 3 pages.
Reply to official communication for EP Application No. 05783232.1, dated Apr. 30, 2008.
Reply to the invitation to remedy deficiencies for EP Application No. 06023078.6, dated Jan. 11, 2007.
Request for accelerated examination in KR Application No. 10-2012-7003846, dated Jun. 18, 2014, 29 pages (with English translation).
Request for amendment of the text intended for grant and translation of claims for EP Application No. 04025700.8, dated Feb. 1, 2008.
Request for amendment of the text intended for grant and translation of claims for EP Application No. 06023078.6, dated Nov. 5, 2008.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Request for Continued Examination (RCE) transmittal for U.S. Appl. No. 12/864,817, filed Dec. 22, 2011.
Request for correction of errors in filed documents for EP Application No. 06023078.6, dated Feb. 13, 2007.
Request for Examination in CA Application No. 2713930, dated Oct. 21, 2013, 8 pages.
Request for Re-Examination in CN ApplicationA1452:A1470780017371.9, dated Oct. 11, 2013, 9 pages (with English translation).
Request for Substantive Examination for ID Application No. W-00201201031, filed Jun. 3, 2013, 6 pages (with English translation).
Request for Substantive Examination for UA Application No. a201203132, filed Apr. 15, 2013, 14 pages (with English translation).
Request for Voluntary Amendments filed May 10, 2012, in Ukraine Patent Application No. a 2012 03132, with English Abstract.
Request to Amend Complete Specification dated Feb. 15, 2013 for AU Application No. 2008325608, 23 pages.
Request to Amend Complete Specification dated May 9, 2013 for AU Application No. 2009210098, 22 pages.
Response and Amended Claims filed in EP Application No. 08846814.5, filed Aug. 1, 2013, 14 pages.
Response and Amended Claims filed in EP Application No. 10809938.3, filed Jul. 19, 2013, 7 pages.
Response and Amendment for CA Application No. 2652442, dated Sep. 5, 2013, 17 pages.
Response filed in CA Application No. 2652442, dated Jan. 8, 2014, 5 pages.
Response filed in CO Application No. 12-022608, dated Nov. 13, 2013, 13 pages (with English translation).
Response filed in IL Application No. 195282, filed Jul. 11, 2013, 13 pages (with English translation).
Response filed in IN Application No. 1571/CHENP/2007, dated Oct. 30, 2013, 9 pages.
Response filed in KR Application No. 10-2009-7005657, dated Nov. 21, 2013, 46 pages (with English translation).
Response filed in MX Application No. MX/a/2010/008187, dated Nov. 4, 2013, 21 pages (with English translation).
Response filed in PH Application No. 1-2011-502441, dated Feb. 28, 2014, 4 pages.

(56) References Cited

OTHER PUBLICATIONS

Response filed in PH Application No. 1-2011-502441, dated Nov. 4, 2013, 28 pages.
Response filed in U.S. Appl. No. 10/797,903, dated Dec. 29, 2010, 13 pages.
Response filed in VN Application No. 1-2011-03484, dated Feb. 28, 2014, 40 pages (with English translation).
Response filed on Apr. 11, 2006 for CN Application No. 01819710.8 (with English translation).
Response filed on Apr. 17, 2007 for PH Application No. 1-2003-500266.
Response filed on Apr. 27, 2006 for AU Application No. 2001295986.
Response filed on Apr. 30, 2008 for PH Application No. 1-2003-500266.
Response filed on Aug. 13, 2009 for CA Application No. 2426461.
Response filed on Aug. 14, 2006 for PH Application No. 1-2003-500266.
Response filed on Aug. 18, 2008 for NO Application No. 20031731 (with English translation).
Response filed on Aug. 21, 2006 for MX Application No. PA/a/2003/003362 (with English translation).
Response filed on Aug. 26, 2004 for NZ Application No. 525324.
Response filed on Aug. 5, 2003 for PH Application No. 1-2003-500266.
Response filed on Dec. 11, 2007 for TW Application No. 90125928 (with English translation).
Response filed on Dec. 15, 2005 for MX Application No. PA/a/2003/003362 (with English translation).
Response filed on Dec. 4, 2007 for IL Application No. 155447 (with English translation).
Response filed on Feb. 23, 2009 for CA Application No. 2426461.
Response filed on Feb. 26, 2008 for U.S. Appl. No. 11/293,785.
Response filed on Jan. 11, 2010 for CN Application No. 200580026468.7 (with English translation).
Response filed on Jan. 21, 2005 for NZ Application No. 525324.
Response filed on Jan. 26, 2010 for CN Application No. 200710007097.9 (with English translation).
Response filed on Jan. 26, 2011 for IL Application No. 181697 (with English translation).
Response filed on Jul. 1, 2005 for U.S. Appl. No. 10/420,466.
Response filed on Jul. 2, 2009 for CN Application No. 200710007097.9 (with English translation).
Response filed on Jul. 26, 2006 for AU Application No. 2001295986.
Response filed on Jul. 31, 2007 for PH Application No. 1-2003-500266.
Response filed on Jun. 22, 2010 for CN Application No. 200710007097.9 (with English translation).
Response filed on Mar. 17, 2005 for RU Application No. 2003114740 (with English translation).
Response filed on May 13, 2009 for IL Application No. 189677 (with English translation).
Response filed on May 16, 2008 for CA Application No. 2426461.
Response filed on May 20, 2010 for CA Application No. 2426461.
Response filed on May 7, 2008 for NO Application No. 20031731 (with English translation).
Response filed on May 8, 2008 for AU Application No. 2006236039.
Response filed on Nov. 19, 2009 for CN Application No. 200710007097.9 (with English translation).
Response filed on Nov. 30, 2004 for RU Application No. 2003114740 (with English translation).
Response filed on Oct. 13, 2008 for NO Application No. 20031731 (with English translation).
Response filed on Oct. 15, 2007 for PH Application No. 1-2003-500266.
Response filed on Oct. 8, 2004 for U.S. Appl. No. 10/420,466.
Response filed on Oct. 9, 2006 for CN Application No. 01819710.8 (with English translation).
Response filed on Sep. 10, 2007 for NO Application No. 20031731 (with English translation).
Response filed on Sep. 13, 2005 for CN Application No. 01819710.8 (with English translation).
Response filed on Sep. 15, 2003 for PH Application No. 1-2003-500266.
Response filed on Sep. 21, 2011 for CA Application No. 2579810.
Response filed on Sep. 23, 2009 for CN Application No. 200580026468.7 (with English translation).
Response filed on Sep. 8, 2003 for PH Application No. 1-2003-500266.
Response in Chinese Patent Application No. 201510031628.2, dated Aug. 11, 2017, 8 pages (English Translation).
Response in EP Application No. 06796594.7, dated Mar. 31, 2008, 3 pages.
Response in EP Application No. 12774278.1, dated Oct. 13, 2014, 4 pages.
Response in Indian Patent Applciation No. 5287/CHENP/2010, dated Sep. 12, 2017, 6 pages (English Translation).
Response in U.S. Appl. No. 13/923,858 dated Oct. 3, 2017, 29 pages.
Response to Advisory Action in U.S. Appl. No. 12/315,291, dated Mar. 31, 2011, 6 pages.
Response to AU OA for AU 2008211952 filed on Jun. 28, 2012, 36 pages.
Response to Australian Office Action filed on Apr. 29, 2010 for corresponding AU Application No. 2006285673.
Response to Australian Office Action filed on Jul. 28, 2010 for corresponding AU Application No. 2006285673.
Response to Australian Office Action filed on Oct. 16, 2009 for corresponding AU Application No. 2006285673.
Response to Canadian Office Action filed Feb. 13, 2012, in Canadian Application No. 2,620,594.
Response to Canadian Office Action filed on Jun. 21, 2010 for corresponding CA Application No. 2,620,594.
Response to Chinese Office Action filed on Mar. 5, 2010 for corresponding CN Application No. 200680036592.6, with English translation.
Response to Chinese Office Action for CN 200680020317.5 dated Sep. 11, 2012, 7 pages with English translation.
Response to Chinese Office Action, filed Jul. 11, 2012 for Chinese Patent Application No. 200680036592.6, with English translation.
Response to CN OA for CN200880003336.6 filed on May 3, 2012, 15 pages.
Response to Communication in EP App. Ser. 07743994.1, dated Dec. 22, 2014, 62 pages.
Response to EESR in EP Application No. 09713617.0, dated Sep. 2, 2011, 12 pages.
Response to EP OA for EP 07806561.2 filed on Apr. 18, 2012, 8 pages.
Response to Examination Report in AU Application No. 2005217325, dated Oct. 26, 2007, 33 pages.
Response to Examination Report in AU Application No. 2005217328, dated Sep. 20, 2007, 6 pages.
Response to Examination Report in AU Application No. 2007288793, dated Mar. 30, 2012, 5 pages.
Response to Examination Report in Australian Patent Application No. 2012246490, dated Jul. 15, 2016, 30 pages.
Response to Examiner's Substantive Report in CL Application No. 2012-00412, dated Nov. 28, 2014, 39 pages (with English translation).
Response to Extended European Search Report in EP Application No. 07793075.8, dated Nov. 8, 2010, 11 pages.
Response to Extended European Search Report in EP Application No. 07805959.9, dated Mar. 29, 2011, 2 pages.
Response to Hearing Notice in IN Application No. 1424/CHENP/2008, dated Sep. 11, 2012, 14 pages.
Response to IL OA for IL 195282 filed on May 28, 2012, 5 pages.
Response to Indian Office Action dated Feb. 2, 2012, dated Jun. 22, 2012, for Application No. 1908/DELNP/2008.
Response to Israeli Office Action filed on Sep. 7, 2010 for the corresponding Israeli Application No. 189589.
Response to Israeli Office Action, filed Jul. 24, 2012 for corresponding Israeli Patent Application No. 189589.

(56) References Cited

OTHER PUBLICATIONS

Response to Japanese Office Action dated Jul. 17, 2012 for Japanese Application No. 2007-533350 with English translation.
Response to Japanese Office Action filed on Jan. 9, 2013 for corresponding Japanese Application JP-2007-533350.
Response to Korean Office Action filed on Feb. 24, 2010 for corresponding KR Application No. 10-2008-7005195, with English translation.
Response to Korean Office Action filed on Jul. 29, 2010 for corresponding KR Application No. 10-2008-7005195, with English translation.
Response to Notice of Allowability filed on Dec. 13, 2007 for PH Application No. 1-2003-500266.
Response to Notice of Allowance in U.S. Appl. No. 13/205,328, dated Jul. 8, 2014, 7 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination filed in IL Application No. 217197, filed Jul. 31, 2013, 9 pages (with English translation).
Response to Notice Prior to Examination filed on Apr. 22, 2009 for IL Application No. 181697 (with English translation).
Response to Notice Prior to Examination filed on Jan. 11, 2009 for IL Application No. 189677 (with English translation).
Response to Notice Prior to Examination in IL Application No. 188670, dated Nov. 22, 2009, 29 pages (with English translation).
Response to Notice Prior to Examination in IL Application No. 197002, dated Oct. 13, 2010, 18 pages (with English translation).
Response to Notice Prior to Examination in IL Application No. 197141, dated Jun. 1, 2010, 22 pages (with English translation).
Response to OA for EP 10015141 filed on Mar. 5, 2012, 47 pages.
Response to Office Action dated Feb. 7, 2013 for CN Application No. 201080030508.6, 17 pages (with English translation).
Response to Office Action dated Jul. 5, 2012 for CN Application No. 200880115011.7 (with English translation).
Response to Office Action dated Nov. 30, 2012 for CN Application No. 200780017371.9, 4 pages (with English translation).
Response to Office Action filed in EP Application No. 04807580.8, dated May 16, 2014, 13 pages.
Response to Office Action filed on Jan. 25, 2013 for CA Application No. 2627598, 9 pages.
Response to Office Action filed on Jul. 11, 2012 for CN Application No. 200880003336.6 (with English translation).
Response to Office Action filed on May 29, 2012 for RU Application No. 2012103471 (with English translation).
Response to Office Action for Australian Application No. 2006309551, filed on Mar. 28, 2012.
Response to Office Action for CA Application No. 2661702, filed Jul. 16, 2013, 13 pages.
Response to Office Action for EP Applciation No. 0870437.6, dated Jan. 2, 2013, 22 pages.
Response to Office Action for IL 199907 filed on Oct. 11, 2010, 4 pages with English translation.
Response to Office Action for Israeli Application No. 205512, filed on Mar. 11, 2012 (with English translation).
Response to Office Action for Israeli Application No. 207089, filed on Mar. 11, 2012, with English translation.
Response to Office Action for MX Application No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005.
Response to Office Action in AU Application No. 2006282456, dated Jul. 16, 2009, 2 pages.
Response to office action in AU Application No. 2007289787, dated Feb. 16, 2012, 27 pages.
Response to office action in AU Application No. 2010285740, dated Oct. 28, 2014, 14 pages.
Response to Office Action in BD Application No. 184/2006, dated Dec. 13, 2007, 2 pages.
Response to Office Action in CA Application No. 2605854, dated Oct. 8, 2009, 18 pages.
Response to Office Action in CA Application No. 2661333, dated Nov. 12, 2013, 18 pages.
Response to Office Action in CA Application No. 2676796, dated Jun. 27, 2014, 18 pages.
Response to Office Action in CA Application No. 2704000, dated Dec. 19, 2014, 13 pages.
Response to Office Action in CA Application No. 2704000, dated Dec. 24, 2015, 11 pages.
Response to Office Action in CA Application No. 2771403, dated Sep. 10, 2014, 11 pages.
Response to Office Action in Canadian Patent Application No. 2704000, dated May 19, 2016, 11 pages.
Response to Office Action in CN Application No. 200680020317.5 filed on Jan. 9, 2014, 7 pages (with English translation).
Response to Office Action in CN Application No. 200680021939.X, dated Jul. 27, 2010, 44 pages (with English translation).
Response to Office Action in CN Application No. 200680021939.X, dated May 20, 2011, 39 pages (with English translation).
Response to Office Action in CN Application No. 200680021939.X, dated Oct. 28, 2010, 40 pages (with English translation).
Response to office action in CN Application No. 200780019200.X, dated Jul. 24, 2012, 49 pages (with English translation).
Response to office action in CN Application No. 200780019520.5, dated Dec. 3, 2010, 28 pages (with English translation).
Response to office action in CN Application No. 200780019520.5, dated Feb. 21, 2011, 7 pages (with English translation).
Response to Office Action in CN Application No. 201180030568.2 filed on Jan. 13, 2014, 46 pages (with English translation).
Response to Office Action in CN Application No. 201180030568.2 filed on May 14, 2014, 10 pages (with English translation).
Response to Office Action in CN Application No. 201280010427.9, dated Jun. 12, 2014, 13 pages (with English translation).
Response to office action in CN Application No. 201280010898.X, dated Nov. 25, 2014, 7 pages (with English translation).
Response to Office Action in EP Application No. 03791389.4, dated Jul. 25, 2014, 75 pages.
Response to office action in EP Application No. 05719973.9, dated Dec. 21, 2011, 150 pages.
Response to office action in EP Application No. 05719973.9, dated May 24, 2011, 26 pages.
Response to Office Action in EP Application No. 07793075.8, dated May 27, 2011, 17 pages.
Response to Office Action in EP Application No. 08704376.6, dated Apr. 30, 2014, 73 pages.
Response to Office Action in EP Application No. 08846814.5, dated Jul. 24, 2014, 71 pages.
Response to Office Action in European Patent Application No. 12786619.2, dated Apr. 15, 2016, 41 pages.
Response to Office Action in European Patent Application No. 12793322.4, dated Apr. 8, 2016, 10 pages.
Response to office action in ID App. Ser No. W-00 2008 00601, dated Jun. 18, 2012, 3 pages (with English translation).
Response to office action in IL Application No. 188670, dated Aug. 15, 2011, 43 pages (with English translation).
Response to office action in IL Application No. 197002, dated Feb. 29, 2012, 7 pages (with English translation).
Response to office action in IL Application No. 197141, dated Jun. 6, 2012, 10 pages (with English translation).
Response to office action in IL Application No. 217197, dated Nov. 26, 2014, 7 pages (with English translation).
Response to office action in JP Application No. 2008-530917, dated Dec. 13, 2012, 9 pages (with English translation).
Response to office action in JP Application No. P2009-510543, dated Nov. 9, 2009, 12 pages (with English translation).
Response to Office Action in JP Application No. P2009-540099, dated Apr. 28, 2014, 9 pages (with English Translation).
Response to office action in KR Application No. 10-2006-7013907, dated Sep. 28, 2007, 10 pages (with English translation).

(56) References Cited

OTHER PUBLICATIONS

Response to office action in KR Application No. 10-2006-7013940, dated Oct. 1, 2007, 20 pages (with English translation).
Response to Office Action in MX Application No. MX/a/2010/008187, dated Feb. 17, 2014, 7 pages (with English translation).
Response to Office Action in MX Application No. MX/a/2010/008187, dated Jun. 25, 2014, 5 pages (with English translation).
Response to Office Action in MX Application No. MX/a/2012/002011 filed on Jan. 16, 2014, 20 pages (with English translation).
Response to Office Action in MX Application No. MX/a/2012/014776, dated Jan. 7, 2015, 20 pages (with English translation).
Response to Office Action in MX Application No. MX/a/2012/014776, dated Jun. 20, 2014, 16 pages (with English translation).
Response to Office Action in MX Application No. MX/a/2013/009931, dated Dec. 9, 2014, 24 pages (with English translation).
Response to office action in NZ Application No. 566793, dated Jan. 17, 2010, 17 pages.
Response to office action in PH Application No. 1-2007-502319, dated Feb. 6, 2012, 19 pages.
Response to office action in PK Application No. 1024/2006, dated Apr. 20, 2009, 14 pages.
Response to office action in PK Application No. 1024/2006, dated Apr. 7, 2008, 17 pages.
Response to office action in PK Application No. 1024/2006, dated Jan. 29, 2009, 6 pages.
Response to office action in PK Application No. 155/2005, dated Jan. 4, 2008, 34 pages.
Response to office action in PK Application No. 375/2008, dated Apr. 8, 2009, 19 pages.
Response to office action in PK Application No. 375/2008, dated Dec. 20, 2008, 1 page.
Response to office action in PK Application No. 375/2008, dated Sep. 1, 2009, 20 pages.
Response to office action in RU Application No. 2006134254, dated Dec. 15, 2006, 23 pages (with English translation).
Response to office action in RU Application No. 2006134254, dated Nov. 20, 2007, 32 pages (with English translation).
Response to office action in RU Application No. 2008110932, dated Jan. 26, 2009, 29 pages (with English translation).
Response to Office Action in RU Application No. 2012103471, dated Jul. 21, 2014, 7 pages (with English translation).
Response to office action in RU Application No. 2012103471, dated Nov. 18, 2014, 17 pages (with English translation).
Response to Office Action in RU Application No. 2013139556, dated Dec. 25, 2013, 10 pages (with English translation).
Response to Office Action in SG Application No. 201108602-2, dated May 22, 2014, 37 pages.
Response to office action in TW Application No. 095130665, dated May 28, 2012, 379 pages (with English translation).
Response to Office Action in U.S. Appl. No. 13/870,507, dated May 17, 2016, 12 pages.
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to Office Action in U.S. Appl. No. 11/662,425, filed on May 20, 2014, 8 pages.
Response to office action in U.S. Appl. No. 12/031,568, dated Aug. 12, 2011, 12 pages.
Response to office action in U.S. Appl. No. 12/031,568, dated Jun. 2, 2010, 13 pages.
Response to Office Action in U.S. Appl. No. 12/039,381, dated Apr. 3, 2014, 7 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 21 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 13/983,891, dated Feb. 27, 2014, 6 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to office action in VN Application No. 1-2008-00723, dated May 10, 2010, 7 pages (with English translation).
Response to Office Action under 37 C.F.R. §1.111 for U.S. Appl. No. 12/523,495, filed Dec. 7, 2011.
Response to Office Action under 37 C.F.R. §1.111 for U.S. Appl. No. 13/083,338, filed Apr. 8, 2011, 6 pages.
Response to Office Action under 37 C.F.R. §1.111 for U.S. Appl. No. 13/083,338, filed Sep. 6, 2012.
Response to Office Action under 37 C.F.R.S 1.111 and Information Disclosure Statement for U.S. Appl. No. 11/997,719, filed Jul. 3, 2013, 26 pages.
Response to Restriction Requirement for U.S. Appl. No. 11/997,543, filed Mar. 22, 2011.
Response to Restriction Requirement for U.S. Appl. No. 12/301,353, filed Nov. 23, 2010.
Response to Restriction Requirement for U.S. Appl. No. 12/524,754, filed Dec. 1, 2011.
Response to Restriction Requirement in U.S. Appl. No. 11/065,631, dated Nov. 26, 2007, 16 pages.
Response to Restriction Requirement in U.S. Appl. No. 11/892,785, dated Oct. 30, 2009, 16 pages.
Response to Restriction Requirement in U.S. Appl. No. 13/238,085, dated Oct. 4, 2013, 3 pages.
Response to Restriction Response in U.S. Appl. No. 13/805,826, dated Jun. 2, 2014, 2 pages.
Response to the European Search Report for European Application No. 06782407 filed on Nov. 8, 2010.
Response to the Office Action for European Application No. 06782407 filed on Jan. 23, 2012, 17 pages.
Response to the Office Action issued for IN Application No. 6415/CHENP/2008 filed on Jan. 17, 2014, 16 pages.
Response to the Office Action issued for Japanese Application No. 2007-529565 filed on Feb. 3, 2012, 44 pages with English full translation.
Restriction Requirement for U.S. Appl. No. 11/997,543, dated Feb. 23, 2011.
Restriction Requirement for U.S. Appl. No. 12/092,539, dated Oct. 29, 2010.
Restriction Requirement for U.S. Appl. No. 12/301,353, dated Oct. 29, 2010.
Restriction Requirement for U.S. Appl. No. 12/439,339, dated Jul. 29, 2011.
Restriction Requirement for U.S. Appl. No. 12/524,754, dated Nov. 3, 2011.
Restriction Requirement in U.S. Appl. No. 11/065,631, dated Oct. 25, 2007, 8 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Roberts et al., "Antiangiogenic and Antitumor Activity of a Selective PDGFR Tyrosine Kinase Inhibitor, CP-673,451", Cancer Research., 65, 957-966, 2005.
Robinson et al, "Characterization of Tumor Size Changes Over Time From the Phase 3 Study of (E7080) Lenvatinib in Differentiated Cancer of the Thyroid (Select)", The Poster, No. 1031P, presented at European Society for Medical Oncology 2014 Congress, Sep. 26-30, 2014, 1 page.
Rosen and Goldberg, "Scatter Factor and Angiogenesis," *Advances in Cancer Research*, 1995, 67:257-279.

(56) References Cited

OTHER PUBLICATIONS

Rowe, R.C. et al. (ed.), Handbook of Pharmaceutical Excipients, 5th ed. Pharmaceutical Press, London, 2006, pp. 336-343.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Russian Decision of Grant directed at Appl. No. 2008149948115(065561), 16 pages with English translation.
Russian Notice of Allowance in Application No. 2012158142, dated May 5, 2015, 14 pages, with English translation.
Russian Office Action dated Apr. 11, 2012 for Application No. 2012103471, (with English translation).
Russian Office Action dated Jan. 19, 2005 for Application No. 2003114740 (with English translation).
Russian Office Action dated Jun. 29, 2004 for Application No. 2003114740 (with English translation).
Russian Office Action in Application No. 2012158142, dated Feb. 12, 2015, 21 pages, with English translation.
Russian Response to Office Action in Application No. 2012158142, dated Apr. 13, 2015, with English translation.
Russian Submission Documents in Application No. 2015148193, dated Apr. 27, 2016, 10 pages, with English translation.
Saeki et al., "Concurrent overexpression of Ets-1 and c-Met correlates with a phenotype of high cellular motility in human esophageal cancer," International J Cancer, 2002, 98(1):8-13.
Saito et al., "Angiogenic factors in normal endometrium and endometrial adenocarcinoma," Pathology International, 57: 140-147, 2007.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," Cancer Invest., 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Sandler et al, "Paclitaxel-carboplatin alone or with bevacizumab for non-small-cell lung cancer," N Engl J Med, 355(24):2542-2550, Dec. 14, 2006.
Sandler et al., "Phase III trial of gemcitabine plus cisplatin versus cisplatin alone in patients with locally advanced or metastatic non-small-cell lung cancer," J. Clin. Oncol., 18(1):122-130 (2000).
Sanger et al., "DNA sequencing with chain-terminating inhibitors", Proc. Natl. Acad. Sci. USA 74:5463 (1977).
Santoro et al., "Drug insight: Small-molecule inhibitors of protein kinases in the treatment of thyroid cancer," Nat. Clin. Pract. Endocrinol. Metab., 2(1):42-52 (2006).
Santoro et al., "Minireview: RET: normal and abnormal functions," Endocrinology, 145:5448-5451 (2004).
Santoro et al., "Molecular Mechanisms of RET Activation in Human Cancer," Ann. N.Y. Academy of Sciences, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," Oncogene, 21:3314-3333 (2002).
Schlumberger et al, "Lenvatinib versus Placebo in Radioiodine-Refracto ly Thyroid Cancer (with supplementary material)", The New England Journal of Medicine 2015; 372, Feb. 12, 2015, p. 621-p. 630.
Schlumberger et al., "A phase 3, multicenter, double-blind, placebo-controlled trial of lenvatinib (E7080) in patients with $^{131}$I-refractory differentiated thyroid cancer (SELECT)," Am Soc Clin Oncol., Annual Meeting Abstract LBA6008, 2012, 4 pages.
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Schoepp and Conn, "Metabotropic glutamate receptors in brain function and pathology," Trends in Pharmacological Sciences, 1993, pp. 13-20.
Search Report in EP Application No. 09705712.9, dated Aug. 7, 2014, 6 pages.
Search Report in EP Application No. 11798224.9, dated Mar. 21, 2014, 1 page.
Search Report in EP Application No. 11798224.9, dated Mar. 4, 2014, 6 pages.
Search Report in EP Application No. 12774278.1, dated Aug. 14, 2014, 8 pages.
Search Report in EP Application No. 12786619.2, dated Dec. 15, 2014, 6 pages.
Search Report in EP Application No. 16802790.2, dated Oct. 9, 2018, 10 pages.
Search Report in European Patent Application No. 14873998.0, dated May 29, 2017, 6 pages.
Search Report in European Patent Application No. 15836577.5, dated Jun. 28, 2018, 9 pages.
Search Report in European Patent Application No. 16814346.9, dated Nov. 15, 2018, 8 pages.
Search Report in European Patent Application No. 16837135.9, dated Mar. 18, 2019, 10 pages.
Search Report in European Patent Application No. 16837150.8, dated Mar. 22, 2019, 7 pages.
Search Report in European Patent Application No. 18197141.7, dated Jan. 21, 2019, 6 pages.
Search Report in European Patent Application No. 19151846.3, dated Jun. 3, 2019, 13 pages.
Second Preliminary Amendment and Response to Restriction Requirement for U.S. Appl. No. 12/092,539, filed Nov. 22, 2010.
Sekido et al., "Preferential Expression of c-kit Protooncogene Transcripts in Small Cell Lung Cancer," Cancer Res., 51:2416-2418 (1991).
Sennino and McDonald, "Controlling escape from angiogenesis inhibitors", Nature Rev Cancer, 12:699-709, Oct. 2012.
Sharma et al., "Thyroid Cancer," Feb. 18, 2015, pp. 1-16.
Sherman et al., "A phase II trial of the multitargeted kinase inhibitor E7080 in advanced radioiodine (RAI)-refractory differentiated thyroid cancer (DTC)," Journal of Clinical Oncology, 29(15):5503A, May 2011.
Shiang et al., "Mutations in the transmembrane domain of FGFR3 cause the most common genetic form of dwarfism, achondroplasia," Cell., 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," Bioorganic and Medicinal Chemistry Letters, 14(4):875-879 (2004).
Shirai, Y., et al., "Role of low-substituted hydroxypropylcellulose in dissociation and bioavalability of novel fine granule system for masking bitter taste," Biol. Pharm. Bull, 17(3): 427-431 (1994).
Shitashige et al., "Traf2- and Nck-Interacting Kinase Is Essential for Wnt Signaling and Colorectal Cancer Growth," Cancer Res., 2010, 70:5024-5033.
Shumaker et al., "Effect of lenvatinib (E7080) on the QTc interval: results from a thorough QT study in healthy volunteers," Cancer Chemother Pharmacol., published online Mar. 23, 2014, 9 pages (with English abstract).
Siegel et al., "Sorafenib: Where Do We Go from Here?," Hepatology, 52:360-369 (2010).

(56) References Cited

OTHER PUBLICATIONS

Siemeister et al., "ZK304709, the oral Multitarget Tumor Growth Inhibitor™, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Singaporean Submission Documents in Application No. 11201706630U, dated Aug. 21, 2018, 9 pages.
Soh et al, "Neutralizing vascular endothelial growth factor activity inhibits thyroid cancer growth in vivo", Surgery, 2000:1059-1066.
Sondergaard et al., Differential sensitivity of melanoma cell lines with BRAF$^{V600E}$ mutation to the specific Raf inhibitor PLX4032, J Translational Med., 2010, 8:39, 11 pages.
Spacey et al., "Indolocarbazoles, Potent and Selective Inhibitors of Platelet-Derived Growth Factor Receptor Autophosphorylation," Biochemical Pharmacology, 55:261-271 (1998).
St. Bernard et al., "Fibroblast Growth Factor Receptors as Molecular Targets in Thyroid Carcinoma," Endocrinology, Mar. 2005, 146(3):1145-1153.
Stahl and Wermuth, "Handbook of Pharmaceutical Salts: Properties, selection, and use," 2002, pp. 117-122.
Stahl et al., "Handbook of Pharmaceutical Salts, Properties, Selection and Use," Publisher—Wiley-VCH-2002, Cover pp. 2002, 6 pages.
Stahl et al., "Handbook of Pharmaceutical Salts, Properties, Selection and Use," Publisher—Wiley-VCH-2002, Chapters 5, 6, 7 and 8, 2002, 110 pages.
Stahl, "Preparation of water-soluble compounds through salt formation," edited by Camille G. Wermuth, The Practice of Medicinal Chemistry Second Edition, 2003, 601-615.
Stinchcombe "Targeted therapy of advanced non-small cell lung cancer: the role of bevacizumab," Biologics: Targets & Therapy 1(3):185-194, 2007.
Stinchcombe and Scoinski, "Bevacizumab in the treatment of non-small-cell lung cancer," Oncogene 26:3691-3698, May 28, 2007.
Stjepanovic and Capdevila, "Multikinase inhibitors in the treatment of thyroid cancer: specific role of lenvatinib," Biologics: Targets and Therapy, 8:129-139, Aug. 2014.
Strohmeyer et al., "Expression of the hst-1 and c-kit Protoonocogenes in Human Testicular Germ Cell Tumors," Cancer Res., 51:1811-1816 (1991).
Submission Document(s) Before the Patent Office for IL Application No. 200090, dated Dec. 23, 2012, 16 pages, with English translation.
Submission Document Before the Patent Office dated Apr. 22, 2013 for IL Application No. 207089, 7 pages (with English translation).
Submission Document Before the Patent Office dated Mar. 14, 2013 for IL Application No. 205512, 12 pages (with English translation).
Submission Document Before the Patent Office for CL Application No. 2012-00412, dated Aug. 31, 2012, 6 pages (with English translation).
Submission Document Before the Patent Office for EP Application No. 03791389.4, dated Dec. 20, 2012, 4 pages.
Submission Document Before the Patent Office for EP Application No. 08846814.5, dated Jan. 3, 2013, 102 pages.
Submission Document Before the Patent Office for EP Application No. 8704376.6, dated Jan. 2, 2013, 22 pages.
Submission Document Before the Patent Office re Observation dated Feb. 16, 2013 for CN Application No. 200980103218.7, 8 pages (with English translation).
Submission Document Before the Patent Office re RCE in U.S. Appl. No. 13/205,328, dated Sep. 10, 2013, 12 pages.
Submission Document in Algerian Patent Application No. 120036, dated Feb. 22, 2018, 16 pages (English Translation).
Submission Document in Australian Patent Application No. 2013364953, dated Apr. 13, 2017, 15 pages.
Submission Document in Australian Patent Application No. 2014371148, date Jul. 10, 2018, 8 pages.
Submission Document in Canadian Patent Application No. 201380054667.3, dated Apr. 12, 2017, 9 pages.
Submission Document in Chilean Patent Application No. 2012-00412, dated Mar. 6, 2017, 9 pages (English Translation).
Submission Document in Chilean Patent Application No. 2012-00412, dated Mar. 21, 2019, 24 pages.
Submission Document in Chilean Patent Application No. 201601419, dated Jul. 13, 2018, 30 pages (English Translation).
Submission Document in Chinese Patent Application No. 201480026871.9, dated May 8, 2017, 10 pages (English Translation).
Submission Document in Chinese Patent Application No. 201480067017.7, dated Jun. 5, 2017, 7 pages, (English Translation).
Submission Document in Chinese Patent Application No. 201510031628.2, dated Oct. 10, 2018, 8 pages (English Translation).
Submission Document in Chinese Patent Application No. 201510031628.2, dated Apr. 30, 2019, 7 pages (with English Translation).
Submission Document in Chinese Patent Application No. 201680027234.2, dated Mar. 6, 2019, 16 pages (with English Translation).
Submission Document in Chinese Patent Application No. 201780020786.5, dated Mar. 18, 2019, 35 pages (with English Translation).
Submission Document in CL Application No. 2012-00412, dated Aug. 12, 2014, 2 pages (with English translation).
Submission Document in Colombian Patent Application No. 16147681, date Oct. 30, 2017, 39 pages (English Translation).
Submission Document in Egyptian Patent Application No. PCT 283/2012, dated May 9, 2018, 13 pages (English Translation).
Submission Document in European Patent Application No. 08846814.5, dated Mar. 31, 2017, 45 pages.
Submission Document in European Patent Application No. 12793322.4, dated Apr. 19, 2018, 8 pages.
Submission Document in European Patent Application No. 14873998.0, dated Dec. 13, 2017, 11 pages.
Submission Document in European Patent Application No. 16755489.8, dated Feb. 7, 2019, 10 pages.
Submission Document in European Patent Application No. 16814346.9, dated Feb. 22, 2019, 9 pages.
Submission Document in European Patent Application No. 16837135.9, dated Sep. 18, 2018, 2 pages.
Submission Document in European Patent Application No. 16837150.8, dated Sep. 19, 2018, 2 pages.
Submission Document in Gulf Cooperation Council Patent Application No. GC2015-29939, dated May 21, 2018, 6 pages (English Translation).
Submission Document in Indian Patent Application No. 10502/CHENP/2012, dated May 3, 2018, 10 pages (English Translation).
Submission Document in Indian Patent Application No. 10502/CHENP/2012, dated Apr. 26, 2019, 1 page.
Submission Document in Indian Patent Application No. 2371/CHENP/2012, dated Apr. 19, 2018, 21 pages (English Translation).
Submission Document in Indian Patent Application No. 2371/CHENP/2012, dated Jun. 15, 2018, 14 pages (English Translation).
Submission Document in Indian Patent Application No. 2371/CHENP/2012, dated Jan. 8, 2018, 10 pages (English Translation).
Submission Document in Indian Patent Application No. 2371/CHENP/2012, dated Oct. 22, 2018, 276 pages (English Translation).
Submission Document in Indian Patent Application No. 2371/CHENP/2012, dated Sep. 12, 2018, 18 pages (English Translation).
Submission Document in Indian Patent Application No. 2371/CHENP/2012, dated Aug. 21, 2018, 1 page (English Translation).
Submission Document in Indian Patent Application No. 2371/CHENP/2012, dated Jan. 11, 2019, 31 pages.
Submission Document in Indian Patent Application No. 2371/CHENP/2012, dated Jun. 5, 2019, 15 pages.
Submission Document in Indian Patent Application No. 2793/CHENP/2013, dated Apr. 20, 2018, 4 pages (English Translation).

(56) References Cited

OTHER PUBLICATIONS

Submission Document in Indian Patent Application No. 2793/CHENP/2013, dated Dec. 13, 2017, 10 pages (English Translation).
Submission Document in Indian Patent Application No. 3334/CHENP/2010, dated Jul. 26, 2017, 59 pages (English Translation).
Submission Document in Indian Patent Application No. 6415/CHENP/2008, dated Apr. 18, 2017, 317 pages (English Translation).
Submission Document in Indian Patent Application No. 7026/CHENP/2013, dated Jul. 9, 2018, 15 pages.
Submission Document in Israeli Patent Application No. 242519, dated Nov. 29, 2017, 13 pages (English Translation).
Submission Document in Israeli Patent Application No. 250454, dated Dec. 2, 2018, 5 pages (with English Translation).
Submission Document in Israeli Patent Application No. 253946, dated Feb. 5, 2019, 6 pages.
Submission Document in Israeli Patent Application No. 255564, dated Dec. 10, 2018, 4 pages.
Submission Document in Israeli Patent Application No. 257292, dated Apr. 16, 2019, 6 pages (with English Translation)\.
Submission Document in Israeli Patent Application No. 257433, dated Apr. 16, 2019, 6 pages (with English Translation).
Submission Document in Japanese Patent Application No. P2017-546133, dated Apr. 2, 2019, 7 pages (with English Translation).
Submission Document in Jordan Patent Application No. 55/2011, dated Apr. 9, 2017, 7 pages (English Translation).
Submission Document in Jordan Patent Application No. 55/2011, dated Mar. 29, 2017, 5 pages (English Translation).
Submission Document in Korean Patent Application 10-2017-7032771, dated Jan. 8, 2018, 11 pages (English Translation).
Submission Document in Malaysian Patent Application No. PI2016702025, dated Oct. 4, 2018, 2 pages.
Submission Document in MX Application No. MX/a/2014/010594, dated Sep. 4, 2014, 70 pages (with English translation).
Submission Document in MY Application No. PI2011700172, dated Nov. 4, 2014, 3 pages.
Submission Document in New Zealand Patent Application No. 714049, dated Mar. 13, 2019, 7 pages.
Submission Document in Pakistani Patent Application No. 907/2014, dated Nov. 23, 2016, 6 pages (English Translation).
Submission Document in PH App Ser. No. 1-2011-502441, dated May 22, 2015, 25 pages.
Submission Document in Russian Patent Application No. 2015148193, dated Mar. 23, 2018, 17 pages (English Translation).
Submission Document in Russian Patent Application No. 2016122867, dated Aug. 31, 2018, 8 pages.
Submission Document in Singaporean Patent Application No. 11201700855X, dated Jun. 11, 2019, 33 pages.
Submission Document in Taiwanese Patent Application No. 103144928, dated Sep. 5, 2018, 32 pages (English Translation).
Submission Document in Thailand Patent Application No. 1201000221, dated Mar. 12, 2018, 3 pages (English Translation).
Submission Document in U.S. Appl. No. 13/870,507, dated Apr. 11, 2017, 4 pages.
Submission Document in U.S. Appl. No. 13/923,858, dated Jan. 2, 2019, 11 pages.
Submission Document in U.S. Appl. No. 14/122,339, date Jun. 12, 2017, 5 pages.
Submission Document in U.S. Appl. No. 14/122,339, dated Mar. 1, 2018, 15 pages.
Submission Document in U.S. Appl. No. 14/122,339, dated Mar. 27, 2017, 14 pages.
Submission Document in U.S. Appl. No. 14/890,207, dated Sep. 21, 2018, 40 pages.
Submission Document in U.S. Appl. No. 14/890,207, dated Feb. 14, 2019, 1 page.
Submission Document in U.S. Appl. No. 15/460,629, dated Nov. 28, 2018, 2 pages.
Submission Document in U.S. Appl. No. 15/503,108, dated Apr. 17, 2018, 5 pages.
Submission Document in U.S. Appl. No. 15/503,108, dated Aug. 9, 2018, 15 pages.
Submission Document in U.S. Appl. No. 15/503,108, dated Nov. 28, 2018, 11 pages.
Submission Document in U.S. Appl. No. 15/503,108, dated May 28, 2019, 4 pages.
Submission Document in U.S. Appl. No. 15/550,124, dated Mar. 14, 2018, 3 pages.
Submission Document in U.S. Appl. No. 15/748,980, dated Feb. 15, 2019, 3 pages.
Submission Document in U.S. Appl. No. 15/750,712, dated Feb. 25, 2019, 1 page.
Submission Document in U.S. Appl. No. 15/934,242, dated Mar. 23, 2018, 10 pages.
Submission Document in U.S. Appl. No. 16/038,710, dated Feb. 8, 2019, 5 pages.
Submission Document in U.S. Appl. No. 16/229,805, dated May 30, 2019, 11 pages.
Submission Document in Vietnamese Patent Application No. 1-2016-02104, dated Jun. 5, 2018, 18 pages (English Translation).
Submission Document re figures in AR Application No. P110100513, dated Oct. 22, 2014, 3 pages.
Submission Document re Petition on Oct. 2, 2013 in CL Application No. 2012-00412, 22 pages (with English translation).
Submission Document re RCE and Amendment in U.S. Appl. No. 12/031,568, dated Oct. 26, 2010, 23 pages.
Submission Document re RCE and Information Disclosure Statement in U.S. Appl. No. 11/065,631, dated Oct. 8, 2008, 7 pages.
Submission Document re RCE and Information Disclosure Statement in U.S. Appl. No. 12/558,982, dated May 9, 2012, 36 pages.
Submission Document re RCE and Information Disclosure Statement on Oct. 18, 2013, in U.S. Appl. No. 12/524,754, 17 pages.
Submission Document re RCE and Information Disclosure Statment on Sep. 19, 2013 in U.S. Appl. No. 12/741,682, 19 pages.
Submission Document re RCE in U.S. Appl. No. 12/031,568, dated Aug. 30, 2012, 12 pages.
Submission Document re RCE in U.S. Appl. No. 12/031,568, dated Jan. 18, 2012, 11 pages.
Submission Document re RCE in U.S. Appl. No. 12/558,982, dated Nov. 29, 2011, 13 pages.
Submission Document re RCE in U.S. Appl. No. 12/741,682, dated Aug. 14, 2014, 1 page.
Submission Documents Before the Patent Office for CN Application No. 201080030508.6, dated May 27, 2013, 7 pages (with English translation).
Submission Documents Before the Patent Office for GC Patent Application No. GC2011-17812, dated Oct. 24, 2018, 13 pages.
Submission Documents Before the Patent Office for KR Application No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents in Canadian Patent Application No. 2828946, dated Feb. 5, 2016, 6 pages.
Submission Documents in Chinese Patent Application No. 201380054667.3, dated Nov. 17, 2016, 8 pages (English Translation).
Submission Documents in Chinese Patent Application No. 201480026871.9, dated Nov. 14, 2016, 11 pages (English Translation).
Submission Documents in Chinese Patent Application No. 201510031628.2, dated Nov. 29, 2016, 8 pages (English Translation).
Submission Documents in European Patent Applciaiton No. 08846814.5, dated Mar. 2, 2017, 18 pages.
Submission Documents in European Patent Application No. 13865671.5, dated Jul. 7, 2016, 3 pages.
Submission Documents in European Patent Application No. 14727633.1, dated Feb. 2, 2017, 12 pages.
Submission Documents in European Patent Application No. 14727633.1, dated Jul. 18, 2016, 8 pages.
Submission Documents in Indian Patent Application No. 1511/CHENP/2009, dated Aug. 18, 2017, 55 pages (English Translation.

(56) References Cited

OTHER PUBLICATIONS

Submission Documents in Indian Patent Application No. 5022/CHENP/2009, dated Sep. 23, 2016, 9 pages (English Translation).
Submission Documents in Indonesia Patent Application No. W-00201201031, dated Aug. 11, 2016, 13 pages (English Translation).
Submission Documents in Indonesia Patent Application No. W-00201201031, dated Dec. 9, 2016, 4 pages (English Translation).
Submission Documents in Israel Patent Application No. 223695, dated Dec. 22, 2016, 5 pages (English Translation).
Submission Documents in Israel Patent Application No. 227558, dated Jul. 12, 2016, 6 pages (English Translation).
Submission Documents in Israeli Patent Application No. 227558, dated Nov. 30, 2015, 3 pages.
Submission Documents in Israeli Patent Application No. 242519, dated Apr. 13, 2016, 4 pages (English Translation).
Submission Documents in Korean Patent Application No. 10-2013-7020616, dated Feb. 13, 2017, 47 pages (English Translation).
Submission Documents in Mexican Patent Application No. MX/a/2014/010594, dated Oct. 20, 2016, 15 pages (English Translation).
Submission Documents in Norwegian Patent Application No. 20063383, dated Jun. 15, 2016, 181 pages.
Submission Documents in Russian Patent Application No. 2015148193, dated Aug. 5, 2016, 16 pages (English Translation).
Submission Documents in U.S. Appl. No. 14/117,276, dated Jul. 18, 2016, 3 pages.
Submission Documents in U.S. Appl. No. 14/890,207, dated Nov. 30, 2017, 15 pages.
Submission Documents re New Claim Set Before the Patent Office for AR Application No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission documents re RCE filed in U.S. Appl. No. 11/997,719, dated Dec. 11, 2013, 10 pages.
Submission Documents re RCE filed in U.S. Appl. No. 12/524,754, dated May 13, 2014, 1 page.
Submission documents re RCE filed in U.S. Appl. No. 12/741,682, dated Jan. 17, 2014, 1 page.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Submission documents re RCE in U.S. Appl. No. 12/439,339, dated Jan. 27, 2014, 1 page.
Submission documents re RCE in U.S. Appl. No. 12/524,754, filed Feb. 3, 2014, 1 page.
Submission Documents re Request for Continued Examination filed in U.S. Appl. No. 12/741,682, dated May 6, 2014, 1 page.
Submission Documents re Request for Continued Examination filed in U.S. Appl. No. 13/083,338, dated May 6, 2014, 1 page.
Submission documents re Request for Continued Examination in U.S. Appl. No. 13/205,328, dated Apr. 28, 2014, 1 page.
Submission in EP Application No. 04807580.8, dated Jun. 13, 2014, 18 pages.
Submission of Amendments and Complete Specification dated Apr. 10, 2013 for IN Application No. 1571/CHENP/2007, 15 pages.
Submission of Claims in IL Application No. 223695, dated Jan. 17, 2015, 16 pages.
Submission of Document Before the Patent Office re Request for Voluntary Amendments dated Jan. 30, 2013 for NZ Application No. 598291, 8 pages.
Submission of Document re Claims filed in Response to Second Office Action for CN Application No. 200880115011.7, filed on Nov. 20, 2012.
Submission of Document re Request for Examination in CO Application No. 12-022608, submitted on Jun. 12, 2012.
Submission of Documents before the Patent Office for CN Application No. 200880115011.7, dated Apr. 11, 2013, 10 pages (with English translation).
Submission of Documents before the Patent Office for CN Application No. 200980103218.7, dated Mar. 13, 2013, 6 pages (with English translation).
Submission of Documents Before the Patent Office for IL Application No. 175363, dated Feb. 27, 2013, 23 pages.
Submission of Documents re Amendment in UA Application No. a2012 03132, submitted on May 22, 2012.
Submission of Documents re Claim 3 and Figure 3 for KR Application No. 10-2009-7005657, filed on Jul. 13, 2012.
Submission of Reference Materials in KR Application No. 10-2008-7013685, filed Jul. 5, 2013, 43 pages, (with English translation).
Sun et al., "Design, synthesis, and evaluations of substituted 3-[(3- or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119 (2003).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplemental Notice of Allowance in U.S. Appl. No. 12/315,291, dated Jul. 21, 2011, 4 pages.
Supplemental Search Report in EP Application No. 05719973.9, dated Dec. 6, 2007, 3 pages.
Supplemental Search Report in EP Application No. 05719976.2, dated Dec. 6, 2007, 3 pages.
Supplementary European Search Report for Application No. 01976786.2, dated Jul. 6, 2004.
Supplementary European Search Report for Application No. 08 70 4376, dated Jun. 14, 2012.
Supplementary European Search Report for Application No. 08846814.5, dated Jun. 18, 2012.
Supplementary European Search Report dated Jul. 5, 2012, in European Patent Application No. 08846814.5.
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Taguchi et al., "A novel orally active inhibitor of VEGF receptor tyrosine kinases KRN951: Anti-angiogenic and anti-tumor activity against human solid tumors," Proceedings of the AACR Annual Meeting, 45:595 (Mar. 2004) ( XP002536608).
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 24 pages.
Taiwanese Notice of Allowance in Application No. 100104281, dated Jun. 9, 2015, 4 pages, with English translation.
Taiwanese Submission Documents in Application No. 100104281, dated Mar. 9, 2015, 12 pages, with English translation.
Takahashi et al, "Phase II Study of Lenvatinib, A Multitargeted Tyrosine Kinase Inhibitor, in Patients With All Histologic Subtypes of Advanced Thyroid Cancer (Differentiated, Medullary, and Anaplastic)", The Poster, presented at the European Society for Medical Oncology 2014 Congress, Sep. 26-30, 2014, 1 page.
Takahashi et al., "Preclinical Study of VEGFR and EGFR Inhibitor—Are They Potential Therapeutic Targets in Biliary Tract Carcinoma?", The Biliary Tract & Pancreas, Feb. 2015 vol. 36 No. 2, p. 153-p. 160 (Machine Translation).
Takahashi et al., "A case of inoperable scirrhous gastric cancer that responded remarkably to a combination of TS-1+paclitaxel and

(56) References Cited

OTHER PUBLICATIONS showed complete loss of ascites," Japanese Journal of Cancer and Chemotherapy, 31(7):1093-1095 (2004).
Takeda et al., "AZD2171 shows potent anti-tumor activity against gastric cancer expressing variant K-SAM/FGFR2," Abstract #3785, Proceeding of the American Association for Cancer Research, 47:890 (2006).
Tamai et al., "Developmental strategy of Lenvatinib and developmental status in gastrointestinal cancer", BIO Clinica, 2014 vol. 29 No. 2, p. 61-p. 65 (Machine Translation).
Tamura et al., "Molecular Characterization of Undifferentiated-Type Gastric Carcinoma," Laboratory Investigation, 81(4):593-598, Apr. 2001.
Tan et al., "Randomized study of vinorelbine-gemcitabine versus vinorelbine-cathoplatin in patients with advanced non-small cell lung cancer," Lung Cancer, 49(2):233-240 (2005).
Tanaka et al., "Biological Equivalence Test on Tandospirone Citrate 10 mg Tablet "AMEL"," Journal of New Remedies & Clinics, 57(6):936-951 (Jun. 2008) (Partial English Translation).
Taniguchi et al., "Effect of c-kit Mutation on Prognosis of Gastrointestinal Stromal Tumors," Cancer Res., 59:4297-4300 (1999).
Thailand Request for Examination in Application No. 0401005163, dated Aug. 21, 2015, 29 pages, with English translation.
The ESMO/European Sarcoma Network Working Group, "Bone sarcomas: ESMO Clinical Practice Guideline for diagnosis, treatment and follow-up", Annals of Oncology, vol. 23, supplement 7, 2012, pvii100-pvii109.
The Pharmacology of Monoclonal Antibody, vol. 113, Chapter 11, Rosenburg and Moore ed., Springer Verlag (1994) pp. 269-315.
Third Office Action dated Feb. 25, 2013 for CN Application No. 200880115011.7, 6 pages (with English translation).
Thomas et al., "The Eosinophil and its Role in Asthma," Gen. Pharmac., 27(4)593-597 (1996).
Thyroid Cancers, Endocrine and Metabolic Disorders, http://www.merkmanuals.com/professional/print/sec12/ch152/ch152j.html Mar. 16, 2011.
Tian et al., "Activating c-kit Gene Mutations in Human Germ Cell Tumors," American Journal of Pathology, 154(6):1643-1647 (1999).
To and Tsao, "The roles of hepatocyte growth factor/scatter factor and Met receptor in human cancers (Review)," *Oncology Reports*, 1998, 5:1013-1024.
Tohyama et al, "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis," Int. J. Cancer, 89:242-250 (2000).
Tong et al., "Vascular normalization by vascular endothelial growth factor receptor 2 blockade induces a pressure gradient across the vasculature and improves drug penetration in tumors," Cancer Res., 64:3731-3736 (2004).
Toshiyuki et al., "Thermal recording materials with improved background stability," Database CA (Online) Chemical Abstracts Service, Columbus, OH, US (Feb. 20, 1996) (XP002443195).
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011.
Traxler et al., "AEE788; A dual family epidermal growth factor receptor/ErbB2 and vascular endothelial growth factor receptor tyrosine kinase inhibitor with antitumor and antiangiogenic activity," Cancer Res., 64:4931-4941 (2004).
Trudel et al., "CHIR-258, a novel, multitargeted tyrosine kinase inhibitor for the potential treatment of t(4;14) multiple myeloma," Blood, 105:2941-2948 (2005).

"Inhibition of fibroblast growth factor receptor 3 induces differentiation and apoptosis in t(4;14) myeloma," Blood, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signalling: from development to cancer," Nature Reviews, Cancer, 10:116-129 (2010).
U.S. Certificate of Correction in U.S. Appl. No. 12/524,754, dated Aug. 11, 2015, 1 page.
U.S. Certificate of Correction in U.S. Appl. No. 12/741,682, dated Aug. 4, 2015, 2 pages.
U.S. Certificate of Correction in U.S. Appl. No. 13/624,278, dated Aug. 18, 2015, 1 page.
U.S. Notice of Allowance for U.S. Appl. No. 12/244,227, dated Oct. 22, 2010.
U.S. Notice of Allowance in U.S. Appl. No. 14/438,366, dated Feb. 12, 2016, 7 pages.
U.S. Notice of Panel Decision from Pre-Appeal Brief Review in U.S. Appl. No. 12/039,381, dated Mar. 4, 2016, 2 pages.
U.S. Office Action for U.S. Appl. No. 10/420,466, dated Apr. 13, 2005.
U.S. Office Action for U.S. Appl. No. 10/577,531, dated Sep. 23, 2008.
U.S. Office Action for U.S. Appl. No. 10/797,903, dated Jul. 23, 2008, 11 pages.
U.S. Office Action for U.S. Appl. No. 10/797,903, dated Apr. 1, 2010.
U.S. Office Action for U.S. Appl. No. 10/797,903, dated Aug. 20, 2009.
U.S. Office Action for U.S. Appl. No. 10/797,903, dated Dec. 11, 2007.
U.S. Office Action for U.S. Appl. No. 10/797,903, dated Sep. 1, 2010.
U.S. Office Action for U.S. Appl. No. 11/293,785, dated Sep. 4, 2007.
U.S. Office Action for U.S. Appl. No. 11/347,749, dated Feb. 9, 2009.
U.S. Office Action for U.S. Appl. No. 11/662,425, dated May 3, 2010.
U.S. Office Action for U.S. Appl. No. 11/662,425, dated Sep. 28, 2010.
U.S. Office Action for U.S. Appl. No. 11/997,543, dated Feb. 23, 2011.
U.S. Office Action for U.S. Appl. No. 11/997,543, dated May 19, 2011.
U.S. Office Action for U.S. Appl. No. 11/997,543, dated Nov. 9, 2011.
U.S. Office Action for U.S. Appl. No. 11/997,719, dated Apr. 6, 2011.
U.S. Office Action for U.S. Appl. No. 11/997,719, dated Sep. 3, 2010.
U.S. Office Action for U.S. Appl. No. 12/092,539, dated Jan. 7, 2011.
U.S. Office Action for U.S. Appl. No. 12/092,539, dated Jun. 28, 2011.
U.S. Office Action for U.S. Appl. No. 12/092,539, dated May 9, 2011.
U.S. Office Action for U.S. Appl. No. 12/094,492, dated Mar. 24, 2011.
U.S. Office Action for U.S. Appl. No. 12/301,353, dated Jan. 24, 2011.
U.S. Office Action for U.S. Appl. No. 12/400,562, dated Mar. 31, 2010.
U.S. Office Action for U.S. Appl. No. 12/439,339, dated Mar. 30, 2012.
U.S. Office Action for U.S. Appl. No. 12/439,339, dated Nov. 14, 2011.
U.S. Office Action for U.S. Appl. No. 12/523,495, dated Dec. 27, 2011.
U.S. Office Action for U.S. Appl. No. 12/523,495, dated Sep. 27, 2011.

(56) References Cited

OTHER PUBLICATIONS

U.S. Office Action for U.S. Appl. No. 12/524,754, dated Dec. 19, 2011.
U.S. Office Action for U.S. Appl. No. 12/741,682, dated Apr. 30, 2012.
U.S. Office Action for U.S. Appl. No. 12/864,817, dated Dec. 16, 2011.
U.S. Office Action for U.S. Appl. No. 12/864,817, dated May 19, 2011.
U.S. Office Action for U.S. Appl. No. 12/864,817, dated Nov. 3, 2011.
U.S. Office Action for U.S. Appl. No. 13/083,338, dated Apr. 12, 2012.
U.S. Office Action for U.S. Appl. No. 13/083,338, dated Jun. 8, 2012.
U.S. Office Action for U.S. Appl. No. 13/083,338, dated Nov. 23, 2012.
U.S. Office Action for U.S. Appl. No. 13/205,328, dated Jan. 12, 2012.
U.S. Office Action for U.S. Appl. No. 13/205,328, dated May 1, 2012.
U.S. Office Action for U.S. Appl. No. 13/322,961, dated Sep. 25, 2012.
U.S. Office Action in U.S. Appl. No. 12/039,381, dated Feb. 26, 2015, 13 pages.
U.S. Office Action in U.S. Appl. No. 12/092,539, dated May 9, 2011.
U.S. Office Action in U.S. Appl. No. 13/870,507, dated Apr. 1, 2015, 82 pages.
U.S. Office Action in U.S. Appl. No. 14/862,349, dated Mar. 10, 2016, 11 pages.
U.S. Response to Office Action in U.S. Appl. No. 12/039,381, dated Dec. 22, 2015, 10 pages.
U.S. Response to Office Action in U.S. Appl. No. 13/923,858, filed Apr. 1, 2015, 12 pages.
U.S. Response to Restriction Requirement in U.S. Appl. No. 13/870,507, dated Jan. 27, 2015, 3 pages.
U.S. Submission Documents in U.S. Appl. No. 13/870,507, dated Jun. 18, 2015, 13 pages.
Ueda et al., "VGA1155, a Novel Binding Antagonist of VEGF, Inhibits Angiogenesis In Vitro and In Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
U.S. Office Action for U.S. Appl. No. 11/997,543, dated Sep. 30, 2013, 88 pages.
U.S. Response to Notice of Non-Compliant Amendment dated Jan. 18, 2005 for U.S. Appl. No. 10/420,466.
Valle et al., Cisplatin plus Gemcitabine versus Gemcitabine for Biliary Tract Cancer, The New England Journal of Medicine, Apr. 8, 2010 vol. 362, p. 1273-p. 1281.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Van Oers et al., "A simple and fast method for the simultaneous detection of nine fibroblast growth factor receptor 3 mutations in bladder cancer and voided urine," Clin. Cancer Res., 11:7743-7748 (2005).
Varvoglis et al., "Chemical Transformations Induced by Hypervalent Iodine Reagents," Tetrahedron, 1997, 53(4):1179-1255.
Vergote et al., "A phase II trial of lenvatinib in patients with advanced or recurrent endometrial cancer: Angiopoietin-2 as a predictive marker for clinical outcomes.", J. Clin. Oncol, vol. 31, No. 15 supplement, 5520, May 20, 2013, XP002728918.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.
Vianna et al, "The histological rarity of thyroid cancer," Braz J Otorhinolaryngol 78(4):48-51, Jul.-Aug. 2012.
Vieira et al, "Expression of vascular endothelial growth factor (VEGF) and its receptors in thyroid carcinomas of follicular origin: a potential autocrine loop", European Journal of Endocrinology, 2005;153:701-709.
Vippagunta et al., "Crystalline solids," Advanced Drug Delivery Reviews, 48:3-26 (2001).
Vogel et al. "Sensing extracellular matrix: an update on discoidin domain receptor function," Cell Signaling, 18:1108-1116 (2006).
Voluntary Amendment filed in CA Application No. 2704000, filed Aug. 6, 2013, 6 pages.
Voluntary Amendment filed in CA Application No. 2802644, dated Nov. 22, 2013, 25 pages.
Voluntary Amendment filed on Aug. 11, 2010 for CN Application No. 200710007097.9 (with English translation).
Voluntary Amendment filed on Aug. 19, 2010 for CA Application No. 2426461.
Voluntary Amendment filed on Aug. 30, 2006 for AU Application No. 2006203099.
Voluntary Amendment filed on Feb. 16, 2012 for BR Patent App. No. BR112012003592-4 (with partial English translation).
Voluntary Amendment filed on Feb. 21, 2007 for AU Application No. 2006203099.
Voluntary Amendment filed on Feb. 27, 2007 for AU Application No. 2006236039.
Voluntary Amendment filed on Feb. 9, 2010 for AU Application No. 2005283422.
Voluntary Amendment filed on Jul. 6, 2010 for AU Application No. 2005283422.
Voluntary Amendment filed on Sep. 10, 2010 for HU Application No. P0302603 (with English tmnslation).
Voluntary Amendment for Australian Application No. 2010285740, filed on Nov. 21, 2011.
Voluntary Amendment for Chinese counterpart of App. No. PCT/JP2010/063804, filed on Jan. 5, 2012 (with English translation).
Voluntary Amendment for counterpart Canadian patent application, filed on Feb. 16, 2012.
Voluntary Amendment for Russian Application No. 2012103471, filed on Feb. 1, 2012 (with English translation).
Voluntary Amendment for Thailand Application No. 1201000221, filed on Feb. 17, 2012.
Voluntary Amendment in ID Application No. W-00201201031, dated Nov. 5, 2014, 2 pages (with English translation).
Voluntary Amendment in MX Application No. MX/a/2014/010594, dated Oct. 23, 2014, 4 pages (with English translation).
Waaler et al., "Novel Synthetic Antagonists of Canonical Wnt Signaling Inhibit Colorectal Cancer Cell Growth," Cancer Res., 2011, 71:197-205.
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14):2398-2406 (1994) (English abstract).
Wang et al., "KRAS, BRAF, PIK3CA mutations and Pten Expression in Human Colorectal Cancer—Relationship with Metastatic Colorectal Cancer," Ann Oncol., 2010, 21(Supp 6):V164.
Wang et al., "Renal cell carcinoma: diffusion-weighted MR imaging for subtype differentiation at 3.0 T," Radiology, 2010, 257(1):135-143.
Wang et al., "The Role of Angiopoietins as Potential Therapeutic Targets in Renal Cell Carcinoma", Translational Oncology, vol. 7, No. 2, Apr. 1, 2014, p. 188-p. 195, XP055218621.
Wang et al., "A Convenient Set of Bidentate Pyridine Ligands for Combinatorial Synthesis," Tetrahedron Lett., 40:4779-1478 (1999).
Wang et al., "Phase II study of gemcitabine and carboplatin in patients with advanced non-small-cell lung cancer," Cancer Chemother Pharmacol., 60(4):601-607 (2007).

(56) References Cited

OTHER PUBLICATIONS

Wang et al., "The Expression of the Proto-Oncogene C-Kit in the Blast Cells of Acute Myeloblastic Leukemia," Leukemia, 3(10):699-702 (1989).
Wang, "Drugs of Today, Everolimus in renal cell carcinoma," Journals on the Web, Aug. 2010, vol. 46, issue 8, 1 page (abstract only).
Waterman, M., "Computer Analysis of Nucleic Acid Sequences", Methods in Enzymology, 164:765-793 (1988).
Watson et al., "Inhibition of c-Met as a therapeutic strategy for esophageal adenocarcinoma," Neoplasia, 2006, 8(11):949-955.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 24-28, 2001, New Orleans, LA, USA, abstract 3126, 2 pages.
Wells et al., "Targeting the RET Pathway in Thyroid Cancer," Clin. Cancer Res., 15:7119-7123 (2009).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Went et al, "Prevalence of KIT Expression in Hnman Tumor", Journal of Clinical Oncology, Nov. 15, 2004, 4514-4522.
Werner et al., "Gastric adenocarcinoma: pathomorphology and molecular pathology," J. Cancer Res. Clin. Oncology, 127:207-216 (2001) (English abstract).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. and Lipman, DJ., "Rapid similarity searches of nucleic acid and protein data banks", Natl. Acad. Sci, U.S.A. 80:726-730 (1983).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Wirth et al, "Treatment-Emergent Hypertension and Efficacy in the Phase 3 Study of (E7080) Lenvatinib in Differentiated Cancer of the Thyroid (Select)", The Poster, No. 1030P, presented at the European Society for Medical Oncology 2014 Congress, Sep. 26-30, 2014, 1 page.
Wisniewski et al.,"Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Woyach et al., "New therapeutic advances in the management of progressive thyroid cancer," XP055539661, Endocrine-related cancer, 2009, 16(3):715-731.
Wozniak et al., "Randomized trial comparing cisplatin with cisplatin plus vinorelbine in the treatment of advanced non-small-cell lung cancer: a Southwest Oncology Group study," J. Clin. Oncol., 16(7):2459-2465 (1998).
Written Amendment filed on Jun. 16, 2009 for JP Application No. 2009-123432 (with English translation).
Written Amendment filed on Sep. 21, 2011 for JP Application No. 2011-527665 (with English translation).
Written Submission in Indian Patent Application No. 5022/CHENP/2009, dated Aug. 8, 2017, 16 pages (English Translation).
Written Submission regarding hearing in IN Application No. 1571/CHENP/2007 filed on Jan. 23, 2014, 8 pages.
Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Yamada et al, "Phase I Dose-Escalation Study and Biomarker Analysis of E7080 in Patients with Advanced Solid Tumors," Clin Cancer Res 17(8):2528-2537, Mar. 3, 2011.
Yamada et al., "Antitumor and antiangiogenesis activities of E7386, an orally active CBP/β-catenin modulator, as a single agent and in combination with lenvatinib in human HCC xenograft models," Eisai, 2018, 1 page.
Yamada et al., "New technique for staining," Monthly Medical Technology Supplementary Volume (Apr. 1999) (with English translation).
Yamamoto et al., "Plasma biomarkers predictive for disease control duration in the phase I study of E7080, a multitarget kinase inhibitor," ASCO Annual Meeting Proceedings(Post Meeting Edition), Jonrnal of Clinical Oncology, 27:15S, 2009, 1 page.
Yamamoto et al., "E7080 (ER-203492-00), a Novel VEGF Receptor Tyrosine Kinase Inhibitor—III. Significant prolongation of life span in mice transplanted with human ovarian carcinoma based on inhibition of VEGF signaling," Abstract #50, AACR, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, AACR, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, 97th Annual Meeting AACR, Washington, DC. (Apr. 1-5, 2006).
Yamamoto et al., "E7080, an oral multi-targeted tyrosine kinase inhibitor, has direct anti-tumor efficacy via inhibition of KIT signaling in small cell lung cancer," Proceedings of the American Association for Cancer Research,45:1070-1071 (Mar. 2004).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066 (was listed as vol. 38).
Yanagihara et al., "Development and biological analysis of peritoneal metastasis mouse models for human scirrhous stomach cancer," Cancer Sci., 96(6):323-332 (2005).
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yao et al., "AV-65, a novel Wnt/β-catenin signal inhibitor, successfully suppresses progression of multiple myeloma in a mouse model," Blood Cancer J, 2011, 1:e43, 9 pages.

(56) References Cited

OTHER PUBLICATIONS

Yigitbasi et al., "Tumor Cell and Endothelial Cell Therapy of Oral Cancer by Dual Tyrosine Kinase Receptor Blockade", Cancer Research, 64, 7977-7984, 2004.
Yokota, "ASCO report: Gastrointestinal Cancer field/ASCO Hokoku Shokakigan Ryoiki," Gan Bunshi Hyoteki Chiryo, 2010, 8(4):271-283.
Yu, "Amorphous Pharmaceutical Solids:Preparation Characterization and Stabilization," Advanced Drug Delivery Reviews, 48:27-42 (2001) (XP009065056).
Zhang et al., "Stage 1 in vivo evaluation of multi-receptor tyrosine-kinase inhibitor lenvatinib in osteosarcoma patient derived mouse xenograft models", AACR 2017, Abstract 697, Jul. 2017.
Zhang et al., "Induction of apoptosis in EMT-6 breast cancer cell in line by a Sigma-2 selective ligand," Am. Assoc. Cancer Research, Abstract 5353, 2005, 2 pages.
Zhang et al., "Inhibition of both autocrine and paracrine growth and propagation of human myeloid, leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor a in Endothelial Cells of Hepatocellular Carcinoma Associated with High Metastatic Potential," Clin. Cancer Res., 11(24):8557-8563 (2005).
Zhang et al., "Synergic antiproliferative effect of DNA methyltransferase inhibitor in combination with anticancer drugs in gastric carcinoma," Cancer Sci., Sep. 2006, 97(9):938-944.
Zhao et al., "Basics for the design and development of new drugs," Shandong University Press, 2015, p. 93-p. 94 (with English Translation).
Zhong et al., "Mechanisms underlying the synergistic effect of SU5416 and cisplatin on cytotoxicity in human ovarian tumor cells," Inter'l J Oncol., 25(2):445-451, 2001 2004.
Zhou et al., "Correlation Research on VEGF Testing in Primary Gastric Cancer and Clinical Pathology Factor," Journal of Practical Oncology, 20(2):103-105 (Apr. 25, 2006) with English translation.
Zhu et al., "Fibroblast growth factor receptor 3 inhibition by short hairpin RNAs leads to apoptosis in multiple myeloma," Mol. Cancer Ther., 4(5):787-798 (2005).
Zhu et al., "Inhibition of human leukemia in an animal model with human antibodies directed against vascular endothelial growth factor receptor 2. Correlation between antibody affinity and biological activity," Leukemia, 17:604-611 (2003).
Zieger et al., "Role of activating fibroblast growth factor receptor 3 mutations in the development of bladder tumors," Clin. Cancer Res., 11:7709-7719 (2005).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
Zurita et al., "A cytokine and angiogenic factor (CAF) analysis in plasma for selection of sorafenib therapy in patients with metastatic renal cell carcinoma," Annals of Oncology, 23(1):46-52, Apr. 4, 2011.
Zurita et al., "Circulating biomarkers for vascular endothelial growth factor inhibitors in renal cell carcinoma," Cancer 115(S10):2346-2354, May 15, 2009.
International Preliminary Report on Patentability in International Application No. PCT/JP2018/004007, dated Aug. 22, 2019, 7 pages.
Notice of Allowance in Japanese Patent Application No. P2017-535558, dated Jul. 2, 2019, 6 pages (with English Translation).
Notice of Allowance in Japanese Patent Application No. P2018-567437, dated Aug. 27, 2019, 5 pages (with English Translation).
Notice of Allowance in Mexican Patent Application No. MX/a/2015/015605, dated Jul. 24, 2019, 4 pages (with English Translation).
Notice of Allowance in U.S. Appl. No. 15/750,712, dated Jul. 8, 2019, 11 pages.
Notice of Allowance in U.S. Appl. No. 16/229,805, dated Jun. 24, 2019, 10 pages.
Office Action in Australian Patent Application No. 2014266223, dated Jun. 14, 2019, 4 pages.
Office Action in Chinese Patent Application No. 201510031628.2, dated May 27, 2019, 16 pages (with English Translation).
Office Action in Chinese Patent Application No. 201680027234.2, dated Jun. 19, 2019, 9 pages (with English Translation).
Office Action in Gulf Cooperation Council Patent Application No. GC2015-29939, dated Jul. 4, 2019, 9 pages (English Translation).
Office Action in Indian Patent Application No. 1511/CHENP/2009, dated Jul. 31, 2019, 2 pages.
Office Action in Japanese Patent Application No. P2016-545564, dated Aug. 20, 2019, 7 pages (with English Translation).
Office Action in U.S. Appl. No. 15/554,577, dated Jul. 17, 2019, 321 pages.
Office Action in U.S. Appl. No. 15/748,980, dated Jun. 3, 2019, 25 pages.
Office Action in U.S. Appl. No. 16/092,245, dated Aug. 22, 2019, 6 pages.
Official Notification in Indian Patent Application No. 6415/CHENP/2008, dated Jul. 15, 2019, 2 pages.
Submission Document in Argentine Patent Application No. P110100513, dated Aug. 2, 2019, 52 pages (with English Translation).
Submission Document in Brazilian Patent Application No. PI0418200-6, dated Jul. 10, 2019, 16 pages (with English Translation).
Submission Document in Egyptian Patent Application No. PCT 283/2012, dated Jul. 17, 2019, 14 pages (English Translation).
Submission Document in European Patent Application No. 16837135.9, dated Aug. 27, 2019, 21 pages.
Submission Document in European Patent Application No. 16837150.8, dated Aug. 28, 2019, 13 pages.
Submission Document in European Patent Application No. 18197141.7, Aug. 13, 2019, 41 pages.
Submission Document in Indian Patent Application No. 10502/CHENP/2012, dated Jul. 17, 2019, 13 pages.
Submission Document in Indian Patent Application No. 2371/CHENP/2012, dated Aug. 21, 2019, 9 pages.
Submission Document in International Patent Application No. PCT/US2019/031967, dated Jul. 8, 2019, 5 pages.
Submission Document in Japanese Patent Application No. P2018-567437, dated Jul. 30, 2019, 15 pages (with English Translation).
Submission Document in Mexican Patent Application No. MX/a/2015/015605, dated Jun. 25, 2019, 11 pages (with English Translation).
Submission Document in U.S. Appl. No. 15/460,629, dated Aug. 5, 2019, 2 pages.
Submission Document in U.S. Appl. No. 15/554,577, dated Jul. 3, 2019, 35 pages.
Submission Document in U.S. Appl. No. 15/748,980, dated Aug. 23, 2019, 10 pages.
Submission Document in U.S. Appl. No. 15/750,712, dated Jun. 27, 2019, 26 pages.
[No Author], "Study of Pembrolizumab (MK-3475) in Participants With Advanced Solid Tumors (MK-3475-012/KEYNOTE-012)," Apr. 2014, [Retrieved on Feb. 25, 2020], retrieved from, URL<https://clinicaltrials.gov/ct2/show/study/NCT01848834?term=01848834&draw=1&rank=1>, 38 pages.
[No Author], "Highlights of Prescribing Information: Lenvima," U.S. Food and Drug Administration, revised Feb. 2017, 34 pages.
[No Author], "Pharmaceuticals Interview Form: Lenvima" Pharmaceuticals and Medical Devices Agency, Version No. 5, 2018, 248 pages (with English Translation).
[No Author], "Pharmaceuticals Interview Form: Lenvima" Pharmaceuticals and Medical Devices Agency, Version No. 1, 2015, 165 pages (with English Translation).
Amin et al., "Nivolumab (ANTI-PD-1; BMS-936558, ONO-4538) in Combination With Sunitinib or Pazopanib in Patients (PTS) With Metastatic Renal Cell Carcinoma (MRCC)," Abstract, Journal of Clinical Oncology, 2014, 32(15_suppl):5010, 2 pages.
Anzeninfo.mhlw.go.jp [online]. "Report No. 166; Strong Mutagenic Chemical Substance," Ministry of Health, Labor and Welfare of

(56) References Cited

OTHER PUBLICATIONS

Japan, Dec. 11, 2012, retrieved from: URL<https://anzeninfo.mhlw.go.jp/user/anzen/kag/20121211_heni.html>, 46 pages (with Partial Translation).
Baj-Krzyworzeka et al., "Elevated level of some chemokines in plasma of gastric cancer patients," Central European Journal of Immunology, 2016, 41(4):358-362, XP002793963.
Cainap et al., "Linifanib Versus Sorafenib in Patients With Advanced Hepatocellular Carcinoma: Results of a Randomized Phase III Trial," Journal of Clinical Oncology, 2015, 33(2):172-179.
Cheng et al., "Sunitinib Versus Sorafenib in Advanced Hepatocellular Cancer: Results of a Randomized Phase III Trial," Journal of Clinical Oncology, 2013, 31(32):4067-4075.
ClinicalTrials.gov [online], "A Phase 1 Study of BMS-936558 Plus Sunitinib or Pazopanib in Subjects With Metastatic Renal Cell Carcinoma," Nov. 2011, retrieved from: URL<https://clinicaltrials.gov/archive/NCT01472081/2011_11_15>, 4 pages.
ClinicalTrials.gov [online], "A Phase I/II Study to Assess the Safety and Efficacy of Pazopanib and MK 3475 in Subjects With Advanced Renal Cell Carcinoma," Dec. 2013, retrieved from: URL<https://clinicaltrials.gov/archive/NCT02014636/2013_12_17>, 8 pages.
Complete Specification in Indian Patent Application No. 6415/CHENP/2008, "Antitumor Agent for Thyroid Cancer," dated Nov. 24, 2008, 53 pages.
FDA.gov [online], "Prescribing Information of Afinitor (everolimus) tablets for oral administration, Afinitor Disperz (Everolimus Tablets for Oral Suspension)," Feb. 2016, [Retrieved on Jan. 27, 2020], retrieved from: URL<https://www.accessdata.fda.gov/drugsatfda_docs/label/2016/022334s036lbl.pdf>, 44 pages.
FDA.gov [online], "Prescribing Information of Lenvima (lenvatinib) capsules, for oral use," Feb. 2015, [Retrieved on Jan. 27, 2020], retrieved from: URL<https://www.accessdata.fda.gov/drugsatfda_docs/label/2015/206947s000lbl.pdf>, 25 pages.
Ikeda et al., "Phase 2 study of lenvatinib in patients with advanced hepatocellular carcinoma," J. Gastroenterol., 2016, 52:512-519.
Ikeda et al., "Safety and Pharmacokinetics of Lenvatinib in Patients with Advanced Hepatocellular Carcinoma," Clinical Cancer Research, 2015, 22:1385-1394.
International Search Report and Written Opinion in International Application No. PCT/US2019/031967, dated Sep. 17, 2019, 15 pages.
International Search Report and Written Opinion in International Application No. PCT/JP2018/018810, dated Aug. 7, 2018, 7 pages.
Johnson et al., "Brivanib Versus Sorafenib As First-Line Therapy in Patients With Unresectable, Advanced Hepatocellular Carcinoma: Results From the Randomized Phase III BRISK-FL Study," Journal of Clinical Oncology, 2013, 31(28):3517-3524.
Kudo et al., "Lenvatinib versus sorafenib in first-line treatment of patients with unresectable hepatocellular carcinoma: a randomised phase 3 non-inferiority trial," Lancet, 2018, 391:1163-1173.
Llovet et al., "Sorafenib in advanced hepatocellular carcinoma," New England Journal of Medicine, 2008, 359(4):378-390.
Mizushima, "Drug Repositioning," Bio Industry, 2014, 31(11):4-10 (with English Translation).
Motzer et al., "Independent assessment of lenvatinib plus everolimus in patients with metastatic renal cell carcinoma," Lancet Oncol., 2016, 17(1), p. E4-p. E5.
Motzer et al., "Lenvatinib, everolimus, and the combination in patients with metastatic renal cell carcinoma: a randomised, phase 2, open-label, multicentre trial," Lancet Oncol., 2015, 16(15):1473-1482.
Notice of Allowance in Australian Patent Application No. 2015309862, dated Mar. 31, 2020, 3 pages.
Notice of Allowance in Japanese Patent Application No. P2016-545564, dated Feb. 4, 2020, 5 pages (with English Translation).
Notice of Allowance in Pakistani Patent Application No. 94/2011, dated Oct. 21, 2019, 2 pages.
Notice of Allowance in Russian Patent Application No. 2018104697, dated Feb. 3, 2020, 13 pages (with English Translation).
Notice of Allowance in U.S. Appl. No. 14/890,207, dated Aug. 28, 2019, 9 pages.
Notice of Allowance in U.S. Appl. No. 15/750,712, dated Oct. 22, 2019, 10 pages.
Office Action in Argentine Patent Application No. P110100513, dated Nov. 11, 2019, 12 pages (with English Translation).
Office Action in Australian Patent Application No. 2016273230, dated Mar. 3, 2020, 1 page.
Office Action in Brazilian Patent Application No. BR112012003592-4, dated Jan. 28, 2020, 11 pages (with English Translation).
Office Action in Brazilian Patent Application No. PI0906576-08, dated Sep. 10, 2019, 8 pages.
Office Action in Brazilian Patent Application No. PI0906576-08, dated Mar. 17, 2020, 7 pages.
Office Action in Canadian Patent Application No. 2889866, dated Sep. 25, 2019, 5 pages.
Office Action in Chinese Patent Application No. 201580042365.3, dated Feb. 21, 2020, 17 pages (with English Translation).
Office Action in Chinese Patent Application No. 201680009824.2, dated Dec. 18, 2019, 31 pages (with English Translation).
Office Action in Chinese Patent Application No. 201680027234.2, dated Feb. 19, 2020, 7 pages (with English Translation).
Office Action in Chinese Patent Application No. 201680044979.X, dated Mar. 12, 2020, 13 pages (with English Translation).
Office Action in Egyptian Patent Application No. PCT 283/2012, dated Oct. 23, 2019, 10 pages (with English Translation).
Office Action in European Patent Application No. 16755489.8, dated Mar. 19, 2020, 8 pages.
Office Action in European Patent Application No. 16802790.2, dated Sep. 19, 2019, 6 pages.
Office Action in European Patent Application No. 16837150.8, dated Apr. 8, 2020, 3 pages.
Office Action in Gulf Cooperation Council Patent Application No. GC2011-17812, dated Oct. 16, 2019, 9 pages (with English Translation).
Office Action in Indian Patent Application No. 1511/CHENP/2009, dated Nov. 21, 2019, 23 pages.
Office Action in Indian Patent Application No. 201747004829, dated Nov. 6, 2019, 1 page.
Office Action in Indian Patent Application No. 201747028834, dated Feb. 20, 2020, 276 pages.
Office Action in Indian Patent Application No. 201747040368, dated Jan. 3, 2020, 19 pages.
Office Action in Indian Patent Application No. 201847003846, dated Mar. 2, 2020, 27 pages.
Office Action in Indian Patent Application No. 201847003846, dated Mar. 3, 2020, 6 pages (with English Translation).
Office Action in Indian Patent Application No. 201847004787, dated Jan. 30, 2020, 5 pages.
Office Action in Indian Patent Application No. 201847037747, dated Dec. 3, 2019, 25 pages.
Office Action in Indian Patent Application No. 2371/CHENP/2012, dated Jan. 10, 2020, 1 page.
Office Action in Indian Patent Application No. 2371/CHENP/2012, dated Apr. 18, 2020, 190 pages.
Office Action in Indian Patent Application No. 6971/CHENP/2015, dated Sep. 13, 2019, 6 pages (with English Translation).
Office Action in Israeli Patent Application No. 262076, dated Nov. 24, 2019, 5 pages (with English Translation).
Office Action in Israeli Patent Application No. 267159, dated Feb. 5, 2020, 5 pages (with English Translation).
Office Action in Japanese Patent Application No. P2017-502388, dated Dec. 17, 2019, 9 pages (with English Translation).
Office Action in Japanese Patent Application No. P2017-546075, dated Jan. 7, 2020, 6 pages (with English Translation).
Office Action in Japanese Patent Application No. P2017-546133, dated Mar. 10, 2020, 10 pages (with English Translation).
Office Action in Japanese Patent Application No. P2017-560343, dated Mar. 10, 2020, 5 pages (with English Translation).
Office Action in Jordan Patent Application No. 203/2015, dated Mar. 8, 2020, 2 pages (with English Translation).
Office Action in Korean Patent Application No. 10-2015-7009430, dated Dec. 26, 2019, 3 pages (with English Translation).

(56) References Cited

OTHER PUBLICATIONS

Office Action in Korean Patent Application No. 10-2015-7032202, dated Mar. 10, 2020, 11 pages (with English Translation).
Office Action in Mexican Patent Application No. MX/a/2018/001439, dated Dec. 3, 2019, 11 pages (with English Translation).
Office Action in Mexican Patent Application No. MX/a/2018/001658, dated Dec. 6, 2019, 7 pages (with English Translation).
Office Action in New Zealand Patent Application No. 714049, dated Dec. 23, 2019, 2 pages.
Office Action in Russian Patent Application No. 2017139090, dated Nov. 12, 2019, 16 pages (with English Translation).
Office Action in Russian Patent Application No. 2018103737, dated Oct. 11, 2019, 20 pages (with English Translation).
Office Action in Russian Patent Application No. 2018103737, dated Jan. 28, 2020, 16 pages (with English Translation).
Office Action in Russian Patent Application No. 2018104697, dated Oct. 24, 2019, 12 pages (with English Translation).
Office Action in Singaporean Patent Application No. 11201706630U, dated Nov. 5, 2019, 7 pages.
Office Action in Taiwanese Patent Application No. 104127982, dated Dec. 18, 2019, 10 pages (with English Translation).
Office Action in U.S. Appl. No. 15/737,197, dated Feb. 14, 2020, 21 pages.
Office Action in U.S. Appl. No. 13/923,858, dated Feb. 21, 2020, 9 pages.
Office Action in U.S. Appl. No. 15/749,980, dated Nov. 29, 2019, 15 pages.
Office Action in U.S. Appl. No. 15/934,242, dated Jan. 3, 2020, 7 pages.
Office Action in U.S. Appl. No. 16/559,293, dated Dec. 12, 2019, 129 pages.
Official Notification in European Patent Application No. 16755489.8, dated Oct. 30, 2019, 9 pages.
Official Notification in U.S. Appl. No. 16/038,710, dated Dec. 30, 2019, 3 pages.
Ribas et al., "Oncolytic Virotherapy Promotes Intratumoral T Cell Infiltration and Improves Anti-PD-1 Immunotherapy," Cell Elsevier, 2017, 170(6):1109-1119, XP085189788.
Ruiz-Garcia et al., "Gene expression profiling identifies Fibronectin 1 and CXCL9 as candidate biomarkers for breast cancer screening," British Journal of Cancer, 2010, 102(3):462-468, XP055403533.
Sacher et al., "Biomarkers for the Clinical Use of PD-1/PD-L1 Inhibitors in Non-Small-Cell Lung Cancer: A Review," JAMA Oncology, 2016, 2(9):1217-1222, XP055617261.
Search Report in European Patent Application No. 17782552.8 dated Nov. 12, 2019, 4 pages.
Submission Document in Australian Patent Application No. 2015309862, dated Mar. 20, 2020, 28 pages.
Submission Document in Brazilian Patent Application No. BR112012003592-4, dated Apr. 13, 2020, 13 pages (with English Translation).
Submission Document in Brazilian Patent Application No. PI0906576-08, dated Dec. 4, 2019, 124 pages (with English Translation).
Submission Document in Chinese Patent Application No. 201580042365.3, dated Sep. 18, 2019, 26 pages (with English Translation).
Submission Document in Chinese Patent Application No. 201680009824.2, dated Apr. 7, 2020, 28 pages (with English Translation).
Submission Document in Chinese Patent Application No. 201680027234.2, dated Oct. 21, 2019, 19 pages (with English Translation).
Submission Document in Egyptian Patent Application No. PCT 283/2012, dated Jan. 21, 2020, 11 pages (with English Translation).
Submission Document in European Patent Application No. 16802790.2, Jan. 28, 2020, 12 pages.
Submission Document in European Patent Application No. 19151846.3, dated Feb. 10, 2020, 27 pages.
Submission Document in Gulf Cooperation Council Patent Application No. GC2015-29939, dated Sep. 26, 2019, 17 pages (with English Translation).
Submission Document in Gulf Cooperation Council Patent Application No. GC2011-17812, dated Oct. 28, 2019, 3 pages (with English Translation).
Submission Document in Indian Patent Application No. 1511/CHENP/2009, dated Oct. 29, 2019, 83 pages.
Submission Document in Indian Patent Application No. 1511/CHENP/2009, dated Feb. 20, 2020, 49 pages.
Submission Document in Indian Patent Application No. 201747004829, dated Feb. 4, 2020, 24 pages.
Submission Document in Indian Patent Application No. 2371/CHENP/2012, dated Mar. 24, 2020, 121 pages.
Submission Document in Indian Patent Application No. 6971/CHENP/2015, dated Mar. 4, 2020, 10 pages.
Submission Document in Israeli Patent Application No. 255564, dated Dec. 9, 2019, 16 pages (with English Translation).
Submission Document in Japanese Patent Application No. P2016-545564, dated Dec. 19, 2019, 23 pages (with English Translation).
Submission Document in Mexican Patent Application No. MX/a/2018/001658, dated Jan. 8, 2020, 5 pages (with English Translation).
Submission Document in Mexican Patent Application No. MX/a/2018/001439, dated Feb. 4, 2020, 10 pages (with English Translation).
Submission Document in New Zealand Patent Application No. 714049, dated Dec. 16, 2019, 13 pages.
Submission Document in New Zealand Patent Application No. 714049, dated Mar. 18, 2020, 1 page.
Submission Document in Russian Patent Application No. 2017128583, dated Mar. 13, 2020, 18 pages (with English Translation).
Submission Document in Russian Patent Application No. 2017139090, dated Feb. 6, 2020, 13 pages (with English Translation).
Submission Document in Russian Patent Application No. 2018103737, dated Dec. 26, 2019, 10 pages (with English Translation).
Submission Document in Russian Patent Application No. 2018104697, dated Jan. 20, 2020, 8 pages (with English Translation).
Submission Document in Singaporean Patent Application No. 11201709335X, dated Sep. 19, 2019, 5 pages.
Submission Document in Singaporean Patent Application No. 11201706630U, dated Feb. 17, 2020, 12 pages.
Submission Document in Singaporean Patent Application No. 11201801083U, dated Jan. 6, 2020, 10 pages.
Submission Document in Singaporean Patent Application No. 11201904020S, dated Jan. 31, 2020, 14 pages.
Submission Document in Sri Lankan Patent Application No. 16523, dated Oct. 10, 2019, 3 pages.
Submission Document in Taiwanese Patent Application No. 104127982, dated Oct. 30, 2019, 26 pages (with English Translation).
Submission Document in Taiwanese Patent Application No. 104127982, dated Feb. 10, 2020, 6 pages (with English Translation).
Submission Document in U.S. Appl. No. 13/923,858, dated Sep. 5, 2019, 11 pages.
Submission Document in U.S. Appl. No. 13/923,858, dated Oct. 28, 2019, 2 pages.
Submission Document in U.S. Appl. No. 15/750,712, dated Oct. 7, 2019, 15 pages.
Submission Document in U.S. Appl. No. 15/750,712, dated Jan. 17, 2020, 18 pages.
Submission Document in U.S. Appl. No. 16/038,710, dated Oct. 22, 2019, 46 pages.
Submission Document in U.S. Appl. No. 16/038,710, dated Jan. 30, 2020, 3 pages.
Submission Document in U.S. Appl. No. 16/092,245, dated Jan. 22, 2020, 17 pages.
Tahara et al., "Exploratory analysis of biomarkers associated with clinical outcomes from the study of lenvatinib in differentiated cancer of the thyroid," European Journal of Cancer, 2017, 75:213-221, XP029959213.
Tass.ru [online], "Combination of lenvatinib with everolimus increases progression-free survival in subjects with renal cell carcinoma,"

(56) References Cited

OTHER PUBLICATIONS

Jun. 2015, [Retrieved on Oct. 17, 2019], retrieved from: URL<https://tass.ru/press-relizy/2010118>, 20 pages (with English Translation).
Taylor et al., "A phase 1 trial of lenvatinib plus pembrolizumab in patients with selected solid tumors," Annals of Oncology, 2006, 27:XP002793962, 1 page.
Yang et al., "Improvement of Sirolimus Oral Dosing Method," Journal of Nursing Science (Surgery Edition), 2009, 24(18), 2 pages (with Partial Translation).
Yoshikawa et al., "Clinicopathological and prognostic significance of EGFR, VEGF, and HER2 expression in cholangiocarcinoma," XP002789353, British Journal of Cancer, 2008, 98(2):418-425.
Zhu et al., "SEARCH: A Phase III, Randomized, Double-Blind, Placebo-Controlled Trial of Sorafenib Plus Erlotinib in Patients With Advanced Hepatocellular Carcinoma," Journal of Clinical Oncology, 2015, 33(6):559-566.
[No Author], "Unique Protocol ID: E7080-G000-207; Phase 1/2 Study of Lenvatinib in Children and Adolescents with Refractory or Relapsed Solid Malignancies and Young Adults with Osteosarcoma," ClinicalTrials.gov PRS, results summary NIH resolution Review 1, Last Update: Aug. 10, 2020, 117 pages.
Notice of Allowance in Australian Patent Application No. 2014266223, dated Jun. 10, 2020, 3 pages.
Notice of Allowance in Brazilian Patent Application No. BR112012003592-4, dated Jun. 9, 2020, 2 pages (with English Translation).
Notice of Allowance in European Patent Application No. 16802790.2, dated Aug. 14, 2020, 35 pages.
Notice of Allowance in European Patent Application No. 18197141.7, dated Jun. 25, 2020, 83 pages.
Notice of Allowance in Israeli Patent Application No. 257433, dated Jul. 21, 2020, 8 pages (with English Translation).
Notice of Allowance in Japanese Patent Application No. P2017-560343, dated Aug. 4, 2020, 5 pages (with English Translation).
Notice of Allowance in New Zealand Patent Application No. 714049, dated May 21, 2020, 1 page.
Notice of Allowance in Russian Patent Application No. 2018103737, dated May 22, 2020, 12 pages (with English Translation).
Notice of Allowance in U.S. Appl. No. 15/750,712, dated Jul. 22, 2020, 12 pages.
Notice of Allowance in U.S. Appl. No. 16/038,710, dated Jun. 30, 2020, 32 pages.
Notice of Allowance in U.S. Appl. No. 16/559,293, dated Jun. 16, 2020, 5 pages.
Office Action in Argentine Patent Application No. P110100513, dated Jul. 23, 2020, 6 pages (with English Translation).
Office Action in Argentine Patent Application No. P20150102731, dated Jun. 10, 2020, 6 pages (with English Translation).
Office Action in Australian Patent Application No. 2016224583, dated Jun. 30, 2020, 4 pages.
Office Action in Brazilian Patent Application No. BR112013021941-6, dated May 26, 2020, 4 pages (with English Translation).
Office Action in Canadian Patent Application No. 2912219, dated Aug. 31, 2020, 4 pages.
Office Action in Chinese Patent Application No. 201680009824.2, dated Jun. 3, 2020, 26 pages (with English Translation).
Office Action in Chinese Patent Application No. 201680046598.5, dated Mar. 23, 2020, 17 pages (with English Translation).
Office Action in Chinese Patent Application No. 201680046598.5, dated Aug. 14, 2020, 8 pages (with English Translation).
Office Action in Chinese Patent Application No. 201780020786.5, dated Apr. 17, 2020, 19 pages (with English Translation).
Office Action in Egyptian Patent Application No. D1 PCT 283/2012, dated Apr. 29, 2020, 6 pages (with English Translation).
Office Action in Egyptian Patent Application No. PCT 283/2012, dated May 4, 2020, 10 pages (with English Translation).
Office Action in European Patent Application No. 16802790.2, dated Apr. 1, 2020, 6 pages.
Office Action in European Patent Application No. 19151846.3, dated Jul. 22, 2020, 5 pages.
Office Action in Gulf Cooperation Council Patent Application No. GC2015-29939, dated Apr. 8, 2020, 9 pages (with English Translation).
Office Action in Indian Patent Application No. 1511/CHENP/2009, dated Aug. 11, 2020, 3 pages (with English Translation).
Office Action in Indian Patent Application No. 201847004787, dated Jul. 10, 2020, 2 pages (with English Translation).
Office Action in Indian Patent Application No. 2371/CHENP/2012, dated May 21, 2020, 191 pages.
Office Action in Israeli Patent Application No. 257292, dated May 14, 2020, 7 pages (with English Translation).
Office Action in Israeli Patent Application No. 257433, dated Apr. 1, 2020, 5 pages (with English Translation).
Office Action in Israeli Patent Application No. 270317, dated Aug. 23, 2020, 5 pages (with English Translation).
Office Action in Japanese Patent Application No. P2017-502388, dated Jun. 2, 2020, 6 pages (with English Translation).
Office Action in Japanese Patent Application No. P2017-535551, dated Jun. 16, 2020, 8 pages (with English Translation).
Office Action in Japanese Patent Application No. P2017-546075, dated Jul. 21, 2020, 5 pages (with English Translation).
Office Action in Jordan Patent Application No. 203/2015, dated Jul. 26, 2020, 2 pages (with English Translation).
Office Action in Mexican Patent Application No. MX/a/2017/010474, dated Aug. 11, 2020, 8 pages (with English Translation).
Office Action in Mexican Patent Application No. MX/a/2018/001439, dated Jul. 23, 2020, 8 pages (with English Translation).
Office Action in Mexican Patent Application No. MX/a/2018/001658, dated Jul. 13, 2020, 6 pages (with English Translation).
Office Action in Mexican Patent Application No. MX/a/2018/012193, dated Jul. 15, 2020, 8 pages (with English Translation).
Office Action in New Zealand Patent Application No. 714049, dated Apr. 23, 2020, 1 page.
Office Action in Russian Patent Application No. 2017104496, dated Jun. 23, 2020, 9 pages (with English Translation).
Office Action in Russian Patent Application No. 2017128583, dated Apr. 30, 2020, 19 pages (with English Translation).
Office Action in Russian Patent Application No. 2017139090, dated Apr. 2, 2020, 10 pages (with English Translation).
Office Action in Russian Patent Application No. 2018134943, dated May 26, 2020, 16 pages (with English Translation).
Office Action in U.S. Appl. No. 15/573,197, dated Feb. 14, 2020, 21 pages.
Office Action in U.S. Appl. No. 13/923,858, dated Aug. 27, 2020, 25 pages.
Office Action in U.S. Appl. No. 15/554,577, dated May 1, 2020, 38 pages.
Office Action in U.S. Appl. No. 15/748,980, dated Aug. 6, 2020, 150 pages.
Office Action in U.S. Appl. No. 15/748,980, dated Nov. 29, 2019, 15 pages.
Office Action in U.S. Appl. No. 15/934,242, dated Jun. 15, 2020, 6 pages.
Office Action in U.S. Appl. No. 16/092,245, dated Apr. 30, 2020, 7 pages.
Official Notification in U.S. Appl. No. 15/748,980, dated Jun. 23, 2020, 3 pages.
Oikonomopoulos et al., "Lenvatinib: a potential breakthrough in advanced hepatocellular carcinoma?," Future Oncology, 2016, 12(4):465-476.
Submission Document in Argentine Patent Application No. P110100513, dated Apr. 6, 2020, 21 pages (with English Translation).
Submission Document in Australian Patent Application No. 2014266223, dated May 22, 2020, 14 pages.
Submission Document in Australian Patent Application No. 2015309862, dated Jul. 3, 2020, 30 pages.
Submission Document in Brazilian Patent Application No. PI0906576-08, dated May 28, 2020, 61 pages (with English Translation).
Submission Document in Chinese Patent Application No. 201580042365.3, dated Jul. 6, 2020, 170 pages (with English Translation).

(56) References Cited

OTHER PUBLICATIONS

Submission Document in Chinese Patent Application No. 201680027234.2, dated Apr. 29, 2020, 16 pages (with English Translation).
Submission Document in Chinese Patent Application No. 201680044979.X, dated Jul. 3, 2020, 14 pages (with English Translation).
Submission Document in Chinese Patent Application No. 201880028701.2, dated Jun. 4, 2020, 110 pages (with English Translation).
Submission Document in Egyptian Patent Application No. D1 PCT 283/2012, dated Jul. 20, 2020, 17 pages (with English Translation).
Submission Document in European Patent Application No. 16755489.8, dated Jul. 16, 2020, 5 pages.
Submission Document in European Patent Application No. 16837150.8, dated Aug. 7, 2020, 6 pages.
Submission Document in European Patent Application No. 17782552.8, dated Jun. 5, 2020, 4 pages.
Submission Document in Indian Patent Application No. 201747004829, dated Apr. 16, 2020, 29 pages.
Submission Document in Indian Patent Application No. 201747028834, dated May 13, 2020, 21 pages.
Submission Document in Indian Patent Application No. 201847003846, dated May 29, 2020, 39 pages.
Submission Document in Israeli Patent Application No. 267159, dated May 28, 2020, 4 pages (with English Translation).
Submission Document in Japanese Patent Application No. P2017-502388, dated Apr. 3, 2020, 13 pages (with English Translation).
Submission Document in Japanese Patent Application No. P2017-502388, dated Jul. 17, 2020, 9 pages (with English Translation).
Submission Document in Korean Patent Application No. 10-2015-7032202, dated May 19, 2020, 23 pages (with English Translation).
Submission Document in Russian Patent Application No. 2017104496, dated Apr. 24, 2020, 42 pages (with English Translation).
Submission Document in Russian Patent Application No. 2017139090, dated Jul. 2, 2020, 14 pages (with English Translation).
Submission Document in Russian Patent Application No. 2018103737, dated Apr. 3, 2020, 9 pages (with English Translation).
Submission Document in U.S. Appl. No. 13/923,858, dated May 13, 2020, 8 pages.
Submission Document in U.S. Appl. No. 15/573,197, dated Jun. 15, 2020, 21 pages.
Submission Document in U.S. Appl. No. 15/934,242, dated Apr. 22, 2020, 6 pages.
Submission Document in U.S. Appl. No. 16/559,293, dated Jun. 2, 2020, 9 pages.
Xu et al., "Research on novelty issue of method claims including use feature, " Paper of IP Forum of 5th Annual Conference of ACPAA, Part III, 20140401, pp. 1-5 (with Full English Translation).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, Sep. 2014, 6(1), 19 pages.
De Araujo et al., "Polymorphism in drug production," Journal of Basic and Applied Pharmaceutical Sciences—Revista de Ciências Farmacêuticas Básica e Aplicada, Dec. 6, 2019, pp. 27-36 (with English Translation).
Examination Decision and Determination in Chinese Patent Application No. 201380034056.2, dated Jun. 10, 2019, 18 pages (with English Translation).
Notice of Allowance in Israeli Patent Application No. 255564, dated Dec. 1, 2020, 8 pages (with English Translation).
Notice of Allowance in Japanese Patent Application No. P2017-502388, dated Nov. 4, 2020, 5 pages (with English Translation).
Notice of Allowance in Japanese Patent Application No. P2017-546133, dated Oct. 6, 2020, 8 pages (with English Translation).
Notice of Allowance in Korean Patent Application No. 10-2015-7032202, dated Oct. 21, 2020, 3 pages (with English Translation).
Notice of Allowance in Mexican Patent Application No. MX/a/2018/001439, dated Nov. 13, 2020, 6 pages.
Notice of Allowance in Singaporean Patent Application No. 11201700855X, dated Nov. 26, 2020, 4 pages.
Office Action in Brazilian Patent Application No. PI0418200-6, dated Jul. 28, 2020, 60 pages (with English Translation).
Office Action in Brazilian Patent Application No. PI0906576-08, dated Oct. 27, 2020, 6 pages (with English Translation).
Office Action in Brazilian Patent Application No. PI0906576-08, dated Oct. 28, 2020, 6 page (with English Translation).
Office Action in Canadian Patent Application No. 2957005, dated Oct. 15, 2020, 4 pages.
Office Action in Chinese Patent Application No. 201580042365.3, dated Oct. 30, 2020, 13 pages (with English Translation).
Office Action in Chinese Patent Application No. 201680009824.2, dated Sep. 27, 2020, 14 pages (with English Translation).
Office Action in Chinese Patent Application No. 201680027234.2, dated Sep. 27, 2020, 12 pages (with English Translation).
Office Action in Chinese Patent Application No. 201680044979.X, dated Oct. 13, 2020, 9 pages (with English Translation).
Office Action in European Patent Application No. 16837135.9, dated Sep. 28, 2020, 4 pages.
Office Action in Indian Patent Application No. 201847037747, dated Sep. 9, 2020, 5 pages (with English Translation).
Office Action in Indian Patent Application No. 7026/CHENP/2013, dated Sep. 18, 2020, 16 pages.
Office Action in Mexican Patent Application No. MX/a/2019/006504, dated Sep. 3, 2020, 10 pages (with English Translation).
Office Action in Russian Patent Application No. 2017139090, dated Sep. 1, 2020, 9 pages (with English Translation).
Office Action in Russian Patent Application No. 2018134943, dated Nov. 23, 2020, 13 pages (with English Translation).
Office Action in U.S. Appl. No. 15/554,577, dated Nov. 23, 2020, 51 pages.
Office Action in U.S. Appl. No. 16/092,245, dated Oct. 7, 2020, 6 pages.
Official Notification in Indian Patent Application No. 201847037747, dated Sep. 9, 2020, 28 pages.
Search Report in European Patent Application No. 18751614.1, dated Nov. 5, 2020, 8 pages.
Submission Document in Argentine Patent Application No. P20150102731, dated Oct. 7, 2020, 67 pages (with English Translation).
Submission Document in Brazilian Patent Application No. PI0418200-6, dated Oct. 20, 2020, 112 pages (with English Translation).
Submission Document in Canadian Patent Application No. 2978226, dated Sep. 21, 2020, 12 pages.
Submission Document in Chinese Patent Application No. 201680009824.2, dated Nov. 20, 2020, 49 pages (with English Translation).
Submission Document in Chinese Patent Application No. 201680027234.2, dated Dec. 7, 2020, 39 pages (with English Translation).
Submission Document in Chinese Patent Application No. 201680044979.X, dated Dec. 7, 2020, 10 pages (with English Translation).
Submission Document in Chinese Patent Application No. 201680046598.5, dated Oct. 13, 2020, 9 pages (with English Translation).
Submission Document in European Patent Application No. 18751614.1, dated Dec. 18, 2020, 6 pages.
Submission Document in European Patent Application No. 19151846.3, dated Nov. 17, 2020, 9 pages.
Submission Document in Indian Patent Application No. 201847004787, dated Aug. 21, 2020, 6 pages.
Submission Document in Indian Patent Application No. 2371/CHENP/2012, dated Aug. 19, 2020, 39 pages.
Submission Document in Israeli Patent Application No. 253946, dated Dec. 10, 2020, 5 pages (with English Translation).
Submission Document in Israeli Patent Application No. 262076, Request for Delayed Examination, dated Sep. 22, 2020, 3 pages (with English Translation).
Submission Document in Israeli Patent Application No. 262076, Section 18 Requirements, dated Sep. 22, 2020, 4 pages (with English Translation).

(56) References Cited

OTHER PUBLICATIONS

Submission Document in Israeli Patent Application No. 270317, dated Dec. 16, 2020, 14 pages (with English Translation).
Submission Document in Japanese Patent Application No. P2017-535551, dated Aug. 12, 2020, 8 pages (with English Translation).
Submission Document in Korean Patent Application No. 10-2017-7027616, dated Oct. 20, 2020, 18 pages (with English Translation).
Submission Document in Mexican Patent Application No. MX/a/2017/010474, dated Oct. 8, 2020, 21 pages (with English Translation).
Submission Document in Mexican Patent Application No. MX/a/2018/001439, dated Sep. 24, 2020, 10 pages (with English Translation).
Submission Document in Mexican Patent Application No. MX/a/2019/006504, dated Oct. 23, 2020, 14 pages (with English Translation).
Submission Document in Russian Patent Application No. 2018134943, dated Sep. 24, 2020, 46 pages (with English Translation).
Submission Document in U.S. Appl. No. 13/923,858, dated Nov. 4, 2020, 6 pages.
Submission Document in U.S. Appl. No. 15/554,577, dated Aug. 31, 2020, 21 pages.
Submission Document in U.S. Appl. No. 15/748,980, dated Oct. 28, 2020, 8 pages.
Submission Document in U.S. Appl. No. 15/750,712, dated Oct. 20, 2020, 53 pages.
Submission Document in U.S. Appl. No. 15/934,242, dated Dec. 9, 2020, 13 pages.
Submission Document in U.S. Appl. No. 17/022,675, dated Sep. 16, 2020, 85 pages.
Submission Document in U.S. Appl. No. 17/022,675, dated Oct. 20, 2020, 10 pages.
Notice of Allowance in Australian Patent Application No. 2016224583, dated May 20, 2021, 3 pages.
Notice of Allowance in Australian Patent Application No. 2016309356, dated Jun. 10, 2021, 4 pages.
Notice of Allowance in Mexican Patent Application No. MX/a/2017/010474, dated Jun. 14, 2021, 5 pages (with English Translation).
Notice of Allowance in Singaporean Patent Application No. 11201801083U, dated Aug. 16, 2021, 4 pages.
Office Action in Chinese Patent Application No. 201880005026.1, dated Jul. 29, 2021, 10 pages (with English Translation).
Office Action in U.S. Appl. No. 17/228,025, dated Aug. 18, 2021, 5 pages.
Submission Document in Mexican Patent Application No. MX/a/2017/001980, dated Jul. 30, 2021, 19 pages (with English Translation).
Submission Document in U.S. Appl. No. 15/750,712, dated Jul. 26, 2021, 5 pages.
Office Action in Gulf Cooperation Council Patent Application No. GC2015-40053, dated Jun. 20, 2021, 6 pages (with English Translation).
Submission Document in Brazilian Patent Application No. PI0418200-6, dated Jun. 14, 2021, 10 pages (with English Translation).
Decision to Grant Patent in European Patent Application No. 16811667.1, dated Jul. 1, 2021, 3 pages.
Decision to Grant Patent in Russian Patent Application No. 2018100944, dated Jun. 19, 2020, 10 pages (with English Translation).
Intimation of Grant in Indian Patent Application No. 201847001060, dated Feb. 18, 2021, 2 pages (with English Translation).
Notice of Allowance in European Patent Application No. 16811667.1, dated Jan. 13, 2021, 28 pages.
Office Action in Australian Patent Application No. 2016279474, dated Feb. 12, 2021, 5 pages.
Submission Document in Australian Patent Application No. 2016279474, dated Jan. 21, 2021, 10 pages.
Submission Document in Chinese Patent Application No. 201680035322.7, dated Jan. 18, 2021,11 pages (with English Translation).
Submission Document in European Patent Application No. 16811667.1, dated Jul. 25, 2019, 7 pages.
Submission Document in European Patent Application No. 16811667.1, dated Aug. 24, 2020, 40 pages.
Submission Document in Indian Patent Application No. 201847001060, dated Feb. 3, 2021, 9 pages.
Submission Document in Israeli Patent Application No. 256148, dated Dec. 22, 2020, 12 pages (with English Translation).
Submission Document in Mexican Patent Application No. MX/a/2018/012193, dated Jul. 1, 2021, 48 pages (with English Translation).
Submission Document in Russian Patent Application No. 2018100944, dated Jun. 4, 2020, 9 pages (with English Translation).
Submission Document in Singaporean Patent Application No. 11201710198Y, dated Dec. 8, 2020, 6 pages.
Submission Document in U.S. Appl. No. 16/809,301, dated Jun. 22, 2021, 6 pages.
Boulter et al., "WNT signaling drives cholangiocarcinoma growth and can be pharmacologically inhibited," J Clin Invest, 125(3): 1269-85 (Mar. 2, 2015).
Driessens et al., "β-Catenin Inhibits T Cell Activation by Selective Interference with Linker for Activation of T Cells-Phospholipase C-γ1 Phosphorylation," J Immunol, 186:784-790 (2011).
El-Khouelry et al., "A phase I first-in-human study of PRI-724 in patients (pts) with advanced solid tumors," J Clin Oneal, 31: suppl; abstr 2501 (2013).
Grigson et al., "Canonical Wnt Pathway Inhibitor ICG-001 Induces Cytotoxicity of Multiple Myeloma Cells in Wnt-Independent Manner, " PLOS One, 2015, 10(1), e0117693, 15 pages.
International Search Report and Written Opinion in International Application No. PCT/US2020/057650, dated Feb. 12, 2021, 16 pages.
Kim et al., "Combining targeted therapy and immune checkpoint inhibitors in the treatment of metastatic melanoma," Cancer Biol. Med., 11(4):237-246 (Dec. 2014).
Kondo, "Molecular Target Drugs for Renal Cell Carcinoma—Angiogenesis Inhibitor; The role of VEGFR-TKI's in the treatment of renal cell carcinoma, " The Japanese Journal of Nephrology, 2012, 54(5):574-580 (with English Translation).
Lenz et al., "Safely targeting cancer stem cells via selective catenin coactivator antagonism," Cancer Sci., 105(9):1087-1092 (Sep. 2014).
Leonetti et al., "Clinical use of lenvatinib in combination with everolimus for the treatment of advanced renal cell carcinoma," Therapeutics and Clinical Risk Management, 2017, 13:799-806.
Mahoney et al., "The Next Immune-Checkpoint Inhibitors: PD-1/PD-L1 Blockade in Melanoma," Clin. Ther., 37(4):764-782 (Apr. 2015).
Miyuki Azuma, Journal of Clinical and Experimental Medicine, 2013.03.02 Vol.244, No. 9, p. 809-815 (with partial English translation).
Notice of Allowance in Canadian Patent Application No. 2912219, dated May 18, 2021, 1 page (with English Translation).
Notice of Allowance in Chinese Patent Application No. 201680027234.2, dated Jan. 28, 2021, 4 pages (with English Translation).
Notice of Allowance in Chinese Patent Application No. 201680046598.5, dated Dec. 31, 2020, 4 pages (with English Translation).
Notice of Allowance in European Patent Application No. 16837150.8, dated Feb. 11, 2021, 27 pages.
Notice of Allowance in Mexican Patent Application No. MX/a/2018/001658, dated Mar. 2, 2021, 5 pages (with English Translation).
Notice of Allowance in Mexican Patent Application No. MX/a/2019/006504, dated Jan. 13, 2021, 6 pages (with English Translation).
Notice of Allowance in Russian Patent Application No. 2017139090, dated Jan. 25, 2021, 8 pages.
Notice of Allowance in Taiwanese Patent Application No. 104127982, dated Jan. 26, 2021, 5 pages (with English Translation).
Notice of Allowance in U.S. Appl. No. 15/750,712, dated Jan. 13, 2021, 19 pages.
Notice of Allowance in U.S. Appl. No. 15/750,712, dated Apr. 30, 2021, 14 pages.

(56) References Cited

OTHER PUBLICATIONS

Notice of Allowance in U.S. Appl. No. 16/038,710, dated Jan. 6, 2021, 16 pages.
Notice of Opposition in Indian Patent Application No. 201747040368, dated Dec. 31, 2020, 1 page.
Office Action and Search Report in Chinese Patent Application No. 201680035322.7, dated Apr. 3, 2020, 10 pages (with English Translation).
Office Action and Search Report in Russian Patent Application No. 2018100944, dated Dec. 17, 2019, 12 pages (with English Translation).
Office Action in Australian Patent Application No. 2016224583, dated Mar. 30, 2021, 4 pages.
Office Action in Australian Patent Application No. 2016279474, dated Sep. 21, 2020, 6 pages.
Office Action in Australian Patent Application No. 2016308390, dated Feb. 2, 2021, 5 pages.
Office Action in Australian Patent Application No. 2016309356, dated Feb. 3, 2021, 4 pages.
Office Action in Brazilian Patent Application No. BR112012032462-4, dated Jan. 19, 2021, 3 pages (with English Translation).
Office Action in Brazilian Patent Application No. BR112012032462-4, dated Jan. 26, 2021, 8 pages (with English Translation).
Office Action in Brazilian Patent Application No. PI0418200-6, dated Apr. 27, 2021, 29 pages (with English Translation).
Office Action in Canadian Patent Application No. 2957005, dated Apr. 9, 2021, 4 pages.
Office Action in Chinese Patent Application No. 201580042365.3, dated Mar. 12, 2021, 67 pages (with English Translation).
Office Action in Chinese Patent Application No. 201680009824.2, dated Jan. 12, 2021, 15 pages (with English Translation).
Office Action in Chinese Patent Application No. 201680035322.7, dated Nov. 3, 2020, 7 pages (with English Translation).
Office Action in Chinese Patent Application No. 201680044979.X, dated Mar. 25, 2021, 8 pages (with English Translation).
Office Action in European Patent Application No. 16755489.8, dated May 14, 2021, 9 pages.
Office Action in European Patent Application No. 16811667.1, dated Jun. 24, 2020, 5 pages.
Office Action in European Patent Application No. 16837135.9, dated May 10, 2021, 4 pages.
Office Action in European Patent Application No. 17782552.8, dated Mar. 16, 2021, 4 pages.
Office Action in Gulf Cooperation Council Patent Application No. GC2015-40053, dated Jan. 26, 2021, 9 pages (with English Translation).
Office Action in Indian Patent Application No. 201747040368, dated Dec. 31, 2020, 8 pages (with English Translation).
Office Action in Indian Patent Application No. 201847001060, dated Aug. 5, 2020, 7 pages (with English translation).
Office Action in Indian Patent Application No. 201947022655, dated Jan. 19, 2021, 5 pages (with English Translation).
Office Action in Indian Patent Application No. 2371/CHENP/2012, dated Jan. 4, 2021, 1 page.
Office Action in Israeli Patent Application No. 256148, dated Sep. 8, 2020, 6 pages (with English Explanation).
Office Action in Israeli Patent Application No. 257292, dated Jan. 27, 2021, 8 pages (with English Translation).
Office Action in Japanese Patent Application No. P2017-525268, dated Mar. 31, 2020, 10 pages (with Machine Translation).
Office Action in Japanese Patent Application No. P2017-535551, dated Dec. 15, 2020, 6 pages (with English Translation).
Office Action in Japanese Patent Application No. P2017-546075, dated Mar. 23, 2021, 8 pages (with English Translation).
Office Action in Japanese Patent Application No. P2018-552092, dated Feb. 2, 2021, 10 pages (with English Translation).
Office Action in Japanese Patent Application No. P2018-552092, dated May 11, 2021, 10 pages (with English Translation).
Office Action in Jordan Patent Application No. 203/2015, dated Dec. 28, 2020, 2 pages (with English Translation).
Office Action in Jordan Patent Application No. 225/2020, dated Jan. 5, 2021, 2 pages (with English Translation).
Office Action in Korean Patent Application No. 10-2017-7003226, dated Dec. 9, 2020, 15 pages (with English Translation).
Office Action in Mexican Patent Application No. MX/a/2017/010474, dated Nov. 27, 2020, 8 pages (with English Translation).
Office Action in Mexican Patent Application No. MX/a/2017/010474, dated Apr. 16, 2021, 10 pages (with English Translation).
Office Action in Mexican Patent Application No. MX/a/2017/014540, dated Feb. 8, 2021, 15 pages (with English Translation).
Office Action in Mexican Patent Application No. MX/a/2017/015896, dated Oct. 15, 2019, 6 pages (with English Translation).
Office Action in Mexican Patent Application No. MX/a/2018/012193, dated Feb. 23, 2021, 10 pages (with English Translation).
Office Action in Russian Patent Application No. 2019120680, dated Dec. 28, 2020, 18 pages (with English Translation).
Office Action in Russian Patent Application No. 2019120680, dated May 12, 2021, 13 pages (with English Translation).
Office Action in Singaporean Patent Application No. 11201706630U, dated Feb. 8, 2021, 7 pages.
Office Action in Singaporean Patent Application No. 11201904020S, dated May 19, 2021, 5 pages.
Office Action in Thai Patent Application No. 0401005163, dated Dec. 15, 2020, 14 pages (with English Translation).
Office Action in U.S. Appl. No. 13/923,858, dated Dec. 14, 2020, 9 pages.
Office Action in U.S. Appl. No. 15/573,197, dated May 13, 2021, 30 pages.
Office Action in U.S. Appl. No. 15/748,980, dated Apr. 2, 2021, 25 pages.
Office Action in U.S. Appl. No. 15/934,242, dated Jan. 26, 2021, 18 pages.
Office Action in U.S. Appl. No. 16/609,895, dated Feb. 22, 2021, 143 pages.
Office Action in U.S. Appl. No. 16/809,301. dated Mar. 22, 2021, 10 pages.
Office Action in U.S. Appl. No. 17/228,025, dated Jun. 4, 2021, 3 pages.
Official Notification in Brazilian Patent Application No. PI0418200-6, dated Jan. 26, 2021, 28 pages (with English Translation).
Official Notification in Indian Patent Application No. 1511/CHENP/2009, dated Feb. 1, 2021, 6 pages.
Search Report in European Patent Application No. 16811667.1, dated Jan. 16, 2019, 8 pages.
Search Report in European Patent Application No. 18801285.0, dated Jan. 20, 2021, 6 pages.
Search Report in European Patent Application No. 20207489.4, dated Mar. 10, 2021, 7 pages.
Shah et al., "CTLA-4 is a direct target of Wnt/β-catenin signaling and is expressed in human melanoma tumors," Journal of Investigative Dermatology, 2008, 128(12):2870-2879.
Spranger et al., "Melanoma-intrinsic β-catenin signalling prevents anti-tumour immunity," Nature, 231-235 (May 11, 2015) doi: 10.1038/nature 14404.
Submission Document in Australian Patent Application No. 2016224583, dated Mar. 2, 2021, 53 pages.
Submission Document in Australian Patent Application No. 2016224583, dated May 11, 2021, 7 pages.
Submission Document in Australian Patent Application No. 2016308390, dated May 11, 2021, 9 pages.
Submission Document in Australian Patent Application No. 2016309356, dated Apr. 27, 2021, 7 pages.
Submission Document in Australian Patent Application No. 2017249459, dated Mar. 17, 2021, 36 pages.
Submission Document in Brazilian Patent Application No. BR112012032462-4, dated Apr. 16, 2021, 29 pages (with English Translation).
Submission Document in Brazilian Patent Application No. BR1120190141278, dated Dec. 16, 2020, 16 pages (with English Translation).
Submission Document in Brazilian Patent Application No. BR1120190230645, dated Apr. 28, 2021. 148 pages (with English Translation).

(56) References Cited

OTHER PUBLICATIONS

Submission Document in Canadian Patent Application No. 2957005, dated Feb. 8, 2021, 19 pages.
Submission Document in Canadian Patent Application No. 2957005, dated May 12, 2021, 16 pages.
Submission Document in Chinese Patent Application No. 201580042365.3, dated Apr. 27, 2021, 22 pages (with English Translation).
Submission Document in Chinese Patent Application No. 201680027234.2, dated Dec. 25, 2020, 12 pages (with English Translation).
Submission Document in European Patent Application No. 16837135.9, dated Jan. 20, 2021, 6 pages.
Submission Document in Gulf Cooperation Council Patent Application No. GC2015-40053, dated Apr. 22, 2021, 10 pages (with English Translation).
Submission Document in Indian Patent Application No. 1511/CHENP/2009, dated Jan. 27, 2021, 72 pages.
Submission Document in Indian Patent Application No. 1511/CHENP/2009, dated Mar. 18, 2021, 79 pages.
Submission Document in Indian Patent Application No. 201747040368, dated Apr. 1, 2021, 38 pages.
Submission Document in Indian Patent Application No. 201947022655, dated Apr. 16, 2021, 9 pages.
Submission Document in Indian Patent Application No. 201947044328, dated May 10, 2021, 95 pages.
Submission Document in Indian Patent Application No. 2371/CHENP/2012, dated Jan. 28, 2021, 74 pages.
Submission Document in Indian Patent Application No. 7026/CHENP/2013, dated Dec. 16, 2020, 682 pages.
Submission Document in Israeli Patent Application No. 257292, dated Apr. 29, 2021, 6 pages (with English Translation).
Submission Document in Jordan Patent Application No. 225/2020, dated Jan. 10, 2021, 106 pages (with English Translation).
Submission Document in Korean Patent Application No. 10-2019-7032983, dated May 6, 2021, 41 pages (with English Translation).
Submission Document in Mexican Patent Application No. MX/a/2017/010474, dated Jan. 25, 2021, 5 pages (with English Translation).
Submission Document in Mexican Patent Application No. MX/a/2017/014540, dated Apr. 15, 2021, 16 pages (with English Translation).
Submission Document in Mexican Patent Application No. MX/a/2018/012193, dated Dec. 3, 2020, 48 pages (with English Translation).
Submission Document in Russian Patent Application No. 2017139090, dated Dec. 25, 2020, 16 pages (with English Translation).
Submission Document in Russian Patent Application No. 2019120680, dated Mar. 17, 2021, 10 pages (with English Translation).
Submission Document in Singaporean Patent Application No. 10202100272R, dated Jan. 11, 2021, 43 pages.
Submission Document in U.S. Appl. No. 15/554,577, dated May 24, 2021, 15 pages.
Submission Document in U.S. Appl. No. 15/750,712, dated Apr. 9, 2021, 5 pages.
Submission Document in U.S. Appl. No. 16/038,710, dated Sep. 29, 2020, 5 pages.
Submission Document in U.S. Appl. No. 16/038,710, dated Apr. 1, 2021, 5 pages.
Submission Document in U.S. Appl. No. 16/092,245, dated Mar. 31, 2021, 4 pages.
Sugiyama et al., "Potent in vitro and in vivo antitumor activity of sorafenib against human intrahepatic cholangiocarcinoma cells," Journal of Gastroenterology, 2011, 46:779-789.
Takahashi et al., "Axitinib (AG-013736), an oral specific VEGFR TKI, shows potential therapeutic utility against cholangiocarcinoma," Japanese Journal of Clinical Oncology, 2014, 44(6):570-578.
Tamai et al., "Suppressive expression of CD274 increases tumorigenesis and cancer stem cell phenotypes in cholangiocarcinoma," Cancer Sci, 105:667-674 (2014).
Ueno et al., "Phase 2 study of lenvatinib monotherapy as second-line treatment in unresectable biliary tract cancer: primary analysis results," BMC Cancer, 2020, 20:1105.
Wend et al., "Wnt/β-catenin signaling induces MLL to create epigenetic changes in salivary gland tumours," The EMBO Journal 2013, 1-13 (Oct. 2012).
Written Opinion in Singaporean Patent Application No. 11201710198Y, dated Jul. 22, 2020, 7 pages.
Yamada et al., "E7386, a selective inhibitor of the interaction between β-catenin and CBP, exerts antitumor activity in tumor models with activated canonical Wnt signaling," Cancer Research, Manuscript Published Jan. 6, 2021, 45 pages.
Notice of Allowance in Canadian Patent Application No. 2957005, dated Aug. 3, 2021, 1 page (with English Translation).
Office Action in European Patent Application No. 19151846.3, dated Aug. 6, 2021, 7 pages.
Eisai.mediaroom.com [online], "Positive Topline Results of Large Phase 3 Trial Show Eisai's Lenvatinib Meets Primary Endpoint in Unresectable Hepatocellular Carcinoma," Jan. 25, 2017, retrieved from: URL<https://eisai.mediaroom.com/2017-01-25-Positive-Topline-Results-of-Large-Phase-3-Trial-Show-Eisais-Lenvatinib-Meets-Primary-Endpoint-in-Unresectable-Hepatocellular-Carcinoma>, 4 pages.
Notice of Allowance in Korean Patent Application No. 10-2017-7003226, dated Aug. 18, 2021, 4 pages (with English Translation).
Office Action in Russian Patent Application No. 2019134940, dated Aug. 20, 2021, 30 pages (with English Translation).
Office Action in U.S. Appl. No. 17/022,675, dated Aug. 20, 2021, 149 pages.
Notice of Allowance in U.S. Appl. No. 15/554,577, dated Jun. 8, 2021, 32 pages.
Office Action in Japanese Patent Application No. P2017-535551, dated Aug. 3, 2021, 2 pages (with English Translation).
Office Action in Mexican Patent Application No. MX/a/2019/013014, dated Jul. 6, 2021, 16 pages (with English Translation).
Submission Document in Korean Patent Application No. 10-2017-7003226, dated Jul. 26, 2021, 17 pages (with English Translation).
Submission Document in Singaporean Patent Application No. 11201801083U, dated Aug. 3, 2021, 9 pages.
Office Action in Singaporean Patent Application No. 11201801083U, dated Jun. 16, 2021, 6 pages.
Submission Document in U.S. Appl. No. 15/934,242, dated Jul. 20, 2021, 7 pages.
Submission Document in U.S. Appl. No. 16/038,710, dated Jul. 9, 2021, 7 pages.
Office Action in Korean Patent Application No. 10-2017-7003226, dated Jun. 24, 2021, 12 pages (with English Translation).
Office Action in Singaporean Patent Application No. 11201709335X, dated Jun. 28, 2021, 7 pages.
Notice of Allowance in Japanese Patent Application No. P2017-546075, dated Aug. 31, 2021, 6 pages (with English Translation).
Submission Document in Thai Patent Application No. 0401005163, dated Aug. 4, 2021, 33 pages (with English Translation).
Notice of Allowance in Chinese Patent Application No. 201580042365.3, dated Jun. 2, 2021, 4 pages (with English Translation).
Notice of Allowance in Mexican Patent Application No. MX/a/2017/014540, dated Apr. 28, 2021, 4 pages (with English Translation).
Office Action in Brazilian Patent Application No. BR112012032462-4, dated May 18, 2021, 11 pages (with English Translation).
Office Action in Indian Patent Application No. 201947044328, dated Jun. 8, 2021, 7 pages (with English Translation).
Submission Document in Mexican Patent Application No. MX/a/2017/010474, dated Jun. 11, 2021, 25 pages (with English Translation).
Submission Document in Brazilian Patent Application No. BR112012032462-4, dated Aug. 12, 2021, 14 pages (with English Translation).
Office Action in Australian Patent Application No. 2015384801, dated Dec. 17, 2020, 6 pages.
Submission Document in U.S. Appl. No. 16/609,895, dated Aug. 20, 2021, 5 pages.

(56) References Cited

OTHER PUBLICATIONS

Notice of Allowance in U.S. Appl. No. 16/038,710, dated Jul. 1, 2021, 19 pages.
Notice of Allowance in U.S. Appl. No. 15/750,712, dated Aug. 26, 2021, 11 pages.
Decision to Grant Patent in Japanese Patent Application No. P2017-525268, dated Aug. 4, 2020, 4 pages (with English Translation).
Decision to Grant Patent in Mexican Patent Application No. MX/a/2017/015896, dated Mar. 6, 2020, 9 pages (with English Translation).
Notice of Allowance in Chinese Patent Application No. 201680035322.7, dated Mar. 30, 2021, 4 pages (with English Translation).
Office Action in Japanese Patent Application No. P2017-525268, dated Mar. 31, 2020, 11 pages (with English Translation).
Submission Document in Australian Patent Application No. 2016279474, dated Aug. 23, 2021, 5 pages.
Submission Document in Chinese Patent Application No. 201680035322.7, dated Aug. 13, 2020, 16 pages (with English Translation).
Submission Document in Mexican Patent Application No. MX/a/2017/015896, dated Dec. 13, 2019, 7 pages (with English Translation).
Submission Document in Japanese Patent Application No. P2017-525268, dated May 27, 2020, 12 pages (with English Translation).
Submission Document in Egyptian Patent Application No. PCT 283/2012, dated Jun. 28, 2021, 3 pages (with English Translation).
Submission Document in Singaporean Patent Application No. 11201904020S, dated Jul. 1, 2021, 13 pages.
Submission Document in U.S. Appl. No. 13/923,858, dated Jun. 14, 2021, 7 pages.
Office Action in Egyptian Patent Application No. PCT 283/2012, dated Apr. 13, 2021, 10 pages (with English Translation).
Office Action in Australian Patent Application No. 2016308390, dated Jun. 2, 2021, 3 pages.
Submission Document in U.S. Appl. No. 17/228,025, dated Jun. 24, 2021, 3 pages.
Office Action in Australian Patent Application No. 2016273230, dated Jun. 21, 2021, 4 pages.
Office Action in Mexican Patent Application No. MX/a/2017/001980, dated May 27, 2021, 7 pages (with English Translation).
Office Action in U.S. Appl. No. 16/092,245, dated Jun. 25, 2021, 30 pages.
Submission Document in U.S. Appl. No. 17/228,025, dated Jun. 15, 2021, 10 pages.
[No. Author], "Report on the Deliberation Results—Brand Name: Lenvima Capsules 4mg, Lenvima Capsules 10 mg," Evaluation and Licensing Division, Pharmaceutical and Food Safety Bureau, Ministry of Health, Labour and Welfare, Jan. 26, 2015, 100 pages.
[No. Author], "Study NCT02014636—A Phase I/II Study to Assess the Safety and Efficacy of Pazopanib and MK 3475 in Subjects With Advanced Renal Cell Carcinoma," v12, Sponsored by GlaxoSmithKline, Nov. 13, 2014, 11 pages.
[No. Author], "Study NCT02133742—A Phase 1b, Open Label, Dose Finding Study to Evaluate Safety, Pharmacokinetics and Pharmacodynamics of Axitinib (Ag-013736) in Combination with MK-3475 in Patients with Advanced Renal Cell Cancer," v11, Sponsored by Pfizer, Feb. 10, 2015, 8 pages.
Gaspar et al., "Lenvatinib with etoposide plus ifosfamide in patients with refractory or relapsed osteosarcoma (ITCC-050): a multicentre, open-label, multicohort, phase 1/2 study," The Lancet Oncology, 2021, 22(9): 1312-1321.
Notice of Allowance in Singaporean Patent Application No. 11201904020S, dated Sep. 30, 2021, 4 pages.
Notice of Allowance in U.S. Appl. No. 17/022,675, dated Sep. 22, 2021, 17 pages.
Notice of Allowance in U.S. Appl. No. 17/022,675, dated Nov. 4, 2021, 5 pages.
Notification of Information Provision in Canadian Patent Application No. 2978226, dated Sep. 28, 2021, 15 pages.
Notification of Information Provision in European Patent Application No. 16755489.8, dated Oct. 25, 2021, 77 pages.
Notification of Information Provision in Japanese Patent Application No. P2020-182679, dated Oct. 12, 2021, 2 pages (with English Translation).
Office Action in Brazilian Patent Application No. BR112012032462-4, dated Aug. 31, 2021, 9 pages (with English Translation).
Office Action in Brazilian Patent Application No. BR112015009004-4, dated Sep. 21, 2021, 11 pages (with English Translation).
Office Action in Brazilian Patent Application No. BR1120170028271, dated Sep. 21, 2021, 5 pages (with English Translation).
Office Action in Brazilian Patent Application No. BR1120170174286, dated Sep. 21, 2021, 9 pages (with English Translation).
Office Action in Brazilian Patent Application No. BR1120170241960, dated Sep. 21, 2021, 9 pages (with English Translation).
Office Action in Canadian Patent Application No. 2978226, dated Nov. 1, 2021, 5 pages.
Office Action in Egyptian Patent Application No. PCT 283/2012, dated Aug. 8, 2021, 9 pages (with English Translation).
Office Action in European Patent Application No. 17782552.8, dated Oct. 15, 2021, 2 pages.
Office Action in Indian Patent Application No. 201747040368, dated Sep. 29, 2021, 16 pages.
Office Action in Indian Patent Application No. 201947022655, dated Oct. 25, 2021, 2 pages (with English Translation).
Office Action in Israeli Patent Application No. 267159, dated Oct. 6, 2021, 8 pages (with English Translation).
Office Action in Japanese Patent Application No. P2020-182679, dated Oct. 12, 2021, 10 pages (with English Translation).
Office Action in Korean Patent Application No. 10-2018-7028053, dated Nov. 12, 2021, 6 pages (with English Translation).
Office Action in Mexican Patent Application No. MX/a/2017/001980, dated Oct. 5, 2021, 6 pages (with English Translation).
Office Action in Mexican Patent Application No. MX/a/2018/012193, dated Aug. 18, 2021, 13 pages (with English Translation).
Office Action in Mexican Patent Application No. MX/a/2019/013014, dated Nov. 8, 2021, 4 pages (with English Translation).
Office Action in Pakistani Patent Application No. 548/2015, dated Nov. 5, 2021, 14 pages.
Office Action in U.S. Appl. No. 16/809,301, dated Sep. 13, 2021, 26 pages.
Office Action in U.S. Appl. No. 17/228,025, dated Nov. 19, 2021, 8 pages.
Office Action in U.S. Appl. No. 17/407,742, dated Oct. 22, 2021, 18 pages.
Office Action in U.S. Appl. No. 17/407,742, dated Sep. 1, 2021, 2 pages.
Pfizer.com [Online], "Press Release—Pfizer and Merck to Collaborate on Innovative Anti-Cancer Combination Studies," Feb. 5, 2014, [Retrieved on Dec. 1, 2021], retrieved from: URL<https://www.pfizer.com/news/press-release/press-release-detail/pfizer_and_merck_to_collaborate_on_innovative_anti_cancer_combination_studies>, 5 pages.
Submission Document in Australian Patent Application No. 2015384801, dated Nov. 8, 2021, 17 pages.
Submission Document in European Patent Application No. 16755489.8, dated Sep. 6, 2021, 65 pages.
Submission Document in European Patent Application No. 20207489.4, dated Oct. 29, 2021, 45 pages.
Submission Document in European Patent Application No. 20207489.4, dated Nov. 8, 2021, 12 pages.
Submission Document in Gulf Cooperation Council Patent Application No. GC2015-40053, dated Sep. 16, 2021, 104 pages (with English Translation).
Submission Document in Indian Patent Application No. 201947044328, dated Oct. 22, 2021, 4 pages.
Submission Document in Singaporean Patent Application No. 11201709335X, dated Sep. 23, 2021, 10 pages.
Submission Document in U.S. Appl. No. 15/573,197, dated Nov. 12, 2021, 21 pages.
Submission Document in U.S. Appl. No. 17/022,675, dated Sep. 3, 2021, 53 pages.

(56) References Cited

OTHER PUBLICATIONS

Submission Document in U.S. Appl. No. 17/022,675, dated Oct. 25, 2021, 7 pages.
Submission Document in U.S. Appl. No. 17/228,025, dated Oct. 5, 2021, 4 pages.
Thornton, "Nivolumab, a Novel Anti-PD-1 Monoclonal Antibody for the Treatment of Solid and Hematologic Malignancies," Personalized Medicine in Oncology, Part 2, 2014, 13 pages.
Walsh et al., "Playing hide and seek with poorly tasting paediatric medicines: Do not forget the excipients," Advanced Drug Delivery Reviews, 2014, 73:14-33.
Submission Document in U.S. Appl. No. 15/750,712, dated Nov. 22, 2021, 5 pages.
Submission Document in Brazilian Patent Application No. BR1120170174286, dated Dec. 14, 2021, 26 pages (with English Translation).
Office Action in Brazilian Patent Application No. BR1120180027324, dated Sep. 21, 2021, 12 pages (with English Translation).
Office Action in Mexican Patent Application No. MX/a/2019/013014, dated Nov. 18, 2021, 15 pages (with English Translation).
Office Action in Russian Patent Application No. 2017104496, dated Nov. 3, 2021, 11 pages (with English Translation).
Notice of Allowance in Israeli Patent Application No. 256148, dated Dec. 12, 2021, 9 pages (with English Translation).
Office Action in Brazilian Patent Application No. BR112017027227-0, dated Sep. 14, 2021, 8 pages (with Partial English Translation).
Office Action in Chinese Patent Application No. 201880005026.1, dated Dec. 9, 2021, 17 pages (with English Translation).
Office Action in Chinese Patent Application No. 201880005026.1, dated Dec. 21, 2021, 6 pages (with English Translation).
Office Action in European Patent Application No. 17782552.8, dated Dec. 21, 2021, 65 pages.
Submission Document in Brazilian Patent Application No. BR112017027227-0, dated Dec. 20, 2021 12 pages (with Partial English Translation).
Submission Document in Brazilian Patent Application No. BR1120180027324, dated Dec. 16, 2021, 20 pages (with English Translation).
Submission Document in European Patent Application No. 19151846.3, dated Dec. 29, 2021, 98 pages.
Submission Document in Indian Patent Application No. 202148057534, dated Dec. 10, 2021, 129 pages.
Notice of Allowance in U.S. Appl. No. 15/750,712, dated Dec. 8, 2021, 11 pages.
Office Action in Australian Patent Application No. 2016273230, dated Dec. 21, 2021, 19 pages.
Submission Document in Indian Patent Application No. 201947022655, dated Dec. 10, 2021, 5 pages.
Official Notification in Egyptian Patent Application No. PCT 283/2012, dated Apr. 11, 2022, 2 pages (with English Translation).
Official Notification in Brazilian Patent Application No. PI0418200-6, dated May 31, 2022, 15 pages (with English Translation).
Office Action in Israeli Patent Application No. 250454, dated Apr. 6, 2022, 4 pages.
Office Action in U.S. Appl. No. 15/573,197, dated May 3, 2022, 43 pages.
Office Action in Australian Patent Application No. 2017249459, dated Mar. 16, 2022, 3 pages.
Office Action in Mexican Patent Application No. MX/a/2017/001980, dated Mar. 28, 2022, 9 pages (with English Translation).
Submission Document in Israeli Patent Application No. 253946, dated Apr. 24, 2022, 16 pages (with English Translation).
Office Action in U.S. Appl. No. 13/923,858, dated May 20, 2022, 10 pages.
Notice of Allowance in U.S. Appl. No. 15/750,712, dated Jun. 23, 2022, 8 pages.
Notice of Allowance in Mexican Patent Application No. MX/a/2017/001980, dated May 30, 2022, 4 pages (with English Translation).
Office Action in Korean Patent Application No. 10-2017-7027616, dated May 11, 2022, 27 pages (with English Translation).
Office Action in Canadian Patent Application No. 2976325, dated Apr. 1, 2022, 5 pages.
Submission Document in U.S. Appl. No. 15/750,712, dated Jun. 14, 2022, 5 pages.
Office Action in Japanese Patent Application No. P2020-182679, dated Jun. 7, 2022, 2 pages (with English Translation).
Office Action in U.S. Appl. No. 15/934,242, dated Apr. 6, 2022, 21 pages.
Submission Document in Canadian Patent Application No. 3019682, dated Apr. 14, 2022, 22 pages.
Notice of Allowance in Australian Patent Application No. 2015384801, dated Dec. 16, 2021, 3 pages.
Notice of Allowance in Australian Patent Application No. 2016273230, dated Jan. 14, 2022, 3 pages.
Notice of Allowance in Chinese Patent Application No. 201880005026.1, dated Feb. 25, 2022, 8 pages (with English Translation).
Notice of Allowance in Egyptian Patent Application No. PCT 283/2012, dated Feb. 1, 2022, 2 pages (with English Translation).
Notice of Allowance in European Patent Application No. 17782552.8, dated Jan. 5, 2022, 1 page.
Notice of Allowance in European Patent Application No. 19151846.3, dated Feb. 25, 2022, 41 pages.
Notice of Allowance in Israeli Patent Application No. 267159, dated Mar. 2, 2022, 6 pages (with English Translation).
Notice of Allowance in Thai Patent Application No. 0401005163, dated Feb. 9, 2022, 2 pages (with English Translation).
Notice of Allowance in U.S. Appl. No. 15/554,577, dated Jan. 31, 2022, 19 pages.
Notice of Allowance in U.S. Appl. No. 15/750,712, dated Mar. 15, 2022, 5 pages.
Office Action in Brazilian Patent Application No. BR112017027227-0, dated Sep. 21, 2021, 8 pages (with Partial English Translation).
Office Action in Canadian Patent Application No. 2985596, dated Mar. 7, 2022, 5 pages.
Office Action in Indian Patent Application No. 202148057534, dated Feb. 4, 2022, 5 pages (with English Translation).
Office Action in Israeli Patent Application No. 253946, dated Dec. 27, 2021, 11 pages (with English Translation).
Office Action in Korean Patent Application No. 10-2018-7028053, dated Nov. 12, 2021, 11 pages (with English Translation).
Office Action in Mexican Patent Application No. MX/a/2018/012193, dated Jan. 12, 2022, 13 pages (with English Translation).
Office Action in Russian Patent Application No. 2017104496, dated Mar. 11, 2022, 17 pages (with English Translation).
Office Action in Russian Patent Application No. 2018134943, dated Dec. 23, 2021, 85 pages (with English Translation).
Office Action in Russian Patent Application No. 2018134943, dated Feb. 22, 2022, 17 pages (with English Translation).
Office Action in Singaporean Patent Application No. 10202010137Y, dated Mar. 2, 2022, 7 pages.
Office Action in U.S. Appl. No. 13/923,858, dated Jan. 24, 2022, 2 pages.
Office Action in U.S. Appl. No. 16/092,245, dated Dec. 22, 2021, 13 pages.
Office Action in U.S. Appl. No. 16/092,245, dated Jan. 24, 2022, 29 pages.
Office Action in U.S. Appl. No. 17/228,025, dated Mar. 25, 2022, 12 pages.
Official Notification in European Patent Application No. 19151846.3, dated Dec. 17, 2021, 2 pages.
Submission Document in Brazilian Patent Application No. BR1120170241960, dated Dec. 20, 2021, 28 pages (with English Translation).
Submission Document in Chinese Patent Application No. 201880005026.1, dated Feb. 14, 2022, 17 pages (with English Translation).
Submission Document in European Patent Application No. 19151846.3, dated Jan. 10, 2022, 95 pages.
Submission Document in Indian Patent Application No. 201947044328, dated Jan. 3, 2022, 3 pages.

(56) References Cited

OTHER PUBLICATIONS

Submission Document in Israeli Patent Application No. 250454, dated Mar. 27, 2022, 3 pages (with English Translation).
Submission Document in Mexican Patent Application No. MX/a/2018/012193, dated Dec. 17, 2021, 24 pages (with English Translation).
Submission Document in Mexican Patent Application No. MX/a/2019/013014, dated Jan. 21, 2022, 34 pages (with English Translation).
Submission Document in Russian Patent Application No. 2017104496, dated Jan. 12, 2022, 20 pages (with English Translation).
Submission Document in U.S. Appl. No. 13/923,858, dated Jan. 14, 2022, 20 pages.
Submission Document in U.S. Appl. No. 13/923,858, dated Feb. 1, 2022, 5 pages.
Submission Document in U.S. Appl. No. 15/750,712, dated Mar. 4, 2022. 5 pages.
Submission Document in U.S. Appl. No. 15/934,242, dated Feb. 18, 2022, 16 pages.
Submission Document in U.S. Appl. No. 17/228,025, dated Feb. 18, 2022, 7 pages.
Office Action in Mexican Patent Application No. MX/a/2019/013014, dated Mar. 2, 2022, 12 pages (with English Translation).
Submission Document in Korean Patent Application No. 10-2018-7028053, dated May 11, 2022, 86 pages (with English Translation).
Notice of Allowance in European Patent Application No. 16755489.8, dated Apr. 12, 2022, 49 pages.
Notice of Allowance in Russian Patent Application No. 2018134943, dated Oct. 19, 2022, 20 pages (with English Translation).
Imai et al., "Different types of reactions to E7386 among colorectal cancer patient-derived organoids and corresponding CAFs," Oncology Letters, 2022, 24:221.
Kanda et al., "NF-$_k$B suppression synergizes with E7386, an inhibitor of CBP/βcatenin interaction, to block proliferation of patient-derived colon cancer spheroids," Biochemical and Biophysical Research Communications, 2022, 586, p. 93-p. 99.
Kawazoe et al., "A Phase 1 Study of E7386, a CREB-Binding Protein/β-Catenin Interaction Inhibitor, in Patients With Advanced Solid Tumors Including Colorectal Cancer," Presented at the European Society for Medical Oncology Virtual Congress, Sep. 16-21, 2021, 1 page.
Yoshino et al., "An Open-label, Multicenter, Phase 1b/2 Study of E7386 (Wnt/β-catenin pathway inhibitor) + Pembrolizumab in Patients With Pretreated Advanced Solid Tumors," Presented at the American Association for Cancer Research (AACR) annual meeting; New Orleans, LA, Apr. 8-13, 2022.
Notice of Allowance in Russian Patent Application No. 2017104496, dated Oct. 18, 2022, 18 pages (with English Translation).
Submission Document in Brazilian Patent Application No. BR1120190141278, dated Oct. 19, 2022, 4 pages (with English Translation).
Submission Document in Indian Patent Application No. 202148057534, dated Oct. 28, 2022, 5 pages.
Notice of Allowance in European Patent Application No. 16755489.8, dated Oct. 10, 2022, 49 pages.
Notice of Allowance in U.S. Appl. No. 15/554,577, dated Jul. 28, 2022, 13 pages.
Notice of Allowance in U.S. Appl. No. 15/750,712, dated Oct. 6, 2022, 10 pages.
Office Action in Brazilian Patent Application No. BR112013021941-6, dated Jun. 7, 2022, 9 pages.
Office Action in Brazilian Patent Application No. BR1120190141278, dated Jul. 26, 2022, 8 pages (with English Translation).
Office Action in Canadian Patent Application No. 2994224, dated Sep. 12, 2022, 4 pages.
Office Action in Canadian Patent Application No. 2994925, dated Sep. 15, 2022, 3 pages.
Office Action in European Patent Application No. 19733190.3, dated Jul. 5, 2022, 4 pages.
Office Action in Israeli Patent Application No. 253946, dated Jun. 19, 2022, 12 pages (with English Translation).
Office Action in Korean Patent Application No. 10-2018-7028053, dated Sep. 20, 2022, 7 pages (with English Translation).
Office Action in Korean Patent Application No. 10-2021-7037538, dated Sep. 23, 2022, 4 pages.
Office Action in Singaporean Patent Application No. 11201709335X, dated Jul. 15, 2022, 5 pages.
Office Action in U.S. Appl. No. 17/511,773, dated Sep. 6, 2022, 160 pages.
Search Report in European Patent Application No. 22180987.4, dated Sep. 26, 2022, 9 pages.
Submission Document in Brazilian Patent Application No. BR112013021941-6, dated Aug. 29, 2022, 22 pages (with English Translation).
Submission Document in Canadian Patent Application No. 2976325, dated Jul. 21, 2022, 13 pages.
Submission Document in European Patent Application No. 16755489.8, dated Aug. 18, 2022, 6 pages.
Submission Document in European Patent Application No. 16837150.8, dated Aug. 19, 2022, 68 pages.
Submission Document in Indian Patent Application No. 201947022655, dated Aug. 17, 2022, 45 pages.
Submission Document in Israeli Patent Application No. 250454, dated Jul. 31, 2022, 79 pages (with English Translation).
Submission Document in Israeli Patent Application No. 253946, dated Oct. 11, 2022, 5 pages.
Submission Document in Russian Patent Application No. 2017104496, dated Sep. 6, 2022, 13 pages.
Submission Document in Russian Patent Application No. 2018134943, dated Aug. 22, 2022, 23 pages (with English Translation).
Submission Document in Singaporean Patent Application No. 10202010137Y, dated Aug. 2, 2022, 20 pages.
Submission Document in U.S. Appl. No. 13/923,858, dated Jul. 20, 2022, 14 pages.
Submission Document in U.S. Appl. No. 15/750,712, dated Sep. 22, 2022, 5 pages.
Submission Document in U.S. Appl. No. 16/092,245, dated Jul. 25, 2022, 6 pages.
Submission Document in U.S. Appl. No. 17/228,025, dated Sep. 23, 2022, 6 pages.
Notice of Allowance in Brazilian Patent Application No. BR112013021941-6, dated Oct. 11, 2022, 2 pages (with English Translation).
Submission Document in U.S. Appl. No. 15/934,242, dated Oct. 6, 2022, 13 pages.
[No. Author], "Assessment Report: Lenvima—Procedure No. EMEA/H/C/003727/0000," European Medicines Agency, Science Medicines Health, Committee for Medicinal Products for Human Use (CHMP), 2015, 169 pages.
[No. Author], "Bone sarcomas: ESMO Clinical Practice Guidelines for diagnosis, treatment and follow-up," Annals of Oncology, ESMO (European Sarcoma Network Working Group), 2014, 25(Supplement 3):iii113-iii123.
[No. Author], "Guidance for Industry—Genotoxic and Carcinogenic Impurities in Drug Substances and Products: Recommended Approaches," U.S. Department of Health and Human Services, Food and Drug Administration, Center for Drug Evaluation and Research (CDER), Pharmacology and Toxicology, Dec. 2008, 16 pages.
[No. Author], "International Conference on Harmonisation; Draft Guidance on Specifications: Test Procedures and Acceptance Criteria for New Drug Substances and New Drug Products: Chemical Substances," Food and Drug Administration HHS, Federal Register, 1997, 62(227):62890-62910.
[No. Author], "Material Safety Data Sheet for 4-Chloroquinoline," Supplier: Santa Cruz Biotechnology, Inc., Oct. 29, 2009, 10 pages.
Anderson's Practical Process Research & Development—A guide for Organic Chemists, 2nd ed., Cover Page with Table of Content, Academic Press, 7 pages.
Benigni et al., "Structural alerts of mutagens and carcinogens," Current Computer-Aided Drug Design, 2006, 2:169-176.

(56) References Cited

OTHER PUBLICATIONS

Botter et al., "Recent advances in osteosarcoma," Current Opinion in Pharmacology, 2014, 16:15-23.
ClinicalTrials.gov [online], "History of Changes for Study: NCT02432274—Study of Lenvatinib in Children and Adolescents With Refractory or Relapsed Solid Malignancies," Version: Jun. 1, 2015, (Latest Version Submitted Sep. 2, 2021), [Retrieved on Feb. 21, 2022], retrieved from: URL<https://clinicaltrials.gov/ct2/history/NCT02432274?A=2&B=2&C=merged#StudyPageTop>, 8 pages.
Gaspar et al., "A Multicenter, Open-label, Randomized, Phase 2 Study to Compare the Efficacy and Safety of Lenvatinib in Combination With Ifosfamide and Etoposide Versus Ifosfamide and Etoposide in Children, Adolescents, and Young Adults With Relapsed or Refractory Osteosarcoma (OLIE)," Poster presented at: the Connective Tissue Oncology Society Annual Meeting; Nov. 16-19, 2022, 1 page.
Kamiya et al., "Antimutagenic Structure Modification of Quinoline: Fluorine-Substitution at Position-3," Antimutagenesis and Anticarcinogenesis Mechanisms II, 1990, pp. 441-446.
Kondo et al., "A Phase 1 Study of E7386, a CREB-Binding Protein/β-Catenin Interaction Inhibitor, in Patients With Advanced Solid Tumors Including Colorectal Cancer: Updated Dose-Escalation Part," Poster Presentation, Presented at the American Society of Clinical Oncology Gastrointestinal Cancers Symposium, San Francisco, CA USA, Jan. 19-21, 2023, 1 page.
Kondo et al., "A Phase 1b Study of E7386, a CREB-Binding Protein (CBP)/β-Catenin Interaction Inhibitor, in Combination With Lenvatinib in Patients With Advanced Solid Tumors," Poster Presentation, Presented at ESMO Asia Congress, Singapore, Dec. 2-4, 2022, 1 page.
Lund's The Pharmaceutical Codex—Principles and Practice of Pharmaceutics, 12th Ed., The Pharmaceutical Press, 1994, pp. 342-349.
Mutschler et al.'s Mutschler Drug Reactions, Pharmacological and Toxicological Textbook, 8th Ed., Wissenschaftliche Verlagsgesellschaft mbH, 2001, pp. 882-891 (with Partial Translation).
Mutschler et al.'s Mutschler Drug Reactions, Pharmacological and Toxicological Textbook, 8th Ed., Wissenschaftliche Verlagsgesellschaft mbH, 2001, pp. 123-124 (with Partial Translation).
Notice of Allowance in Gulf Cooperation Council Patent Application No. GC2015-29939, dated Nov. 13, 2022, 2 pages (with English Translation).
Notice of Allowance in Gulf Cooperation Council Patent Application No. GC2015-40053, dated Nov. 13, 2022, 2 pages (with English Translation).
Notice of Allowance in Gulf Cooperation Council Patent Application No. GC2011-17812, dated Nov. 13, 2022, 2 pages (with English Translation).
Notice of Allowance in U.S. Appl. No. 15/934,242, dated Nov. 9, 2022, 12 pages.
Office Action in Brazilian Patent Application No. BR1120170028271, dated Nov. 16, 2022, 12 pages (with English Translation).
Office Action in Brazilian Patent Application No. BR1120170174286, dated Dec. 6, 2022, 7 pages (with English Translation).
Office Action in Canadian Patent Application No. 2978226, dated Oct. 3, 2022, 3 pages.
Office Action in European Patent Application No. 16755489.8, dated Dec. 23, 2022, 2 pages.
Office Action in European Patent Application No. 16837150.8, dated Jan. 19, 2023, 11 pages.
Office Action in European Patent Application No. 17782552.8, dated Nov. 28, 2022, 4 pages.
Office Action in Indian Patent Application No. 201747028834, dated Nov. 9, 2022, 3 pages (with English Translation).
Office Action in Korean Patent Application No. 10-2019-7016853, dated Jan. 8, 2023, 7 pages (with English Translation).
Office Action in U.S. Appl. No. 13/923,858, dated Dec. 21, 2022, 7 pages.
Office Action in U.S. Appl. No. 17/407,742, dated Dec. 8, 2022, 169 pages.
Official Notification in Indian Patent Application No. 201747028834, dated Jan. 2, 2023, 2 pages.
Robinson, "Control of genotoxic impurities in active pharmaceutical ingredients: a review and perspective," Organic Process Research & Development, 2010, 14(4):946-959.
Sadineni et al., "Novel method for the synthesis of lenvatinib using 4-nitrophenyl cyclopropylcarbamate and their pharmaceutical salts," Chemical Papers, 2021, 75:1475-1483.
Submission Document in Canadian Patent Application No. 2994925, dated Dec. 30, 2022, 8 pages.
Submission Document in Indian Patent Application No. 201747028834, dated Dec. 19, 2022, 15 pages.
Submission Document in Korean Patent Application No. 10-2021-7037538, dated Nov. 9, 2022, 31 pages (with English Translation).
Submission Document in U.S. Appl. No. 15/934,242, dated Nov. 18, 2022, 3 pages.
Submission Document in U.S. Appl. No. 17/692,698, dated Oct. 21, 2022, 11 pages.
Yamada et al., "E7386 Opportunity Overview—Inhibitor of Protein-Protein Interaction of CBP/β-catenin as a Wnt Signaling Modulator," Presentation Slides, Eisai, Dec. 2022, 29 pages.
Zheng et al., "The mechanism of solvent-mediated desolvation transformation of lenvatinib mesylate from dimethyl sulfoxide solvate to form D," Acta Crystallographica Section B: Structural Science, Crystal Engineering and Materials, 2020, B76:343-352.
Notice of Allowance in U.S. Appl. No. 15/750,712, dated Jan. 25, 2023, 11 pages.
Office Action in European Patent Application No. 16837150.8, dated Jan. 30, 2023, 5 pages.
Office Action in Indian Patent Application No. 201847003846, dated Jan. 19, 2023, 3 pages (with English Translation).
Submission Document in Brazilian Patent Application No. BR1120170028271, dated Feb. 14, 2023, 54 pages (with English Translation).
Submission Document in European Patent Application No. 16755489.8, dated Feb. 17, 2023, 6 pages.
Submission Document in U.S. Appl. No. 15/750,712, dated Jan. 6, 2023, 3 pages.
Notice of Allowance in Korean Patent Application No. 10-2021-7037538, dated Jan. 31, 2023, 7 pages (with English Translation).
Official Notification in U.S. Appl. No. 13/923,858, dated Jan. 19, 2023, 2 pages.
Submission Document in Australian Patent Application No. 2017249459, dated Feb. 22, 2023, 89 pages.
Submission Document in European Patent Application No. 19733190.3, dated Jan. 13, 2023, 10 pages.
Office Action in Brazilian Patent Application No. BR122023002744-2, dated May 30, 2023, 10 pages (with English Translation).
Office Action in Brazilian Patent Application No. BR122023002748-5, dated May 30, 2023, 10 pages (with English Translation).
Office Action in U.S. Appl. No. 17/228,025, dated May 23, 2023, 18 pages.
Notice of Allowance in European Patent Application No. 16755489.8, dated May 24, 2023, 51 pages.
Notice of Opposition in European Patent Application No. 19151846.3, Opponent: Accord Healthcare, Ltd, dated May 10, 2023, 19 pages.
Notice of Opposition in European Patent Application No. 19151846.3, Opponent: Aechter, Mr Bernd, dated May 10, 2023, 15 pages.
Notice of Opposition in European Patent Application No. 19151846.3, Opponent: Elkington and Fife LLP, dated May 4, 2023, 28 pages.
Notice of Opposition in European Patent Application No. 19151846.3, Opponent: Generics (UK) Limited, dated May 10, 2023, 23 pages.
Notice of Opposition in European Patent Application No. 19151846.3, Opponent: Hansen Norbert, dated May 9, 2023, 354 pages.
Notice of Opposition in European Patent Application No. 19151846.3, Opponent: Maiwald GmbH, dated May 10, 2023, 23 pages.
Notice of Opposition in European Patent Application No. 19151846.3, Opponent: Stada Arzneimittel AG, dated May 10, 2023, 22 pages.
Notice of Opposition in European Patent Application No. 19151846.3, Opponent: Teva Pharmaceutical Industries Ltd., dated May 9, 2023, 24 pages.

(56) References Cited

OTHER PUBLICATIONS

Notice of Opposition in European Patent Application No. 19151846.3, Opponent: Welding GmbH & Co. KG, dated May 10, 2023, 22 pages.
Office Action in Canadian Patent Application No. 3019682, dated May 31, 2023, 3 pages.
Office Action in Korean Patent Application No. 10-2017-7022544, dated Apr. 14, 2023, 12 pages (with English Translation).
Opposition, [No. Author Listed], "Assessment Report—Lenvima (lenvatinib)," European Medicines Agency, Mar. 26, 2015, Exhibit HW5 in European Patent Application No. 19151846.3, Opponent: Welding GmbH & Co. KG, dated May 10, 2023, 170 pages.
Opposition, [No. Author Listed], "Datasheet for Decision; Lenvatinib mesylate polymorphs—Crystal of salt of 4-(3-chloro-4-(cyclopropylaminocarbonyl)amino-phenoxy)-7-methoxy-6-quinolinecarboxamide or of solvate thereof and processes for producing these," Board of Appeal of The European Patent Office, Jun. 18, 2014, Exhibit D10 in European Patent Application No. 19151846.3, Opponent: Generics (UK) Limited, dated May 10, 2023, 16 pages.
Opposition, [No. Author Listed], "Drugs@FDA: FDA-Approved Drugs Lenvima," NDA: 206947, Company: Eisai Inc, FDA Drug Database, Exhibit D12 in European Patent Application No. 19151846.3, Opponent: Maiwald GmbH, dated May 10, 2023, 4 pages.
Opposition, [No. Author Listed], "Experimental Data," Exhibit D11 in European Patent Application No. 19151846.3, Opponent: Maiwald GmbH, dated May 10, 2023, 3 pages.
Opposition, [No. Author Listed], "Experimental Report—Purge of Compound (I) from Lenvatinib," Exhibit E17 in European Patent Application No. 19151846.3, Opponent: Hansen Norbert, dated May 9, 2023, 5 pages.
Opposition, [No. Author Listed], "Guideline on the limits of genotoxic impurities," Committee for Medicinal Products for Human Use, European Medicines Agency, Jun. 28, 2006, Exhibit HW3 in European Patent Application No. 19151846.3, Opponent: Welding GmbH & Co. KG, dated May 10, 2023, 8 pages.
Opposition, [No. Author Listed], "ICH guideline M7 on assessment and control of DNA reactive (mutagenic) impurities in pharmaceuticals to limit potential carcinogenic risk," European Medicines Agency, May 2013, Exhibit E10 in European Patent Application No. 19151846.3, Opponent: HANSEN Norbert, dated May 9, 2023, 27 pages.
Opposition, [No. Author Listed], "Translation of JP 2014-174062 (first priority)," Aug. 28, 2014, Exhibit E1 in European Patent Application No. 19151846.3, Opponent: Hansen Norbert, dated May 9, 2023, 43 pages.
Opposition, [No. Author Listed], "Translation of JP 2015-034729 (second priority), " Feb. 25, 2015, Exhibit E2 in European Patent Application No. 19151846.3, Opponent: Hansen Norbert, dated May 9, 2023, 51 pages.
Opposition, [No. Author Listed], "Transmittal of Annual Reports for Drugs and Biologics for Human Use—Summary of Manufacturing Changes," Department of Health and Human Services, Food and Drug Administration, Feb. 13, 2018, Exhibit E13 in European Patent Application No. 19151846.3, Opponent: HANSEN Norbert, dated May 9, 2023, 9 pages.
Opposition, Ahuja et al.'s, Handbook of Pharmaceutical Analysis by HPLC, 1st ed., Elsevier, 2005, Exhibit D9 in European Patent Application No. 19151846.3, Opponent: Teva Pharmaceutical Industries Ltd., dated May 9, 2023, pp. 19-22, 43, 44, 123-127, 133, 134, 200-203, 212, 262, 274, 275, 370-377.
Opposition, anzeninfo.mhlw.go.jp [Online], "Newly notified chemical substances (36 substances) confirmed to have mutagenicity," Dec. 11, 2012, [Retrieved on or before May 9, 2023], retrieved from: URL<https://anzeninfo.mhlw.go.jp/user/anzen/kag/20121211_heni.html>, Exhibits E11 & E11a in European Patent Application No. 19151846.3, Opponent: HANSEN Norbert, dated May 9, 2023, 7 pages (with English Translation).
Opposition, Eisai.com [Online], "U.S. FDA Approves Anticancer Agent Lenvima (Lenvatinib Mesylate) as Treatment for Radioactive Iodine-Refractory Differentiated Thyroid Cancer, " Feb. 16, 2015, [Retrieved on or before May 4, 2023], retrieved from: URL<https://www.eisai.com/news/news201510.html>, Exhibit D10 in European Patent Application No. 19151846.3, Opponent: Elkington and Fife LLP, dated May 4, 2023, 2 pages.
Opposition, Honma, "AMES/QSAR International Collaborative Study," with Class A list, Division of Genetics and Mutagenesis, National Institute of Health Sciences, Jun. 2019, [Retrieved on or before May 9, 2023], retrieved from: URL<http://www.nihs.go.jp/dgm/amesqsar.html>, Exhibits E12 & E12a in European Patent Application No. 19151846.3, Opponent: Hansen Norbert, dated May 9, 2023, 20 pages.
Opposition, Jeffery et al.'s, Vogel's Textbook of Quantitative Chemical Analysis, 5th ed., Longman Scientific & Technical, 1989, Exhibit D10 in European Patent Application No. 19151846.3, Opponent: Teva Pharmaceutical Industries Ltd., dated May 9, 2023, pp. 216, 220-229, 232-233.
Opposition, Müller et al., "A rationale for determining, testing, and controlling specific impurities in pharmaceuticals that possess potential for genotoxicity," Regulatory Toxicology and Pharmacology, 2006, Exhibit HW4 in European Patent Application No. 19151846.3, Opponent: Welding GmbH & Co. KG, dated May 10, 2023, 44:198-211.
Opposition, Patentee's Brief, dated Dec. 9, 2021, Exhibit D13 in European Patent Application No. 19151846.3, Opponent: Teva Pharmaceutical Industries Ltd., dated May 9, 2023, 11 pages.
Opposition, Shumaker et al., "Effect of Rifampicin on the Pharmacokinetics of Lenvatinib in Healthy Adults," Clin. Drug Investig., 2014, Exhibit D10 in European Patent Application No. 19151846.3, Opponent: Maiwald GmbH, dated May 10, 2023, 34:651-659.
Opposition, Snyder's Practical HPLC Method Development, 2nd ed., John Wiley & Sons Inc., 1998, Exhibit D9 in European Patent Application No. 19151846.3, Opponent: Elkington and Fife LLP, dated May 4, 2023, pp. 1-14, 292-317.
Opposition, Waters.com [Online], "X-Bridge HPLC cols. Brochure," Feb. 2015, [Retrieved on or before May 4, 2023], retrieved from: URL<https://www.waters.com/webassets/cms/library/docs/720001255en.pdf>, Exhibit D8 in European Patent Application No. 19151846.3, Opponent: Elkington and Fife LLP, dated May 4, 2023, 23 pages.
Submission Document in Australian Patent Application No. 2018219637, dated Jun. 7, 2023, 17 pages.
Submission Document in Brazilian Patent Application No. BR112018002732-4, dated May 29, 2023, 64 pages (with English Translation).
Submission Document in Korean Patent Application No. 10-2017-7022544, dated Jun. 9, 2023, 40 pages (with English Translation).
Adachi et al., "E7386, a selective inhibitor of the interaction between β-catenin and CREB-binding protein (CBP), enhances antitumor activity in combination with lenvatinib (LEN), and LEN + anti-PD-1 antibody in a preclinical tumor model," Poster_1837, Presented at AACR 2023, Jun. 2-6, 2023, 1 page.
Ikeda et al., "A Phase 1b Study of E7386, a CREB-Binding Protein/β-Catenin Interaction Inhibitor, in Combination With Lenvatinib in Patients With Advanced Hepatocellular Carcinoma, " Abstract #4075, Presented at The American Society for Clinical Oncology Symposium, Jun. 2-6, 2023, 1 page.
Kawano et al., "E7386, a selective inhibitor of the interaction between β-catenin and CREB-binding protein (CBP), in combination with lenvatinib (LEN), exerts antitumor activity in preclinical tumor models with prior immune checkpoint inhibitor (ICI)-based combination treatment," Poster_1830, Presented at AACR 2023, Jun. 2-6, 2023, 1 page.
Notice of Allowance in Brazilian Patent Application No. BR1120170028271, dated Mar. 7, 2023, 7 pages (with English Translation).
Notice of Allowance in Canadian Patent Application No. 2976325, dated Feb. 16, 2023, 4 pages (with English Translation).
Notice of Allowance in Canadian Patent Application No. 2976325, dated Apr. 18, 2023, 6 pages.
Notice of Allowance in Canadian Patent Application No. 2994925, dated Apr. 24, 2023, 1 page.

(56) References Cited

OTHER PUBLICATIONS

Notice of Allowance in Israeli Patent Application No. 250454, dated Feb. 27, 2023, 5 pages (with English Translation).
Notice of Allowance in Korean Patent Application No. 10-2019-7016853, dated Mar. 24, 2023, 7 pages (with English Translation).
Notice of Allowance in U.S. Appl. No. 15/750,712, dated May 9, 2023, 11 pages.
Notice of Allowance in U.S. Appl. No. 17/511,773, dated Mar. 15, 2023, 14 pages.
Office Action in Australian Patent Application No. 2017249459, dated Feb. 24, 2023, 3 pages.
Office Action in Australian Patent Application No. 2018219637, dated Mar. 14, 2023, 9 pages.
Office Action in Brazilian Patent Application No. BR1120180027324, dated Feb. 28, 2023, 12 pages (with English Translation).
Office Action in Indian Patent Application No. 202148057534, dated Mar. 14, 2023, 2 pages (with English Translation).
Office Action in Indian Patent Application No. 202148057534, dated May 1, 2023, 2 pages.
Office Action in Japanese Patent Application No. P2020-560740, dated May 16, 2023, 4 pages (with English Translation).
Office Action in Korean Patent Application No. 10-2018-7003723, dated May 8, 2023, 5 pages (with English Translation).
Office Action in U.S. Appl. No. 13/923,858, dated Mar. 1, 2023, 13 pages.
Search Report in European Patent Application No. 17782552.8, dated May 19, 2023, 6 pages.
Submission Document in European Patent Application No. 19151846.3, dated May 17, 2023, 203 pages.
Submission Document in European Patent Application No. 22180987.4, dated May 15, 2023, 116 pages.
Submission Document in Korean Patent Application No. 10-2019-7016853, dated Mar. 7, 2023, 25 pages (with English Translation).
Submission Document in U.S. Appl. No. 13/923,858, dated Jan. 10, 2023, 4 pages.
Submission Document in U.S. Appl. No. 15/750,712, dated Apr. 24, 2023, 5 pages.
Submission Document in U.S. Appl. No. 16/092,245, dated Feb. 14, 2023, 21 pages.
Submission Document in U.S. Appl. No. 17/228,025, dated Apr. 20, 2023, 13 pages.
Submission Document in U.S. Appl. No. 17/511,773, dated Mar. 3, 2023, 17 pages.
Notice of Allowance in European Patent Application No. 18751614.1, dated Jun. 26, 2023, 66 pages.
Office Action in Israeli Patent Application No. 302218, dated Apr. 19, 2023, 5 pages (with English Translation).
Office Action in U.S. Appl. No. 16/092,245, dated Jun. 8, 2023, 17 pages.
Official Notification in U.S. Appl. No. 13/923,858, dated Jun. 13, 2023, 19 pages.
Official Notification in U.S. Appl. No. 13/923,858, dated May 23, 2023, 2 pages.
Office Action in Indian Patent Application No. 201747004829, dated Oct. 9, 2023, 2 pages.
Submission Document in Canadian Patent Application No. 3019682, dated Sep. 28, 2023, 22 pages.
Submission Document in U.S. Appl. No. 17/228,025, dated Sep. 22, 2023, 1 page.
Bruheim et al., "Antitumor activity of oral E7080, a novel inhibitor of multiple tyrosine kinases, in human sarcoma xenografts," International Journal of Cancer, 2011, 129:742-750.
Fleuren et al., "Targeting receptor tyrosine kinases in osteosarcoma and Ewing sarcoma: Current hurdles and future perspectives," Biochimica et Biophysica Acta, 2014, 1845:266-276.
Gaspar et al., "Lenvatinib with etoposide plus ifosfamide in patients with refractory or relapsed osteosarcoma (ITCC-050):a multicentre, open-label, multicohort, phase 1/2 study "Supplementary appendix"," Lancet Oncol, Aug. 17, 2021, 179 pages.
Mutschler et al., "Mutschler Drug Effects," Textbook of Pharmacology and Toxicology, 2001, Chapter 10, pp. 120-122 (with English Translation).
Notice of Allowance in Korean Patent Application No. 10-2018-7003723, dated Sep. 7, 2023, 7 pages (with English Translation).
Notice of Allowance in Thai Patent Application No. 1201000221, dated Jul. 25, 2023, 2 pages (with English Translation).
Notice of Allowance in U.S. Appl. No. 15/750,712, dated Aug. 17, 2023, 14 pages.
Notice of Allowance in U.S. Appl. No. 17/511,773, dated Jul. 20, 2023, 14 pages.
Office Action in Australian Patent Application No. 2018219637, dated Jun. 30, 2023, 3 pages.
Office Action in European Patent Application No. 16837150.8, dated Jul. 12, 2023, 20 pages.
Office Action in Indian Patent Application No. 201747040368, dated Jul. 6, 2023, 2 pages.
Office Action in Israeli Patent Application No. 253946, dated Jul. 17, 2023, 13 pages (with English Translation).
Office Action in Korean Patent Application No. 10-2023-7009398, dated Jul. 31, 2023, 4 pages (with English Translation).
Office Action in Singaporean Patent Application No. 10202010137Y, dated Jul. 28, 2023, 8 pages.
Office Action in U.S. Appl. No. 17/228,025, dated Sep. 11, 2023, 19 pages.
Official Notification in European Patent Application No. 16837150.8, dated Jul. 21, 2023, 3 pages.
Official Notification in Jordan Patent Application No. 225/2020, dated Sep. 4, 2023, 2 pages (with English Translation).
Reed et al., "β-catenin/CBP activation of mTORC1 signaling promotes partial epithelial-mesenchymal states in head and neck cancer," Translational Research, Jun. 21, 2023, 1-15.
Submission Document in Brazilian Patent Application No. BR122023002744-2, dated Aug. 24, 2023, 46 pages (with English Translation).
Submission Document in Brazilian Patent Application No. BR122023002748-5, dated Aug. 25, 2023, 33 pages (with English Translation).
Submission Document in European Patent Application No. 16837150.8, dated Jul. 5, 2023, 10 pages.
Submission Document in Korean Patent Application No. 10-2018-7003723, dated Jun. 29, 2023, 14 pages (English Translation).
Submission Document in U.S. Appl. No. 15/750,712, dated Aug. 8, 2023, 1 page.
Submission Document in U.S. Appl. No. 17/228,025, dated Aug. 7, 2023, 37 pages.
Submission Document in U.S. Appl. No. 17/407,742, dated Jun. 7, 2023, 6 pages.
Van Winkle et al., "Ifosfamide, Carboplatin, and Etoposide (ICE) Reinduction Chemotherapy in a Large Cohort of Children and Adolescents With Recurrent/Refractory Sarcoma: The Children's Cancer Group (CCG) Experience," Pediatr. Blood Cancer, 2005, 44:338-347.
Official Notification in European Patent Application No. 16837150.8, dated Sep. 29, 2023, 43 pages.
Kudo et al., "Analysis of Tumor Biomarkers in Patients with Advanced Hepatocellular Carcinoma from a Phase 1b Study of E7386, a CREB-Binding Protein/β-Catenin Interaction Inhibitor, in Combination with Lenvatinib—Abstract #535," Poster, ASCO Gastrointestinal Cancers Symposium, Jan. 18-20, 2024, San Francisco, CA, USA, 1 page.
Kudo et al., "Analysis of Tumor Biomarkers in Patients with Advanced Hepatocellular Carcinoma from a Phase 1b Study of E7386, a CREB-Binding Protein/β-Cantenin Interaction Inhibitor, in Combination with Lenvatinib—Abstract #535," Slideshow, ASCO Gastrointestinal Cancers Symposium, Jan. 18-20, 2024, San Francisco, CA, USA, 6 pages.
Office Action in European Patent Application No. 17782552.8, dated Dec. 18, 2023, 7 pages.
Office Action in Israeli Patent Application No. 262076, dated Dec. 18, 2023, 4 pages.
Office Action in U.S. Appl. No. 16/092,245, dated Dec. 22, 2023, 33 pages.

(56) References Cited

OTHER PUBLICATIONS

Office Action in U.S. Appl. No. 17/052,133, dated Jan. 8, 2024, 9 pages.
Submission Document in European Patent Application No. 16837150.8, dated Dec. 1, 2023, 9 pages.
Submission Document in U.S. Appl. No. 15/750,712, dated Nov. 16, 2023, 14 pages.
Submission Document in U.S. Appl. No. 16/092,245, dated Nov. 30, 2023, 6 pages.
[No Author Listed], "Original Specification of Opposed Application," EISAI R&D Management Co. Ltd, Jun. 7, 2019, 40 pages.
EU Clinical Trials (2012-002992-33), 2013, 18 pages.
Notice of Allowance in U.S. Appl. No. 15/750,712, dated Feb. 2, 2024, 11 pages.
Office Action in Canadian Patent Application No. 3044658, dated Feb. 20, 2024, 4 pages.
Office Action in Indian Patent Application No. 201947022655, dated Feb. 13, 2024, 335 pages.
Office Action in Indian Patent Application No. 6971/CHENP/2015, dated Feb. 22, 2024, 5 pages.
Office Action in Singaporean Patent Application No. 10202010137Y, dated Feb. 6, 2024, 9 pages.
Office Action in U.S. Appl. No. 17/407,742, dated Feb. 1, 2024, 29 pages.
Office Action in U.S. Appl. No. 17/407,742, dated Feb. 14, 2024, 7 pages.
Submission Document in Brazilian Patent Application No. B112018002732-4, dated Jan. 22, 2024, 32 pages (with English Translation).
Submission Document in Israeli Patent Application No. 302218, dated Feb. 15, 2024, 20 pages (with English Translation).
Office Action in Brazilian Patent Application No. BR122023002744-2, dated Feb. 15, 2024, 20 pages (with English Translation).
Office Action in Brazilian Patent Application No. BR122023002748-5, dated Feb. 15, 2024, 19 pages (with English Translation).
[No Author], "Chromatograhic Purification of Lenvatinib," Experiment Report, Aug. 2023, 2 pages.
[No Author], "Experimental Data," provided as Evidence 12 by the Cancellation Petitioner on Feb. 17, 2024, in Taiwanese Patent Application No. 104127982, 3 pages.
[No Author], "Information of compound (I)," on the NITE Chemical Risk Information Platform website, Dec. 11, 2012, 3 pages (with English Translation).
[No Author], "Purified Lenvatinib analysis report," Experimental Report, Mar. 2024, 1 page.
[No Author], "Report on the Regulatory Uses and Applications in OECD Member Countries of (Quantitative) Structure-Activity Relationship [(Q)SAR] Models in the Assessment of New and Existing Chemicals," ENV/JM/MONO(2006)25, OECD, 2007, Paris France, available from URL: <http://oecd.org/>, 79 pages.
ClinicalTrials.gov [online], NCT database, "A Multicenter, Randomized, Double-Blind, Placebo-Controlled, Trial of Lenvatinib(E7080) in 131I-Refractory Differentiated Thyroid Cancer(DTC)(SELECT)," NCT01321554, Dec. 18, 2014, retrieved from: URL <https://clinicaltrials.gov/study/NCT01321554?cond=NCT01321554&rank=1&tab=histo ry&a=19>, 17 pages.
ClinicalTrials.gov [online], NCT database, "A Phase 1, Open-Label, Single-Dose, Pharmacokinetic and Safety Study of E7080(24mg) Administered to Subjects With Mild, Moderate, and Severe Renal Impairment and to Healthy Subjects," NCT02199379, Feb. 12, 2015, retrieved form: URL <https://clinicaltirals.gov/study/NCT02199379?intr=Lenvatinib&term=dose&rank=26&ta b=history&a=>, 13 pages.
ClinicalTrials.gov [online], NCT database, "A Study of E7080 in Subjects With Solid Tumor," NCT01268293, Feb. 21, 2015, retrieved from: URL <https://clinicaltrials.gov/study/NCT01268293?intr=Lenvatinib&studyComp=2016-02-10&rank=2&tab=history&a=6>, 20 pages.

Fisher et al., "Targeting Epigenetic Activity of β-Catenin/CBP Impedes Oral Cancer Progression," Poster, AACR Annual Meeting 2024, San Diego, California, Apr. 5-10, 2024, 1 page.
Herestch, "Experimental Report—Synthesis of Lenvatinib mesylate following prior art patent US 2007/0078159 A1—Prof. Heretsch with Annexes 1-3," Mar. 12, 2024, 23 pages.
Khan et al., "Reducing the effect of cellular stress in murine oral tumors with pharmacological blockade of β-catenin/CBP activity," Poster, AACR Annual Meeting 2024, San Diego, California, Apr. 5-10, 2024, 1 page.
Kume et al., "Single-cell RNA-sequencing analysis of tumor endothelial cells reveals suppression of specific endothelial subtypes by the combination treatment of Wnt/β-catenin signaling modulator E7386 plus lenvatinib," Poster, AACR Annual Meeting 2024, San Diego, California, Apr. 5-10, 2024, 1 page.
Lee et al., "Dose-Expansion Part of a Phase 1b Global Study of E7386 in Combination With Lenvatinib in Patients With Hepatocellular Carcinoma and Other Solid Tumors Including Enodmetrial Cancer," Poster, ASCO Annual Meeting 2024, Chicago, Illinois, May 31-Jun. 4, 2024, 7 pages.
Lee et al., "Dose-Expansion Part of a Phase 1b Global Study of E7386 in Combination With Lenvatinib in Patients With Hepatocellular Carcinoma and Other Solid Tumors Including Endometrial Cancer," Slidedeck, ASCO Annual Meeting 2024, Chicago, Illinois, May 31-Jun. 4, 2024, 7 pages.
Notice of Allowance in Israeli Patent Application No. 302218, dated Feb. 20, 2024, 3 pages.
Notice of Allowance in Japanese Patent Application No. P2022-161848, dated May 28, 2024, 8 pages (with English Translation).
Notice of Allowance in U.S. Appl. No. 15/750,712, dated May 15, 2024, 13 pages.
Notice of Allowance in U.S. Appl. No. 17/511,773, dated May 20, 2024, 4 pages.
Notice of Allowance in U.S. Appl. No. 17/511,773, dated May 6, 2024, 27 pages.
Office Action in Argentinian Patent Application No. P190102193, dated May 16, 2024, 11 pages (with English Translation).
Office Action in Brazilian Application No. BR122023002744-2, dated Jun. 4, 2024, 8 pages (with English Translation).
Office Action in Brazilian Application No. BR122023002748-5, dated Jun. 4, 2024, 8 pages (with English Translation).
Office Action in Canadian Patent Application No. 3019682, dated Apr. 4, 2024, 4 pages.
Office Action in Chinese Patent Application No. 202110939882.8, dated Apr. 11, 2024, 17 pages (with English Translation).
Office Action in European Patent Application No. 19151846.3, dated Apr. 2, 2024, 21 pages.
Office Action in European Patent Application No. 20207489.4, dated Jun. 3, 2024, 5 pages.
Office Action in Indian Patent Application No. 201947022655, dated May 14, 2024, 2 pages.
Office Action in Indian Patent Application No. 6971/CHENP/2015, dated Mar. 22, 2024, 10 pages.
Office Action in Tawiwanese Patent Application No. 104127982, dated Feb. 17, 2024, 178 pages (with English Translation).
Official Notification in European Patent Application No. 17782552.8, dated Jun. 5, 2024, 3 pages.
Official Notification in European Patent Application No. 19151846.3, dated May 23, 2024, 37 pages.
PubChem Substance Record for SID 135264024, "Lenvatinib Mesylate," National Library of Medicine, Mar. 21, 2012, 8 pages.
Shen et al., "E7386, a Wnt/β-catenin signaling modulator, suppresses the differentiation of regulatory T cells in combination with lenvatinib plus anti-PD-1 antibody," Poster, AACR Annual Meeting 2024, San Diego, California, Apr. 5-10, 2024, 1 page.
Submission Document in Brazilian Patent Application No. BR122023002744-2, dated May 15, 2024, 65 pages (with Englsh Translation).
Submission Document in Brazilian Patent Application No. BR122023002748-5, dated May 15, 2024, 54 pages (with English Translation).
Submission Document in European Patent Application No. 16837150.8, dated May 29, 2024, 21 pages.

(56) References Cited

OTHER PUBLICATIONS

Submission Document in European Patent Application No. 17782552.8, dated May 17, 2024, 12 pages.
Submission Document in European Patent Application No. 19151846.3, dated Mar. 12, 2024, 10 pages.
Submission Document in European Patent Application No. 19151846.3, dated Mar. 13, 2024, 25 pages.
Submission Document in European Patent Application No. 22867352.1, dated May 17, 2024, 8 pages.
Submission Document in Indian Patent Application No. 201947022655, dated May 10, 2024, 19 pages.
Submission Document in Indian Patent Application No. 201947022655, dated May 28, 2024, 9 pages.
Submission Document in Israeli Patent Application No. 262076, dated Apr. 11, 2024, 29 pages (with English Translation).
Submission Document in Japanese Patent Application No. P2022-161848, dated Mar. 27, 2024, 9 pages (with English Translation).
Submission Document in U.S. Appl. No. 15/750,712, dated May 1, 2024, 23 pages.
Submission Document in U.S. Appl. No. 17/228,025, dated Apr. 18, 2024, 11 pages.
Submission Document in U.S. Appl. No. 17/407,742, dated Jan. 5, 2024, 42 pages.
Waters.com [online], "Waters Chromatography Columns and Supplies," 2009, retrieved form: URL <https://www.waters.com/webassets/cms/library/docs/720002784en>, 9 pages.
Submission Document in Canadian Patent Application No. 3044658, dated Jun. 17, 2024, 12 pages.
[No Author], "Guideline on pharmaceutical development of medicines for paediatric use," European Medicines Agency, Aug. 2013, 24 pages.
[No Author], "How to give medicines: tablets," Medicines for Children, Dec. 2011, 2 pages.
Aulton et al., "Pharmaceutics: The Science of Dosage Form Design," Churchill Livingstone, 2002, Chapters 1, 23, 27 and 29; 96 pages.
Burger et al., "Hunnius Pharmazeuticals Worterbuch," Berlin, New York: Walter de Gruyte, 1993, Ed. 7, p. 221, 8 pages (Partial Translation).
Felton, "Remington Essentials of Pharmaceutics," Pharmaceutical Press, 2013, Chapters 17 and 20; 71 pages.
Lynch et al., "The Sense of Taste," Nova Science Publishers, 2012, pp. 237-276.
Notice of Allowance in U.S. Appl. No. 17/407,742, dated Aug. 29, 2024, 15 pages.
Notice of Allowance in U.S. Appl. No. 17/511,773, dated Aug. 14, 2024, 21 pages.
Notice of Opposition in European Patent Application No. 16755489.8, Opponent: Accord Healthcare Ltd, dated Jul. 30, 2024, 26 pages.
Notice of Opposition in European Patent Application No. 16755489.8, Opponent: Generics [UK] Limited, dated Jul. 31, 2024, 24 pages.
Notice of Opposition in European Patent Application No. 16755489.8, Opponent: Maiwald GmbH, dated Jul. 26, 2024, 27 pages.
Office Action in Argentinian Patent Application No. P20150102731, dated Jul. 26, 2024, 7 pages (with English Translation).
Office Action in Indian Patent Application No. 201947022655, dated Aug. 6, 2024, 2 pages.
Office Action in Indian Patent Application No. 201947022655, dated Jul. 3, 2024, 2 pages.
Office Action in Israeli Patent Application No. 253946, dated Jul. 25, 2024, 9 pages (with English Translation).
Office Action in Signaporean Patent Application No. 10202100272R, dated Jul. 30, 2024, 10 pages.
Official Notification in European Patent Application No. 16755489.8, dated Aug. 6, 2024, 2 pages.
Official Notification in European Patent Application No. 16755489.8, dated Jul. 17, 2024, 26 pages.
Official Notification in European Patent Application No. 16755489.8, dated Jun. 26, 2024, 31 pages.
Official Notification in European Patent Application No. 18751614.1, dated Sep. 3, 2024, 26 pages.
Olivieri et al., "Dasatinib: a new step in molecular target therapy," Annals of Oncology, Jun. 2007, 18(Supplement 6):vi42-46.
Padma, "An overview targeted cancer therapy," BioMedicine, Dec. 2015, 5(4):1-6.
Pydi, "Amino Acid Derivatives as Bitter Taste Receptor (T2R) Blockers," Journal of Biochemistry, Sep. 5, 2014, 289(36):25054-25066.
Row et al., "Handbook of Pharmaceutical Excipients," Pharmaceutical Press, 2009, Sixth ed., pp. 400-402.
Rowe et al., "Handbook of Pharmaceutical Excipients," Pharmaceutical Press, 2009, Sixth ed., pp. 86-89.
Submission Document in Brazilian Patent Application No. BR122023002744-2, dated Aug. 2, 2024, 37 pages (with English Translation).
Submission Document in Brazilian Patent Application No. BR122023002748-5, dated Aug. 2, 2024, 36 pages (with English Translation).
Submission Document in Chinese Patent Application No. 202110939882.8, dated Aug. 9, 2024, 44 pages (with English Translation).
Submission Document in Korean Patent Application No. 10-2017-7022544, dated Jul. 23, 2024, 19 pages (with English Translation).
Swarbrick, "Encyclopedia of Pharmaceutical Technology," CRC Press, 2006, Third ed., vol. 1, 16 pages.
Tai et al., "Targeting the WNT Signaling Pathway in Cancer Therapeutics," The Oncologist, Oct. 2015, 20(10):1189-1198.
White et al., "Handbook of Drug Administration via Enteral Feeding Tubes," Pharmaceutical Press, 2007, 22 pages.
Wikipedia.org [online], "Alkaloid," Extract of the Internet Archive website, Feb. 23, 2015, 19 pages.
ClinicalTrials.gov [online], "Study of Lenvatinib in Children and Adolescents With Refractory or Relapsed Solid Malignancies and Young Adults With Osteosarcoma," NCT02432274, Jan. 26, 2016, Version 6, retrieved from URL <https://clinicaltrials.gov/study/NCT02432274>, 44 pages.
De Gruyter, "Pschyrembel: Klinisches Wörterbuch," bearbeitet von der Wörterbuch-Redaktion des Verlages unter der Leitung von Helmut Hildebrand, 1994, p. 796; 4 pages (with English Translation).
Mitra et al., "Memorandum regarding NDA 206-947: LENVIMA (lenvatinib) capsules 4 and 10 mg, Eisai, Inc., Drug Product Review for Division of Drug Oncology Products (Div 2)," FDA's Chemistry Review, Feb. 5, 2015, 56 pages.
Notice of Allowance in U.S. Appl. No. 15/750,712, dated Aug. 28, 2024, 11 pages.
Notice of Opposition in European Patent Application No. 16755489.8, Opponent: STADA Arzeitmittel AG, dated Jul. 30, 2024, 37 pages.
U.S. Appl. No. 62/120,561, Nagane et al., Method for suppressing bitterness of quinoline derivative, filed Feb. 25, 2015, 64 pages (with Machine Translation).
Azuma, "Cancer Immunotherapy b Blockade of PD-1 Immune Checkpoint," Journal of Clinical and Experimental Medicine, Mar. 2, 2013, 244(9):809-815 (with Full Translation).
Fodde et al., "Wnt/β-catenin signaling in cancer stemness and malignant behavior," Current Opinion in Cell Biology, 2007, 19(2):150-158.
International Preliminary Report on Patentability in International Application No. PCT/JP2022/033458, dated Mar. 21, 2024, 5 pages.
International Search Report in International Application No. PCT/JP2022/033458, mailed on Nov. 22, 2022, 2 pages (English Translation).
International Search Report in International Application No. PCT/JP2023/012957, dated Jun. 20, 2023, 2 pages (English Translation).
Joeng et al., "Interaction between Wnt/β-catenin and RAS-ERK pathways and an anti-cancer strategy via degradations of β-catenin and RAS by targeting the Wnt/β-catenin pathway," NPJ Precision Onc., Feb. 20, 2018, 2(5);1-10.
Mologni et al., "Synergistic Effects of Combined Wnt/KRAS Inhibition in Colorectal Cancer Cells," PLoS One, Dec. 5, 2012, 7(12):1-10.
Notice of Allowance in Argentina Patent Application No. P140104850, dated Mar. 26, 2024, 4 pages (with English Translation).

(56) References Cited

OTHER PUBLICATIONS

Notice of Allowance in Australia Patent Application No. 2016284383, dated Aug. 10, 2020, 47 pages.
Notice of Allowance in Brazilian Patent Application No. BR11201603572-5, dated Mar. 7, 2023, 295 pages (with English Translation).
Notice of Allowance in Brazilian Patent Application No. BR112016013572-5, dated Nov. 8, 2022, 10 pages (with English Translation).
Notice of Allowance in Brazilian Patent Application No. BR112017025519-7, dated Jun. 6, 2023, 7 pages (with English Tranlsation).
Notice of Allowance in Canadian Patent Application No. 2932435, dated Apr. 27, 2021, 2 pages.
Notice of Allowance in Canadian Patent Application No. 2986999, dated Mar. 28, 2023, 1 page.
Notice of Allowance in Chinese Patent Application No. 201680030060.5, Nov. 4, 2019, 4 pages (with English Translation).
Notice of Allowance in European Patent Application No. 16814346.9, dated Nov. 25, 2020, 37 pages.
Notice of Allowance in Indonesian Patent Application No. P00201603922, dated Jul. 15, 2019, 4 pages (wit English Translation).
Notice of Allowance in Israeli Patent Application No. 255901, dated Apr. 27, 2020, 5 pages (with English Translation).
Notice of Allownce in Japanese Patent Application No. P2023-546948, dated Feb. 20, 2024, 6 pages (with English Translation).
Notice of Allowand in Korean Patent Application No. 10-2016-7015608, dated Jun. 29, 2021, 4 pages (with English Translation).
Notice of Allowand in Korean Patent Application No. 10-2017-7033876, dated Jun. 23, 2023, 7 pages (with English Translation).
Notice of Allowand in Malayasian Patent Application No. PI2016702025, dated Feb. 12, 2020, 3 pages.
Notice of Allowand in Mexican Patent Application No. MX/a/2016/007705, dated Apr. 5, 2019, 5 pages (with English Translation).
Notice of Allowand in Mexican Patent Application No. MX/a/2017/015257, dated Apr. 22, 2021, 4 pages (with English Translation).
Notice of Allowand in New Zealand Patent Application No. 720718, dated Oct. 7, 2020, 2 pages.
Notice of Allowand in Russian Patent Application No. 2017141763, dated Apr. 28, 2020, 13 pages (with English Translation).
Notice of Allowand in Singaporean Patent Application No. 11201709593V, dated Jan. 27, 2023, 4 pages.
Notice of Allowand in Taiwanese Patent Application No. 103144928, dated Oct. 31, 2019, 6 pages (with English Translation).
Notice of Allowand in Venezuelan Patent Application No. 2014001560, dated Jul. 22, 2022, 3 pages (with English Translation).
Office Action in Argentina Patent Application No. P140104850, dated Dec. 18, 2019, 4 pages (with English Translation).
Office Action in Argentina Patent Application No. P140104850, dated Sep. 18, 2023, 10 pages (with English Translation).
Office Action in Australian Patent Application No. 2016284383, dated Jun. 3, 2020, 3 pages.
Office Action in Australian Patent Application No. 2016284383, dated Mar. 23, 2020, 3 pages.
Office Action in Brazilian Patent Application No. BR112016013572-5, dated Feb. 11, 2020, 9 pages (with English Translation).
Office Action in Brazilian Patent Application No. BR112017025519-7, dated Feb. 14, 2023, 9 pages (with English Translation).
Office Action in Brazilian Patent Application No. BR112017025519-7, dated Nov. 24, 2020, 9 pages (with English Translation).
Office Action in Canadian Patent Application No. 2932435, dated Oct. 9, 2020, 3 pages (with English Translation).
Office Action in Canadian Patent Application No. 2986999, dated Mar. 25, 2022, 4 pages.
Office Action in Canadian Patent Application No. 2986999, dated Sep. 9, 2022, 3 pages.
Office Action in Chinese Patent Application No. 201680030060.5, dated Jul. 15, 2019, 8 pages (with English Translation).
Office Action in Egyptian Patent Application No. PCT985-2016, dated Jan. 10, 2024, 11 pages (with English Translation).
Office Action in Egyptian Patent Application No. PCT985-2016, dated Jan. 15, 2024, 9 pages (with English Translation).
Office Action in Egyptian Patent Application No. PCT985-2016, dated Jan. 2, 2024, 9 pages (with English Translation).
Office Action in European Patent Application No. 16814346.9, dated Feb. 27, 2020, 3 pages.
Office Action in European Patent Application No. 16814346.9, dated Jun. 26, 2019, 5 pages.
Office Action in Indian Patent Application No. 201647019978, dated Apr. 29, 2019, 6 pages.
Office Action in Indian Patent Application No. 201647019978, dated Sep. 16, 2019, 2 pages.
Office Action in Indian Patent Application No. 201747042429, dated Jan. 28, 2020, 6 pages.
Office Action in Indian Patent Application No. 201747042429, dated Oct. 20, 2022, 2 pages.
Office Action in Indonesian Patent Application No. P00201603922, dated Feb. 21, 2019, 6 pages (with English Translation).
Office Action in Israeli Patent Application No. 255901, dated Nov. 8, 2018, 5 pages (with English Translation).
Office Action in Japanese Patent Application No. P2023-546948, dated Nov. 7, 2023, 6 pages (with English Translation).
Office Action in Jordanian Patent Application No. 3732014, dated Jan. 6, 2020, 2 pages (with English Translation).
Office Action in Korean Patent Application No. 10-2016-7015608, dated Jan. 18, 2021, 5 pages (with English Translation).
Office Action in Korean Patent Application No. 10-2017-7022544, dated Jun. 18, 2024, 11 pages (with English Translation).
Office Action in Korean Patent Application No. 10-2017-7033876, dated Feb. 3, 2023, 9 pages (with English Translation).
Office Action in Mexican Patent Application No. MX/a/2017/015257, dated Feb. 2, 2021, 6 pages (with English Translation).
Office Action in Mexican Patent Application No. MX/a/2017/015257, dated Oct. 2, 2020, 9 pages (with English Translation).
Office Action in Mexican Patent Application No. MX/a/2022/009299, dated Sep. 3, 2024, 10 pages (with English Translation).
Office Action in New Zealand Patent Application No. 720718, dated Aug. 14, 2020, 2 pages.
Office Action in Peruvian Patent Application No. 000711-2016, dated Oct. 11, 2019, 14 pages (with English Translation).
Office Action in Russian Patent Application No. 000711-2016, dated Oct. 11, 2019, 14 pages (with English Translation).
Office Action in Russian Patent Application No. 2017141763, dated Aug. 23, 2019, 16 pages (with English Translation).
Office Action in Russian Patent Application No. 2017141763, dated Jan. 10, 2020, 11 pages (with English Translation).
Office Action in Singaporean Patent Application No. 11201709593V, dated Dec. 24, 2020, 6 pages.
Santos et al., "Structural and functional properties of ras proteins," FASEB J., Aug. 1989, 3(10):2151-2163.
Submission Document in Argentina Patent Application No. P140104850, dated Feb. 6, 2020, 183 pages (with English Translation).
Submission Document in Argentina Patent Application No. P140104850, dated Feb. 6, 2024, 5 pages (with English Translation).
Submission Document in Australian Patent Application No. 2016284383, dated Jul. 31, 2020, 7 pages.
Submission Document in Australian Patent Application No. 2016284383, dated May 12, 2020, 26 pages.
Submission Document in Brazilian Patent Application No. BR11216013572-5, dated May 11, 2020, 22 pages (with English Translation).
Submission Document in Brazilian Patent Application No. BR112017025519-7, dated Feb. 18, 2021, 12 pages (with English Translation).
Submission Document in Brazilian Patent Application No. BR112017025519-7, dated May 12, 2023, 20 pages (with English Translation).
Submission Document in Canadian Patent Application No. 2932435, dated Jan. 26, 2021, 15 pages.
Submission Document in Canadian Patent Application No. 2986999, dated Jun. 6, 2022, 25 pages.

(56) References Cited

OTHER PUBLICATIONS

Submission Document in Canadian Patent Application No. 2986999, dated Nov. 11, 2022, 6 pages.
Submission Document in Chinese Patent Application No. 201680030060.5, dated Aug. 21, 2019, 61 pages (with English Translation).
Submission Document in Egyption Patent Application No. PCT985-2016, dated Apr. 4, 2022, 7 pages (with English Translation).
Submission Document in Egyption Patent Application No. PCT985-2016, dated Apr. 6, 2023, 11 pages (with English Translation).
Submission Document in European Patent Application No. 16814346.9, dated Jun. 18, 2020, 9 pages.
Submission Document in European Patent Application No. 16814346.9, dated Sep. 23, 2019, 45 pages.
Submission Document in Indian Patent Application No. 201647019978, dated Jul. 30, 2019, 28 pages.
Submission Document in Indian Patent Application No. 201647019978, dated Oct. 31, 2019, 11 pages.
Submission Document in Indian Patent Application No. 201747042429, dated Dec. 28, 2022, 14 pages.
Submission Document in Indian Patent Application No. 201747042429, dated Mar. 12, 2020, 9 pages.
Submission Document in Indonesian Patent Application No. P00201603922, dated May 17, 2019, 5 pages (with English Translation).
Submission Document in Israeli Patent Application No. 255901, dated Jan. 21, 2019, 8 pages (with English Translation).
Submission Document in Japanese Patent Application No. P2023-546948, dated Dec. 26, 2023, 4 pages (with English Translation).
Submission Document in Jordan Patent Application No. 3732014, dated Jan. 28, 2020, 2 pages (with English Translation).
Submission Document in Korean Patent Application No. 10-2016-7015608, dated Feb. 19, 2020, 9 pages (with English Translation).
Submission Document in Korean Patent Application No. 10-2016-7015608, Mar. 8, 2021, 12 pages (with English Translation).
Submission Document in Korean Patent Application No. 10-2017-7033876, dated Mar. 22, 2023, 22 pages (with English Translation).
Submission Document in Mexican Patent Application No. MX/a/2017/015257, dated Mar. 10, 2021, 12 pages (with English Translation).
Submission Document in Mexican Patent Application No. MX/a/2017/015257, dated Nov. 26, 2021, 14 pages (with English Translation).
Submission Document in New Zealand Patent Application No. 720718, dated Sep. 28, 2020, 5 pages.
Submission Document in Peruvian Patent Application No. 000711-2016, dated Dec. 23, 2019, 8 pages (with English Translation).
Submission Document in Russian Patent Application No. 201741763, dated Mar. 23, 2020, 12 pages (with English Translation).
Submission Document in Russian Patent Application No. 2017141763, dated Nov. 12, 2019, 15 pages (with English Translation).
Submission Document in Singaporean Patent Application No. 11201709593V, dated Feb. 19, 2021, 18 pages.
Submission Document in U.S. Appl. No. 15/750,712, dated Aug. 14, 2024, 16 pages.
Submission Document in U.S. Appl. No. 17/407,742, dated Aug. 14, 2024, 22 pages.
Submission Document in Venezuelan Patent Application No. 2014001560, dated Mar. 9, 2020, 4 pages (with English Translation).
Turcios et al., "Sorafenib and FH535 in combination act synergistically on hepatocellular carcinoma by targeting cell bioenergetics and mitochondrial function," Digestive and Liver Disease, Jun. 2017, 49(6):697-704.

Van Amerongen et al., "Break the loop, escape the cycle?," The EMBO Journal, Jul. 17, 2023, 32(14):1967-1969.
Hori et al., "Abstract 5172: E7386, an orally active CBP/beta-catenin modulator, induces T cells infiltration into tumor and enhances antitumor activity of anti-PD-1 mAb in Wnt1 tumor syngeneic mice model," Cancer Research, Jul. 2017, 77(13 Supplement):5172, 5 pages.
Lee et al., "Dose-Expansion Part of a Phase 1b Global Study of E7386 in Combination With Lenvatinib in Patients With Hepatocellular Carcinoma and Other Solid Tumors, Including Endometrial Cancer," Abstract ID: 1565, Poster, IGCS 2024 Annual Global Meeting, Dublin, Ireland, Oct. 16-18, 2024, 1 page.
Lee et al., "Global, Phase 1b Dose-Expansion of E7386 + Lenvatinib in—Patients With Advanced Endometrial Cancer That Progressed on Platinum-Based Chemotherapy and an Anti-PD-(L)1 Immunotherapy," Poster, ESMO Congress 2024, Barcelona, Spain, Sep. 13-17, 2024, 1 page.
Notice of Allowance in Israeli Patent Application No. 253946, dated Nov. 6, 2024, 7 pages (with English Translation).
Notice of Allowance in Japanese Patent Application No. P2020-560740, dated Nov. 14, 2023, 5 pages (with English Translation).
Notice of Allowance in Korean Patent Application No. 10-201-7022544, dated Nov. 1, 2024, 7 pages (with English Translation).
Office Action in Chinese Patent Application No. 202110939882.8, dated Oct. 26, 2024, 11 pages (with English Translation).
Office Action in Indian Patent Application No. 201947022655, dated Nov. 21, 2024, 16 pages.
Office Action in Indian Patent Application No. 201947022655, dated Nov. 29, 2024, 17 pages.
Office Action in Israeli Patent Application No. 302218, dated Oct. 18, 2023, 6 pages.
Office Action in Japanese Patent Application No. P2022-161848, dated Oct. 31, 2023, 12 pages (with English Translation).
Office Action in Japanese Patent Application No. P2022-520800, dated Oct. 8, 2024, 9 pages (with English Translation).
Office Action in Korean Patent Application No. 10-2017-022544, dated Oct. 10, 2023, 5 pages (with English Translation).
Office Action in Mexican Patent Application No. MX/a/2022/009300, dated Sep. 5, 2024, 17 pages (with English Translation).
Official Notification in U.S. Appl. No. 17/228,025, dated Oct. 23, 2024, 7 pages.
Submission Document in European Patent Application No. 20207489.4, dated Nov. 27, 2024, 38 pages.
Submission Document in Indian Patent Application No. 201947022655, dated Nov. 29, 2024, 4 pages.
Submission Document in Indian Patent Application No. 201947022655, dated Nov. 4, 2024, 87 pages.
Submission Document in Israeli Patent Application No. 253946, dated Nov. 6, 2023, 8 pages (with English Transportation).
Submission Document in Israeli Patent Application No. 253946, dated Oct. 8, 2024, 6 pages.
Submission Document in Mexican Patent Application No. MX/a/2022/009299, dated Jan. 5, 2023, 43 pages (with English Translation).
Submission Document in Singaporean Patent Application No. 10202100272R, dated Dec. 19, 2024, 13 pages.
Submission Document in U.S. Appl. No. 17/228,025, dated Nov. 14, 2023, 25 pages.
Submission Document in U.S. Appl. No. 17/511,773, dated Nov. 13, 2024, 5 pages.
Office Action in European Patent Application No. 18751614.1, dated Feb. 20, 205, 12 pages.
Opposition, "Lenvima," Exhibit D9 in European Application No. 18751614.1, dated May 20, 2020, 61 pages.
Official Notification in U.S. Appl. No. 17/228,025, dated Nov. 24, 2025, 13 pages.

* cited by examiner

Transgenic mouse (MMTV-Wnt-1) spontaneous breast cancer

Transgenic mouse (MMTV-Wnt-1) spontaneous breast cancer

Transgenic mouse (MMTV-Wnt-1) spontaneous breast cancer

Mouse breast cancer 4T1 cell

Human anaplastic thyroid cancer cell line HTC/C3

Human anaplastic thyroid cancer cell line HTC/C3

Human hepatocellular carcinoma line SNU398 cell

Human renal cell carcinoma line A-498 cell (a) Control group (b) E7386 alone administration group (c) Lenvatinib mesylate alone administration group (d) E7386 and lenvatinib mesylate combined administration group (a) Control group (b) E7386 alone administration group (c) Lenvatinib mesylate alone administration group (d) E7386 and lenvatinib mesylate combined administration group Mouse breast cancer 4T1 cell Mouse breast cancer 4T1 cell Human hepatocellular carcinoma line HepG2 cell Human hepatocellular carcinoma line HepG2 cell

TUMOR-TREATING PHARMACEUTICAL COMPOSITION

TECHNICAL FIELD

The present invention relates to a pharmaceutical composition for treating a tumor, which is used in the combination therapy of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

BACKGROUND ART

Lenvatinib is an oral tyrosine kinase inhibitor having an angiogenesis inhibitory effect (Patent Literature 1) and targeting vascular endothelial growth factor receptors (VEGFRs) 1 to 3, fibroblast growth factor receptors (FGFRs) 1 to 4, rearranged during transfection (RET), KIT and platelet-derived growth factor receptor (PDGFR) a (Patent Literatures 2 to 5), and is known as a therapeutic agent for various tumors such as thyroid cancer, lung cancer, melanoma, endometrial cancer, renal cell carcinoma, glioma, hepatocellular carcinoma, and ovary cancer. The compound name of lenvatinib is 4-(3-chloro-4-(cyclopropylaminocarbonyl)aminophenoxy)-7-methoxy-6-quinolinecarboxamide.

(6S,9aS)—N-Benzyl-8-({6-[3-(4-ethylpiperazin-1-yl)azetidin-1-yl]pyridin-2-yl}methyl)-6-(2-fluoro-1-hydroxybenzyl)-4,7-dioxo-2-(prop-2-en-1-yl)hexahydro-2H-pyrazino[2,1-c][1,2,4]triazine-1(6H)-carboxamide (hereinafter, also referred to as E7386) is known as a compound having a Wnt Pathway modulating effect (Patent Literature 6).

There is no previous report as to whether the combination therapy of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide exhibits any antitumor effect.

In general, a tumor therapeutic agent, when used alone, is often not effective for all patients. Accordingly, an attempt has been made so far to improve a treatment rate by using a plurality of tumor therapeutic agents in combination and achieving enhancement in antitumor effect or alleviation of adverse reactions (Patent Literatures 7 to 9).

CITATION LIST

Patent Literature

Patent Literature 1: U.S. Pat. No. 7,253,286
Patent Literature 2: U.S. Patent Application Publication No. 2004-253205
Patent Literature 3: U.S. Patent Application Publication No. 2010-105031
Patent Literature 4: U.S. Patent Application Publication No. 2009-209580
Patent Literature 5: U.S. Patent Application Publication No. 2009-264464
Patent Literature 6: U.S. Pat. No. 9,174,998
Patent Literature 7: International Publication No. WO 2009/140549
Patent Literature 8: U.S. Patent Application Publication No. 2004-259834
Patent Literature 9: U.S. Pat. No. 6,217,866

SUMMARY OF INVENTION

Technical Problem

Under such circumstances, the further development of new combination therapy of tumor therapeutic agents is anticipated.

Solution to Problem

The present inventors have conducted diligent studies and consequently completed the present invention by finding that the combined administration of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide exhibits an unexpected antitumor effect.

Specifically, the present invention provides the following [1] to [33].

[1] A pharmaceutical composition comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is administered in combination with lenvatinib or a pharmaceutically acceptable salt thereof.

[2] A pharmaceutical composition comprising lenvatinib or a pharmaceutically acceptable salt thereof, wherein lenvatinib or a pharmaceutically acceptable salt thereof is administered in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[3] A pharmaceutical composition for treating a tumor, comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is administered in combination with lenvatinib or a pharmaceutically acceptable salt thereof.

[4] A pharmaceutical composition for treating a tumor, comprising lenvatinib or a pharmaceutically acceptable salt thereof, wherein lenvatinib or a pharmaceutically acceptable salt thereof is administered in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[5] A therapeutic agent for a tumor comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, wherein (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7- dioxo-2-(prop-2-en-1-yl)hexahydro-2H-pyrazino[2,1-c][1,2,4]triazine-1(6H)-carboxamide is administered in combination with lenvatinib or a pharmaceutically acceptable salt thereof.

[6] A therapeutic agent for a tumor comprising lenvatinib or a pharmaceutically acceptable salt thereof, wherein lenvatinib or a pharmaceutically acceptable salt thereof is administered in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[7] A method for treating tumor, comprising administering lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide to a patient in need thereof.

[8] Use of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide for producing a pharmaceutical composition for treating a tumor, wherein (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is administered in combination with lenvatinib or a pharmaceutically acceptable salt thereof.

[9] Use of lenvatinib or a pharmaceutically acceptable salt thereof for producing a pharmaceutical composition for treating a tumor, wherein lenvatinib or a pharmaceutically acceptable salt thereof is administered in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[10] (6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide for treating a tumor, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is administered in combination with lenvatinib or a pharmaceutically acceptable salt thereof.

[11] Lenvatinib or a pharmaceutically acceptable salt thereof for treating a tumor, wherein the lenvatinib or the pharmaceutically acceptable salt thereof is administered in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[12] A kit comprising a formulation comprising lenvatinib or a pharmaceutically acceptable salt thereof, and a formulation comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[13] The kit according to [12], wherein the kit is a kit for treating a tumor.

[14] A pharmaceutical composition comprising lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[15] A pharmaceutical composition for treating a tumor, comprising lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[16] A therapeutic agent for a tumor comprising lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[17] Lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide for use in treating a tumor.

[18] (6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide for use in treating a tumor in combination with lenvatinib or a pharmaceutically acceptable salt thereof.

[19] Lenvatinib or a pharmaceutically acceptable salt thereof for use in treating a tumor in combination with (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[20] Use of lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide for producing a pharmaceutical composition for treating a tumor.

[21] The pharmaceutical composition or the therapeutic agent for a tumor, further comprising an excipient.

[22] The pharmaceutical composition, the therapeutic agent for a tumor, the treatment method, the use, the compound or the kit, wherein the lenvatinib or the pharmaceutically acceptable salt thereof is lenvatinib mesylate.

[23] The pharmaceutical composition, the therapeutic agent for a tumor, the treatment method, the use, the compound or the kit, wherein the lenvatinib or the pharmaceutically acceptable salt thereof, and the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide are administered simultaneously, separately, continuously, or at time intervals.

[24] The pharmaceutical composition, the therapeutic agent for a tumor, the treatment method, the use, the compound or the kit, wherein the tumor is breast cancer, thyroid cancer, hepatocellular carcinoma, colorectal cancer, renal cell carcinoma, head and neck cancer, endometrial cancer or melanoma.

[25] The pharmaceutical composition, the therapeutic agent for a tumor, the treatment method, the use, the compound or the kit according to [24], wherein the tumor is breast cancer.

[26] The pharmaceutical composition, the therapeutic agent for a tumor, the treatment method, the use, the compound or the kit according to [24], wherein the tumor is thyroid cancer.

[27] The pharmaceutical composition, the therapeutic agent for a tumor, the treatment method, the use, the compound or the kit according to [26], wherein the thyroid cancer is anaplastic thyroid cancer.

[28] The pharmaceutical composition, the therapeutic agent for a tumor, the treatment method, the use, the compound or the kit according to [24], wherein the tumor is hepatocellular carcinoma.

[29] The pharmaceutical composition, the therapeutic agent for a tumor, the treatment method, the use, the compound or the kit according to [24], wherein the tumor is colorectal cancer.

[30] The pharmaceutical composition, the therapeutic agent for a tumor, the treatment method, the use, the compound or the kit according to [24], wherein the tumor is renal cell carcinoma.

[31] The pharmaceutical composition, the therapeutic agent for a tumor, the treatment method, the use, the compound or the kit according to [24], wherein the tumor is head and neck cancer.

[32] The pharmaceutical composition, the therapeutic agent for a tumor, the treatment method, the use, the compound or the kit according to [24], wherein the tumor is endometrial cancer.

[33] The pharmaceutical composition, the therapeutic agent for a tumor, the treatment method, the use, the compound or the kit according to [24], wherein the tumor is melanoma.

Advantageous Effects of Invention

The present invention provides a pharmaceutical composition for treating a tumor, which is used in the combination therapy of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide. This pharmaceutical composition for treating a tumor exhibits unexpected antitumor effects for patients in need thereof.

BRIEF DESCRIPTION OF DRAWINGS

FIG. 17(a) is a photograph of a control group, FIG. 17(b) is a photograph of an E7386 alone administration group (25 mg/kg), FIG. 17(c) is a photograph of a lenvatinib mesylate alone administration group (10 mg/kg), and FIG. 17(d) is a photograph of an E7386 (25 mg/kg) and lenvatinib mesylate (10 mg/kg) combined administration group.

FIG. 18(a) is a photograph of a control group, FIG. 18(b) is a photograph of an E7386 alone administration group (25 mg/kg), FIG. 18(c) is a photograph of a lenvatinib mesylate alone administration group (10 mg/kg), and FIG. 18(d) is a photograph of an E7386 (25 mg/kg) and lenvatinib mesylate (10 mg/kg) combined administration group. A microvessel stained with CD31 is indicated by black arrow. A CD31/α-SMA both positive blood vessel is indicated by open arrow.

DESCRIPTION OF EMBODIMENTS

Figure 1:
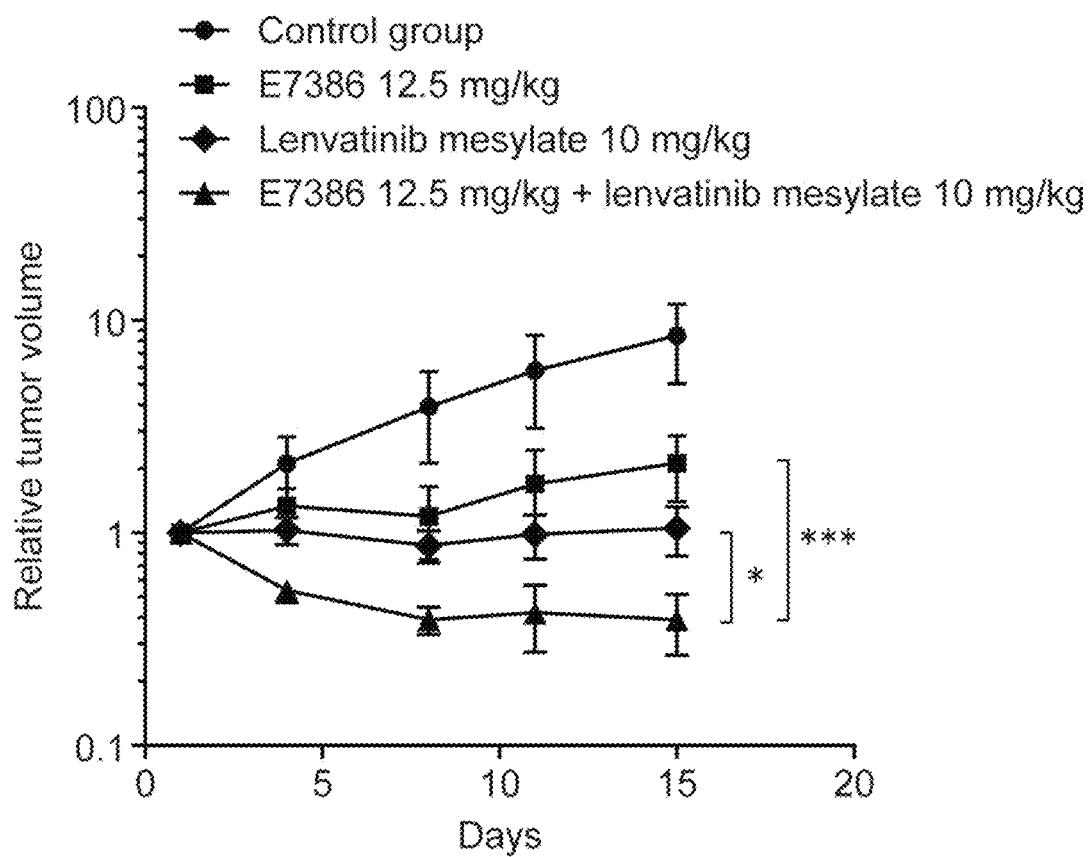
FIG. 1 is a graph showing the antitumor effect of combined use of 12.5 mg/kg E7386 and 10 mg/kg lenvatinib mesylate in serial transplantation models of transgenic mouse (MMTV-Wnt-1) spontaneous breast cancer. In the graph, * and *** show that the combined use of E7386 and lenvatinib mesylate statistically significantly inhibited tumor growth as compared with the case where each of them was administered alone (*: $p<0.05$, ***: $p<0.001$; repeated measures ANOVA followed by Dunnett's type multiple comparison).

Embodiments of the present invention are described below. The following embodiments are only examples for describing the present invention, and it is not intended to limit the present invention only to these embodiments. The present invention can be carried out in various modes without departing from the subject matter of the present invention.

Note that the documents, publications, patent publications, and other patent literatures cited in the present description are incorporated herein by reference.

Lenvatinib refers to 4-(3-chloro-4-(cyclopropylaminocarbonyl)aminophenoxy)-7-methoxy-6-quinolinecarboxamide, and the structural formula thereof is shown in the following formula:

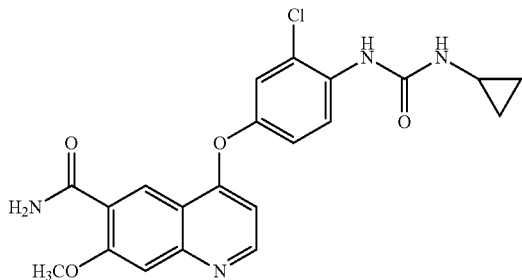 [SMILES: COc1cc2nccc(Oc3ccc(NC(=O)NC4CC4)c(Cl)c3)c2cc1C(N)=O]

Lenvatinib or a pharmaceutically acceptable salt thereof can be produced by a method described in Patent Literature 1. One example of the pharmaceutically acceptable salt of lenvatinib is lenvatinib mesylate. Lenvatinib mesylate is also referred to as E7080 or Lenvima®.

The structural formula of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is shown in the following formula.

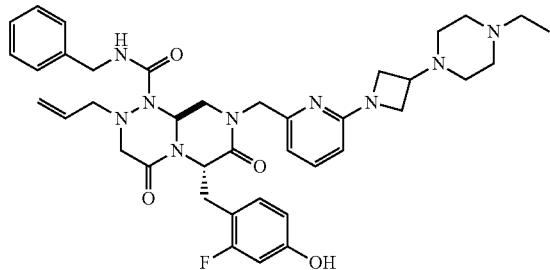

(6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide can be produced by a method described in Patent Literature 6. (6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is also referred to as E7386.

Although the "pharmacologically acceptable salt" is not limited to a specific type of salt, examples thereof include salts with inorganic acids, salts with organic acids, salts with inorganic bases, salts with organic bases, and salts with acidic or basic amino acids.

Examples of salts with inorganic acids include salts with hydrochloric acid, hydrobromic acid, sulfuric acid, nitric acid, and phosphoric acid. Examples of salts with organic acids include salts with acetic acid, succinic acid, fumaric acid, maleic acid, tartaric acid, citric acid, lactic acid, stearic acid, benzoic acid, methanesulfonic acid (mesylic acid), ethanesulfonic acid, and p-toluenesulfonic acid.

Examples of salts with inorganic bases include alkali metal salts, such as sodium salt and potassium salt; alkaline earth metal salts, such as a calcium salt and a magnesium salt; an aluminum salt and an ammonium salt. Examples of salts with organic bases include salts with diethylamine, diethanolamine, meglumine, and N,N-dibenzylethylenediamine.

Examples of salts with acidic amino acids include salts with aspartic acid and glutamic acid. Examples of salts with basic amino acids include salts with arginine, lysine, and ornithine.

Examples of pharmacologically acceptable salts of lenvatinib include salts with organic acids, and one embodiment thereof is methanesulfonate (mesylate).

In the case where solvates and optical isomers of lenvatinib or (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide of the present invention are present, these solvates and optical isomers are included therein. Examples of solvates include hydrate and anhydrate. Examples of solvents include water, alcohols (e.g., methanol, ethanol, and n-propanol), and dimethylformamide.

Moreover, lenvatinib or (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino[2,1-c][1,2,4]triazine-1(6H)-carboxamide of the present invention may be crystalline or amorphous. In the case where polymorphic crystals are present, a single crystal form or a mixture of any of these crystal forms may be used.

The dose of lenvatinib or a pharmacologically acceptable salt thereof can be suitably selected, depending on the degree of symptoms, the development of adverse effects, the age, sex, body weight, and sensitivity difference of the patient, administration route, administration period, administration interval, the type of pharmaceutical formulation, etc.

The dose of lenvatinib or a pharmaceutically acceptable salt thereof is not particularly limited, but is generally, when orally administered to an adult (body weight: 60 kg) or an child, 0.1 to 500 mg, 0.5 to 300 mg, or 1 to 100 mg, per day, or is 0.1 to 500 mg/m$^2$ (body surface area, hereinafter the same), 0.5 to 300 mg/m$^2$, or 1.0 to 100 mg/m$^2$, per day. This dose can be generally administered once a day, or two to three times a day. If the patient has undergone excessive toxicity, it is necessary to reduce the dose. The dose and dosage schedule may be changed when one or more additional chemotherapeutic agents are used, in addition to the combination therapy of the present invention. The dosage schedule can be determined by the physician who is treating the specific patient.

The dose and dosage schedule of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide can be changed according to the specific disease symptoms and the total symptoms of the patient. The dose can be suitably reduced, depending on age, sex, symptoms, development of adverse effects, etc.

The dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is not particularly limited, but is generally 0.1 to 5000 mg, 0.5 to 3000 mg, or 1.0 to 1000 mg per day in the case of oral administration to an adult (body weight: 60 kg) or a child. This can usually be administered in one portion or in two to six divided portions per day or per a plurality of days. The dose and dosage schedule may be changed when one or more additional chemotherapeutic agents are used. The dosage schedule can be determined by the physician who is treating the specific patient.

The dose of lenvatinib or (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide in the combined administration of the present invention can generally be set equal to or lower than the dose when they are administered alone. The specific dose, administration route, administration frequency, administration cycle, etc., are suitably determined, in consideration of the age, sex, and symptoms of the patient, the development of adverse effects, etc.

The mode of administration of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide according to the present invention is not particularly limited, and lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1 (6H)-carboxamide can be administered in combination at the time of administration. For example, lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide are administered to a patient simultaneously, separately, continuously, or at time intervals. Here, the term "simultaneously" means that the ingredients are each administered in the same period or exactly at the same time, or administered through the same route. The term "separately" means that the ingredients are each administered in different intervals or with different frequencies, or administered through different routes. The term "continuously" means that the ingredients are each administered through the same or different routes in an arbitrary order within a predetermined period. The term "at time intervals" means that the ingredients are each administered through the same or different routes at intervals for the respective ingredients. In the combined administration of lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, when lenvatinib is administered during one cycle of administration of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide described above or during a period in which this cycle is repeated, it is determined that lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide are administered in combination. In one mode of administration for the combined administration of the present invention, lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide are orally administered. Moreover, the combined administration of the present invention may be conducted simultaneously, separately, continuously, or at time intervals, together with the administration of a therapeutic agent for a tumor other than lenvatinib and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

The pharmaceutical composition for treating a tumor of the present invention can be formulated by a method described in, for example, the Japanese Pharmacopoeia, 16th edition (JP), the United States pharmacopoeia (USP) or the European pharmacopoeia (EP).

The tumor targeted in the present invention is specifically, for example, breast cancer, thyroid cancer, hepatocellular carcinoma (HCC), colorectal cancer (CRC), renal cell carcinoma (RCC), head and neck cancer, endometrial cancer or melanoma, though not particularly limited to these. The tumor targeted in one aspect of the present invention is thyroid cancer. Also, the thyroid cancer targeted in one aspect of the present invention is anaplastic thyroid cancer (ATC). The tumor targeted in another aspect of the present invention is hepatocellular carcinoma.

EXAMPLES

Specific examples of the present invention are provided below; however, the present invention is not limited thereto.

[Example 1] Antitumor Effect of Combined Use of E7386 and Lenvatinib Mesylate in Serial Transplantation Model of Transgenic Mouse (MMTV-Wnt-1) Spontaneous Breast Cancer Spontaneous breast cancer of a transgenic mouse (MMTV-Wnt-1, The Jackson Laboratory) caused to locally express Wnt-1 in mammary gland epithelial cells was collected, transplanted in a mouse of background strain (C57BL/6J, Charles River Laboratories Japan, Inc.) by using a trocar, and passaged. The tumor thus transplanted and passaged was excised when becoming approximately 1.5 g, and prepared into approximately 30 mg of a fragment, which was subcutaneously transplanted to the sides of the bodies of five mice (C57BL/6J) each of a control group, an E7386 12.5, 25 or 50 mg/kg alone administration group, a lenvatinib mesylate 10 mg/kg alone administration group, and a combined administration group of 12.5, 25 or 50 mg/kg E7386 and 10 mg/kg lenvatinib mesylate. After confirmation of engraftment of the tumor, E7386 (12.5, 25 or 50 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. 0.1 mol/L hydrochloric acid (b.d.s., 14 days) was administered to the control group.

When the start day of administration was defined as day 1, the major axis and minor axis of tumor developed in each mouse were then measured at day 4, day 8, day 11, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm)/2

Figure 2:
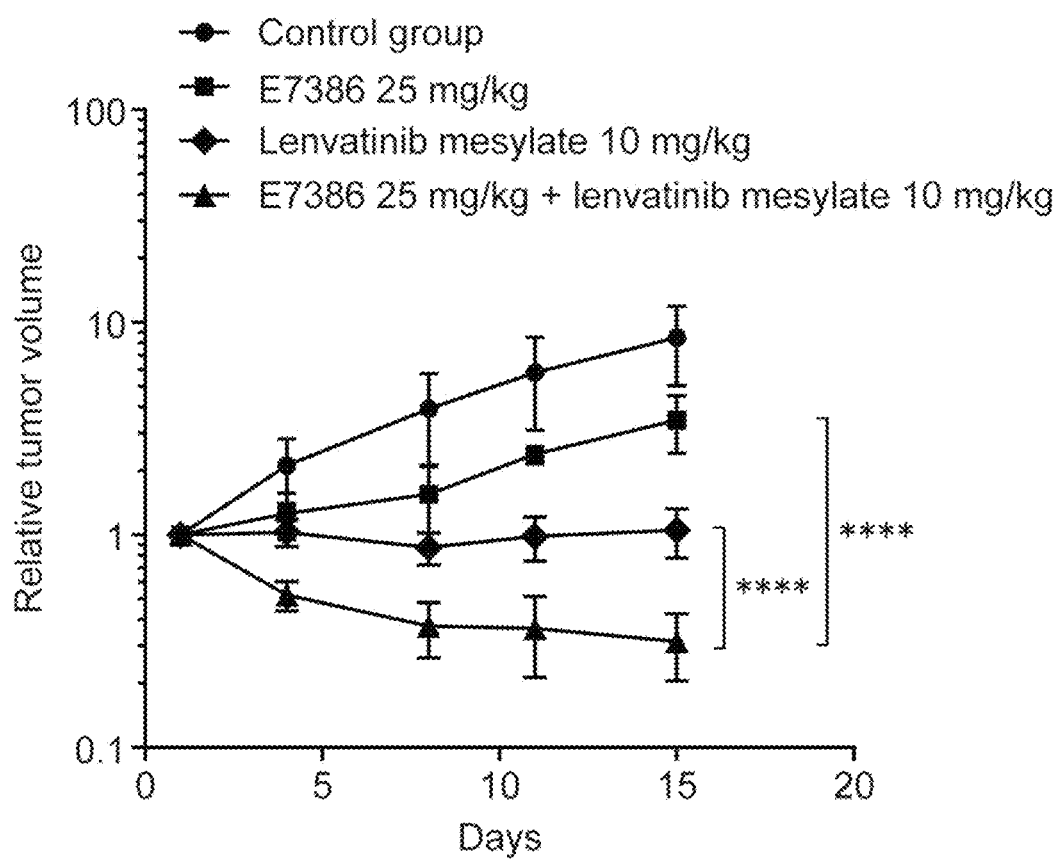
FIG. 2 is a graph showing the antitumor effect of combined use of 25 mg/kg E7386 and 10 mg/kg lenvatinib mesylate in serial transplantation models of transgenic mouse (MMTV-Wnt-1) spontaneous breast cancer. In the graph, ** shows that the combined use of E7386 and lenvatinib mesylate statistically significantly inhibited tumor growth as compared with the case where each of them was administered alone (**: $p<0.0001$; repeated measures ANOVA followed by Dunnetts type multiple comparison).
Figure 3:
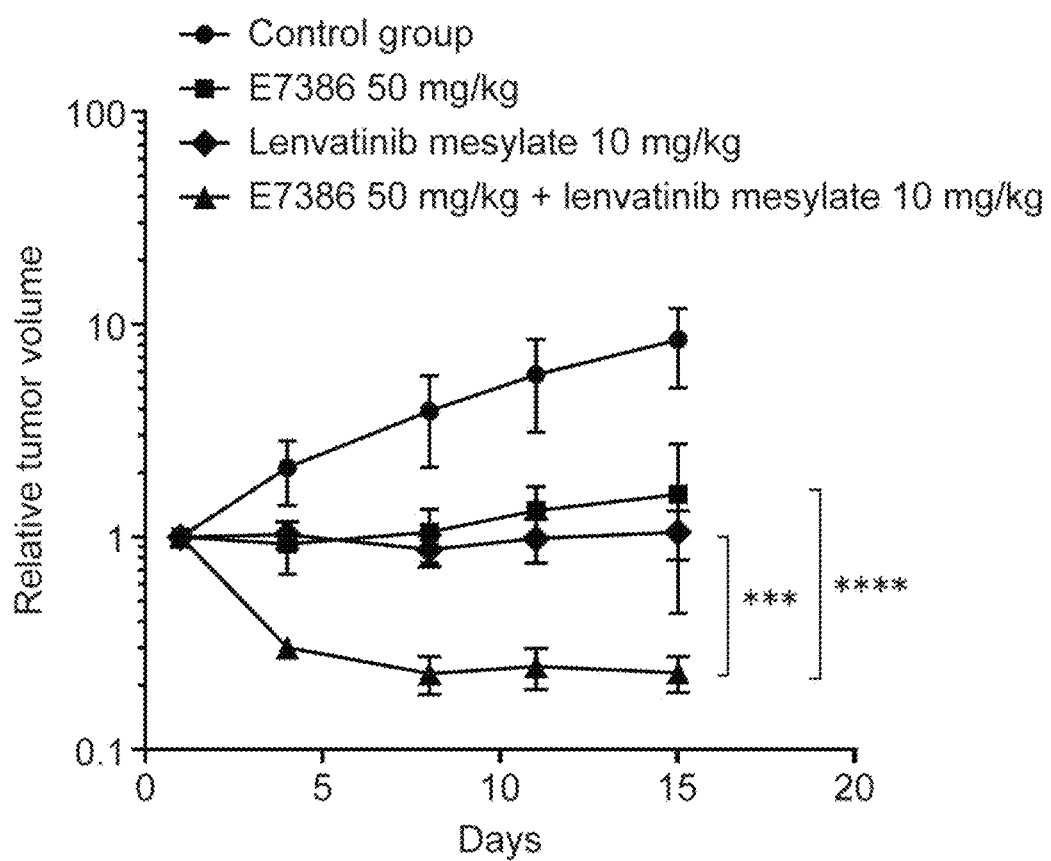
FIG. 3 is a graph showing the antitumor effect of combined use of 50 mg/kg E7386 and 10 mg/kg lenvatinib mesylate in serial transplantation models of transgenic mouse (MMTV-Wnt-1) spontaneous breast cancer. In the graph, * and  show that the combined use of E7386 and lenvatinib mesylate statistically significantly inhibited tumor growth as compared with the case where each of them was administered alone (*: $p<0.001$, ****: $p<0.0001$; repeated measures ANOVA followed by Dunnetts type multiple comparison).

Relative tumor volume (RTV)=Tumor volume at the measurement day/Tumor volume at the start day of administration The results about RTV are shown in Table 1 and FIGS. 1, 2 and 3. Numbers in Table 1 denote mean±standard deviation (SD) of RTV. As a result, combined use of E7386 and lenvatinib mesylate exhibited an excellent antitumor effect in the serial transplantation models of transgenic mouse (MMTV-Wnt-1) spontaneous breast cancer. *, * and  in FIGS. 1, 2 and 3** show that the combined use of E7386 and lenvatinib mesylate statistically significantly inhibited tumor growth as compared with the case where each of them was administered alone (*: $p<0.05$, *: $p<0.001$, **: $p<0.0001$; repeated measures ANOVA followed by Dunnett's type multiple comparison).

TABLE 1

| Group | Day 4 | Day 8 | Day 11 | Day 15 |
|---|---|---|---|---|
| Control group | 2.12 ± 0.64 | 3.93 ± 1.61 | 5.82 ± 2.41 | 8.50 ± 3.10 |
| E7386 12.5 mg/kg group | 1.34 ± 0.25 | 1.20 ± 0.40 | 1.70 ± 0.67 | 2.12 ± 0.65 |
| E7386 25 mg/kg group | 1.26 ± 0.28 | 1.56 ± 0.48 | 2.40 ± 0.22 | 3.69 ± 0.92 |
| E7386 50 mg/kg group | 0.93 ± 0.23 | 1.05 ± 0.26 | 1.34 ± 0.35 | 1.59 ± 1.03 |
| Lenvatinib mesylate 10 mg/kg group | 1.03 ± 0.13 | 0.87 ± 0.13 | 0.98 ± 0.21 | 1.05 ± 0.25 |
| E7386 12.5 mg/kg + lenvatinib mesylate 10 mg/kg group | 0.54 ± 0.06 | 0.39 ± 0.05 | 0.42 ± 0.13 | 0.39 ± 0.11 |
| E7386 25 mg/kg + lenvatinib mesylate 10 mg/kg group | 0.52 ± 0.07 | 0.37 ± 0.10 | 0.36 ± 0.13 | 0.32 ± 0.10 |
| E7386 50 mg/kg + lenvatinib mesylate 10 mg/kg group | 0.30 ± 0.02 | 0.23 ± 0.04 | 0.25 ± 0.05 | 0.23 ± 0.04 |

[Example 2] Antitumor Effect of Combined Use of E7386 and Lenvatinib Mesylate in Mouse Breast Cancer 4T1 Orthotopic Transplantation Model Mouse breast cancer 4T1 cells (ATCC) were cultured by using RPMI1640 medium (Sigma-Aldrich Co. LLC) containing 10% FBS in a 5% $CO_2$ incubator under conditions of 37° C. When the cells became an approximately 80% confluent state, the cells were recovered by using trypsin-EDTA. A suspension was prepared by adding Hank's balanced salt solution so as to be $1.0 \times 10^7$ cells/mL. 0.1 mL of the obtained cell suspension was transplanted to the right third mammary gland fat pads of five mice (C57BL16J, Charles River Laboratories Japan, Inc.) each of a control group, an E7386 25 mg/kg alone administration group, a lenvatinib mesylate 10 mg/kg alone administration group, and a combined administration group of 25 mg/kg E7386 and 10 mg/kg lenvatinib mesylate. From 9 days after the transplantation, E7386 (25 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each mouse were then measured at day 3, day 6, day 9, and day 14 by using Digimatic Caliper (Mitutoyo Corp.).

The tumor volume and the relative tumor volume (RTV) were calculated according to the following expressions.

$$\text{Tumor volume (mm}^3\text{)} = \text{Tumor major axis (mm)} \times \text{Tumor minor axis}^2 \text{ (mm}^2\text{)}/2$$

$$\text{Relative tumor volume (RTV)} = \text{Tumor volume at the measurement day/Tumor volume at the start day of administration}$$

Figure 4:
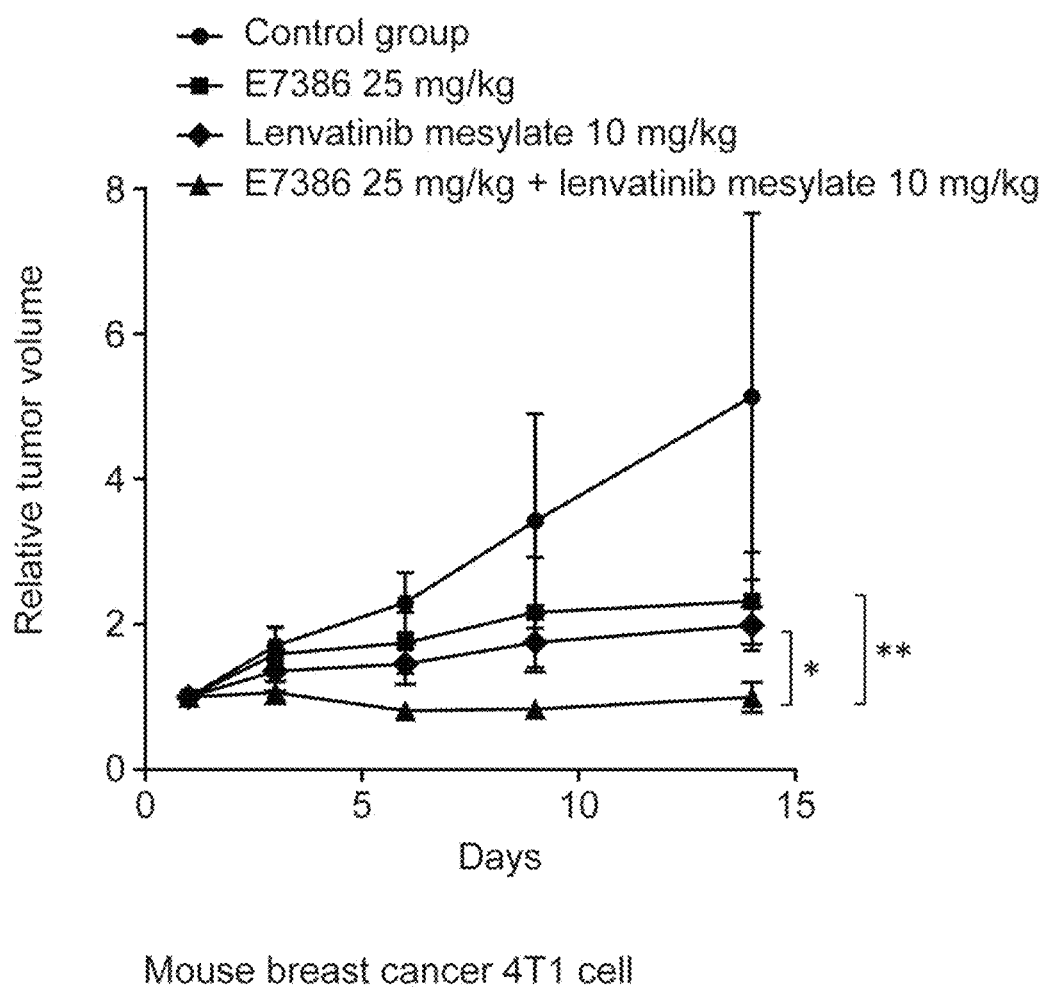
FIG. 4 is a graph showing the antitumor effect of combined use of 25 mg/kg E7386 and 10 mg/kg lenvatinib mesylate in mouse breast cancer 4T1 orthotopic transplantation models. In the graph, * and ** show that the combined use of E7386 and lenvatinib mesylate statistically significantly inhibited tumor growth as compared with the case where each of them was administered alone (*: $p<0.05$, **: $p<0.01$; repeated measures ANOVA followed by Dunnett's type multiple comparison).

The results about RTV are shown in Table 2 and FIG. 4. Numbers in Table 2 denote mean±standard deviation (SD) of RTV As a result, combined use of E7386 and lenvatinib mesylate exhibited an excellent antitumor effect in the mouse breast cancer 4T1 orthotopic transplantation models. * and  in FIG. 4** show that the combined use of E7386 and lenvatinib mesylate statistically significantly inhibited tumor growth as compared with the case where each of them was administered alone (*: $p<0.05$, **: $p<0.01$; repeated measures ANOVA followed by Dunnett's type multiple comparison).

TABLE 2

| Group | Day 3 | Day 6 | Day 9 | Day 14 |
|---|---|---|---|---|
| Control group | 1.71 ± 0.25 | 2.30 ± 0.41 | 3.42 ± 1.48 | 5.14 ± 2.53 |
| Lenvatinib mesylate 10 mg/kg group | 1.36 ± 0.28 | 1.46 ± 0.28 | 1.75 ± 0.41 | 1.99 ± 0.26 |
| E7386 25 mg/kg group | 1.59 ± 0.38 | 1.75 ± 0.42 | 2.17 ± 0.76 | 2.32 ± 0.68 |
| E7386 25 mg/kg + lenvatinib mesylate 10 mg/kg group | 1.06 ± 0.15 | 0.81 ± 0.13 | 0.83 ± 0.13 | 0.99 ± 0.21 |

[Example 3] Antitumor Effect of Combined Use of E7386 and Lenvatinib Mesylate in Human Breast Cancer MDA-MB-231 Transplantation Model Human breast cancer MDA-MB-231 cells (ATCC) were cultured by using RPMI1640 medium (Sigma-Aldrich Co. LLC) containing 10% FBS in a 5% $CO_2$ incubator under conditions of 37° C. When the cells became an approximately 80% confluent state, the cells were recovered by using trypsin-EDTA. A suspension was prepared by adding Hank's balanced salt solution containing 50% Matrigel to the cells so as to be $10.0 \times 10^7$ cells/mL. 0.1 mL of the obtained cell suspension was subcutaneously transplanted to the sides of the bodies of five nude mice (CAnN.Cg-Foxn1$^{nu}$/CrlCrlj, Charles River Laboratories Japan, Inc.) each of a control group, an E7386 25 mg/kg alone administration group, a lenvatinib mesylate 10 mg/kg alone administration group, and a combined administration group of 25 mg/kg E7386 and 10 mg/kg lenvatinib mesylate. From 6 days after the transplantation, E7386 (25 mg/kg, b.d.s., 10 days, oral administration) and lenvatinib mesylate (10 mg/kg, q.d., 10 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each mouse were then measured at day 4, day 7, and day 10 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 5:
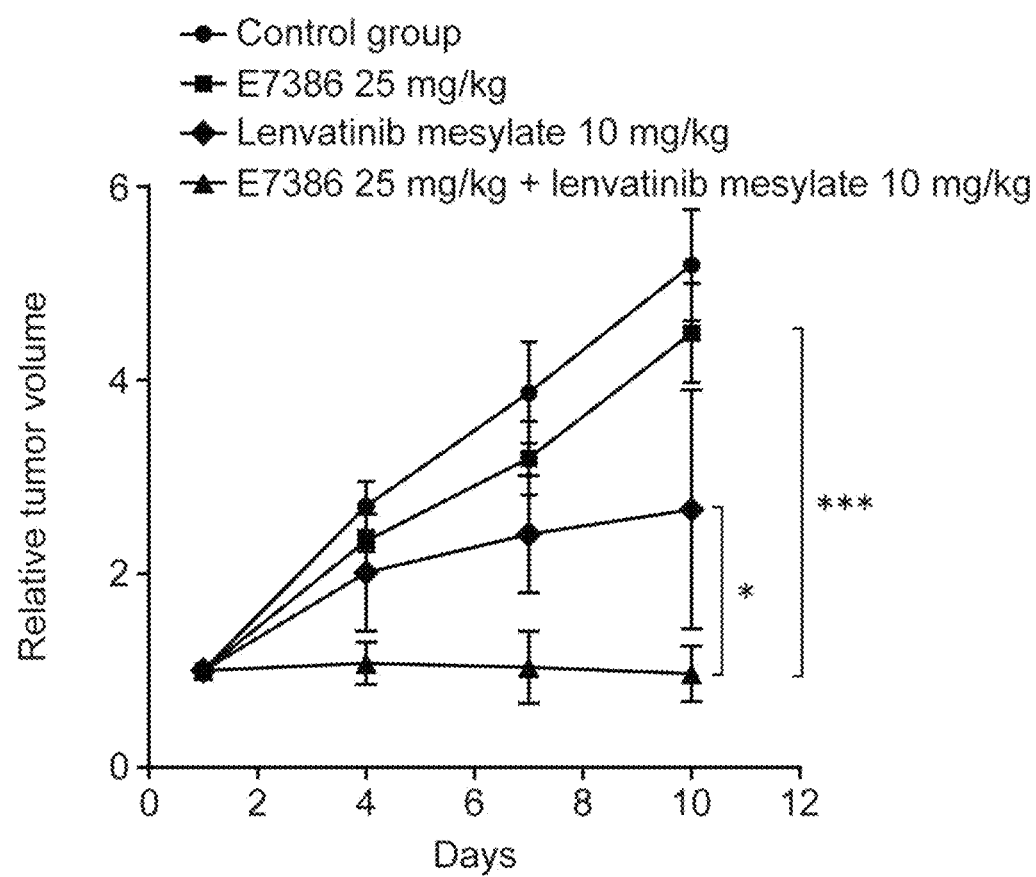
FIG. 5 is a graph showing the antitumor effect of combined use of 25 mg/kg E7386 and 10 mg/kg lenvatinib mesylate in human breast cancer MDA-MB-231 transplantation models. In the graph, * and *** show that the combined use of E7386 and lenvatinib mesylate statistically significantly inhibited tumor growth as compared with the case where each of them was administered alone (*: $p<0.05$, ***: $p<0.001$; repeated measures ANOVA followed by Dunnett's type multiple comparison).

Relative tumor volume (RTV)=Tumor volume at the measurement day/Tumor volume at the start day of administration The results about RTV are shown in Table 3 and FIG. 5. Numbers in Table 3 denote mean±standard deviation (SD) of RTV. As a result, combined use of E7386 and lenvatinib mesylate exhibited an excellent antitumor effect in the human breast cancer MDA-MB-231 transplantation models. * and *** in FIG. 5 show that the combined use of E7386 and lenvatinib mesylate statistically significantly inhibited tumor growth as compared with the case where each of them was administered alone (*: p<0.05, ***: p<0.001; repeated measures ANOVA followed by Dunnett's type multiple comparison).

TABLE 3

| Group | Day 4 | Day 7 | Day 10 |
|---|---|---|---|
| Control group | 2.70 ± 0.26 | 3.87 ± 0.53 | 5.19 ± 0.57 |
| E7386 25 mg/kg group | 2.34 ± 0.11 | 3.19 ± 0.38 | 4.49 ± 0.51 |
| Lenvatinib mesylate 10 mg/kg group | 2.01 ± 0.60 | 2.41 ± 0.60 | 2.67 ± 1.23 |
| E7386 25 mg/kg + lenvatinib mesylate 10 mg/kg group | 1.07 ± 0.22 | 1.04 ± 0.37 | 0.97 ± 0.29 |

[Example 4] Antitumor Effect of Combined Use of E7386 and Lenvatinib Mesylate in Human Melanoma Cell Line SEKI Transplantation Model A human melanoma cell line SEKI (JCRB Cell Bank) was cultured by using RPMI1640 medium (Sigma-Aldrich Co. LLC) containing 10% FBS in a 5% CO$_2$ incubator under conditions of 37° C. When the cells became an approximately 80% confluent state, the cells were recovered by using trypsin-EDTA. A suspension was prepared by adding Hank's balanced salt solution containing 50% Matrigel to the cells so as to be 5.0×10$^7$ cells/mL. 0.1 mL of the obtained cell suspension was subcutaneously transplanted to the sides of the bodies of six nude mice (CAnN.Cg-Foxn1$^{nu}$/CrlCrlj, Charles River Laboratories Japan, Inc.) each of a control group, an E7386 12.5 or 25 mg/kg alone administration group, a lenvatinib mesylate 10 mg/kg alone administration group, and a combined administration group of 12.5 or 25 mg/kg E7386 and 10 mg/kg lenvatinib mesylate. From 13 days after the transplantation, E7386 (12.5 or 25 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. 0.1 mol/L hydrochloric acid (b.d.s., 14 days) was administered to the control group.

When the start day of administration was defined as day 1, the major axis and minor axis of tumor developed in each mouse were then measured at day 4, day 8, day 11, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 6:
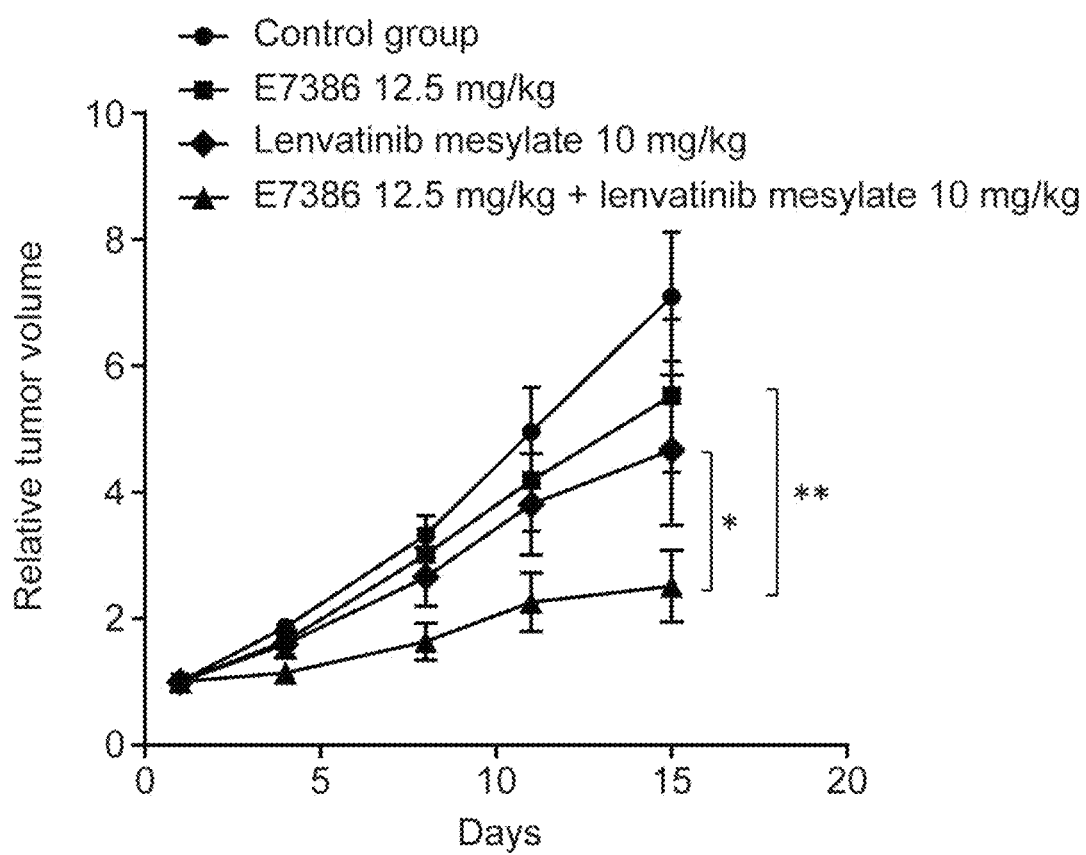
FIG. 6 is a graph showing the antitumor effect of combined use of 12.5 mg/kg E7386 and 10 mg/kg lenvatinib mesylate in human melanoma cell line SEKI transplantation models. In the graph, * and ** show that the combined use of E7386 and lenvatinib mesylate statistically significantly inhibited tumor growth as compared with the case where each of them was administered alone (*: $p<0.05$, **: $p<0.01$; repeated measures ANOVA followed by Dunnett's type multiple comparison).
Figure 7:
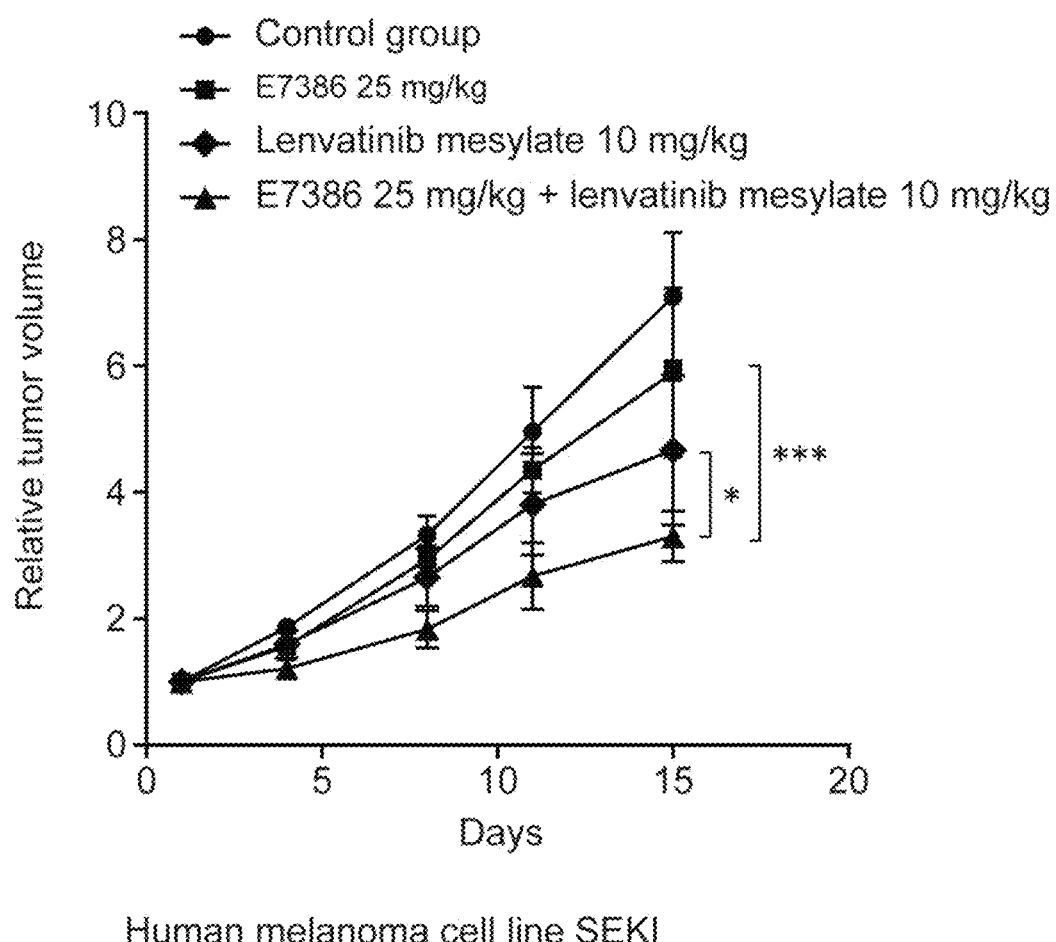
FIG. 7 is a graph showing the antitumor effect of combined use of 25 mg/kg E7386 and 10 mg/kg lenvatinib mesylate in human melanoma cell line SEKI transplantation models. In the graph, * and *** show that the combined use of E7386 and lenvatinib mesylate statistically significantly inhibited tumor growth as compared with the case where each of them was administered alone (*: $p<0.05$, ***: $p<0.001$; repeated measures ANOVA followed by Dunnett's type multiple comparison).

Relative tumor volume (RTV)=Tumor volume at the measurement day/Tumor volume at the start day of administration The results about RTV are shown in Table 4 and FIGS. 6 and 7. Numbers in Table 4 denote mean±standard deviation (SD) of RTV. As a result, combined use of E7386 and lenvatinib mesylate exhibited an excellent antitumor effect in the human melanoma cell line SEKI transplantation models. *,  and * in FIGS. 6 and 7 show that the combined use of E7386 and lenvatinib mesylate statistically significantly inhibited tumor growth as compared with the case where each of them was administered alone (*: p<0.05, : p<0.01, *: p<0.001; repeated measures ANOVA followed by Dunnett's type multiple comparison).

TABLE 4

| Group | Day 4 | Day 8 | Day 11 | Day 15 |
|---|---|---|---|---|
| Control group | 1.87 ± 0.12 | 3.32 ± 0.31 | 4.96 ± 0.71 | 7.10 ± 1.02 |
| E7386 12.5 mg/kg group | 1.65 ± 0.22 | 3.02 ± 0.31 | 4.19 ± 0.80 | 5.53 ± 1.21 |
| E7386 25 mg/kg group | 1.56 ± 0.21 | 2.94 ± 0.22 | 4.35 ± 0.36 | 5.90 ± 1.34 |
| Lenvatinib mesylate 10 mg/kg group | 1.60 ± 0.22 | 2.66 ± 0.46 | 3.81 ± 0.80 | 4.67 ± 1.19 |
| E7386 12.5 mg/kg + lenvatinib mesylate 10 mg/kg group | 1.15 ± 0.10 | 1.64 ± 0.29 | 2.27 ± 0.47 | 2.51 ± 0.57 |
| E7386 25 mg/kg + lenvatinib mesylate 10 mg/kg group | 1.21 ± 0.17 | 1.84 ± 0.30 | 2.68 ± 0.52 | 3.31 ± 0.40 |

[Example 5] Antitumor Effect of Combined Use of E7386 and Lenvatinib Mesylate in Human Anaplastic Thyroid Cancer Cell Line HTC/C3 Transplantation Model A human anaplastic thyroid cancer cell line HTC/C3 (JCBR Cell Bank) was cultured by using D-MEM High Glucose medium (Wako Pure Chemical Industries, Ltd.) containing 10% FBS in a 5% CO$_2$ incubator under conditions of 37° C. When the cells became an approximately 80% confluent state, the cells were recovered by using trypsin-EDTA. A suspension was prepared by adding Hank's balanced salt solution containing 50% Matrigel to the cells so as to be 1.0×10$^7$ cells/mL. 0.1 mL of the obtained cell suspension was subcutaneously transplanted to the sides of the bodies of five nude mice (CAnN.Cg-Foxn1$^{nu}$/CrlCrlj, Charles River Laboratories Japan, Inc.) each of a control group, an E7386 12.5, 25 or 50 mg/kg alone administration group, a lenvatinib mesylate 10 mg/kg alone administration group, and a combined administration group of 12.5, 25 or 50 mg/kg E7386 and 10 mg/kg lenvatinib mesylate. From 11 days after the transplantation, E7386 (12.5, 25, or 50 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. 0.1 mol/L hydrochloric acid (b.d.s., 14 days) was administered to the control group.

When the start day of administration was defined as day 1, the major axis and minor axis of tumor developed in each mouse were then measured at day 4, day 8, day 11, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 8:
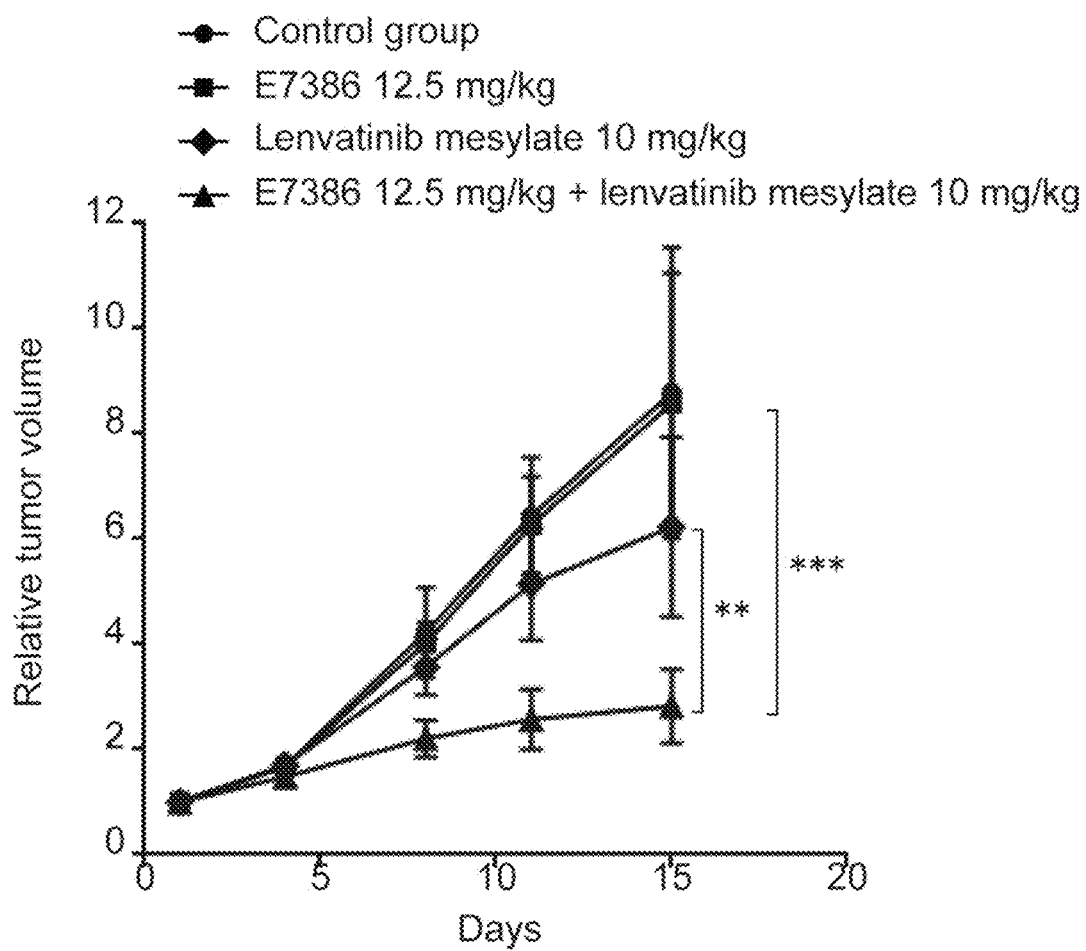
FIG. 8 is a graph showing the antitumor effect of combined use of 12.5 mg/kg E7386 and 10 mg/kg lenvatinib mesylate in human anaplastic thyroid cancer cell line HTC/C3 transplantation models. In the graph,  and * show that the combined use of E7386 and lenvatinib mesylate statistically significantly inhibited tumor growth as compared with the case where each of them was administered alone (: $p<0.01$, *: $p<0.001$; repeated measures ANOVA followed by Dunnett's type multiple comparison).
Figure 9:
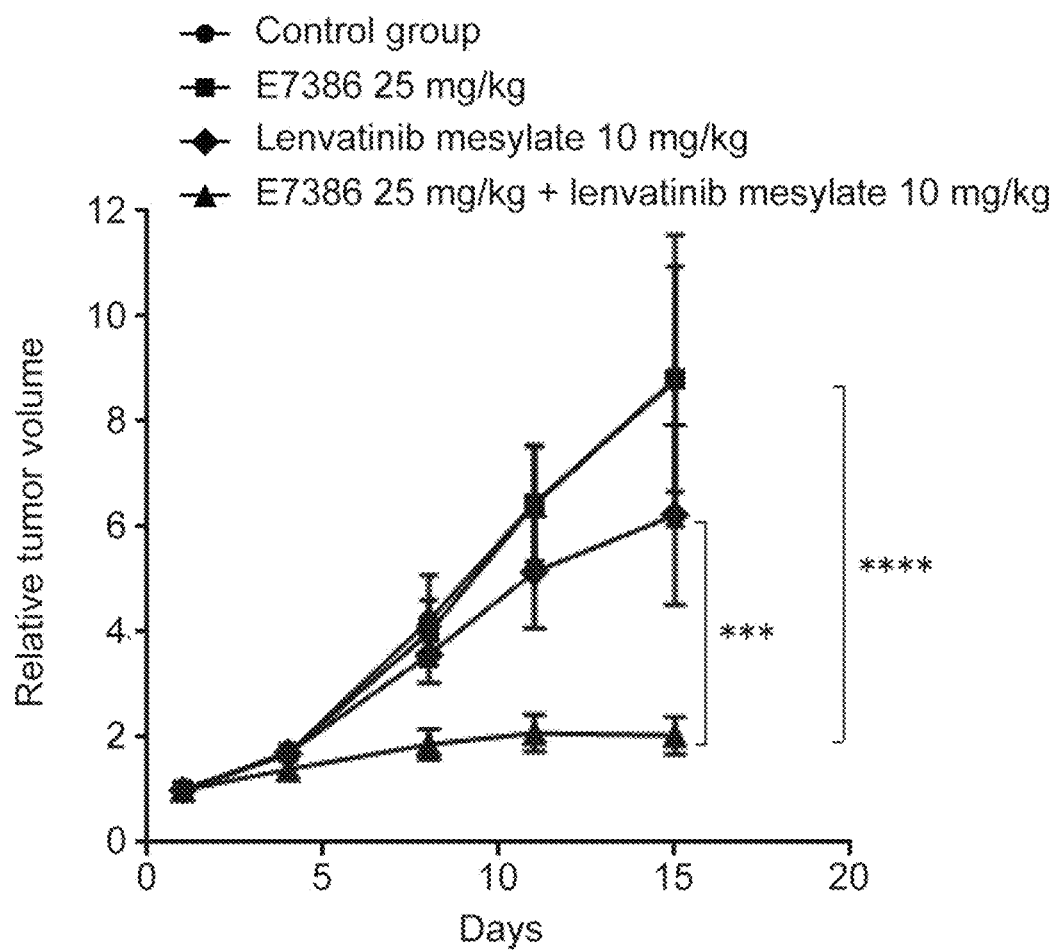
FIG. 9 is a graph showing the antitumor effect of combined use of 25 mg/kg E7386 and 10 mg/kg lenvatinib mesylate in human anaplastic thyroid cancer cell line HTC/C3 transplantation models. In the graph, * and  show that the combined use of E7386 and lenvatinib mesylate statistically significantly inhibited tumor growth as compared with the case where each of them was administered alone (*: $p<0.001$, ****: $p<0.0001$; repeated measures ANOVA followed by Dunnett's type multiple comparison).
Figure 10:
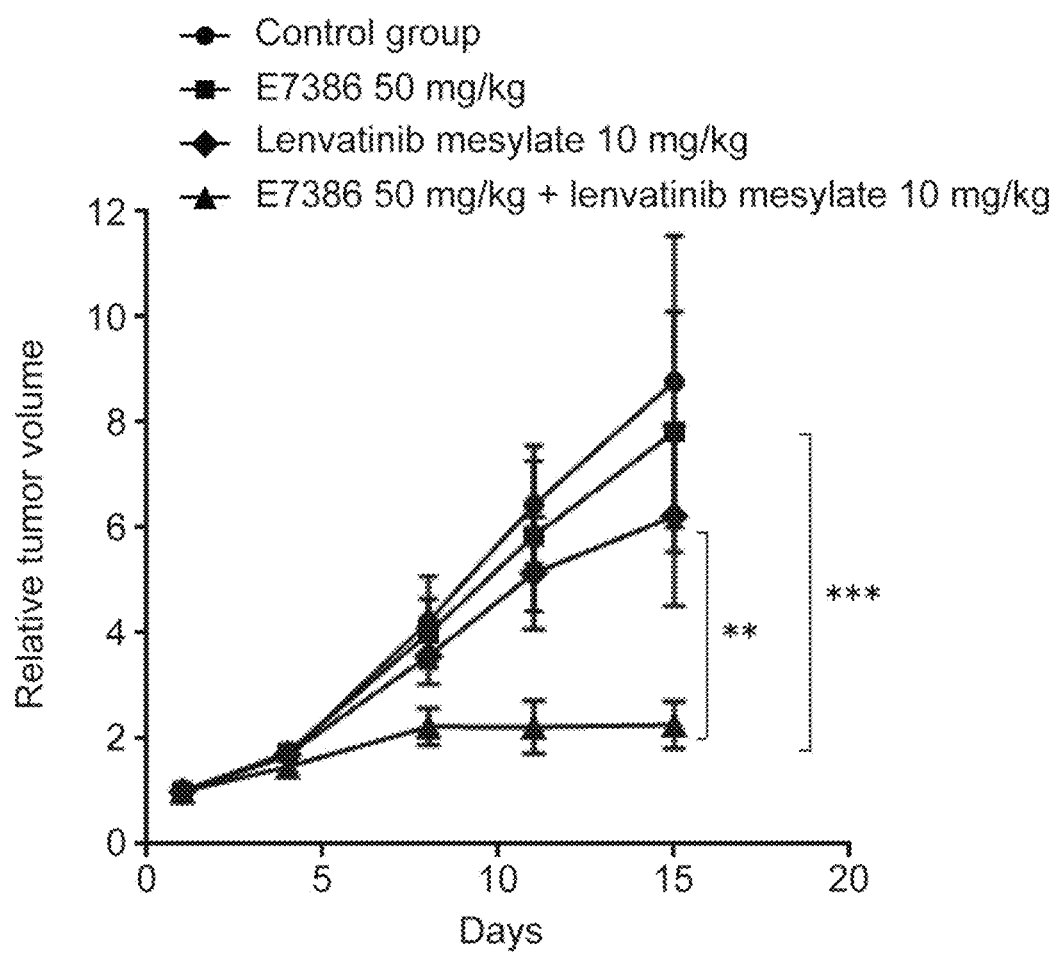
FIG. 10 is a graph showing the antitumor effect of combined use of 50 mg/kg E7386 and 10 mg/kg lenvatinib mesylate in human anaplastic thyroid cancer cell line HTC/C3 transplantation models. In the graph,  and * show that the combined use of E7386 and lenvatinib mesylate statistically significantly inhibited tumor growth as compared with the case where each of them was administered alone (\*\*: p<0.01, \*\*\*: p<0.001; repeated measures ANOVA followed by Dunnett's type multiple comparison).

Relative tumor volume (RTV)=Tumor volume at the measurement day/Tumor volume at the start day of administration The results about RTV are shown in Table 5 and FIGS. 8, 9 and 10. Numbers in Table 5 denote mean±standard deviation (SD) of RTV. As a result, combined use of E7386 and lenvatinib mesylate exhibited an excellent antitumor effect in the human anaplastic thyroid cancer cell line HTC/C3 transplantation models. \*\*, \*\*\* and \*\*\*\* in FIGS. 8, 9 and 10 show that the combined use of E7386 and lenvatinib mesylate statistically significantly inhibited tumor growth as compared with the case where each of them was administered alone (\*\*: p<0.01, \*\*\*: p<0.001, \*\*\*\*: p<0.0001; repeated measures ANOVA followed by Dunnett's type multiple comparison).

TABLE 5

| Group | Day 4 | Day 8 | Day 11 | Day 15 |
|---|---|---|---|---|
| Control group | 1.70 ± 0.12 | 4.23 ± 0.86 | 6.44 ± 1.12 | 8.78 ± 2.76 |
| E7386 12.5 mg/kg group | 1.68 ± 0.13 | 4.02 ± 0.40 | 6.27 ± 0.93 | 8.58 ± 2.48 |
| E7386 25 mg/kg group | 1.72 ± 0.10 | 3.99 ± 0.62 | 6.44 ± 1.09 | 8.81 ± 2.14 |
| E7386 50 mg/kg group | 1.74 ± 0.09 | 4.00 ± 0.66 | 5.85 ± 1.42 | 7.83 ± 2.28 |
| Lenvatinib mesylate 10 mg/kg group | 1.71 ± 0.10 | 3.57 ± 0.54 | 5.15 ± 1.07 | 6.23 ± 1.71 |
| E7386 12.5 mg/kg + lenvatinib mesylate 10 mg/kg group | 1.48 ± 0.17 | 2.21 ± 0.35 | 2.58 ± 0.57 | 2.83 ± 0.70 |
| E7386 25 mg/kg + lenvatinib mesylate 10 mg/kg group | 1.40 ± 0.08 | 1.87 ± 0.29 | 2.08 ± 0.35 | 2.04 ± 0.36 |
| E7386 50 mg/kg + lenvatinib mesylate 10 mg/kg group | 1.48 ± 0.14 | 2.23 ± 0.35 | 2.23 ± 0.50 | 2.27 ± 0.45 |

[Example 6] Antitumor Effect of Combined Use of E7386 and Lenvatinib Mesylate in Human Hepatocellular Carcinoma SNU398 Transplantation Model Human hepatocellular carcinoma SNU398 (ATCC) is cultured by using RPMI1640 medium (Sigma-Aldrich Co. LLC) containing 10% FBS in a 5% $CO_2$ incubator under conditions of 37° C. When the cells become an approximately 80% confluent state, the cells are recovered by using trypsin-EDTA. A suspension is prepared by adding Hanks balanced salt solution containing 50% Matrigel to the cells so as to be 5.0×10$^7$ cells/mL. 0.1 mL of the obtained cell suspension is subcutaneously transplanted to the sides of the bodies of nude mice (CAnN.Cg-Foxn1$^{nu}$/CrlCrlj, Charles River Laboratories Japan, Inc.) each of a control group, an E7386 alone administration group, a lenvatinib mesylate alone administration group, and a combined administration group E7386 and lenvatinib mesylate. After tumorigenesis, E7386 (oral administration) and lenvatinib mesylate (oral administration) are administered alone or in combination to the alone administration group or the combined administration group.

From the start day of administration, the major axis and minor axis of tumor developed in each mouse are measured on a regular basis by using Digimatic Caliper (Mitutoyo Corp.), and the tumor volume and the relative tumor volume (RTV) are calculated. From the results about RTV, the antitumor effect of combined use of E7386 and lenvatinib mesylate can be evaluated.

The tumor volume and the relative tumor volume (RTV) are calculated according to the following expressions.

Tumor volume (mm$^3$)=Tumor major axis (mm)× Tumor minor axis$^2$ (mm$^2$)/2

Relative tumor volume (RTV)=Tumor volume at the measurement day/Tumor volume at the start day of administration

[Example 6-1] Antitumor Effect of Combined Use of E7386 and Lenvatinib Mesylate in Human Hepatocellular Carcinoma Line SNU398 Transplantation Model Human hepatocellular carcinoma line SNU398 cells (ATCC) were cultured by using RPMI1640 medium (Wako Pure Chemical Industries, Ltd.) containing 10% FBS in a 5% $CO_2$ incubator under conditions of 37° C. When the cells became an approximately 80% confluent state, the cells were recovered by using trypsin-EDTA. A suspension was prepared by adding Hank's balanced salt solution containing 50% Matrigel to the cells so as to be 5.0×10$^7$ cells/mL. 0.1 mL of the obtained cell suspension was subcutaneously transplanted to the sides of the bodies of eight nude mice (CAnN.Cg-Foxn1$^{nu}$/CrlCrlj, Charles River Laboratories Japan, Inc.) each of a control group, an E7386 50 mg/kg alone administration group, a lenvatinib mesylate 10 mg/kg alone administration group, and a combined administration group of 12.5, 25 or 50 mg/kg E7386 and 10 mg/kg lenvatinib mesylate. From 9 days after the transplantation, E7386 (12.5, 25, or 50 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each mouse were then measured at day 6, day 9, day 12, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 11:
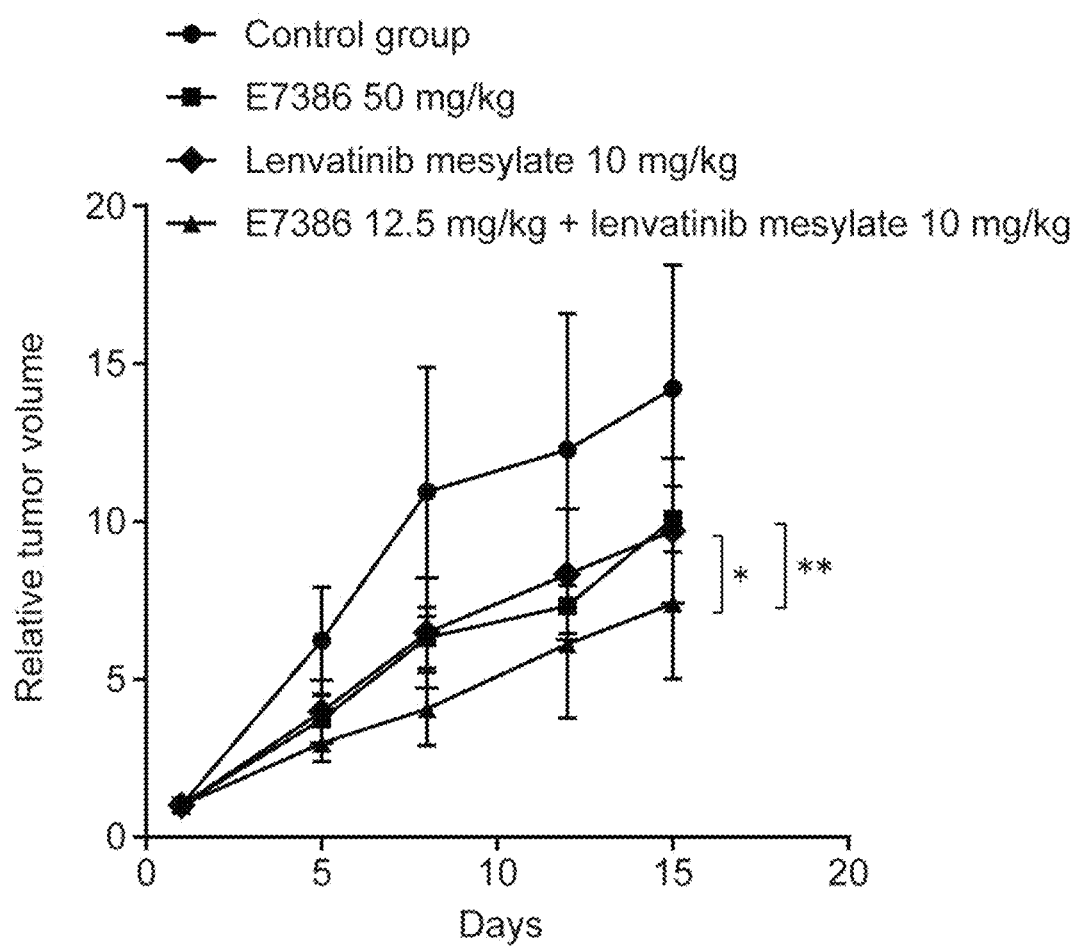
FIG. 11 is a graph showing the antitumor effect of combined use of 12.5 mg/kg E7386 and 10 mg/kg lenvatinib mesylate in human hepatocellular carcinoma line SNU398 transplantation models. In the graph, \* and \*\* show that the combined use of E7386 and lenvatinib mesylate statistically significantly inhibited tumor growth as compared with the case where each of them was administered alone (\*: p<0.05, \*\*: p<0.01; repeated measures ANOVA followed by Dunnetts type multiple comparison).
Figure 12:
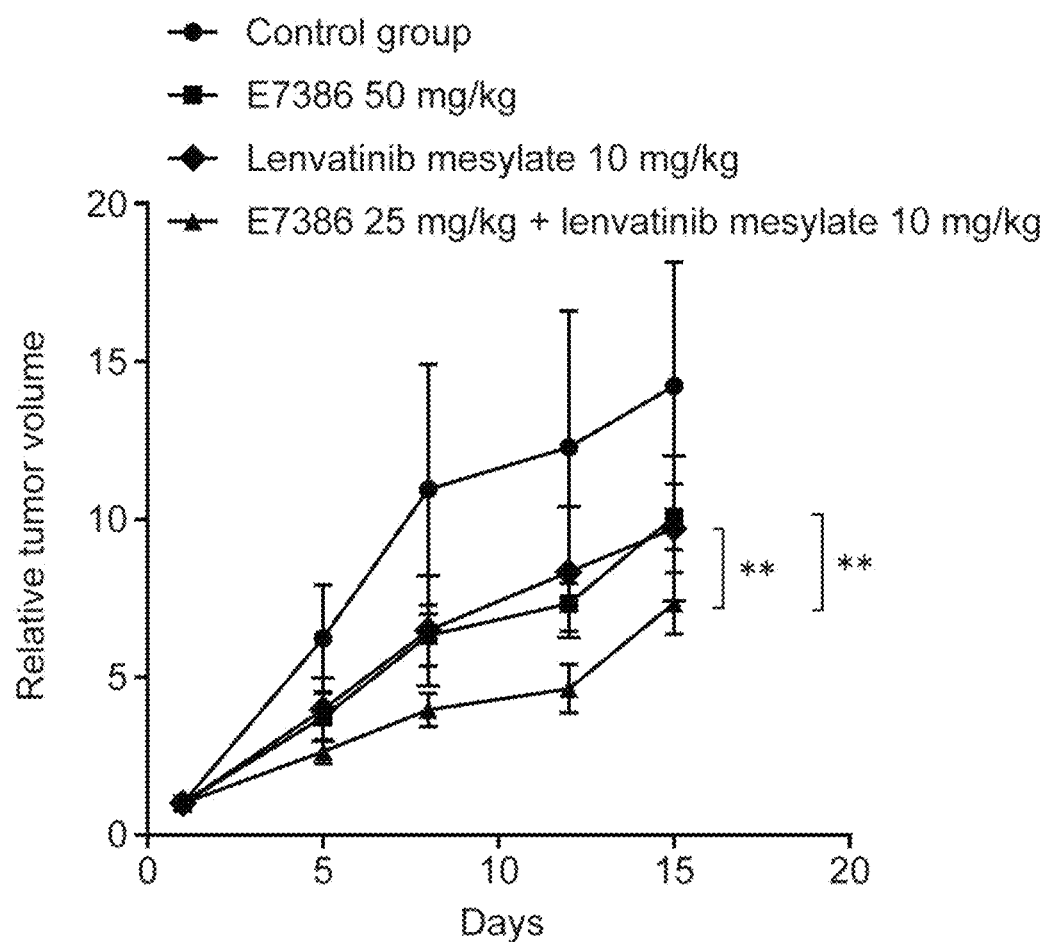
FIG. 12 is a graph showing the antitumor effect of combined use of 25 mg/kg E7386 and 10 mg/kg lenvatinib mesylate in human hepatocellular carcinoma line SNU398 transplantation models. In the graph, \*\* shows that the combined use of E7386 and lenvatinib mesylate statistically significantly inhibited tumor growth as compared with the case where each of them was administered alone (\*\*: p<0.01; repeated measures ANOVA followed by Dunnetts type multiple comparison).
Figure 13:
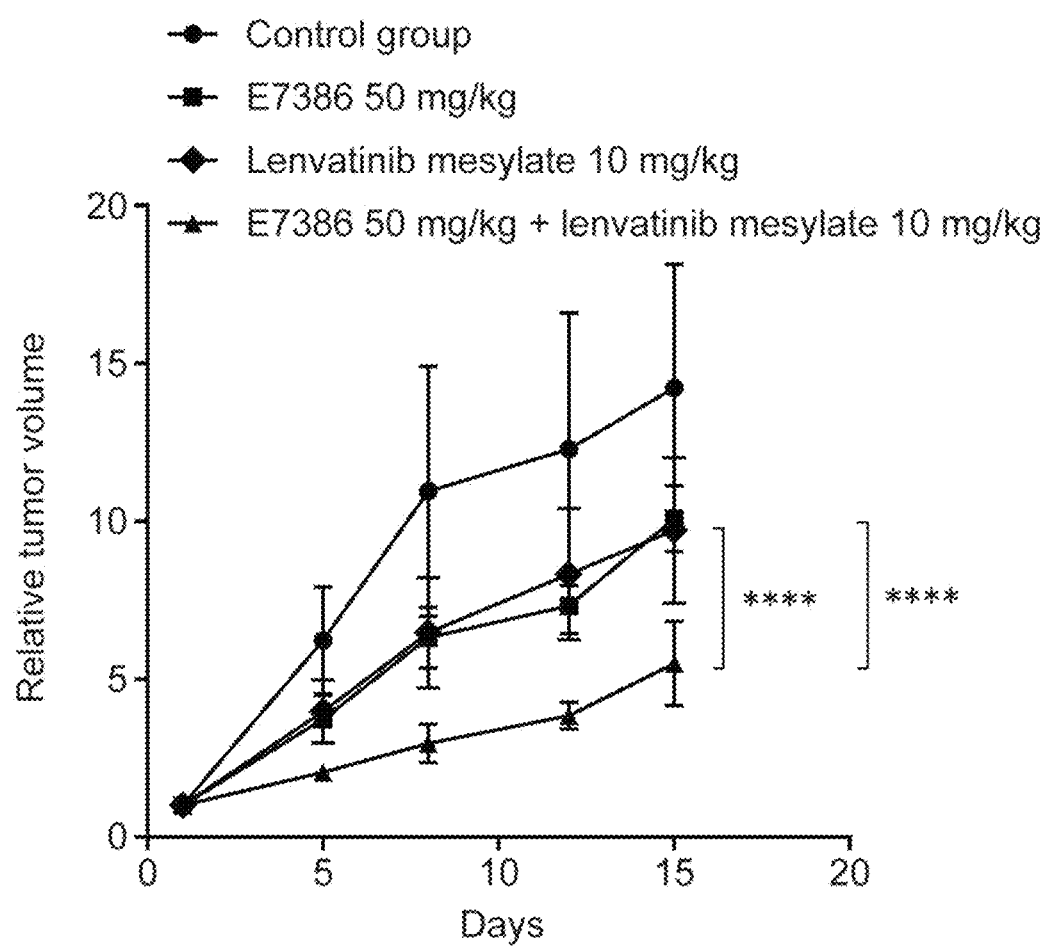
FIG. 13 is a graph showing the antitumor effect of combined use of 50 mg/kg E7386 and 10 mg/kg lenvatinib mesylate in human hepatocellular carcinoma line SNU398 transplantation models. In the graph, \*\*\*\* shows that the combined use of E7386 and lenvatinib mesylate statistically significantly inhibited tumor growth as compared with the case where each of them was administered alone (\*\*\*\*: p<0.0001; repeated measures ANOVA followed by Dunnett's type multiple comparison).

Relative tumor volume (RTV)=Tumor volume at the measurement day/Tumor volume at the start day of administration The results about RTV are shown in Table 6 and FIGS. 11, 12 and 13. Numbers in Table 6 denote mean±standard deviation (SD) of RTV. As a result, combined use of E7386 and lenvatinib mesylate exhibited an excellent antitumor effect in the human hepatocellular carcinoma line SNU398 transplantation models. \*, \*\* and \*\*\*\* in FIGS. 11, 12 and 13 show that the combined use of E7386 and lenvatinib mesylate statistically significantly inhibited tumor growth as compared with the case where each of them was administered alone (\*: p<0.05, \*\*: p<0.01, \*\*\*\*: p<0.0001; repeated measures ANOVA followed by Dunnett's type multiple comparison).

TABLE 6

| Group | Day 6 | Day 9 | Day 12 | Day 15 |
|---|---|---|---|---|
| Control group | 6.22 ± 1.70 | 11.0 ± 3.95 | 12.3 ± 4.31 | 14.2 ± 3.91 |
| E7386 50 mg/kg group | 3.74 ± 0.75 | 6.31 ± 1.74 | 7.33 ± 0.89 | 10.1 ± 1.03 |
| Lenvatinib mesylate 10 mg/kg group | 3.98 ± 1.00 | 6.48 ± 1.74 | 8.33 ± 2.08 | 9.71 ± 2.30 |
| E7386 12.5 mg/kg group + lenvatinib mesylate 10 mg/kg group | 2.98 ± 0.59 | 4.07 ± 1.16 | 6.12 ± 2.34 | 7.41 ± 2.39 |
| E7386 25 mg/kg group + lenvatinib mesylate 10 mg/kg group | 2.48 ± 0.50 | 3.97 ± 0.53 | 4.64 ± 0.76 | 7.35 ± 0.98 |
| E7386 50 mg/kg group + lenvatinib mesylate 10 mg/kg group | 2.06 ± 0.29 | 2.97 ± 0.61 | 3.85 ± 0.43 | 5.50 ± 1.33 | mouse were then measured at day 4, day 7, day 9, day 13, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 14:
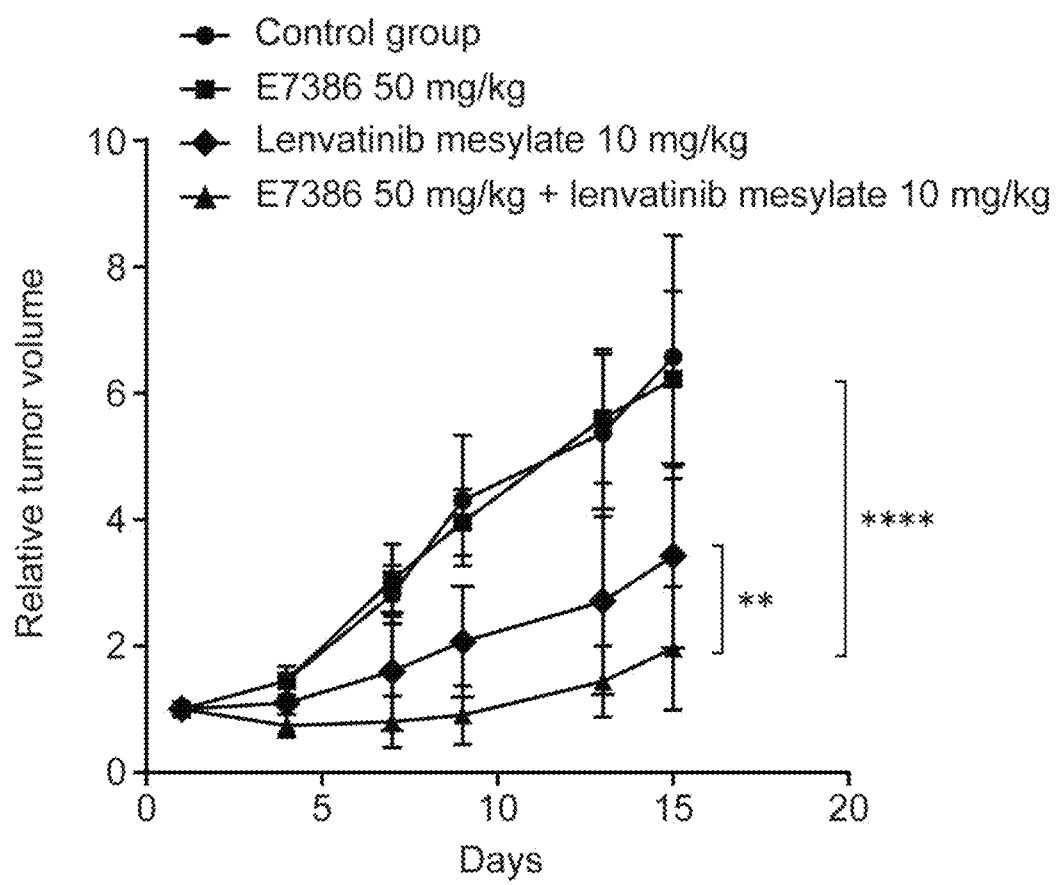
FIG. 14 is a graph showing the antitumor effect of combined use of 50 mg/kg E7386 and 10 mg/kg lenvatinib mesylate in human hepatocellular carcinoma line HepG2 transplantation models. In the graph, \*\* and \*\*\*\* show that the combined use of E7386 and lenvatinib mesylate statistically significantly inhibited tumor growth as compared with the case where each of them was administered alone (\*\*: p<0.01, \*\*\*\*: p<0.0001; repeated measures ANOVA followed by Dunnett's type multiple comparison).

Relative tumor volume (RTV)=Tumor volume at the measurement day/Tumor volume at the start day of administration The results about RTV are shown in Table 7 and FIG. 14. Numbers in Table 7 denote mean±standard deviation (SD) of RTV. As a result, combined use of E7386 and lenvatinib mesylate exhibited an excellent antitumor effect in the human hepatocellular carcinoma line HepG2 transplantation models.  and  in FIG. 14 show that the combined use of E7386 and lenvatinib mesylate statistically significantly inhibited tumor growth as compared with the case where each of them was administered alone (: p<0.01, ****: p<0.0001; repeated measures ANOVA followed by Dunnett's type multiple comparison).

TABLE 7

| Group | Day 4 | Day 7 | Day 9 | Day 13 | Day 15 |
|---|---|---|---|---|---|
| Control group | 1.45 ± 0.12 | 2.82 ± 0.46 | 4.31 ± 1.03 | 5.38 ± 1.32 | 6.58 ± 1.93 |
| E7386 50 mg/kg group | 1.45 ± 0.23 | 3.05 ± 0.57 | 3.96 ± 0.53 | 5.60 ± 1.02 | 6.23 ± 1.39 |
| Lenvatinib mesylate 10 mg/kg group | 1.10 ± 0.08 | 1.60 ± 0.94 | 2.07 ± 0.88 | 2.70 ± 1.47 | 3.43 ± 1.46 |
| E7386 50 mg/kg group + lenvatinib mesylate 10 mg/kg group | 0.74 ± 0.18 | 0.81 ± 0.41 | 0.91 ± 0.47 | 1.44 ± 0.56 | 1.97 ± 0.98 |

[Example 7] Antitumor Effect of Combined Use of E7386 and Lenvatinib Mesylate in Human Hepatocellular Carcinoma Line HepG2 Subcutaneous Transplantation Model Human hepatocellular carcinoma line HepG2 cells (JCRB Cell Bank) were cultured by using DMEM-Low glucose medium (Wako Pure Chemical Industries, Ltd.) containing 10% FBS in a 5% $CO_2$ incubator under conditions of 37° C. When the cells became an approximately 80% confluent state, the cells were recovered by using trypsin-EDTA. A suspension was prepared by adding phosphate-buffered saline containing 50% Matrigel to the cells so as to be 10.0×10$^7$ cells/mL. 0.1 mL of the obtained cell suspension was subcutaneously transplanted to the sides of the bodies of five nude mice (CAnN.Cg-Foxn1$^{nu}$/CrlCrlj, Charles River Laboratories Japan, Inc.) each of a control group, an E7386 50 mg/kg alone administration group, a lenvatinib mesylate 10 mg/kg alone administration group, and a combined administration group of 50 mg/kg E7386 and 10 mg/kg lenvatinib mesylate. From 12 days after the transplantation, E7386 (50 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each

[Example 8] Antitumor Effect of Combined Use of E7386 and Lenvatinib Mesylate in Human Colorectal Cancer Line Colo-205 Transplantation Model Human colorectal cancer line Colo-205 cells (ATCC) were cultured by using RPMI1640 medium (Wako Pure Chemical Industries, Ltd.) containing 10% FBS in a 5% $CO_2$ incubator under conditions of 37° C. When the cells became an approximately 80% confluent state, the cells were recovered by using trypsin-EDTA. A suspension was prepared by adding Hank's balanced salt solution to the cells so as to be 5.0×10$^7$ cells/mL. 0.1 mL of the obtained cell suspension was subcutaneously transplanted to the sides of the bodies of five nude mice (CAnN.Cg-Foxn1$^{nu}$/CrlCrlj, Charles River Laboratories Japan, Inc.) each of a control group, an E7386 50 mg/kg alone administration group, a lenvatinib mesylate 10 mg/kg alone administration group, and a combined administration group of 50 mg/kg E7386 and 10 mg/kg lenvatinib mesylate. From 8 days after the transplantation, E7386 (50 mg/kg, q.d., 11 days, oral administration) and lenvatinib mesylate (10 mg/kg, q.d., 11 days, oral administration) were administered alone or in combination to the alone administration group or the combined administration group. For the administration, E73 86 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each mouse were then measured at day 4, day 8, and day 12 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 15:
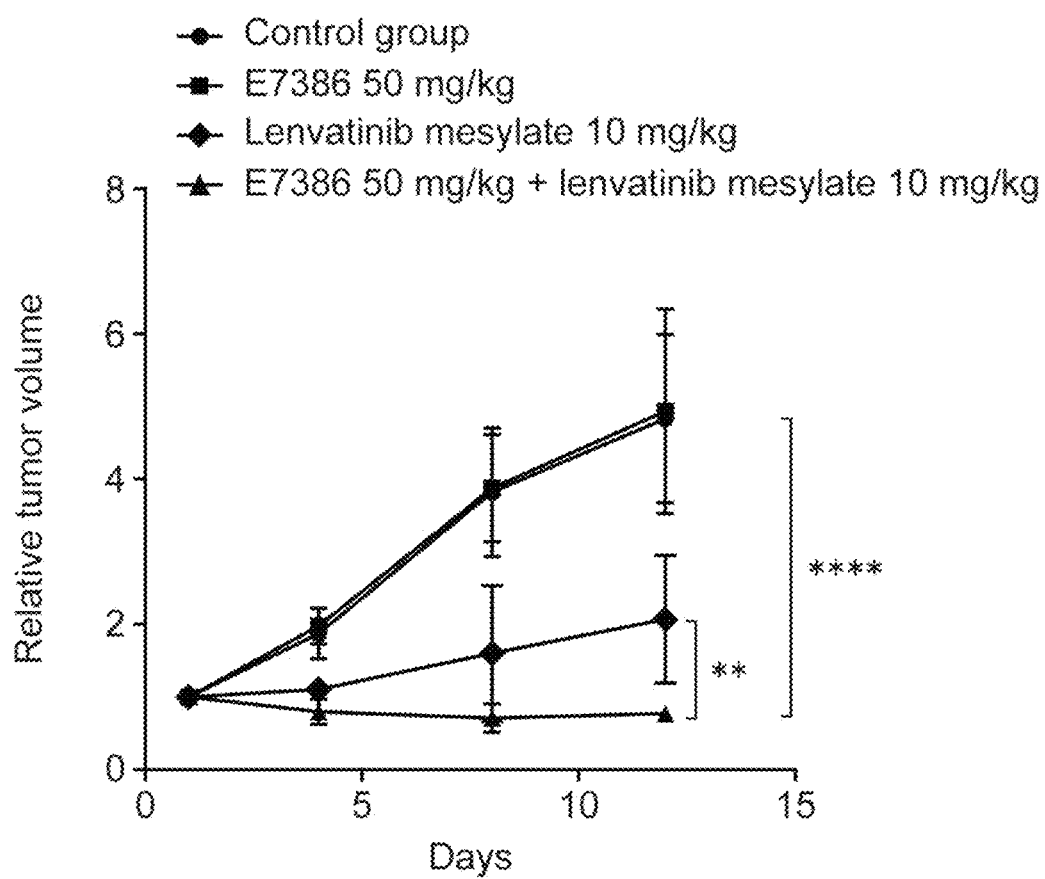
FIG. 15 is a graph showing the antitumor effect of combined use of 50 mg/kg E7386 and 10 mg/kg lenvatinib mesylate in human colorectal cancer line Colo-205 transplantation models. In the graph, \*\* and \*\*\*\* show that the combined use of E7386 and lenvatinib mesylate statistically significantly inhibited tumor growth as compared with the case where each of them was administered alone (\*\*: p<0.01, \*\*\*\*: p<0.0001; repeated measures ANOVA followed by Dunnett's type multiple comparison).

Relative tumor volume (RTV)=Tumor volume at the measurement day/Tumor volume at the start day of administration The results about RTV are shown in Table 8 and FIG. 15. Numbers in Table 8 denote mean±standard deviation (SD) of RTV. As a result, combined use of E7386 and lenvatinib mesylate exhibited an excellent antitumor effect in the human colorectal cancer line Colo-205 transplantation models.  and  in FIG. 15 show that the combined use of E7386 and lenvatinib mesylate statistically significantly inhibited tumor growth as compared with the case where each of them was administered alone (: p<0.01, ****: p<0.0001; repeated measures ANOVA followed by Dunnet's type multiple comparison).

TABLE 8

| Group | Day 4 | Day 8 | Day 12 |
|---|---|---|---|
| Control group | 1.87 ± 0.35 | 3.82 ± 0.89 | 4.83 ± 1.16 |
| E7386 50 mg/kg group | 1.98 ± 0.24 | 3.87 ± 0.74 | 4.94 ± 1.41 |
| Lenvatinib mesylate 10 mg/kg group | 1.41 ± 0.30 | 1.75 ± 0.13 | 1.94 ± 0.31 |
| E7386 50 mg/kg group + lenvatinib mesylate 10 mg/kg group | 0.80 ± 0.18 | 0.71 ± 0.20 | 0.77 ± 0.10 |

[Example 9] Antitumor Effect of Combined Use of E7386 and Lenvatinib Mesylate in Human Renal Cell Carcinoma Line A-498 Subcutaneous Transplantation Model Human renal cell carcinoma line A-498 cells (ATCC) were cultured by using RPMI1640 medium (Wako Pure Chemical Industries, Ltd.) containing 10% FBS in a 5% $CO_2$ incubator under conditions of 37° C. When the cells became an approximately 100% confluent state, the cells were recovered by using trypsin-EDTA. A suspension was prepared by adding RPMI1640 medium containing 50% Matrigel to the cells so as to be 5.0×10$^7$ cells/mL. 0.1 mL of the obtained cell suspension was subcutaneously transplanted to the sides of the bodies of six nude mice (CAnN.Cg-Foxn1$^{nu}$/CrlCrlj, Charles River Laboratories Japan, Inc.) each of a control group, an E7386 50 mg/kg alone administration group, a lenvatinib mesylate 10 mg/kg alone administration group, and a combined administration group of 50 mg/kg E7386 and 10 mg/kg lenvatinib mesylate. From 27 days alter the transplantation, E7386 (50 mg/kg, q.d., 14 days, oral administration) and lenvatinib mesylate (10 mg/kg, q.d, 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

When the start day of administration was defined as day 1, the major axis and minor axis of tumor developed in each mouse were then measured at day 5, day 8, day 12, and day 15 by using Digimatic Caliper (Mitutoyo Corp.).

The tumor volume and the relative tumor volume (RTV) were calculated according to the following expressions.

Tumor volume (mm$^3$)=Tumor major axis (mm)× Tumor minor axis$^2$ (mm$^2$)/2

Figure 16:
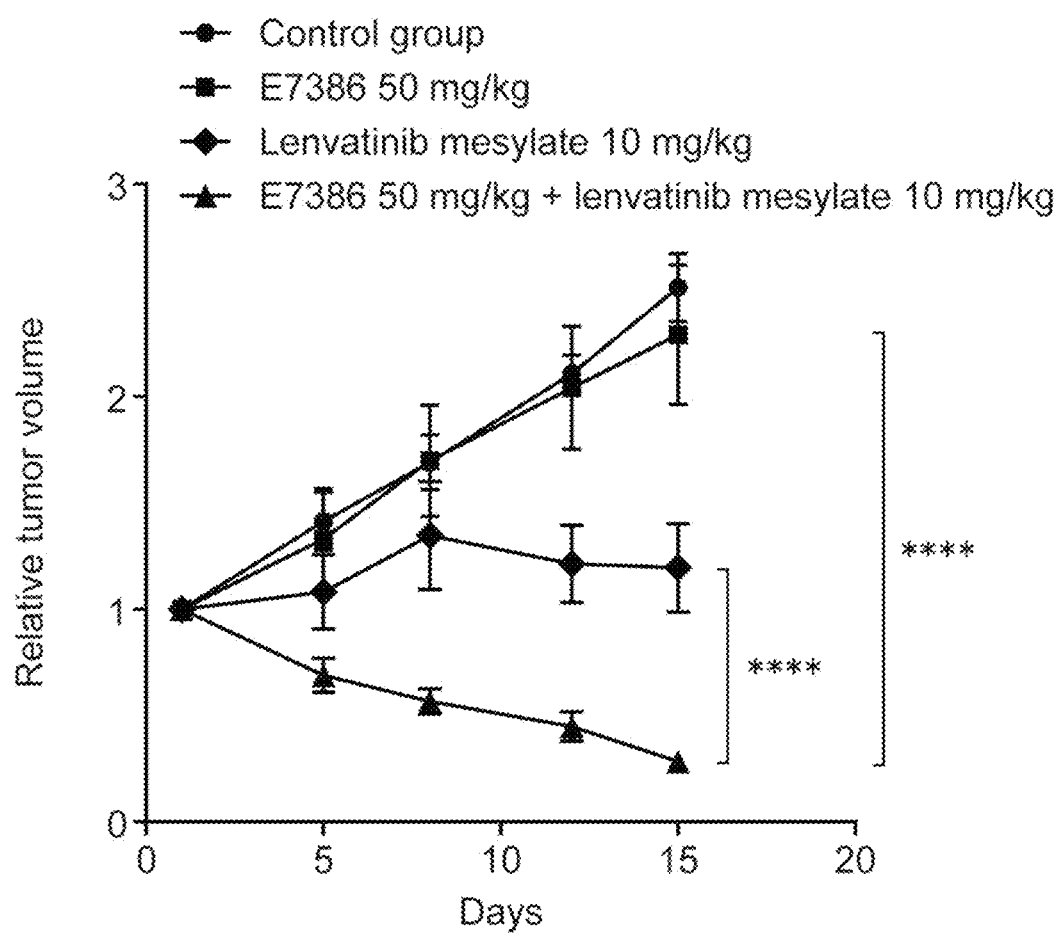
FIG. 16 is a graph showing the antitumor effect of combined use of 50 mg/kg E7386 and 10 mg/kg lenvatinib mesylate in human renal cell carcinoma line A-498 subcutaneous transplantation models. In the graph, \*\*\*\* shows that the combined use of E7386 and lenvatinib mesylate statistically significantly inhibited tumor growth as compared with the case where each of them was administered alone (\*\*\*\*: p<0.0001; repeated measures ANOVA followed by Dunnett's type multiple comparison).

Relative tumor volume (RTV)=Tumor volume at the measurement day/Tumor volume at the start day of administration The results about RTV are shown in Table 9 and FIG. 16. Numbers in Table 9 denote mean±standard deviation (SD) of RTV. As a result, combined use of E7386 and lenvatinib mesylate exhibited an excellent antitumor effect in the human renal cell carcinoma line A-498 subcutaneous transplantation models. ** in FIG. 16 shows that the combined use of E7386 and lenvatinib mesylate statistically significantly inhibited tumor growth as compared with the case where each of them was administered alone (**: p<0.0001; repeated measures ANOVA followed by Dunnetts type multiple comparison).

TABLE 9

| Group | Day 5 | Day 8 | Day 12 | Day 15 |
|---|---|---|---|---|
| Control group | 1.41 ± 0.14 | 1.69 ± 0.13 | 2.11 ± 0.09 | 2.51 ± 0.16 |
| E7386 50 mg/kg group | 1.33 ± 0.24 | 1.70 ± 0.26 | 2.04 ± 0.29 | 2.29 ± 0.33 |
| Lenvatinib mesylate 10 mg/kg group | 1.08 ± 0.18 | 1.35 ± 0.25 | 1.21 ± 0.18 | 1.20 ± 0.21 |
| E7386 50 mg/kg group + lenvatinib mesylate 10 mg/kg group | 0.69 ± 0.08 | 0.57 ± 0.06 | 0.45 ± 0.07 | 0.29 ± 0.05 |

[Example 10] Antitumor Effect of Combined Use of E7386 and Lenvatinib Mesylate in Human Head and Neck Cancer SCC15 Transplantation Model Human head and neck cancer SCC15 cells (ATCC) are cultured by using RPMI1640 medium (Sigma-Aldrich Co. LLC) containing 10% FBS in a 5% $CO_2$ incubator under conditions of 37° C. When the cells become an approximately 80% confluent state, the cells are recovered by using trypsin-EDTA. A suspension is prepared by adding Hank's balanced salt solution containing 50% Matrigel to the cells so as to be 5.0×10$^7$ cells/mL. 0.1 mL of the obtained cell suspension is subcutaneously transplanted to the sides of the bodies of nude mice (CAnN.Cg-Foxn1$^{nu}$/CrlCrlj, Charles River Laboratories Japan, Inc.) each of a control group, an E7386 alone administration group, a lenvatinib mesylate alone administration group, and a combined administration group of E7386 and lenvatinib mesylate. After tumorigenesis, E7386 (oral administration) and lenvatinib mesylate (oral administration) are administered alone or in combination to the alone administration group or the combined administration group.

From the start day of administration, the major axis and minor axis of tumor developed in each mouse are measured on a regular basis by using Digimatic Caliper (Mitutoyo Corp.), and the tumor volume and the relative tumor volume (RTV) are calculated. From the results about RTV, the antitumor effect of combined use of E7386 and lenvatinib mesylate can be evaluated.

The tumor volume and the relative tumor volume (RTV) are calculated according to the following expressions.

Tumor volume (mm$^3$)=Tumor major axis (mm)× Tumor minor axis$^2$ (mm$^2$)/2

Relative tumor volume (RTV)=Tumor volume at the measurement day/Tumor volume at the start day of administration

[Example 11] Antitumor Effect of Combined Use of E7386 and Lenvatinib Mesylate in Human Endometrial Cancer HEC-151 Transplantation Model Human endometrial cancer HEC-151 cells (JCRB Cell Bank) are cultured by using RPMI1640 medium (Sigma-Aldrich Co. LLC) containing 10% FBS in a 5% $CO_2$ incubator under conditions of 37° C. When the cells become an approximately 80% confluent state, the cells are recovered by using trypsin-EDTA. A suspension is prepared by adding Hank's balanced salt solution containing 50% Matrigel to the cells so as to be $5.0 \times 10^7$ cells/mL. 0.1 mL of the obtained cell suspension is subcutaneously transplanted to the sides of the bodies of nude mice (CAnN.Cg-Foxn1$^{nu}$/CrlCrlj, Charles River Laboratories Japan, Inc.) each of a control group, an E7386 alone administration group, a lenvatinib mesylate alone administration group, and a combined administration group of E7386 and lenvatinib mesylate. After tumorigenesis, E7386 (oral administration) and lenvatinib mesylate (oral administration) are administered alone or in combination to the alone administration group or the combined administration group.

From the start day of administration, the major axis and minor axis of tumor developed in each mouse are measured on a regular basis by using Digimatic Caliper (Mitutoyo Corp.), and the tumor volume and the relative tumor volume (RTV) are calculated. From the results about RTV, the antitumor effect of combined use of E7386 and lenvatinib mesylate can be evaluated.

The tumor volume and the relative tumor volume (RTV) are calculated according to the following expressions.

Tumor volume (mm³)=Tumor major axis (mm)× Tumor minor axis² (mm²)/2

Relative tumor volume (RTV)=Tumor volume at the measurement day/Tumor volume at the start day of administration

[Example 12] Tumor Vessel Suppressive Effect of Combined Use of E7386 and Lenvatinib Mesylate in Mouse Breast Cancer 4T1 Orthotopic Transplantation Model Mouse breast cancer 4T1 cells (ATCC) were cultured by using RPMI1640 medium (Sigma-Aldrich Co. LLC) containing 10% FBS in a 5% $CO_2$ incubator under conditions of 37° C. When the cells became an approximately 80% confluent state, the cells were recovered by using trypsin-EDTA. A suspension was prepared by adding Hank's balanced salt solution so as to be $1.0 \times 10^7$ cells/mL. 0.1 mL of the obtained cell suspension was transplanted to the right third mammary gland fat pads of five mice (C57BL/6J, Charles River Laboratories Japan, Inc.) each of a control group, an E7386 25 mg/kg alone administration group, a lenvatinib mesylate 10 mg/kg alone administration group, and a combined administration group of 25 mg/kg E7386 and 10 mg/kg lenvatinib mesylate. From 9 days after the transplantation, E7386 (25 mg/kg, b.d.s., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

After the administration for 14 days, tumor tissues were collected from the mice, the formalin fixation of the tumor tissues was performed, and the tumor tissues were embedded in paraffin. Then, the paraffin-embedded tumor tissues were sliced at a thickness of 4 μm and placed on slide glass, and deparaffinization treatment was performed with xylene/ethanol. Immunostaining was performed by using an antibody (manufactured by Sigma-Aldrich Co. LLC) against α-smooth muscle actin (α-SMA), which is a marker for vascular pericytes, and an antibody (manufactured by Dianova GmbH) against CD31, which is a marker for vascular endothelial cells.

The preparations of CD31/α-SMA co-staining were converted to digital images in a slide scanner (Aperio, Leica Biosystems Nussloch GmbH), and microvessel density (MVD) was measured and analyzed as the amount of CD31-positive blood vessels per unit area (1 mm²) in the whole tumor by using image analysis software (Aperio ImageScope ver 12.3.0.5056, Leica Biosystems Nussloch GmbH).

Figure 17:
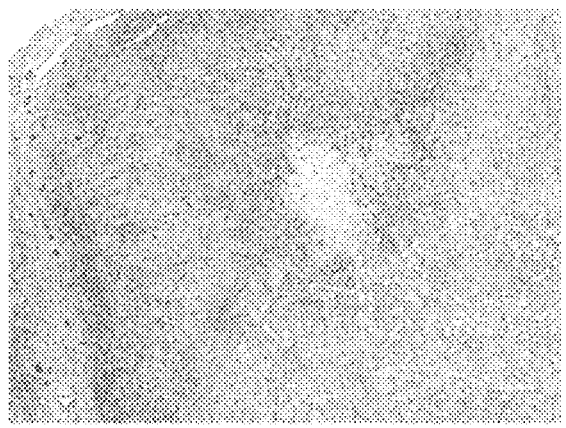
FIG. 17 is a 10× magnified photograph showing the microvessel suppressive effect of combined use of E7386 and lenvatinib mesylate in mouse breast cancer 4T1 orthotopic transplantation models by immunostaining in which CD31/α-SMA co-staining was performed.
Figure 17:
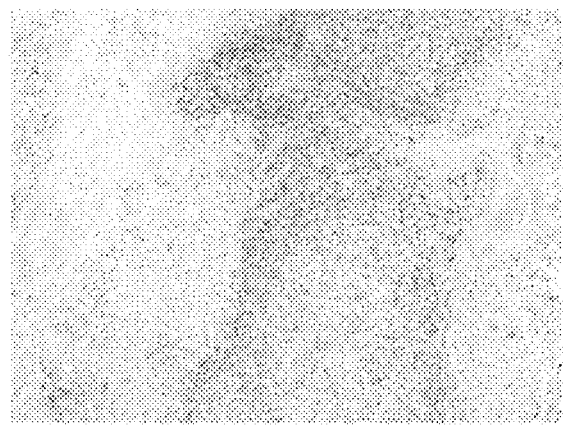
Figure 17:
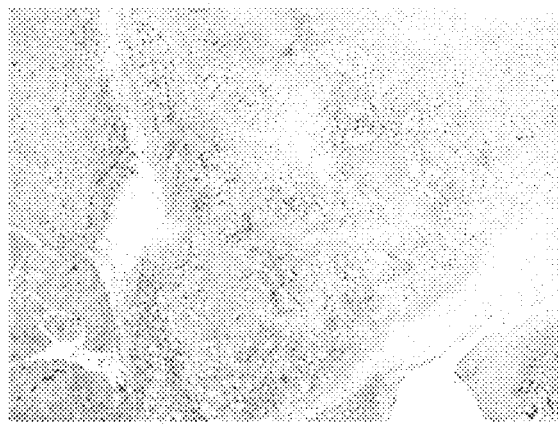
Figure 17:
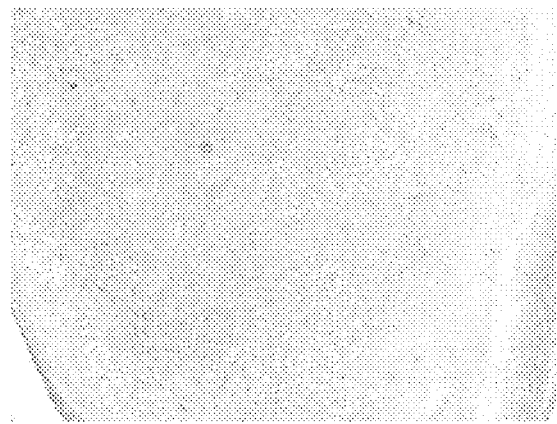

A 10× magnified immunostaining image (in a color photograph, indicated by brown (CD31) and red (α-SMA)) in which CD31/α-SMA co-staining was performed is shown in FIG. 17. FIGS. 17(a), 17(b), 17(c) and 17(d) are the immunostaining images of the control group, the E7386 alone administration group, the lenvatinib mesylate alone administration group, and the combined administration group of E7386 and lenvatinib mesylate, respectively. As a result, for combined use of E7386 and lenvatinib mesylate, marked decrease in MVD was observed, as compared with the control group and the case where each of them was administered alone.

On a 200× magnified image, five regions of 0.2 mm×0.2 mm square with high microvessel density per tumor section were determined as hot spots for vascular property analysis. PCI (pericyte coverage index), which is the amount of CD31/α-SMA both positive blood vessels relative to the amount of CD31-positive blood vessels, in the hot spots for analysis was measured and analyzed by using image analysis software (Aperio ImageScope ver 12.3.0.5056, Leica Biosystems Nussloch GmbH). PCI represents the ratio of blood vessels covered with vascular pericytes to all blood vessels. Mean PCI of the five hot spots for analysis was regarded as a typical value of the tumor section.

Figure 18:
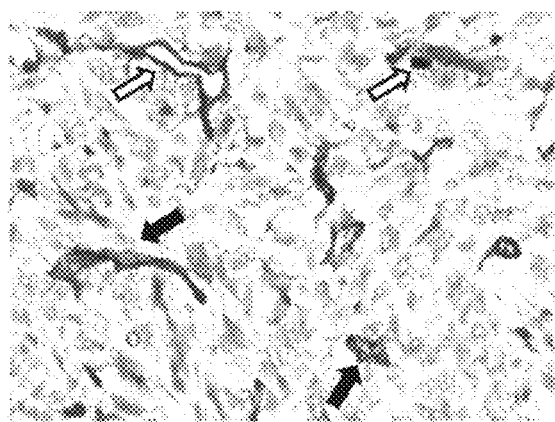
FIG. 18 is a 200× magnified photograph showing the pericyte coverage (coverage of blood vessels with vascular pericytes) suppressive effect of combined use of E7386 and lenvatinib mesylate in mouse breast cancer 4T1 orthotopic transplantation models by immunostaining in which CD31/α-SMA co-staining was performed.
Figure 18:
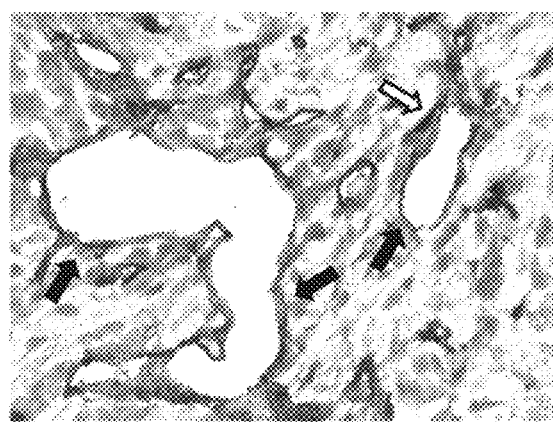
Figure 18:
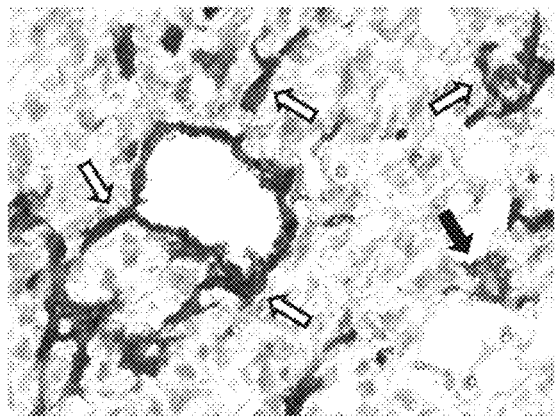
Figure 18:
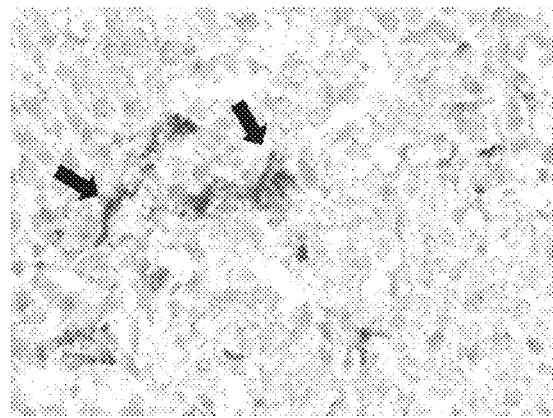

A 200× magnified immunostaining image (in a color photograph, indicated by brown (CD31) and red (α-SMA)) in which CD31/α-SMA co-staining was performed is shown in FIG. 18. FIGS. 18(a), 18(b), 18(c) and 18(d) are the immunostaining images of the control group, the E7386 alone administration group, the lenvatinib mesylate alone administration group, and the combined administration group of E7386 and lenvatinib mesylate, respectively. A microvessel stained with CD31 is indicated by black arrow. A CD31/α-SMA both positive blood vessel is indicated by open arrow. As a result, for combined use of E7386 and lenvatinib mesylate, marked decrease in PCI was observed, as compared with the control group and the case where each of them was administered alone.

Figure 19:
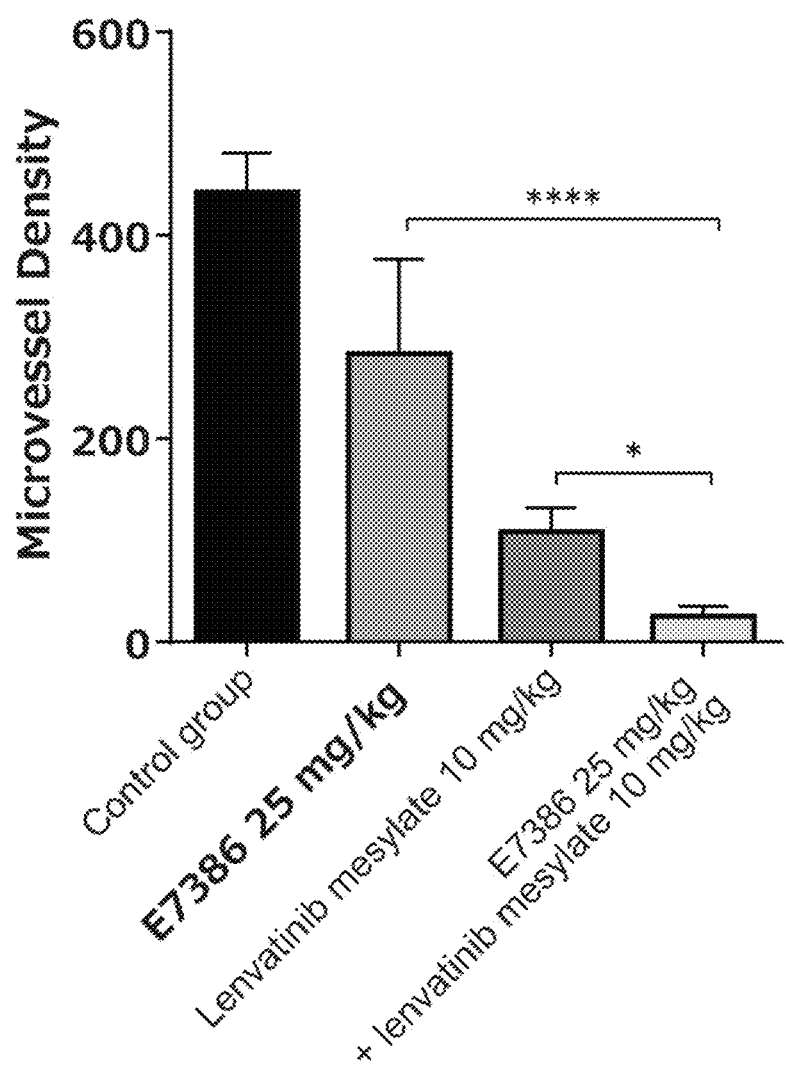
FIG. 19 is a graph showing the microvessel suppressive effect of combined use of 25 mg/kg E7386 and 10 mg/kg lenvatinib mesylate in mouse breast cancer 4T1 orthotopic transplantation models. In the graph, \* and \*\*\*\* show that the combined use of E7386 and lenvatinib mesylate statistically significantly suppressed microvessels as compared with the case where each of them was administered alone (\*: p<0.05, \*\*\*\*: p<0.0001; Dunnett's type multiple comparison).

The results about MVD are shown in FIG. 19. The graph shows a mean of five tumor sections of each administration group, and the error bar shows standard deviation. Combined use of E7386 and lenvatinib mesylate exhibited an excellent microvessel suppressive effect in the mouse breast cancer 4T1 orthotopic transplantation models. * and S*** in FIG. 19 show that the combined use of E7386 and lenvatinib mesylate statistically significantly suppressed microvessels as compared with the case where each of them was administered alone (*: p<0.05, ****: p<0.0001; Dunnett's type multiple comparison).

Figure 20:
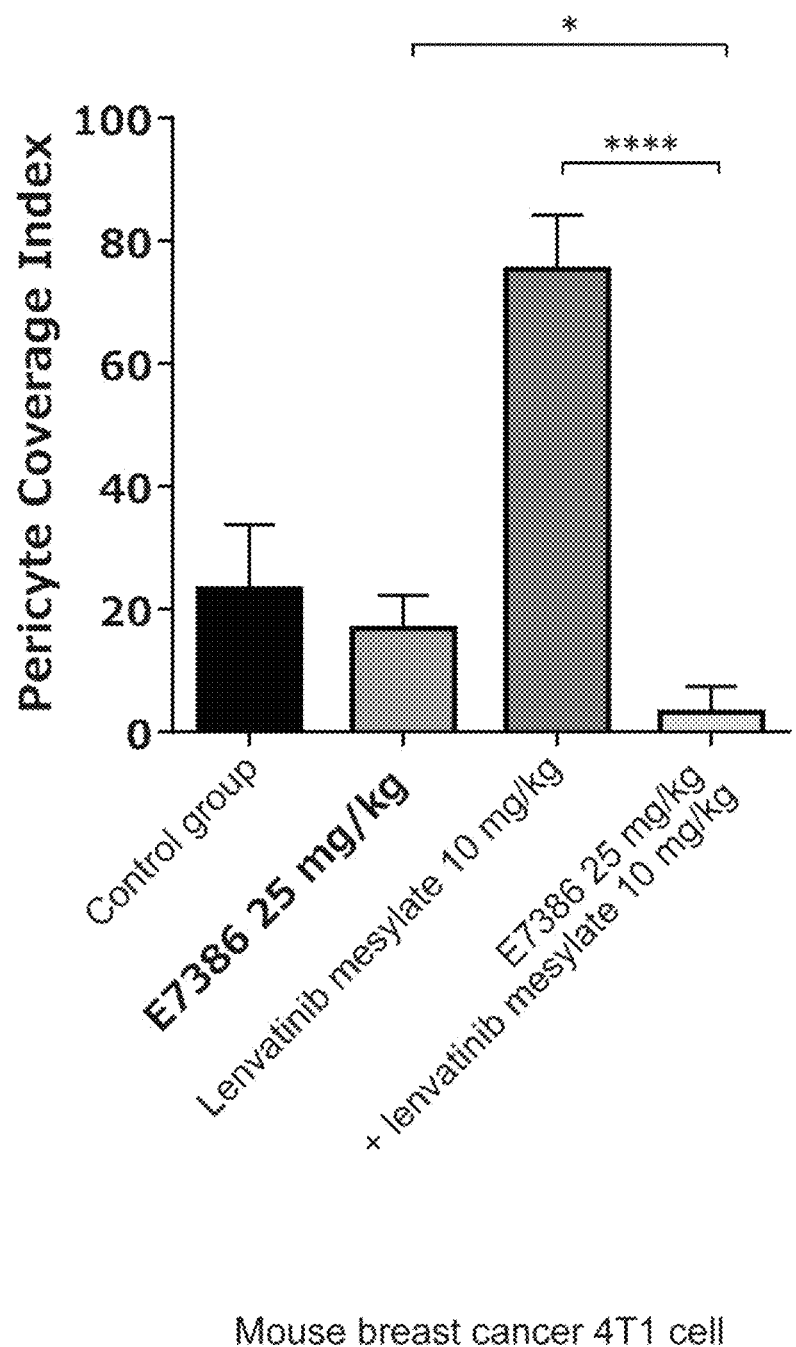
FIG. 20 is a graph showing the pericyte coverage (coverage of blood vessels with vascular pericytes) suppressive effect of combined use of 25 mg/kg E7386 and 10 mg/kg lenvatinib mesylate in mouse breast cancer 4T1 orthotopic transplantation models. In the graph, \* and \*\*\*\* show that the combined use of E7386 and lenvatinib mesylate statistically significantly suppressed pericyte coverage as compared with the case where each of them was administered alone (\*: p<0.05, \*\*\*\*: p<0.0001; Dunnett's type multiple comparison).

The results about PCI are shown in FIG. 20. The graph shows a mean of five tumor sections of each administration group, and the error bar shows standard deviation. Combined use of E7386 and lenvatinib mesylate exhibited an excellent pericyte coverage (coverage of blood vessels with vascular pericytes) suppressive effect in the mouse breast cancer 4T1 orthotopic transplantation models. * and **** in FIG. 20 show that the combined use of E7386 and lenvatinib mesylate statistically significantly suppressed pericyte coverage as compared with the case where each of them was administered alone (*: p<0.05, ****: p<0.0001; Dunnett's type multiple comparison).

[Example 13] Tumor Vessel Suppressive Effect of Combined Use of E7386 and Lenvatinib Mesylate in Human Hepatocellular Carcinoma HepG2 Subcutaneous Transplantation Model 0.1 mL of a cell suspension prepared by using human hepatocellular carcinoma line HepG2 cells (JCRB Cell Bank) as described in Example 7 above was subcutaneously transplanted to the sides of the bodies of five nude mice (CAnN.Cg-Foxn1$^{nu}$/CrlCrlj, Charles River Laboratories Japan, Inc.) each of a control group, an E7386 50 mg/kg alone administration group, a lenvatinib mesylate 10 mg/kg alone administration group, and a combined administration group of 50 mg/kg E7386 and 10 mg/kg lenvatinib mesylate. From 12 days after the transplantation, E7386 (50 mg/kg, q.d., 14 days, oral administration) and lenvatinib mesylate (10 mg/kg, q.d., 14 days, oral administration) were administered alone or in combination to the alone administration group or the combined administration group. For the administration, E7386 was dissolved in 0.1 mol/L hydrochloric acid, and lenvatinib mesylate was dissolved in 3 mmol/L hydrochloric acid. Any drug was not administered to the control group.

After the administration for 14 days, tumor tissues collected from the mice were divided and used as tumor samples for blood vessel analysis. The divided tumor tissues were subjected to formalin fixation and embedded in paraffin. Then, the paraffin-embedded tumor tissues were sliced at a thickness of 4 μm and placed on slide glass, and deparaffinization treatment was performed with xylene/ethanol. Immunostaining was performed by using an antibody (manufactured by Sigma-Aldrich Co. LLC) against α-smooth muscle actin (α-SMA), which is a marker for vascular pericytes, and an antibody (manufactured by Dianova GmbH) against CD31, which is a marker for vascular endothelial cells.

The preparations of CD31/α-SMA co-staining were converted to digital images in a slide scanner (Aperio, Leica Biosystems Nussloch GmbH), and microvessel density (MVD) was measured and analyzed as the amount of CD31-positive blood vessels per unit area (1 mm$^2$) in the whole tumor by using image analysis software (HALO v2.0.1145.38). As a result, for combined use of E7386 and lenvatinib mesylate, marked decrease in MVD was observed, as compared with the control group and the case where each of them was administered alone.

On a 200× magnified image, six regions of 0.5 mm×0.5 mm square with high microvessel density per tumor section were determined as hot spots for vascular property analysis. PCI (pericyte coverage index), which is the amount of CD31/α-SMA both positive blood vessels relative to the amount of CD31-positive blood vessels, in the hot spots for analysis was measured and analyzed by using image analysis software (HALO v2.0.1145.38). PCI represents the ratio (%) of blood vessels covered with vascular pericytes to all blood vessels. Mean PCI of the six hot spots for analysis was regarded as a typical value of the tumor section. As a result, PCI was markedly increased by the administration of lenvatinib mesylate alone, whereas the suppression of increase in PCI to a level equivalent to the control group by combined use of E7386 and lenvatinib mesylate was observed.

Figure 21:
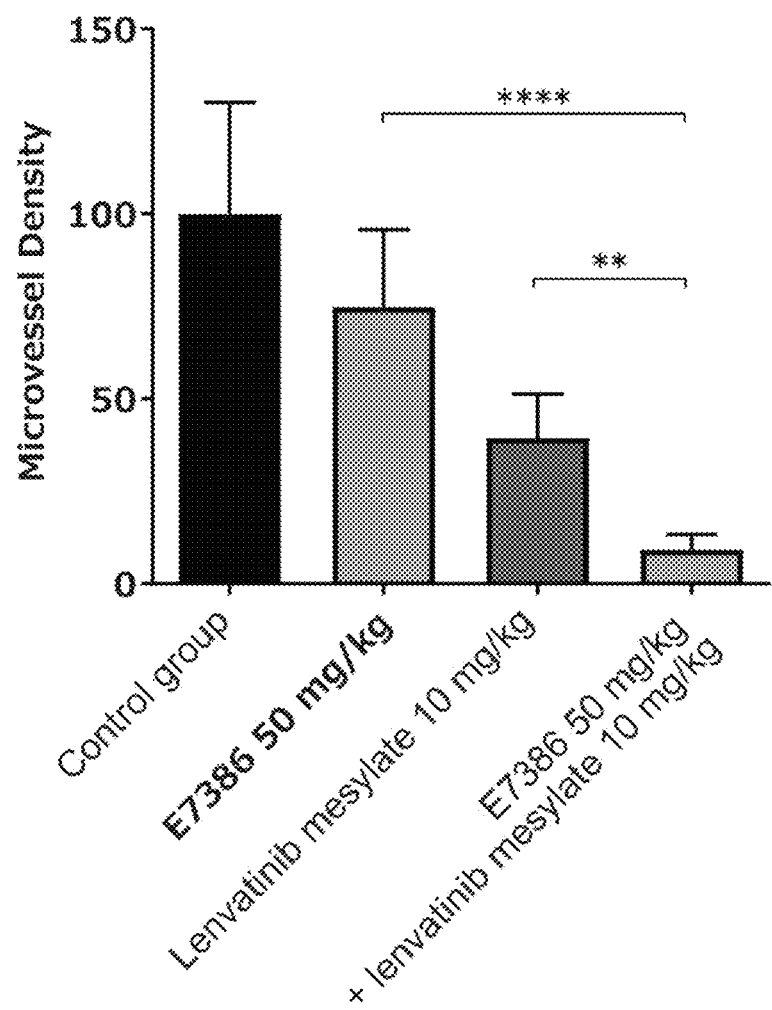
FIG. 21 is a graph showing the microvessel suppressive effect of combined use of 50 mg/kg E7386 and 10 mg/kg lenvatinib mesylate in human hepatocellular carcinoma HepG2 subcutaneous transplantation models. In the graph, \*\* and \*\*\*\* show that the combined use of E7386 and lenvatinib mesylate statistically significantly suppressed microvessels as compared with the case where each of them was administered alone (\*\*: p<0.01, \*\*\*\*: p<0.0001; Dunnett's type multiple comparison).

The results about MVD are shown in FIG. 21. The graph was prepared by measuring a mean of five tumor sections of each administration group, and then calculating a ratio (%) with the value of the control group as a reference value. The error bar shows standard deviation. Combined use of E7386 and lenvatinib mesylate exhibited an excellent microvessel suppressive effect in the human hepatocellular carcinoma HepG2 subcutaneous transplantation models.  and  in FIG. 21 show that the combined use of E7386 and lenvatinib mesylate statistically significantly suppressed microvessels as compared with the case where each of them was administered alone (: p<0.01, ****: p<0.0001; Dunnett's type multiple comparison).

Figure 22:
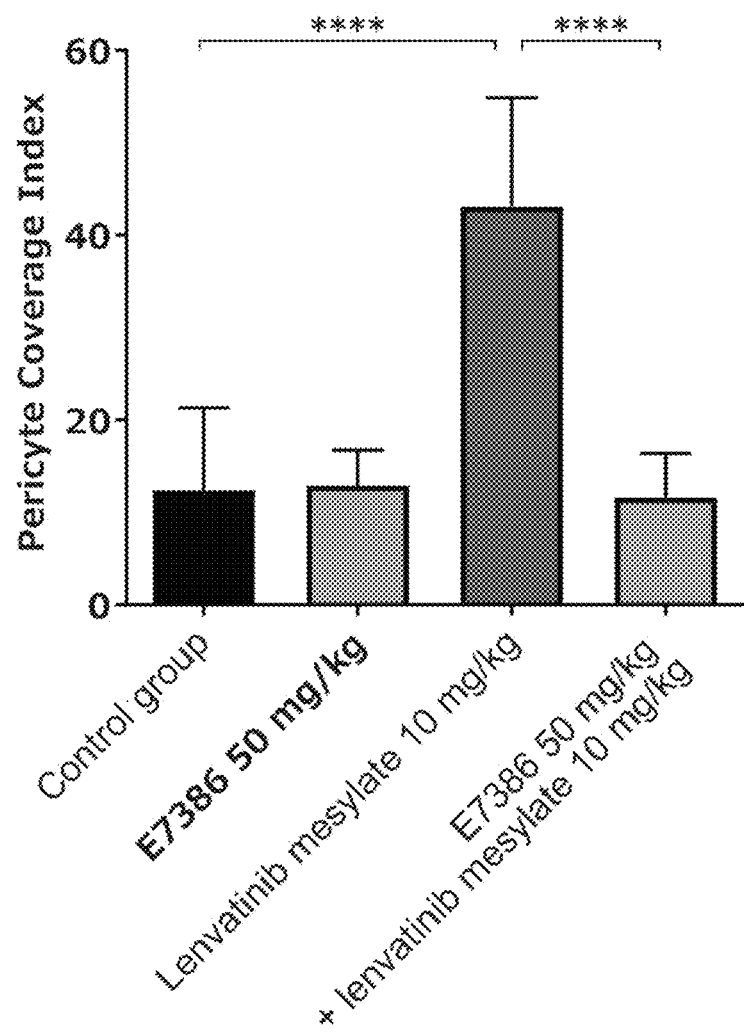
FIG. 22 is a graph showing the pericyte coverage (coverage of blood vessels with vascular pericytes) suppressive effect of combined use of 50 mg/kg E7386 and 10 mg/kg lenvatinib mesylate in human hepatocellular carcinoma HepG2 subcutaneous transplantation models. In the graph, \*\*\*\* shows that the combined use of E7386 and lenvatinib mesylate statistically significantly suppressed pericyte coverage as compared with the case where each of them was administered alone (\*\*\*\*: p<0.0001; Dunnett's type multiple comparison).

The results about PCI are shown in FIG. 22. The graph shows a mean of five tumor sections of each administration group in PCI, and the error bar shows standard deviation. Combined use of E7386 and lenvatinib mesylate exhibited an excellent pericyte coverage (coverage of blood vessels with vascular pericytes) suppressive effect in the human hepatocellular carcinoma HepG2 subcutaneous transplantation models. ** in FIG. 22 shows that the administration of lenvatinib mesylate alone statistically significantly increased pericyte coverage as compared with the control group, and the combined use of E7386 and lenvatinib mesylate statistically significantly suppressed pericyte coverage as compared with the case where lenvatinib mesylate was administered alone (**: p<0.001; Dunnett's type multiple comparison).

The invention claimed is:

1. A method for treating a tumor, comprising administering a therapeutically effective amount of lenvatinib or a pharmaceutically acceptable salt thereof, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide to a patient in need thereof, wherein the tumor is breast cancer, a thyroid cancer, hepatocellular carcinoma, colorectal cancer, renal cell carcinoma, head and neck cancer, endometrial cancer, or melanoma.

2. The method according to claim 1, wherein the lenvatinib or the pharmaceutically acceptable salt thereof is lenvatinib mesylate.

3. The method according to claim 1, wherein the lenvatinib or the pharmaceutically acceptable salt thereof, and the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide are administered simultaneously, separately, continuously, or at time intervals.

4. The method according to claim 1, wherein the tumor is breast cancer.

5. The method according to claim 1, wherein the tumor is a thyroid cancer.

6. The method according to claim 5, wherein the thyroid cancer is anaplastic thyroid cancer.

7. The method according to claim 1, wherein the tumor is hepatocellular carcinoma.

8. The method according to claim 1, wherein the tumor is colorectal cancer.

9. The method according to claim 1, wherein the tumor is renal cell carcinoma.

10. The method according to claim 1, wherein the tumor is head and neck cancer.

11. The method according to claim 1, wherein the tumor is endometrial cancer.

12. The method according to claim 1, wherein the tumor is melanoma.

13. The method according to claim 4, wherein the lenvatinib or the pharmaceutically acceptable salt thereof is lenvatinib mesylate.

14. The method according to claim 5, wherein the lenvatinib or the pharmaceutically acceptable salt thereof is lenvatinib mesylate.

15. The method according to claim 6, wherein the lenvatinib or the pharmaceutically acceptable salt thereof is lenvatinib mesylate.

16. The method according to claim 7, wherein the lenvatinib or the pharmaceutically acceptable salt thereof is lenvatinib mesylate.

17. The method according to claim 8, wherein the lenvatinib or the pharmaceutically acceptable salt thereof is lenvatinib mesylate.

18. The method according to claim 9, wherein the lenvatinib or the pharmaceutically acceptable salt thereof is lenvatinib mesylate.

19. The method according to claim 10, wherein the lenvatinib or the pharmaceutically acceptable salt thereof is lenvatinib mesylate.

20. The method according to claim 11, wherein the lenvatinib or the pharmaceutically acceptable salt thereof is lenvatinib mesylate.

21. The method according to claim 12, wherein the lenvatinib or the pharmaceutically acceptable salt thereof is lenvatinib mesylate.

* * * * *